US008269000B2

(12) United States Patent
Schunk et al.

(10) Patent No.: US 8,269,000 B2
(45) Date of Patent: Sep. 18, 2012

(54) SUBSTITUTED PYRIMIDINE AND TRIAZINE COMPOUNDS

(75) Inventors: Stefan Schunk, Aachen (DE); Melanie Reich, Aachen (DE); Kamila Hennig, Eschweiler (DE); Michael Engels, Turnhout (BE); Tieno Germann, Aachen (DE); Ruth Jostock, Stolberg (DE); Sabine Hees, Aachen (DE)

(73) Assignee: Gruenenthal GmbH, Aachen (DE)

( * ) Notice: Subject to any disclaimer, the term of this patent is extended or adjusted under 35 U.S.C. 154(b) by 276 days.

(21) Appl. No.: 12/604,691

(22) Filed: Oct. 23, 2009

(65) Prior Publication Data

US 2010/0173889 A1    Jul. 8, 2010

Related U.S. Application Data

(60) Provisional application No. 61/107,877, filed on Oct. 23, 2008.

(30) Foreign Application Priority Data

Oct. 23, 2008 (EP) .................................... 08018514

(51) Int. Cl.
| C07D 401/04 | (2006.01) |
| C07D 401/12 | (2006.01) |
| C07D 401/14 | (2006.01) |
| C07D 471/10 | (2006.01) |
| C07D 487/10 | (2006.01) |
| A61K 31/506 | (2006.01) |
| A61P 25/04 | (2006.01) |

(52) U.S. Cl. ........ 544/241; 544/298; 544/322; 514/256; 514/269; 514/275

(58) Field of Classification Search .................. 544/241, 544/298, 322; 514/256, 269, 275
See application file for complete search history.

(56) References Cited

FOREIGN PATENT DOCUMENTS

| WO | WO 01/05783 A1 | 1/2001 |
| WO | WO 2007/101007 A2 | 9/2007 |
| WO | WO 2007/140383 A2 | 12/2007 |
| WO | WO 2007/140383 A3 | 12/2007 |
| WO | WO 2008/040492 A1 | 4/2008 |
| WO | WO 2008/046573 A1 | 4/2008 |

OTHER PUBLICATIONS

Chen et al., Expert Opin. Ther. Targets (2007) 11(1):21-35.*
Campos et al., TRENDS in Pharmacological Sciences vol. 27 No. 12, 646-651.*
Potente et al., Cell 146, 873-887, 2011.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-1010, 1996.*
R. Hayashi et al., "Bradykinin Stimulates IL-6 and IL-8 Production by Human Lung Fibroblasts Through ERK- and p38 MAPK-dependent Mechanisms", European Respiratory Journal, 2000, pp. 452-458, vol. 16, ISSN: 0903-1936.
Bichoy H. Gabra et al., "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.
Joao B. Calixto et al., "Kinin B, Receptors: Key G-protein-coupled Receptors and their Role in Inflammatory and Painful Processes", British Journal of Pharmacology, 2004, pp. 803-818, vol. 143, 2004 Nature Publishing Group.
Sara H. Bengtson et al., "Kinin Receptor Expression During Staphylococcus Aureus Infection", Blood, Sep. 15, 2006, pp. 2055-2063, vol. 108, No. 6, The American Society of Hematology.
Antoni Stadnicki et al., "Immunolocalization and Expression of Kinin $B_1R$ and $B_2R$ Receptors in Human Inflammatory Bowel Disease", Am. J. Physiol. Gastrointest. Liver Physiol, Mar. 31, 2005, pp. G361-G366, vol. 289, American Physiological Society.
Joao B. Pesquero et al., "Genetically Altered Animal Models in the Kallikrein-Kinin System", Biol. Chem., Feb. 2006, pp. 119-126, vol. 387.
A. Prat et al., "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology, ISSN: 0028-3878.
J. Fred Hess et al., "Generation and characterization of a humanized bradykinin B1 receptor mouse", Biol. Chem., vol. 387, pp. 195-201, Feb. 2006.
L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14.

(Continued)

*Primary Examiner* — Venkataraman Balasubramanian
(74) *Attorney, Agent, or Firm* — Crowell & Moring LLP

(57) ABSTRACT

Substituted pyrimidine and triazine compounds corresponding to formula I (I)

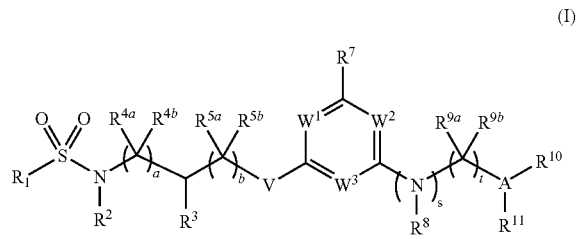

wherein $R^1$, $R^2$, $R^3$, $R^{4a}$, $R^{4b}$, $R^{5a}$, $R^{5b}$, $R^7$, $R^8$, $R^{9a}$, $R^{9b}$, $R^{10}$, $R^{11}$, A, a, b, s, t, V, $W^1$, $W^2$ and $W^3$ have defined meanings, pharmaceutical compositions comprising such compounds, a process for preparing such compounds, and the use of such compounds and compositions to treat or inhibit pain and/or other disorders or disease states.

25 Claims, No Drawings

OTHER PUBLICATIONS

Giselle F. Passos, et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847.

International Search Report with partial translation dated Feb. 1, 2010 (Five (5) pages).
PCT/ISA/237 (Six (6) pages), Feb. 1, 2010.
PCT/ISA/220 (Three (3) pages), Feb. 1, 2010.

* cited by examiner

SUBSTITUTED PYRIMIDINE AND TRIAZINE COMPOUNDS

BACKGROUND OF THE INVENTION

The present invention relates to substituted pyrimidine and triazine derivatives, to a process for their preparation, to medicaments comprising these compounds, and to the use of substituted pyrimidine and triazine derivatives in the preparation of medicaments.

Unlike the constitutive expression of the bradykinin 2 receptor (B2R), the bradykinin 1 receptor (B1R) is not expressed or is expressed only weakly in most tissues. However, the expression of B1R in various cells is inducible. For example, following inflammation reactions there is a rapid and pronounced induction of B1R in neuronal cells but also in various peripheral cells such as fibroblasts, endothelial cells, granulocytes, macrophages and lymphocytes. Accordingly, in the course of inflammation reactions there is a switch from B2R to B1R dominance in the cells that are involved. The cytokines interleukin-1 (IL-1) and tumour necrosis factor alpha (TNFα) play a substantial part in this B1R up-regulation (Passos et al., J. Immunol. 2004, 172, 1839-1847). Following activation with specific ligands, B1R-expressing cells are then themselves able to secrete inflammation-promoting cytokines such as IL-6 and IL-8 (Hayashi et al., Eur. Respir. J. 2000, 16, 452-458). This results in the immigration of further inflammatory cells, for example neutrophilic granulocytes (Pesquero et al., PNAS 2000, 97, 8140-8145). By way of these mechanisms, the bradykinin B1R system can contribute to the chronification of diseases. This is proved by a large number of animal experiments (overviews in Leeb-Lundberg et al., Pharmacol. Rev. 2005, 57, 27-77 and Pesquero et al., Biol. Chem. 2006, 387, 119-126). In humans too, enhanced expression of B1R is found, for example, in enterocytes and macrophages in the affected tissue of patients with inflammatory intestinal diseases (Stadnicki et al., Am. J. Physiol. Gastrointest. Liver Physiol. 2005, 289, G361-366) or in T-lymphocytes of patients with multiple sclerosis (Prat et al., Neurology, 1999; 53, 2087-2092), or activation of the bradykinin B2R-B1R system is found in the course of infections with *Staphylococcus aureus* (Bengtson et al., Blood 2006, 108, 2055-2063). Infections with *Staphylococcus aureus* are responsible for symptoms such as superficial skin infections to septic shock.

Due to the described pathophysiological relationships there is a great therapeutic potential for the use of B1R antagonists in acute and, in particular, chronic inflammatory diseases. These include respiratory diseases (Asthma bronchiale, allergies, COPD/chronic-obstructive pulmonary disease, cystic fibrosis, etc.), inflammatory intestinal diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucosa (Behcet's disease, pelvitis, prostatitis, etc.), rheumatic diseases (rheumatoid arthritis, osteoarthritis, etc.), septic shock and reperfusion syndrome (following heart attack, stroke).

In addition, the bradykinin (receptor) system is also involved in regulating angiogenesis (potential as an angiogenesis inhibitor in cancer and macular degeneration of the eye), and B1R knockout mice are protected against the induction of excess weight as a result of a particularly high-fat diet (Pesquero et al., Biol. Chem. 2006, 387, 119-126). B1R antagonists are therefore suitable also for the treatment of obesity.

B1R antagonists are suitable in particular for the treatment of pain, in particular inflammatory pain and neuropathic pain (Calixto et al., Br. J. Pharmacol. 2004, 1-16), in particular diabetic neuropathy (Gabra et al., Biol. Chem. 2006, 387, 127-143). They are also suitable for the treatment of migraine.

In the development of B1R modulators there is the problem, however, that the human and the rat B1R receptor differ so widely that many compounds which are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect can be investigated on the rat. This has already meant that transgenic animals with human B1 receptors have been produced for animal pharmacology studies (Hess et al., Biol. Chem. 2006; 387(2):195-201). Working with transgenic animals is more expensive, however, than working with the unmodified animals.

Patent applications WO 2008/040492 and WO 2008/046573 describe compounds that exhibit antagonistic activity both on the human B1 receptor and on the B1 receptor of the rat in in vitro assays.

Patent applications WO 2007/140383 and WO 2007/101007 describe compounds that exhibit an antagonistic activity on the macaque B1 receptor in in vitro assays. Experimental data relating to activity on the human B1 receptor or on the B1 receptor of the rat are not disclosed.

There is a continued need for novel B1R modulators, B1R modulators that bind both to the rat receptor and to the human receptor offering particular advantages.

SUMMARY OF THE INVENTION

An object of the present invention was, therefore, to provide novel compounds which are suitable in particular as pharmacological active ingredients in pharmaceutical compositions, especially in medicaments for the treatment of disorders or diseases that are mediated at least in part by B1R receptors.

This and other objects are achieved by providing the substituted pyrimidine and triazine compounds according to the invention.

The invention accordingly provides compounds of the general formula I

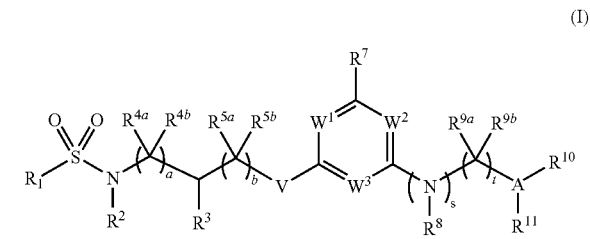

wherein
a represents 0, 1 or 2;
b represents 0, 1 or 2;
$R^1$ represents aryl, heteroaryl, or an aryl or heteroaryl bonded via a $C_{1-3}$-alkylene group;
$R^2$ and $R^3$ are defined as described under (i) or (ii):
(i) $R^2$ represents H, $C_{1-6}$-alkyl, $C_{3-8}$-cycloalkyl, aryl or heteroaryl; or $R^2$ denotes a $C_{3-8}$-cycloalkyl, aryl or heteroaryl bonded via a $C_{1-6}$-alkylene group, $C_{2-6}$-alkenylene group or $C_{2-6}$-alkynylene group;

R³ represents H, F, Cl, Br, I, —CF₃, —OCF₃, OH, O—C₁₋₆-alkyl, C₁₋₆-alkyl, C₃₋₈-cycloalkyl, aryl, heteroaryl; or R³ denotes a C₃₋₈-cycloalkyl, aryl or heteroaryl bonded via a C₁₋₆-alkylene group, C₂₋₆-alkenylene group or C₂₋₆-alkynylene group; or (ii) R² and R³, together with the group —N—(CR⁴ᵃR⁴ᵇ)ₐ—CH— linking them, form a heterocycle which can be substituted on one or more of its carbon ring members by one or more radicals independently selected from the group consisting of F, Cl, Br, I, —CF₃, =O, —O—CF₃, —OH, —SH, —O—C₁₋₆-alkyl, C₁₋₆-alkyl, C₃₋₈cycloalkyl, aryl and heteroaryl and/or can be fused to an aryl or heteroaryl and/or two of its carbon ring members are linked together via a C₁₋₃-alkylene bridge, wherein the heterocycle is saturated or at least monounsaturated but is not aromatic, is 4-, 5-, 6- or 7-membered and can contain, in addition to the N heteroatom to which R² is bonded, one or more heteroatoms or heteroatom groups independently selected from the group consisting of N, NR⁵⁰, O, S, S=O and S(=O)₂; wherein R⁵⁰ denotes H, C₁₋₆-alkyl, —C(=O)—R⁵¹, C₃₋₈-cycloalkyl, aryl, heteroaryl, or a C₃₋₈-cycloalkyl, aryl or heteroaryl bonded via a C₁₋₃-alkylene group, and R⁵¹ denotes C₁₋₆-alkyl, C₃₋₈-cycloalkyl, aryl, heteroaryl, or a C₃₋₈-cycloalkyl, aryl or heteroaryl bonded via a C₁₋₃-alkylene group;

V represents C(R⁶ᵃ)(R⁶ᵇ), NR⁶ᶜ, O or a single bond, wherein R⁶ᶜ represents a radical from the group H, C₁₋₆-alkyl, C₃₋₈-cycloalkyl, aryl, heteroaryl, or represents a C₃₋₈-cycloalkyl, aryl or heteroaryl bonded via a C₁₋₆-alkylene group, C₂₋₆-alkenylene group or C₂₋₆-alkynylene group, R⁴ᵃ, R⁴ᵇ, R⁵ᵃ, R⁵ᵇ, R⁶ᵃ, R⁶ᵇ each independently represent H, F, Cl, Br, I, —CF₃, O—CF₃, OH, SH, O—C₁₋₆-alkyl, C₁₋₆-alkyl, C₃₋₈-cycloalkyl, aryl or heteroaryl; or represents a C₃₋₈-cycloalkyl, aryl or heteroaryl bonded via a C₁₋₆-alkylene group or C₂₋₆-alkenylene group; and R⁶ᵃ and R⁶ᵇ can additionally together denote =O; and/or R⁴ᵃ and R⁴ᵇ, together with the carbon atom linking them, form a saturated ring which is unsubstituted or substituted on one or more, for example 1, 2, 3 or 4, of its carbon ring members by one or more, for example 1, 2, 3 or 4, substituents independently selected from the group consisting of F, CF₃, C₁₋₆-alkyl, O—O₁₋₆-alkyl, OH, OCF₃, aryl and heteroaryl, wherein the ring is 3-, 4-, 5- or 6-membered and can optionally contain one or more, for example 1 or 2, oxygen atoms;

R⁷ represents a substituent from the group H, C₁₋₆-alkyl, —CN, —CF₃, OH, C₁₋₆-alkoxy, —O—CF₃;

W¹, W² and W³ each independently represent N or CR⁶⁰, with the proviso that at least two of W¹, W² and W³ represent N, and R⁶⁰ represents H, C₁₋₆-alkyl, halogen, —CN, CF₃, OH, C₁₋₆-alkoxy or —O—CF₃;

s is 0 or 1, t is 0, 1, 2 or 3,

R⁸ represents H; C₁₋₆-alkyl; C₃₋₈-cycloalkyl; aryl or heteroaryl; C₃₋₈-cycloalkyl, aryl or heteroaryl bonded via a C₁₋₆-alkylene group;

R⁹ᵃ and R⁹ᵇ each independently of the other denotes H; F; Cl; OH; C₁₋₆-alkyl; O—C₁₋₆-alkyl; C₃₋₈-cycloalkyl; aryl or heteroaryl; C₃₋₈-cycloalkyl, aryl or heteroaryl bonded via a C₁₋₆-alkylene group;

A represents N or CH, with the proviso that when s represents 1 and t represents 0, A represents CH; and with the proviso that when s and t each represents 0, A represents N;

R¹⁰ and R¹¹, with the inclusion of A, represent a spirocyclic or cyclic group of one of the general formulas II and III

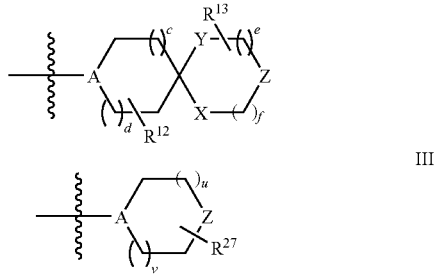

wherein c, d, e, f, u and v each independently denotes 0, 1 or 2;

R¹², R¹³ and R²⁷ each independently represent from 0 to 4 substituents each selected independently of any others from F; Cl; OH; =O; O₁₋₆-alkyl; O—C₁₋₆-alkyl; C₃₋₈-cycloalkyl; aryl or heteroaryl; C₃₋₈-cycloalkyl, aryl or heteroaryl bonded via a C₁₋₆-alkylene group;

and/or in each case two substituents R²⁷ together represent a C₁₋₃-alkylene bridge, so that the ring shown in the general formula III assumes a bicyclically bridged form;

and/or two adjacent substituents R¹³ form a fused aryl or heteroaryl;

and/or two adjacent substituents R²⁷ form a fused aryl or heteroaryl;

X represents CR¹⁴ᵃR¹⁴ᵇ, NR¹⁵ or O;

Y represents CR¹⁶ᵃR¹⁶ᵇ, NR¹⁷ or O;

with the proviso that X does not denote NR¹⁵ when Y denotes NR¹⁷; and with the proviso that X and Y do not simultaneously denote O;

wherein

R¹⁴ᵃ, R¹⁴ᵇ, R¹⁶ᵃ and R¹⁶ᵇ each independently denotes H; F; Cl; OH; C₁₋₆-alkyl; O—C₁₋₆-alkyl; C₃₋₈-cycloalkyl; aryl or heteroaryl; C₃₋₈-cycloalkyl, aryl or heteroaryl bonded via a C₁₋₆-alkylene group;

and/or in each case R¹⁴ᵃ and R¹⁴ᵇ together can represent =O and/or in each case R¹⁶ᵃ and R¹⁶ᵇ together can represent =O;

R¹⁵ and R¹⁷ each independently of the other represents H; C₁₋₆-alkyl; C₃₋₈-cycloalkyl, aryl or heteroaryl; C₃₋₈-cycloalkyl, aryl or heteroaryl bonded via a C₁₋₆-alkylene group;

Z in formula II represents CR¹⁸ᵃR¹⁸ᵇ; NR¹⁹ or O;

Z in formula II, if X represents O and f represents 0, denotes —(C(R¹²⁴)—O(R¹²⁵))—, wherein R¹²⁴ and R¹²⁵, together with the carbon atoms linking them, form a fused aryl or heteroaryl;

or

Z in formula II, if X represents O and f represents 0, denotes =N—(CR¹²⁶)—, wherein the N atom is singly bonded to the O atom, and R¹²⁶ represents H; C₁₋₆-alkyl; C₃₋₈-cycloalkyl; aryl or heteroaryl; C₃₋₈-cycloalkyl, aryl or heteroaryl bonded via a C₁₋₆-alkylene group;

Z in formula III represents CR¹⁸ᵃR¹⁸ᵇ, NR¹⁹, O, S, S(=O) or S(=O)₂;

wherein
R$^{18a}$ represents H; C$_{1-6}$-alkyl; C$_{3-8}$-cycloalkyl; aryl or heteroaryl; C$_{3-8}$-cycloalkyl, aryl or heteroaryl bonded via a C$_{1-6}$-alkylene group;
or R$^{18a}$ represents a group of the general formula IV

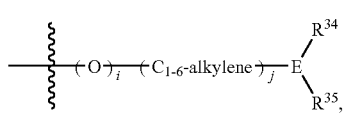

IV wherein
i and j each independently of the other represents 0 or 1;
E represents N or CH,
with the proviso that when i represents 1 and j represents 0, E represents CH;
R$^{34}$ and R$^{35}$ each independently of the other denotes H; C$_{1-6}$-alkyl;
C$_{3-8}$-cycloalkyl; aryl or heteroaryl; aryl, heteroaryl or C$_{3-8}$-cycloalkyl bonded via a C$_{1-3}$-alkylene group; or
R$^{34}$ and R$^{35}$, with the inclusion of E, form a 5- or 6-membered aryl or heteroaryl;
or R$^{34}$ and R$^{35}$, with the inclusion of E, form a saturated heterocycle of the general formula V:

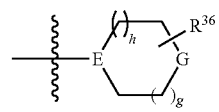

V wherein
h and g each independently denote 0, 1 or 2;
G represents CR$^{37a}$R$^{37b}$, NR$^{38}$, O, S, S=O or S(=O)$_2$, with the proviso that if E represents CH, G is not CR$^{37a}$R$^{37b}$;
R$^{36}$ represents from 0 to 4 substituents each selected independently of any others from F; Cl; Br; I; OH; SH; =O; O—C$_{1-6}$-alkyl; C$_{1-6}$-alkyl; C$_{3-8}$-cycloalkyl; aryl or heteroaryl; C$_{3-8}$-cycloalkyl, aryl or heteroaryl bonded via a C$_{1-6}$-alkylene group; and/or two adjacent substituents R$^{36}$ together represent a fused aryl or heteroaryl;
R$^{37a}$ and R$^{37b}$ each independently of the other denotes H; F; Cl; Br; I; OH; SH; =O; O—C$_{1-6}$-alkyl; C$_{1-6}$-alkyl; C$_{3-8}$-cycloalkyl; aryl or heteroaryl; C$_{3-8}$-cycloalkyl, aryl or heteroaryl bonded via a C$_{1-6}$-alkylene group;
R$^{38}$ represents H; C$_{1-6}$-alkyl; C$_{3-8}$-cycloalkyl; aryl or heteroaryl; aryl, heteroaryl or C$_{3-8}$-cycloalkyl bonded via a C$_{1-3}$-alkylene group;
wherein
R$^{18b}$ represents H; OH; C$_{1-6}$-alkyl; C$_{3-8}$-cycloalkyl; O—C$_{1-6}$-alkyl; O—(C$_{3-8}$-cycloalkyl); (C$_{1-6}$-alkylene)-O—C$_{1-6}$-alkyl; (C$_{1-6}$-alkylene)-O—(C$_{3-8}$-cycloalkyl); aryl or heteroaryl; O-aryl or O-heteroaryl; aryl, O-aryl, heteroaryl or O-heteroaryl bonded via C$_{1-6}$-alkylene;

or R$^{18b}$ represents a group of the general formula VI:

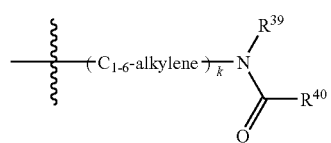

VI wherein
k represents 0 or 1;
R$^{39}$ represents H; C$_{1-6}$-alkyl; C$_{3-8}$-cycloalkyl; aryl or heteroaryl; C$_{3-8}$-cycloalkyl, aryl or heteroaryl bonded via a C$_{1-3}$-alkylene group;
R$^{40}$ represents C$_{1-6}$-alkyl; C$_{3-8}$-cycloalkyl; aryl or heteroaryl; C$_{3-8}$-cycloalkyl, aryl or heteroaryl bonded via a C$_{1-6}$-alkylene group; or
R$^{39}$ and R$^{40}$, together with the N—C(=O) group linking them, form a ring of the general formula VII:

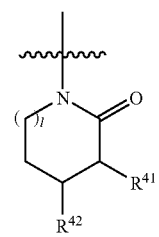

VII wherein
l represents 0, 1 or 2
and R$^{41}$ and R$^{42}$, together with the carbon atoms linking them, form a fused aryl or heteroaryl;
wherein R$^{19}$ represents H; or (P)$_z$—R$^{22}$,
wherein
z represents 0 or 1;
P represents (C=O), S(=O)$_2$ or C(=O)—N(R$^{24}$); wherein the nitrogen atom of the C(=O)—N(R$^{24}$) group is linked to R$^{22}$;
R$^{24}$ represents H; C$_{1-6}$-alkyl; C$_{3-8}$-cycloalkyl; aryl, heteroaryl or C$_{3-8}$-cycloalkyl bonded via a C$_{1-3}$-alkylene group;
R$^{22}$ represents C$_{1-6}$-alkyl; aryl or heteroaryl; aryl or heteroaryl bonded via a C$_{1-6}$-alkylene group; or
R$^{22}$ represents a group of the general formula VIII:

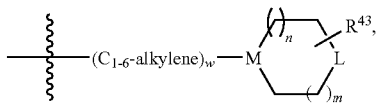

VIII wherein
n represents 0, 1 or 2;
m represents 0, 1 or 2;
w represents 0 or 1,
M represents CH or N;
with the proviso that when P represents C(=O)—NR$^{24}$ and w represents 0, M represents CH; and
with the proviso that when z and w simultaneously represent 0, M represents CH;
L represents CR$^{44a}$R$^{44b}$, NR$^{45}$, O, S, S=O or S(=O)$_2$;

$R^{43}$ represents from 0 to 4 substituents each selected independently of any others from F; Cl; OH; =O; $C_{1-6}$-alkyl; O—$C_{1-6}$-alkyl; $C_{3-8}$-cycloalkyl; aryl or heteroaryl; $C_{3-8}$-cycloalkyl, aryl or heteroaryl bonded via a $C_{1-6}$-alkylene group;

and/or two adjacent radicals $R^{43}$ together represent a fused aryl or heteroaryl;

$R^{44a}$ and $R^{44b}$ each independently of the other represents H; F; Cl; Br; I; OH; $C_{1-6}$-alkyl; O—$C_{1-6}$-alkyl; $C_{3-8}$-cycloalkyl; aryl or heteroaryl; $C_{3-8}$-cycloalkyl, aryl or heteroaryl bonded via a $C_{1-6}$-alkylene group; or $R^{44a}$ and $R^{44b}$ together can represent =O;

$R^{45}$ represents H; $C_{1-6}$-alkyl; $C_{3-8}$-cycloalkyl; aryl or heteroaryl; aryl, heteroaryl or $C_{3-8}$-cycloalkyl bonded via a $C_{1-3}$-alkylene group;

wherein the above-mentioned radicals $C_{1-6}$-alkyl, $C_{1-3}$-alkylene, $C_{1-6}$-alkylene, $C_{2-6}$-alkenylene, $C_{2-6}$-alkynylene, $C_{3-6}$-cycloalkyl, $C_{3-8}$-cycloalkyl, aryl and heteroaryl can in each case be unsubstituted or mono- or poly-substituted by identical or different radicals; the above-mentioned radicals $C_{1-6}$-alkyl, $C_{1-3}$-alkylene, $C_{1-6}$-alkylene, $C_{2-6}$-alkenylene and $C_{2-6}$-alkynylene can in each case be branched or unbranched; in the form of an individual enantiomer or of an individual diastereoisomer, of the racemate, of the enantiomers, of the diastereoisomers, mixtures of the enantiomers and/or diastereoisomers, as well as in each case in the form of their bases and/or physiologically acceptable salts.

In the general formula IV used above, the bonds shown between E and $R^{34}$ and $R^{35}$ are not to be understood solely as being single bonds but may also be part of an aromatic system.

Within the scope of the present invention, the term "halogen" preferably denotes the radicals F, Cl, Br and I, in particular the radicals F and Cl.

Within the scope of this invention, the term "$C_{1-6}$-alkyl" includes acyclic saturated hydrocarbon radicals having 1, 2, 3, 4, 5 or 6 carbon atoms, which can be branched- or straight-chained (unbranched) as well as unsubstituted or substituted one or more times, for example 2, 3, 4 or 5 times, by identical or different radicals. The alkyl radicals can preferably be selected from the group consisting of methyl, ethyl, n-propyl, isopropyl, n-butyl, isobutyl, sec-butyl, tert-butyl, n-pentyl, isopentyl, neopentyl and hexyl. Particularly preferred alkyl radicals can be selected from the group consisting of methyl, ethyl, n-propyl, isopropyl, n-butyl, sec-butyl, isobutyl and tert-butyl.

Within the scope of this invention, the term "$C_{2-6}$-alkenyl" includes acyclic unsaturated hydrocarbon radicals having 2, 3, 4, 5 or 6 carbon atoms, which can be branched- or straight-chained (unbranched) as well as unsubstituted or substituted one or more times, for example 2, 3, 4 or 5 times, by identical or different radicals. Alkenyl radicals contain at least one C=C double bond. Alkenyl radicals can preferably be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl, but-1-en-2-yl, pentenyl and hexenyl. Particularly preferred alkenyl radicals can be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl and but-1-en-2-yl.

Within the scope of this invention, the term "$C_{3-8}$-cycloalkyl" denotes cyclic saturated hydrocarbons having 3, 4, 5, 6, 7 or 8 carbon atoms, which can be unsubstituted or substituted on one or more ring members by one or more, for example by 2, 3, 4 or 5, identical or different radicals. $C_{3-8}$-Cycloalkyl can preferably be selected from the group consisting of cyclopropyl, cyclobutyl, cyclopentyl, cyclohexyl, cycloheptyl and cyclooctyl, in particular cyclopropyl, cyclobutyl, cyclopentyl or cyclohexyl.

Within the scope of this invention, the term "aryl" denotes aromatic hydrocarbons, in particular phenyls and naphthyls. The aryl radicals can also be fused with further saturated, (partially) unsaturated or aromatic ring systems. Each aryl radical can be unsubstituted or substituted one or more times, for example 2, 3, 4 or 5 times, it being possible for the aryl substituents to be identical or different and to be located at any desired and possible position of the aryl. Aryl can advantageously be selected from the group consisting of phenyl, 1-naphthyl and 2-naphthyl, which can in each case be unsubstituted or substituted one or more times, for example by 2, 3, 4 or 5 radicals.

Within the scope of the present invention, the term "heteroaryl" denotes a 5-, 6- or 7-membered cyclic aromatic radical containing at least one, optionally also 2, 3, 4 or 5, heteroatom(s), it being possible for the heteroatoms to be identical or different and for the heteroaryl to be unsubstituted or substituted one or more times, for example 2, 3, 4 or 5 times, by identical or different radicals. The substituents can be bonded at any desired and possible position of the heteroaryl. The heterocycle can also be part of a bi- or polycyclic system, in particular of a mono-, bi- or tri-cyclic system, which can then be more than 7-membered in total, preferably up to 14-membered. Preferred heteroatoms are selected from the group consisting of N, O and S. The heteroaryl radical can preferably be selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phthalazinyl, pyrazolyl, imidazolyl, thiazolyl, oxazolyl, oxadiazolyl, triazolyl, tetrazolyl, isoxazolyl, pyridinyl (pyridyl), pyridazinyl, pyrimidinyl (pyrimidyl), pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, imidazolyl, oxazolyl, quinazolinyl, quinolinyl, isoquinolinyl and oxadiazolyl, it being possible for bonding to the general structure I to take place via any desired and possible ring member of the heteroaryl radical. The heteroaryl radical can particularly preferably be selected from the group consisting of pyridinyl, pyrimidinyl, imidazolyl, thienyl, thiazolyl and triazolyl.

Within the scope of the present invention, the expression "$C_{1-3}$-alkylene group" or "$C_{1-6}$-alkylene group" includes acyclic saturated hydrocarbon radicals having 1, 2 or 3 or having 1, 2, 3, 4, 5 or 6 carbon atoms, which can be branched- or straight-chained (unbranched) as well as unsubstituted or substituted one or more times, for example 2, 3, 4 or 5 times, by identical or different radicals and which link a corresponding radical to the main structure. The alkylene groups can preferably be selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—

$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. Particularly preferably, the alkylene groups can be selected from the group consisting of —$CH_2$—, —$CH_2$—$CH_2$— and —$CH_2$—$CH_2$—$CH_2$—.

Within the scope of the present invention, the expression "—$(O)_{0/1}$—$C_{1-6}$-alkylene group", as well as including the $C_{1-6}$-alkylene groups described above, additionally includes groups in which those groups are linked via an oxygen atom to the main structure.

Within the scope of the present invention, the expression "$C_{2-6}$-alkenylene group" includes acyclic, mono- or poly-unsaturated, for example di-, tri- or tetra-unsaturated, hydrocarbon radicals having 2, 3, 4, 5 or 6 carbon atoms, which can be branched- or straight-chained (unbranched) as well as unsubstituted or substituted one or more times, for example 2, 3, 4 or 5 times, by identical or different radicals and which link a corresponding radical to the main structure. The alkenylene groups contain at least one C=C double bond. The alkenylene groups can preferably be selected from the group consisting of —CH=CH—, —CH=CH—$CH_2$—, —$C(CH_3)$=$CH_2$—, —CH=CH—$CH_2$—$CH_2$—, —$CH_2$—CH=CH—$CH_2$—, —CH=CH—CH=CH—, —$C(CH_3)$=CH—$CH_2$—, —CH=$C(CH_3)$—$CH_2$—, —$C(CH_3)$=$C(CH_3)$—, —$C(CH_2CH_3)$=CH—, —CH=CH—$CH_2$—$CH_2$—$CH_2$—, —$CH_2$—CH=$CH_2$—$CH_2$—$CH_2$—, —CH=CH—CH—$CH_2$—$CH_2$— and —CH=$CH_2$—CH—CH=$CH_2$—.

Within the scope of the invention, the expression "$C_{2-6}$-alkynylene group" includes acyclic, mono- or poly-unsaturated, for example di-, tri- or tetra-unsaturated, hydrocarbon radicals having 2, 3, 4, 5 or 6 carbon atoms, which can be branched- or straight-chained (unbranched) as well as unsubstituted or substituted one or more times, for example 2, 3, 4 or 5 times, by identical or different radicals and which link a corresponding radical to the main structure. The alkynylene groups contain at least one C≡C triple bond. The alkynylene groups can preferably be selected from the group consisting of —C≡O—, —C≡O—$CH_2$—, —C≡O—$CH_2$—$CH_2$—, —C≡C—$CH(CH_3)$—, —$CH_2$—C≡C—$CH_2$—, —C≡C—C≡C—, —C≡C—$C(CH_3)_2$—, —C≡C—$CH_2$—$CH_2$—C≡C—$CH_2$—$CH_2$—, —C≡O—C≡O—$CH_2$— and —C≡C—$CH_2$—C≡C—.

Within the scope of the present invention, the expression "aryl or heteroaryl bonded via a $C_{1-3}$-alkylene group, $C_{1-6}$-alkylene group, $C_{2-6}$-alkenylene group or $C_{2-6}$-alkynylene group" means that the $C_{1-6}$-alkylene groups, $C_{1-3}$-alkylene groups, $C_{2-6}$-alkenylene groups, $C_{2-6}$-alkynylene groups as well as aryl or heteroaryl have the meanings defined above and the aryl or heteroaryl is bonded to the main structure via a $C_{1-3}$-alkylene group, $C_{1-6}$-alkylene group, $C_{2-6}$-alkenylene group or $C_{2-6}$-alkynylene group. Benzyl, phenethyl and phenylpropyl may be mentioned as examples.

Within the scope of the present invention, the expression "$C_{3-8}$-cycloalkyl and heterocycloalkyl bonded via a $C_{1-3}$-alkylene group, $C_{1-6}$-alkylene group, $C_{2-6}$-alkenylene group or $C_{2-6}$-alkynylene group" means that the $C_{1-3}$-alkylene group, $C_{1-6}$-alkylene group, $C_{2-6}$-alkenylene group, $C_{2-6}$-alkynylene group, $C_{3-8}$-cycloalkyl and heterocycloalkyl have the meanings defined above and $C_{3-8}$-cycloalkyl and heterocycloalkyl are bonded to the main structure via a $C_{1-3}$-alkylene group, $C_{1-6}$-alkylene group, $C_{2-6}$-alkenylene group or $C_{2-6}$-alkynylene group.

In connection with "alkyl", "alkenyl", "alkylene", "alkenylene", "alkynylene" and "cycloalkyl", the term "substituted" within the scope of this invention is understood as meaning the substitution of a hydrogen radical by F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl, wherein polysubstituted radicals are to be understood as being radicals which are polysubstituted, for example di- or tri-substituted, either on different atoms or on the same atom, for example trisubstituted on the same carbon atom, as in the case of $CF_3$ or $CH_2CF_3$, or at different positions, as in the case of CH(Cl)—CH=CH—$CHCl_2$. Polysubstitution can be carried out with the same or with different substituents, such as, for example, in the case of CH(OH)—CH=CH—$CHCl_2$. In particular, it is here to be understood as meaning the substitution of one or more hydrogen radicals by F, Cl, $NH_2$, OH, O, —$CF_3$ or O—$C_{1-6}$-alkyl, in particular methoxy.

In relation to "aryl" and "heteroaryl", "substituted" within the scope of this invention is understood as meaning the substitution of one or more hydrogen atoms of the corresponding ring system one or more times, for example 2, 3, 4 or 5 times, by F, Cl, Br, I, CN, $NH_2$, NH—$C_{1-6}$-alkyl, NH—$C_{1-6}$-alkylene-OH, $N(O_{1-6}$-alkyl$)_2$, $N(C_{1-6}$-alkylene-OH$)_2$, NH-aryl$^1$, $N($aryl$^1)_2$, $N(C_{1-6}$-alkyl)aryl$^1$, pyrrolinyl, piperazinyl, morpholinyl; ($C_{1-3}$-alkylene)azetidinyl, -pyrrolidinyl or -piperidinyl, azepanyl, diazepanyl; $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl; pyrrolidinyl, imidazolyl, piperidinyl, benzyloxy, phenoxy, phenyl, naphthyl, pyridinyl, thiazolinyl, —$C_{1-3}$-alkylene-aryl$^1$, benzyl, thienyl, furyl, wherein aryl$^1$ represents phenyl, thiazolyl, thienyl or pyridinyl, on one atom or on different atoms, wherein the above-mentioned substituents—unless indicated otherwise—can themselves optionally be substituted by the mentioned substituents. The polysubstitution of aryl and heteroaryl can be carried out with the same or with different substituents. Preferred substituents for aryl and heteroaryl can be selected from the group consisting of —O—$C_{1-3}$-alkyl, unsubstituted $C_{1-6}$-alkyl, F, Cl, Br, I, CN, $CF_3$, $OCF_3$, OH, SH, —$CH_2$-azetidinyl, —$CH_2$-pyrrolidinyl, —$CH_2$-piperidinyl, —$CH_2$-piperazinyl, —$CH_2$-morpholinyl, phenyl, naphthyl, thiazolyl, thienyl and pyridinyl, in particular from the group consisting of F, Cl, CN, $CF_3$, $CH_3$; $OCH_3$, $OCF_3$ and —$CH_2$-azetidinyl.

In the chemical structural formulas which are used here to describe the compounds according to the invention, the symbol "$R^a$\" is also used to describe one or more substitution patterns, that group, in contrast to the representation of a bond to a specific atom, not being bonded to a specific atom within the chemical structural formula ($R^a$ here represents, for example, a substituent R having a numbering represented by the variable "a").

This will be explained by way of example with reference to the group

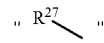

from the general formula III shown above: The definition of $R^{27}$ states that $R^{27}$ can represent from 0 to 4 substituents. $R^{27}$ can, therefore, be absent, or 1, 2, 3 or 4 of the C-bonded hydrogen atoms within the partial structure represented by the general formula III can be replaced by a substituent provided in the definition of $R^{27}$, wherein the substituents in question can be independently selected, that is to say can also have different meanings, and C-bonded hydrogen atoms on one or more carbon atoms can be replaced. As explained in the definition of $R^{27}$, it is also possible for in each case two of the substituents $R^{27}$ together to represent a $C_{1-3}$-alkylene bridge or a fused aryl or heteroaryl (also known as annellated aryl or heteroaryl or fused/annellated aryl or heteroaryl group), so that $R^{27}$ in the general formula III also has the meanings shown by way of example hereinbelow, in which $R^{27}$ represents two substituents on in each case different carbon atoms, which in these cases given solely by way of example together form either a $C_2$-alkylene bridge or a fused benzo group, and in the second example the variable u represents 1:

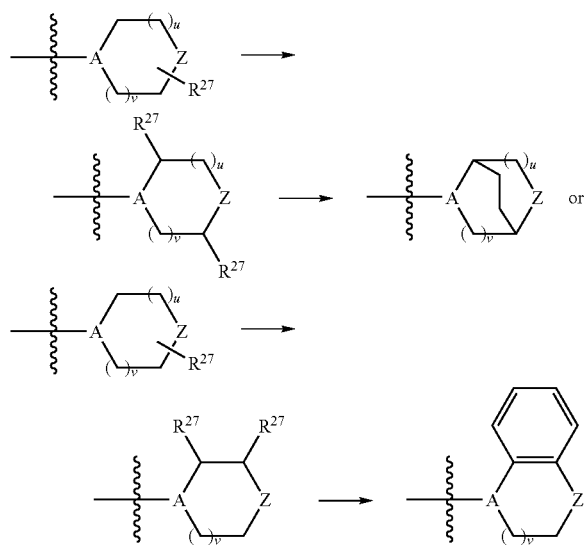

Within the scope of the present invention, the symbol

used in formulas denotes the linking of a corresponding radical to the respective main structure.

Persons skilled in the art will understand that identical radicals used to define different substituents are in each case independent of one another.

Within the scope of this invention, the expression "physiologically acceptable salt" is understood as meaning preferably salts of the compounds according to the invention with inorganic or organic acids which are physiologically acceptable—in particular when used in humans and/or mammals. Examples of suitable acids are hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharinic acid), monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Salts of citric acid (citrates) and hydrochloric acid (hydrochlorides) are particularly preferred.

In preferred embodiments of the compounds according to the invention represented by the general formula I, $W^1$ and $W^3$ represent N and $W^2$ represents $CR^{60}$. Alternatively, $W^1$ and $W^2$ represent N and $W^3$ represents $CR^{60}$. In an alternative variant of the compounds according to the invention, $W^1$, $W^2$ and $W^3$ all represent N. $R^{60}$ can in particular represent H or $C_{1-6}$-alkyl, in particular methyl.

In embodiments of the compounds according to the invention that are likewise preferred, V represents O. In alternative preferred embodiments, V represents $NR^{6c}$. $R^{6c}$ can in particular represent H, methyl or cyclopropyl.

In further preferred embodiments of the compounds according to the invention, V represents $CR^{6a}R^{6b}$. $R^{6a}$ and $R^{6b}$ can in particular represent H.

In the compounds according to the invention, $R^1$ preferably represents phenyl, naphthyl, indolyl, benzofuranyl, benzothiophenyl (benzothienyl); benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl), quinolinyl, isoquinolinyl, phenyl or naphthyl bonded via a $C_{1-3}$-alkylene group, or $CH(phenyl)_2$, preferably phenyl, naphthyl, benzothiophenyl, quinolinyl, isoquinolinyl or thienyl, particularly preferably phenyl, naphthyl or benzothiophenyl (benzothienyl), in each case unsubstituted or mono- or poly-substituted by identical or different substituents, wherein the substituents are selected in particular from —O—$C_{1-3}$-alkyl, $C_{1-6}$-alkyl, F, Cl, Br, $CF_3$, $OCF_3$, OH, phenyl, naphthyl, thienyl, thiazolyl and pyridinyl, and wherein the above-mentioned alkylene groups are in each case unsubstituted or mono- or poly-substituted by identical or different substituents, wherein the substituents are independently selected from the group consisting of —O—$C_{1-3}$-alkyl, F, Cl, Br, $CF_3$, —$OCF_3$, OH, phenyl, phenoxy, naphthyl, furyl, thienyl and pyridinyl.

$R^1$ can in particular represent phenyl or naphthyl, the phenyl or naphthyl being unsubstituted or mono- or poly-substituted, for example substituted 2, 3, 4 or 5 times, by identical or different radicals selected from methyl, methoxy, $CF_3$, $OCF_3$, F and Cl.

In embodiments of the compounds according to the invention that are likewise preferred, $R^1$ is selected from 4-methoxy-2,3,6-trimethylphenyl, 4-methoxy-2,6-dimethylphenyl, 4-methoxy-2,3,5-trimethylphenyl, 2,4,6-trimethylphenyl, 1,3-dichloro-5-(trifluoromethyl)phenyl, 2-chloro-6-methylphenyl, 2,4,6-trichlorophenyl, 2-chloro-6-(trifluoromethyl)phenyl, 2,6-dichloro-4-methoxyphenyl, 2,6-dichloro-4-(trifluoromethyl)phenyl, 2-methyl-1-naphthyl, 2-chloro-1-naphthyl, 2-fluoro-1-naphthyl, 6-methoxy-2-naphthyl, 2-chloro-4-(trifluoromethoxy)phenyl, 4-chloro-2,5-dimethylphenyl, 2,6-dichloro-3-methylphenyl, 2,6-dichlorophenyl, 2,3-dichlorophenyl, 3,4-dichlorophenyl, 2,4-dichlorophenyl, 2-(trifluoromethyl)phenyl, 3-(trifluoromethyl)phenyl, 4-(trifluoromethyl)phenyl, 1-naphthyl and 2-naphthyl; in particular 4-methoxy-2,6-dimethylphenyl, 2-chloro-6-methylphenyl and 2-(trifluoromethyl)phenyl.

In embodiments of the compounds of the general formula I according to the invention that are likewise preferred, the partial structure Ac I shown below:

represents a group of the general formula Ac I.a:

wherein
a represents 0 or 1;
ax represents 0, 1, 2 or 3;
ay represents 0, 1 or 2;
q represents 0 or 1;
with the proviso that a+ax+ay+q≧2;
Q represents $CH_2$, $NR^{50}$, O, S, S=O or $S(=O)_2$, and
$R^{200}$ represents from 0 to 4 substituents independently selected from F, Cl, $-CF_3$, =O, $-O-CF_3$, $-OH$, $-O-C_{1-6}$-alkyl and $C_{1-6}$-alkyl, in particular represents F or $CF_3$, or two of the radicals $R^{200}$ together represent a fused aryl or heteroaryl, in particular a benzo group. If the structure of the N-containing heterocycle permits it, $R^{200}$ can accordingly also represent two aryls, in particular benzo groups, fused to the heterocycle. In specific embodiments, $R^{200}$ represents 0 substituents, that is to say is absent.

In particular, the partial structure Ac I can represent one of the groups listed below:

-continued

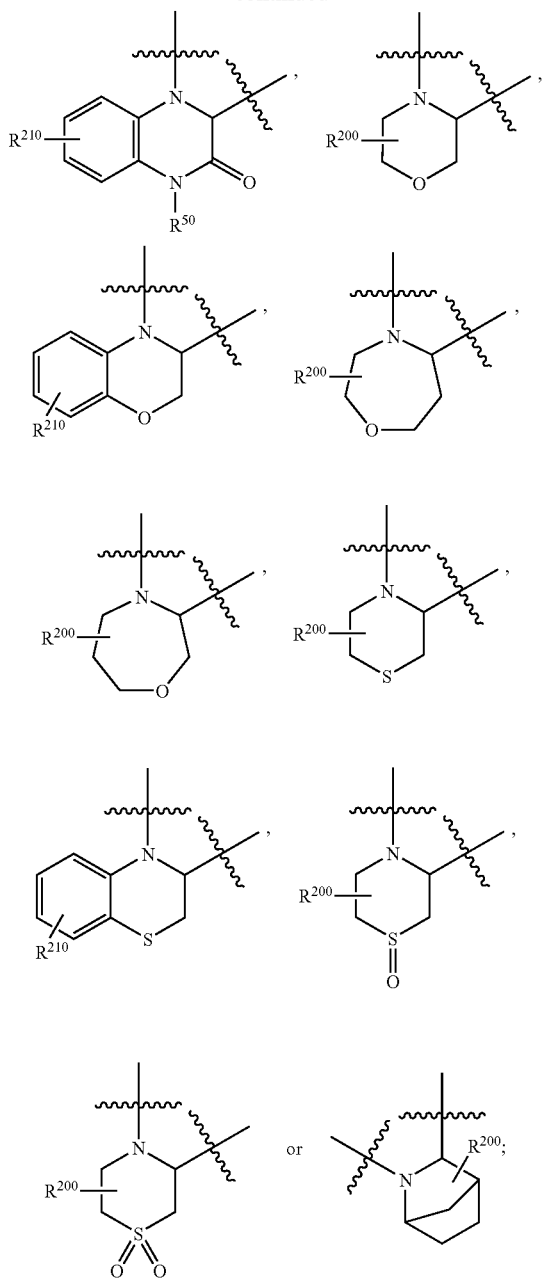

In particular, the partial structure Ac 1 can represent one of the groups listed below:

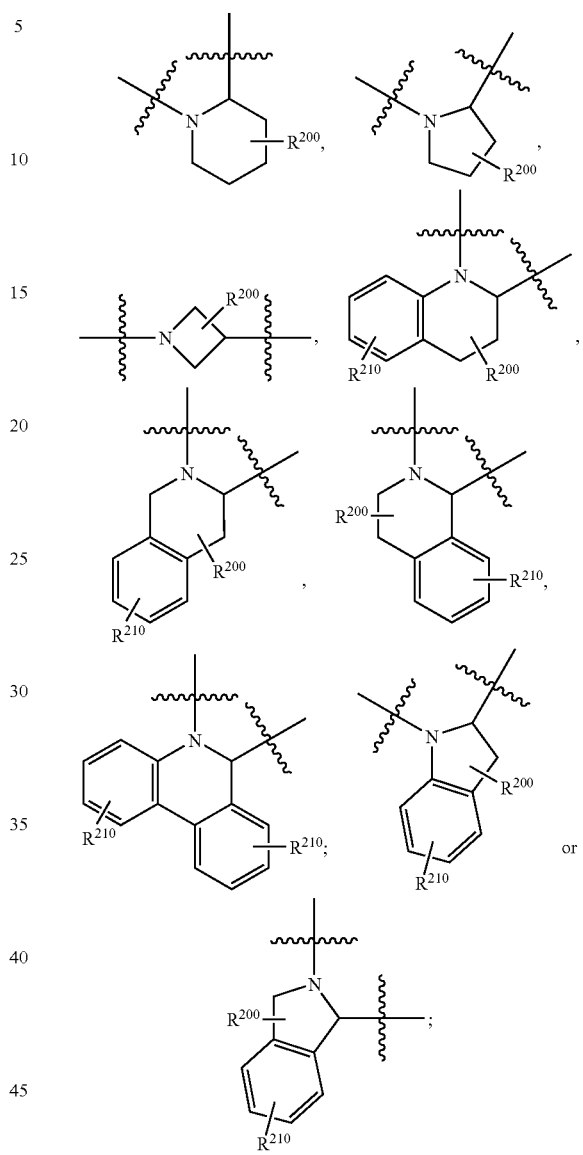

wherein $R^{200}$ and $R^{210}$ preferably have the meanings described above.

wherein $R^{200}$ represents from 0 to 4 substituents independently selected from F, Cl, —CF$_3$, =O, —O—CF$_3$, —OH, —O—C$_{1-6}$-alkyl and C$_{1-6}$-alkyl, in particular represents F or CF$_3$, and/or two adjacent radicals $R^{200}$ together form a fused aryl or heteroaryl, in particular a benzo group;

$R^{210}$ represents from 0 to 4 substituents independently selected from —O—C$_{1-3}$-alkyl, C$_{1-6}$-alkyl, F, Cl, Br, I, CF$_3$, —OCF$_3$, OH, SH, phenyl, naphthyl, furyl, thienyl and pyridinyl, in particular represents methyl, methoxy, CF$_3$, F, Cl, Br and —OCF$_3$.

In specific embodiments of the compounds according to the invention, $R^{200}$ and/or $R^{210}$ represent 0 substituents, that is to say are each absent.

In an embodiment of the compounds according to the invention that is likewise preferred, $R^2$ preferably represents H, C$_{1-6}$-alkyl, C$_{3-6}$-cycloalkyl, aryl, or a C$_{3-6}$-cycloalkyl or aryl bonded via a C$_{1-3}$-alkylene group; in each case unsubstituted or mono- or poly-substituted by identical or different radicals. In particular, $R^2$ can represent H, methyl, ethyl, n-propyl, isopropyl, n-butyl, isobutyl, tert-butyl, cyclopropyl, in each case unsubstituted or mono- or poly-substituted by identical or different radicals selected from F, Cl, OH, OCH$_3$ and OCF$_3$. Or $R^2$ represents phenyl or pyridinyl which is unsubstituted or mono- or poly-substituted by identical or different radicals selected from C$_{1-6}$-alkyl, C$_{1-6}$-alkyl-O—, F, Cl, Br, I, CF$_3$, OCF$_3$, OH and SH, in particular from methyl, methoxy, F, Cl, CF$_3$ and OCF$_3$, wherein phenyl and pyridinyl can be bonded via a C$_{1-3}$-alkylene group.

In an embodiment of the compounds according to the invention that is likewise preferred, $R^3$ preferably represents H, F, Cl, —CF$_3$, —OH, —O—C$_{1-6}$-alkyl, C$_{1-6}$-alkyl, aryl; or an aryl bonded via a C$_{1-3}$-alkylene group, in each case unsubstituted or mono- or poly-substituted by identical or different radicals. In particular, R$^3$ can represent H, F, n-propyl, isopropyl, n-butyl, isobutyl, tert-butyl, cyclopropyl, methoxy or ethoxy, in each case unsubstituted or mono- or poly-substituted by identical or different radicals selected from F, Cl, OH, OCH$_3$ and OCF$_3$. Or R$^3$ represents phenyl or benzyl, in each case unsubstituted or mono- or poly-substituted by identical or different radicals selected from C$_{1-6}$-alkyl, C$_{1-6}$-alkyl-O—, F, Cl, Br, I, CF$_3$, OCF$_3$, OH and SH, in particular from methyl, methoxy, F, Cl, CF$_3$ and OCF$_3$.

Embodiments of the compounds according to the invention that are likewise preferred are those in which R$^{4a}$, R$^{4b}$, R$^{5a}$, R$^{5b}$, R$^{6a}$, R$^{6b}$, R$^{36}$, R$^{37a}$, R$^{37b}$, R$^{44a}$ and R$^{44b}$ each independently is selected from H; F; Cl; OH; =O; O—C$_{1-4}$-alkyl; —OCF$_3$, C$_{1-4}$-alkyl; —CF$_3$, C$_{3-6}$-cycloalkyl; aryl or heteroaryl; C$_{3-6}$-cycloalkyl, aryl or heteroaryl bonded via a C$_{1-6}$-alkylene group.

In embodiments of the compounds according to the invention that are likewise preferred, R$^{4a}$, R$^{4b}$, R$^{5a}$, R$^{5b}$, R$^{6a}$ and/or R$^{6b}$ each independently represents H, F, Cl, —CF$_3$, OH, OCF$_3$ or O—C$_{1-6}$-alkyl, in particular H or F, in particular H.

In preferred embodiments of the compounds according to the invention, R$^{4a}$ and R$^{4b}$ each independently represent H, F, Cl, Br, I, —CF$_3$, O—CF$_3$, OH, SH, O—C$_{1-6}$-alkyl, C$_{1-6}$-alkyl, C$_{3-8}$-cycloalkyl, aryl or heteroraryl, or C$_{3-8}$-cycloalkyl, aryl or heteroaryl bonded via a C$_{1-6}$-alkylene group or C$_{2-6}$-alkenylene group.

In embodiments of the compounds according to the invention that are likewise preferred, R$^{4a}$ and R$^{4b}$, together with the carbon atom linking them, form a saturated C$_{3-6}$-cycloalkyl, in particular cyclopropyl or cyclobutyl. These can be unsubstituted or substituted on one or more, for example 1, 2, 3 or 4, of their carbon ring members by one or more, for example 1, 2, 3 or 4, substituents independently selected from the group consisting of F, CF$_3$, C$_{1-6}$-alkyl, O—C$_{1-6}$-alkyl, OH, OCF$_3$, aryl and heteroaryl.

In further preferred embodiments, R$^{4a}$ and R$^{4b}$ each independently of the other represents H or CH$_3$.

Embodiments of the compounds according to the invention that are likewise preferred are those in which the condition a+b=1, in particular the condition a=0, b=1 or a=1, b=0, is met. In variants of these compounds that are likewise preferred, R$^{4a}$, R$^{4b}$, R$^{5a}$, R$^{5b}$, R$^{6a}$ and/or R$^{6b}$, where present, each independently represent H or F, in particular H.

In further preferred embodiments of the compounds according to the invention, R$^7$ preferably represents H or C$_{1-6}$-alkyl, in each case unsubstituted or mono- or poly-substituted by identical or different substituents, in particular R$^7$ represents H, CF$_3$ or methyl.

In embodiments of the compounds of the general formula I according to the invention that are likewise preferred, the partial structure Ac II shown below:

Ac II

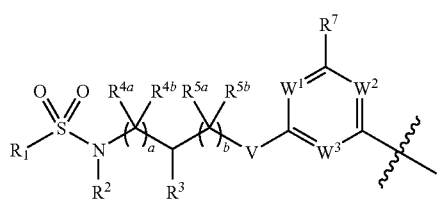

represents one of the following partial structures Ac II.a to Ac.II.h, wherein the radicals, variables and indices have the meanings described above:

Ac II.a

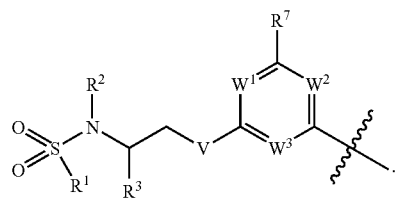

Ac II.b

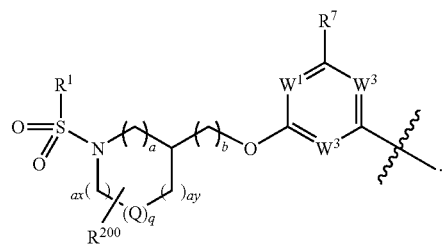

AC II.c

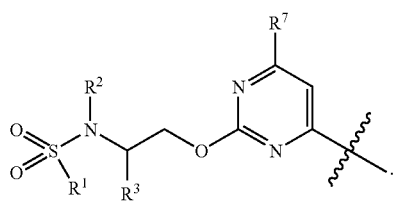

AC II.d

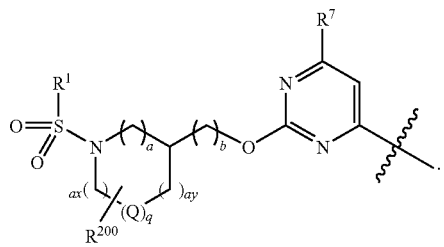

Ac IIe

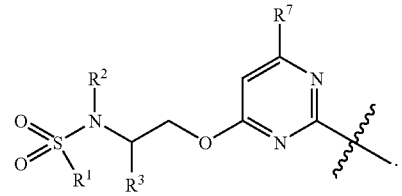

Ac II.f

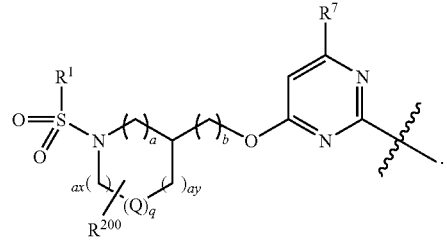

-continued

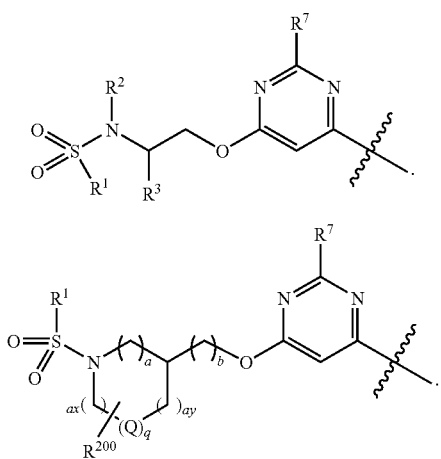

Ac II.g

Ac II.h

Also preferred are embodiments of the compounds according to the invention in which the partial structure Ac II shown above assumes a structure according to formulas Ac II.i and Ac II.j shown below.

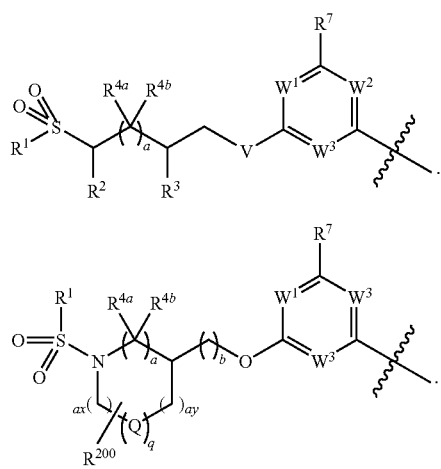

Ac II.i

Ac II.j

In these formulas too, the radicals, variables and indices have the meanings described above.

Embodiments of the compounds according to the invention that are likewise preferred are those in which $R^8$ preferably represents H; $C_{1-6}$-alkyl; in particular methyl, ethyl, n-propyl, isopropyl, n-butyl, isobutyl, sec-butyl, tert-butyl; cyclopropyl, cyclobutyl, cyclopentyl, cyclohexyl, —$CH_2CF_3$, phenyl, benzyl, phenylethyl, phenylpropyl, or cyclopropyl, cyclobutyl, cyclopentyl, cyclohexyl bonded via a $C_{1-3}$-alkylene group, in each case unsubstituted or mono- or poly-substituted by identical or different substituents. In particular, $R^8$ can represent H, methyl, ethyl, isopropyl or cyclopropyl.

Embodiments of the compounds according to the invention that are likewise preferred are those in which $R^{9a}$ and $R^{9b}$ each independently of the other represents H; F; methyl; ethyl, isopropyl, $CF_3$, methoxy; cyclopropyl; phenyl; benzyl, phenylethyl, or a cycloalkyl bonded via a $C_{1-3}$-alkylene group, or —$CF_3$, in each case unsubstituted or mono- or poly-substituted by identical or different substituents. In particular, $R^{9a}$ and $R^{9b}$ represent H.

Embodiments of the compounds according to the invention that are likewise preferred are those in which the general formula II described above assumes the following partial structure IIa:

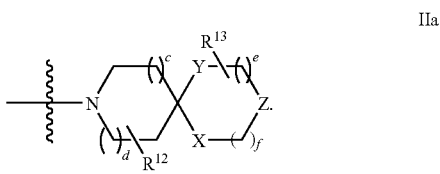

IIa

Embodiments of the compounds according to the invention that are likewise preferred are those in which the general formula III described above assumes one of the following partial structures IIIa or IIIb:

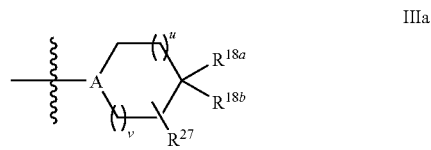

IIIa

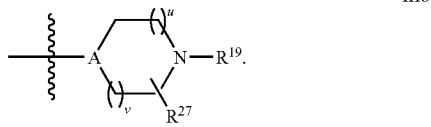

IIIb

Embodiments of the compounds according to the invention that are likewise preferred are those in which the partial structure of formula IIa shown above assumes the following partial structure IIb:

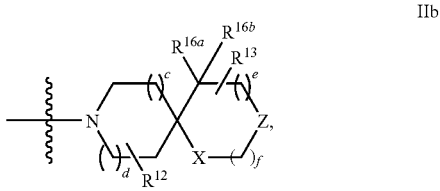

IIb wherein in specific embodiments of these compounds according to the invention $R^8$ represents H, $C_{1-6}$-alkyl or $C_{3-6}$-cycloalkyl, in each case unsubstituted or mono- or poly-substituted by identical or different radicals, and $R^{9a}$ and $R^{9b}$ each represents H.

Embodiments of the compounds according to the invention that are likewise preferred are those compounds in which the partial structures of formulas IIIa and IIIb shown above assume one of the following partial structures IIIc, IIId or IIIe:

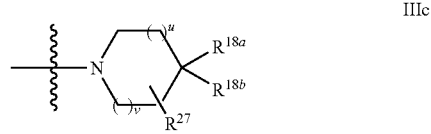

IIIc

-continued

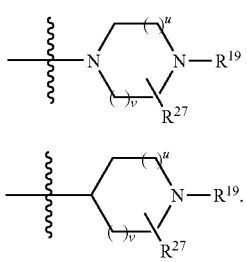

IIId

IIIe

In specific embodiments of these compounds according to the invention, s and t each represent 0.

Embodiments of the compounds according to the invention that are likewise preferred are those in which the partial structures of formulas IIIa and IIIb shown above assume one of the partial structures IIIc or IIId shown above and two of the substituents $R^{27}$ together represent a $C_{1-3}$-alkylene bridge, so that the ring shown in the partial structure IIIc or IIId assumes a bicyclically bridged form. In specific embodiments of these compounds, s and t are each 0.

Embodiments of the compounds according to the invention that are likewise preferred are those in which the partial structures of formulas IIIa and IIIb shown above assume one of the partial structures IIIc or IIIe likewise shown above, s represents 1 and t represents 1, 2 or 3. In specific embodiments of these compounds according to the invention, $R^8$ represents H, $C_{1-6}$-alkyl, $C_{3-6}$-cycloalkyl, in each case unsubstituted or mono- or poly-substituted. In further specific embodiments of the compounds of the invention, $R^{9a}$ and $R^{9b}$ each represent H.

Further preferred embodiments of the compounds according to the invention are those in which the partial structure of formula IIb shown above assumes the following partial structure IIc:

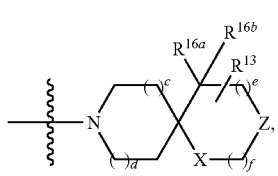

IIc wherein in specific embodiments of these compounds s and t each denotes 0.

In further preferred embodiments of the compounds according to the invention, the partial structures of formulas IIIc or IIId shown above assume one of the following partial structures IIIf or IIIg:

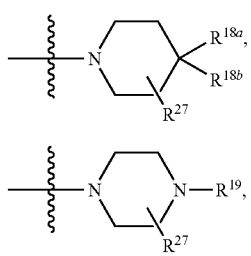

IIIf

IIIg wherein in specific embodiments of these compounds $R^{27}$ represents H or methyl and/or two of the substituents $R^{27}$ form a fused aryl or heteroaryl group, in particular a benzo group.

Further preferred embodiments of the compounds according to the invention are those compounds in which the partial structures IIIc or IIId shown above represent one of the following radicals A to H, in particular G and H:

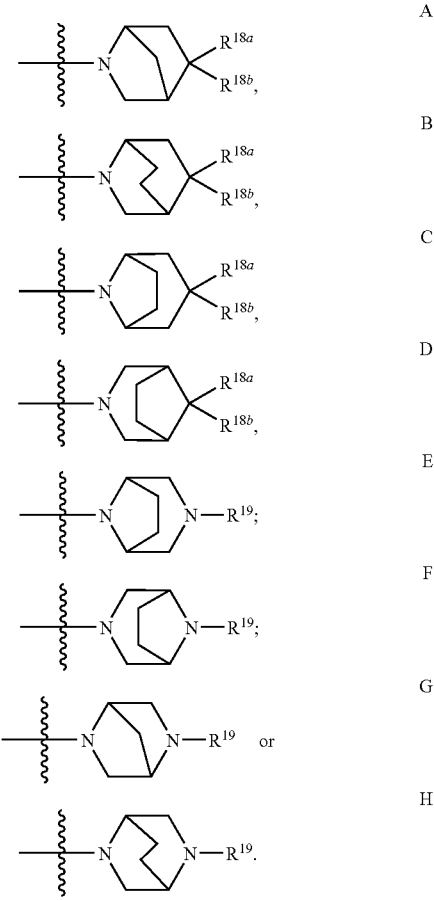

Persons skilled in the art will understand that the representation chosen for the radicals A to H includes all possible stereoisomers of these radicals.

Further preferred embodiments of the compounds according to the invention are those compounds in which partial structures IIIc or IIIe shown above represent a group of one of formulas IIIh or IIIi:

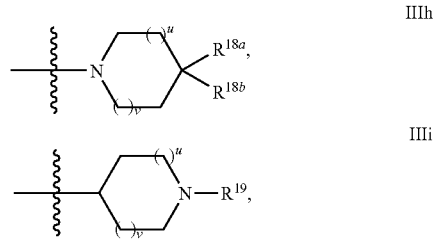

IIIh

IIIi and $R^{9a}$ and $R^{9b}$ each represents H. In specific embodiments of these compounds, u and v each independently of the other represents 0 or 1. In particular, u and v both represent 1.

Further preferred embodiments of the compounds according to the invention are those compounds in which, in partial structure IIc shown above, $R^{16a}$ and $R^{16b}$ each represents H or together form =O; $R^{13}$ represents H, aryl or heteroaryl and/or two of the substituents $R^{13}$ together form =O and/or two adjacent substituents $R^{13}$ together form a fused aryl or heteroaryl, in particular a benzo group, in each case unsubstituted or mono- or poly-substituted by identical or different substituents.

Further preferred embodiments of the compounds according to the invention are those compounds in which, in the partial structures of formulas IIIf or IIIg shown above:

$R^{18a}$ represents H; $C_{1-6}$-alkyl; $C_{3-8}$-cycloalkyl, —NH($C_{1-6}$-alkyl), —N($C_{1-6}$-alkyl)$_2$, phenyl, pyridinyl, pyrimidinyl, imidazolyl, thiazolyl, triazolyl or thienyl, in each case unsubstituted or mono- or poly-substituted; phenyl, pyridinyl, pyrimidinyl, imidazolyl, thiazolyl, triazolyl or thienyl bonded via a —(O)$_{0-1}$—$C_{1-6}$-alkylene group and in each case unsubstituted or mono- or poly-substituted; or $R^{18a}$ represents a radical of the general formula VIIa:

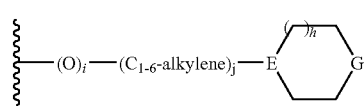

VIIa wherein
i represents 0 or 1;
j represents 0 or 1;
h represents 0 or 1;
E represents N or CH; with the proviso that if i is 1 and j is 0, then E represents CH;
G represents $CR^{37a}R^{37b}$ or $NR^{38}$;
wherein $R^{37a}$ and $R^{37b}$ each independently represent H; F or $C_{1-6}$-alkyl;
$R^{38}$ represents H; $C_{1-6}$-alkyl, $C_{3-6}$-cycloalkyl or pyridyl, in particular pyridin-3-yl or pyridin-4-yl; and
$R^{18b}$ represents H; OH; $C_{1-6}$-alkyl; phenyl, pyridinyl, pyrimidinyl, imidazolyl, thiazolyl, triazolyl or thienyl, in each case unsubstituted or mono- or poly-substituted; phenyl, pyridinyl, pyrimidinyl, imidazolyl, thiazolyl, triazolyl or thienyl, O-phenyl, or O-pyridyl bonded via a $C_{1-6}$-alkylene group and in each case unsubstituted or mono- or poly-substituted by identical or different substituents; phenyl, pyridinyl, pyrimidinyl, imidazolyl, thiazolyl, triazolyl or thienyl bridged via $C_{1-6}$-alkylene-NH(C=O) and in each case unsubstituted or mono- or poly-substituted by identical or different substituents;
$R^{19}$ represents H; $C_{1-6}$-alkyl; $C_{3-8}$-cycloalkyl, or $C_{1-6}$-alkyl bonded via (C=O)$_{0-1}$; phenyl, pyridinyl, pyrimidinyl, imidazolyl, thiazolyl, triazolyl or thienyl; in each case unsubstituted or mono- or poly-substituted by identical or different substituents; phenyl, pyridinyl, pyrimidinyl, imidazolyl, thiazolyl, triazolyl or thienyl bonded via a $C_{1-6}$-alkylene group and in each case unsubstituted or mono- or poly-substituted by identical or different substituents; or $R^{19}$ represents the radical of the general formula VIIIa

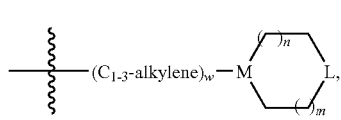

VIIIa wherein
w represents 0 or 1;
n represents 0 or 1;
m represents 0 or 1;
M represents CH or N, with the proviso that if w is 0, M represents CH;
L represents $CR^{44a}R^{44b}$ or $NR^{45}$;
wherein $R^{44a}$ and $R^{44b}$ each independently represent H; F or $C_{1-6}$-alkyl, in each case unsubstituted or mono- or poly-substituted by identical or different substituents;
$R^{45}$ represents H; $C_{1-6}$-alkyl, $C_{3-6}$-cycloalkyl or pyridyl, in each case unsubstituted or mono- or poly-substituted by identical or different substituents.

Further preferred embodiments of the compounds of the invention include those compounds in which the partial structures of formulas IIIc or IIId shown above represent one of the following groups A to H, in particular G or H:

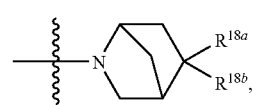
(A)

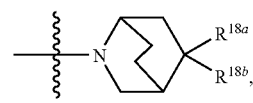
(B)

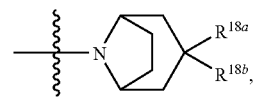
(C)

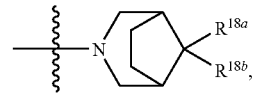
(D)

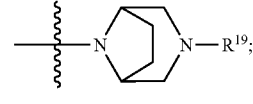
(E)

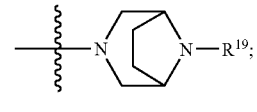
(F)

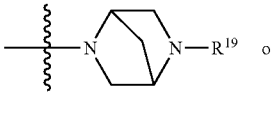
(G)

or

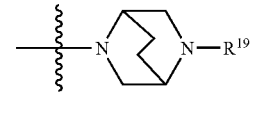
(H)

and wherein
$R^{18a}$ represents H; $C_{1-6}$-alkyl; $C_{3-8}$-cycloalkyl, N($C_{1-6}$-alkyl)$_2$; NH($C_{1-6}$-alkyl); azetidinyl; pyrrolidinyl, piperidinyl, 4-($C_{1-6}$-alkyl)piperazinyl; phenyl, pyridinyl, pyrimidinyl, imidazolyl, thiazolyl, triazolyl or thienyl, in each case unsubstituted or mono- or poly-substituted by identical or different substituents; N(C$_{1-6}$-alkyl)$_2$; NH(C$_{1-6}$-alkyl); azetidinyl; pyrrolidinyl, piperidinyl, 4-(C$_{1-6}$-alkyl)piperazinyl; phenyl, pyridinyl, pyrimidinyl, imidazolyl, thiazolyl, triazolyl or thienyl bonded via a —(O)$_{0-1}$—C$_{1-6}$-alkylene group and in each case unsubstituted or mono- or poly-substituted by identical or different substituents;

R$^{18b}$ m represents H; OH; C$_{1-6}$-alkyl; phenyl, pyridinyl, pyrimidinyl, imidazolyl, thiazolyl, triazolyl or thienyl, in each case unsubstituted or mono- or poly-substituted by identical or different substituents; phenyl, pyridinyl, pyrimidinyl, imidazolyl, thiazolyl, triazolyl or thienyl bonded via a C$_{1-6}$-alkylene group and in each case unsubstituted or mono- or poly-substituted by identical or different substituents;

R$^{19}$ represents H; C$_{1-6}$-alkyl; C$_{3-8}$-cycloalkyl, phenyl, pyridinyl, pyrimidinyl, imidazolyl, thiazolyl, triazolyl or thienyl, in each case unsubstituted or mono- or poly-substituted by identical or different substituents; phenyl, pyridinyl, pyrimidinyl, imidazolyl, thiazolyl, triazolyl or thienyl bonded via a C$_{1-6}$-alkylene group or a (C=O) group and in each case unsubstituted or mono- or poly-substituted by identical or different substituents.

Again, persons skilled in the art will understand that the representation chosen for the radicals A to H includes all possible stereoisomers of those radicals.

Further preferred embodiments of the compounds according to the invention are those compounds in which, in the partial structures of formulas IIIh or IIIi shown above:

R$^{18a}$ represents H; C$_{1-6}$-alkyl; C$_{3-8}$-cycloalkyl, N(C$_{1-6}$-alkyl)$_2$; NH(C$_{1-6}$-alkyl), azetidinyl; pyrrolidinyl, piperidinyl, 4-(C$_{1-6}$-alkyl)piperazinyl; phenyl, pyridinyl, pyrimidinyl, imidazolyl, thiazolyl, triazolyl or thienyl, in each case unsubstituted or mono- or poly-substituted by identical or different substituents; N(C$_{1-6}$-alkyl)$_2$; NH(C$_{1-6}$-alkyl), azetidinyl; pyrrolidinyl, piperidinyl, 4-(C$_{1-6}$-alkyl)piperazinyl; phenyl, pyridinyl, pyrimidinyl, imidazolyl, thiazolyl, triazolyl or thienyl bonded via a —(O)$_{0/1}$—C$_{1-6}$-alkylene group and in each case unsubstituted or mono- or poly-substituted by identical or different substituents;

R$^{18b}$ m represents H; OH; C$_{1-6}$-alkyl; phenyl, pyridinyl, pyrimidinyl, imidazolyl, thiazolyl, triazolyl or thienyl, in each case unsubstituted or mono- or poly-substituted by identical or different substituents; phenyl, pyridinyl, pyrimidinyl, imidazolyl, thiazolyl, triazolyl or thienyl bonded via a C$_{1-6}$-alkylene group and in each case unsubstituted or mono- or poly-substituted by identical or different substituents;

R$^{19}$ represents H; C$_{1-6}$-alkyl; C$_{3-8}$-cycloalkyl, phenyl, pyridinyl, pyrimidinyl, imidazolyl, thiazolyl, triazolyl or thienyl, in each case unsubstituted or mono- or poly-substituted by identical or different substituents; phenyl, pyridinyl, pyrimidinyl, imidazolyl, thiazolyl, triazolyl or thienyl bonded via a C$_{1-6}$-alkylene group or (C=O) group and in each case unsubstituted or mono- or poly-substituted by identical or different substituents.

Further preferred embodiments of the compounds according to the invention are those compounds in which the partial structure of formula IIc shown above can assume one of the following partial structures SP 1 to SP 34:

SP 1
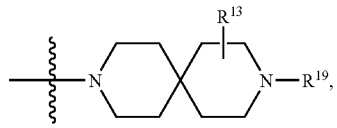

SP 2
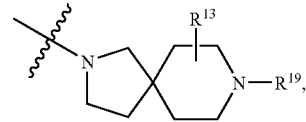

SP 3
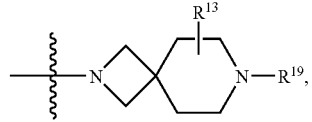

SP 4
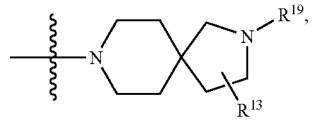

SP 5
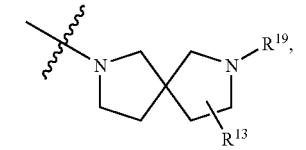

SP 6
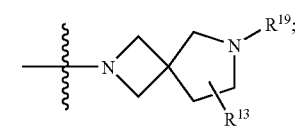

SP 7
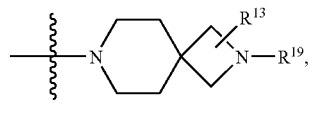

SP 8
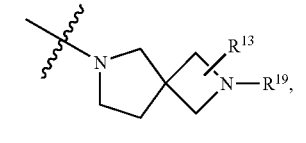

SP 9
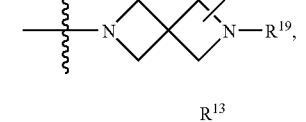

SP 10
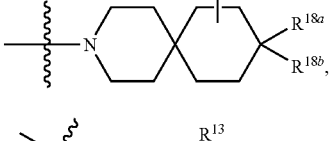

SP 11
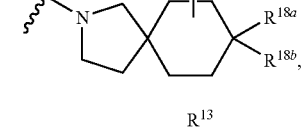

SP 12
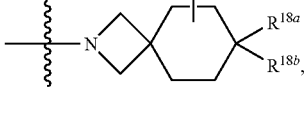

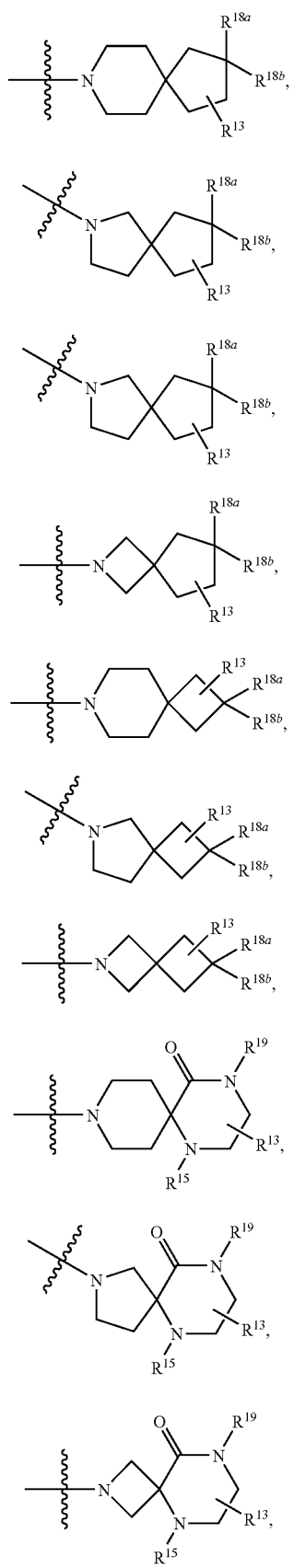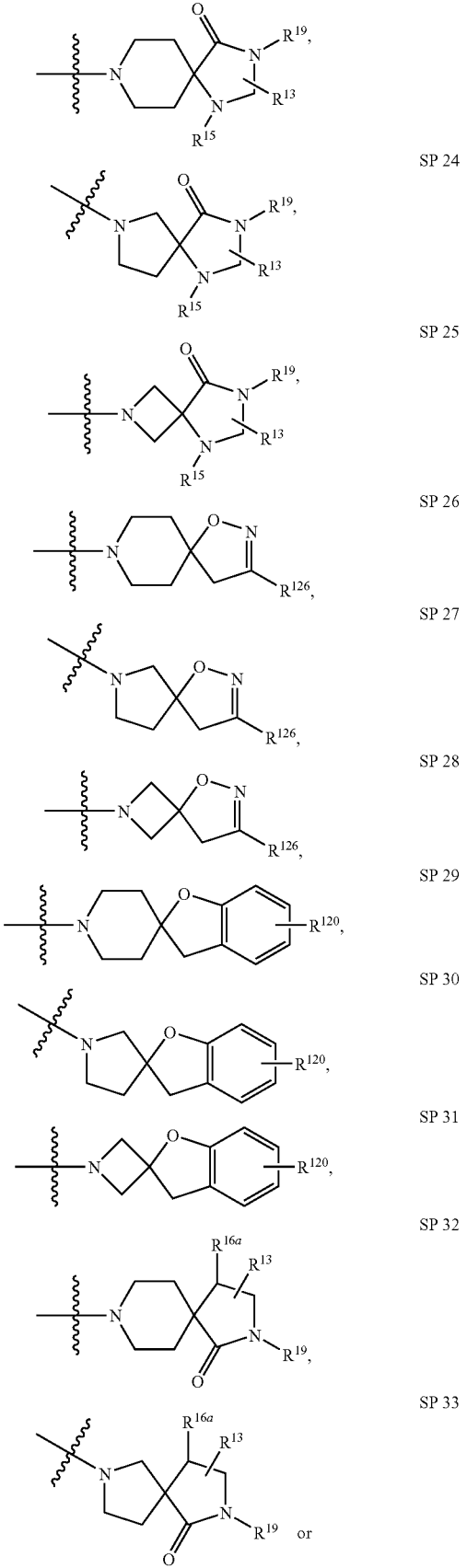

SP 34

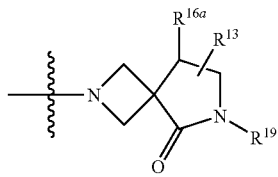

wherein
- $R^{13}$ represents H or phenyl, unsubstituted or mono- or polysubstituted by identical or different substituents; and/or two of the substituents $R^{13}$ together form =O and/or two adjacent substituents $R^{13}$ together form a fused aryl or heteroaryl, in particular a benzo group, in each case unsubstituted or mono- or poly-substituted by identical or different substituents,
- $R^{15}$ represents H; $C_{1-6}$-alkyl; $C_{3-8}$-cycloalkyl, phenyl, pyridinyl, pyrimidinyl, imidazolyl, thiazolyl, triazolyl or thienyl, in each case unsubstituted or mono- or poly-substituted by identical or different substituents; phenyl, pyridinyl, pyrimidinyl, imidazolyl, thiazolyl, triazolyl or thienyl bonded via a $C_{1-6}$-alkylene group and in each case unsubstituted or mono- or poly-substituted by identical or different substituents;
- $R^{16a\ m}$ represents H, $C_{1-6}$-alkyl, phenyl, pyridinyl, pyrimidinyl, imidazolyl, thiazolyl, triazolyl or thienyl, in each case unsubstituted or mono- or poly-substituted by identical or different substituents;
- $R^{18a}$ represents H; $C_{1-6}$-alkyl; $C_{3-8}$-cycloalkyl, $N(C_{1-6}$-alkyl$)_2$; $NH(C_{1-6}$-alkyl), azetidinyl; pyrrolidinyl, piperidinyl, 4-($C_{1-6}$-alkyl)piperazinyl; phenyl, pyridinyl, pyrimidinyl, imidazolyl, thiazolyl, triazolyl or thienyl, in each case unsubstituted or mono- or poly-substituted by identical or different substituents; $N(C_{1-6}$-alkyl$)_2$; $NH(C_{1-6}$-alkyl), azetidinyl; pyrrolidinyl, piperidinyl, 4-($C_{1-6}$-alkyl)piperazinyl; phenyl, pyridinyl, pyrimidinyl, imidazolyl, thiazolyl, triazolyl or thienyl bonded via a —(O)$_{0/1}$— $C_{1-6}$-alkylene group and in each case unsubstituted or mono- or poly-substituted by identical or different substituents;
- $R^{18b\ m}$ represents H; OH; $C_{1-6}$-alkyl; phenyl, pyridinyl, pyrimidinyl, imidazolyl, thiazolyl, triazolyl or thienyl, in each case unsubstituted or mono- or poly-substituted by identical or different substituents; phenyl, pyridinyl, pyrimidinyl, imidazolyl, thiazolyl, triazolyl or thienyl bonded via a $C_{1-6}$-alkylene group and in each case unsubstituted or mono- or poly-substituted by identical or different substituents;
- $R^{19}$ represents H; $C_{1-6}$-alkyl; $C_{3-8}$-cycloalkyl, phenyl, pyridinyl, pyrimidinyl, imidazolyl, thiazolyl, triazolyl or thienyl, in each case unsubstituted or mono- or poly-substituted by identical or different substituents; phenyl, pyridinyl, pyrimidinyl, imidazolyl, thiazolyl, triazolyl or thienyl bonded via a $C_{1-6}$-alkylene group or (C=O) group and in each case unsubstituted or mono- or poly-substituted by identical or different substituents;
- $R^{120}$ represents H; F; Cl; OH; $OCH_3$, O—$CF_3$, $C_{1-6}$-alkyl; $CF_3$, phenyl, unsubstituted or mono- or poly-substituted;
- $R^{126\ m}$ represents H; $C_{1-6}$-alkyl; $C_{3-6}$-cycloalkyl; phenyl, pyridinyl, pyrimidinyl, imidazolyl, thiazolyl, triazolyl or thienyl; $C_{3-6}$-cycloalkyl, phenyl, pyridinyl, pyrimidinyl, imidazolyl, thiazolyl, triazolyl or thienyl bonded via a $C_{1-3}$-alkylene group and in each case unsubstituted or mono- or poly-substituted by identical or different substituents.

Further preferred embodiments of the compounds according to the invention are those compounds in which, in the general formula I shown above, the partial structure (B) shown below:

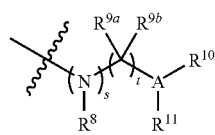

(B)

is selected from one of the following partial structures B.1. to B.45.

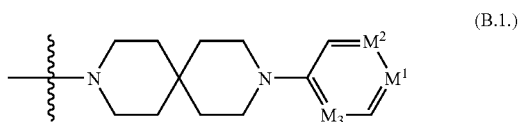

(B.1.)

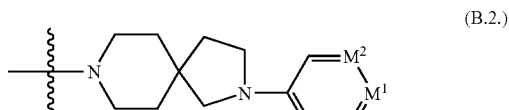

(B.2.)

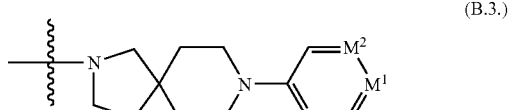

(B.3.)

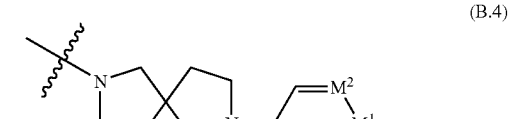

(B.4)

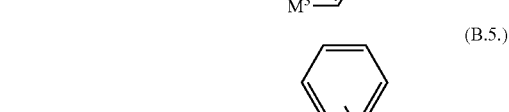

(B.5.)

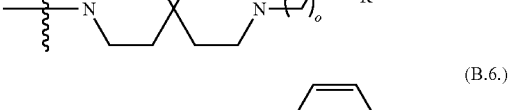

(B.6.)

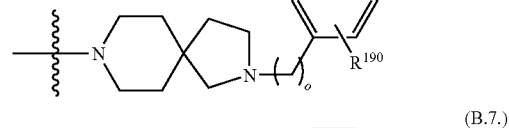

(B.7.)

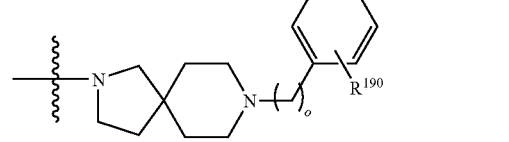

(B.8.)

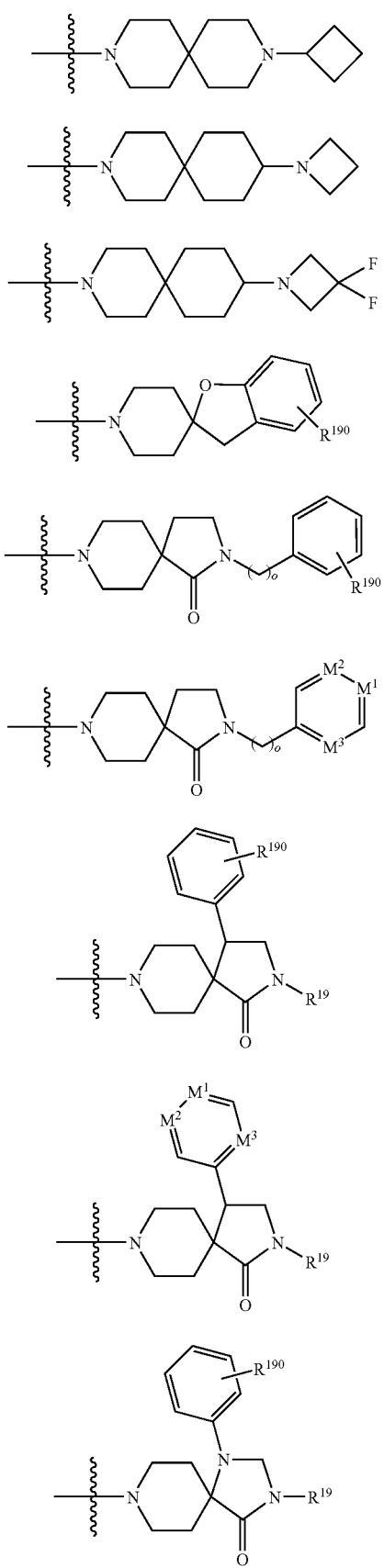
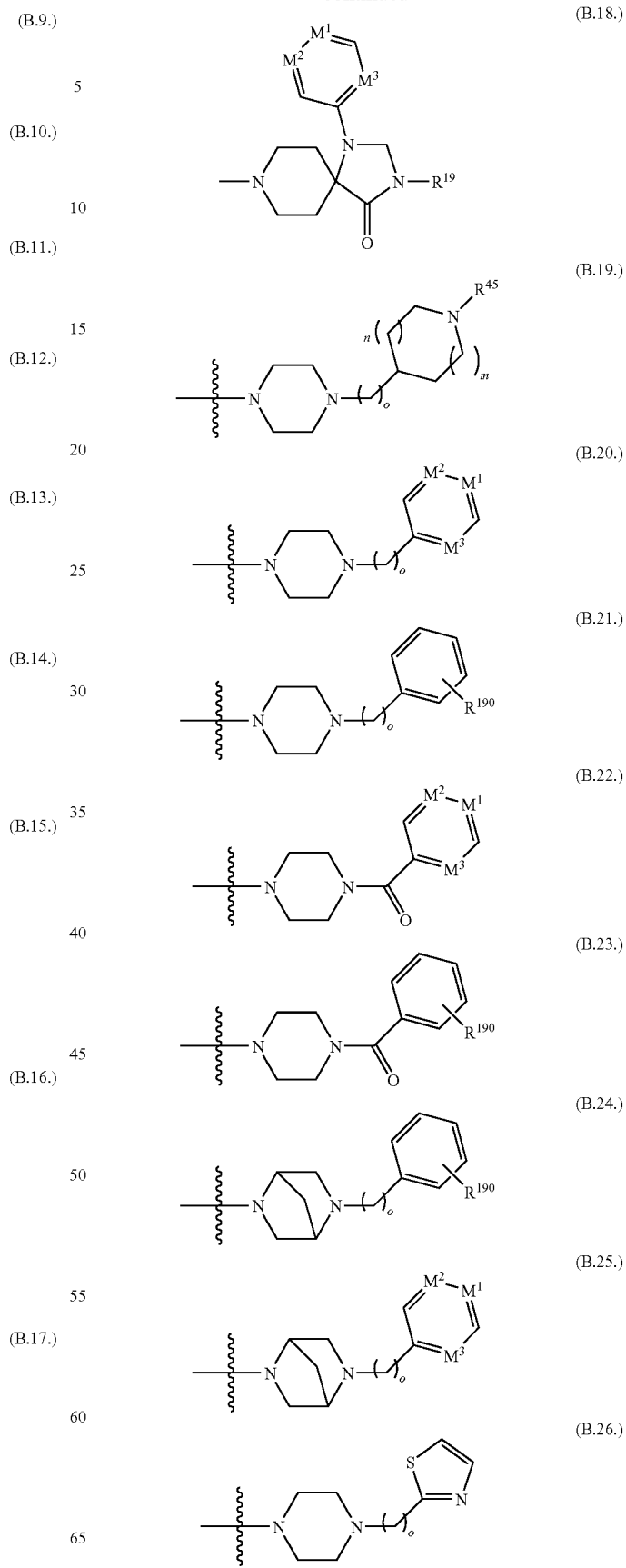

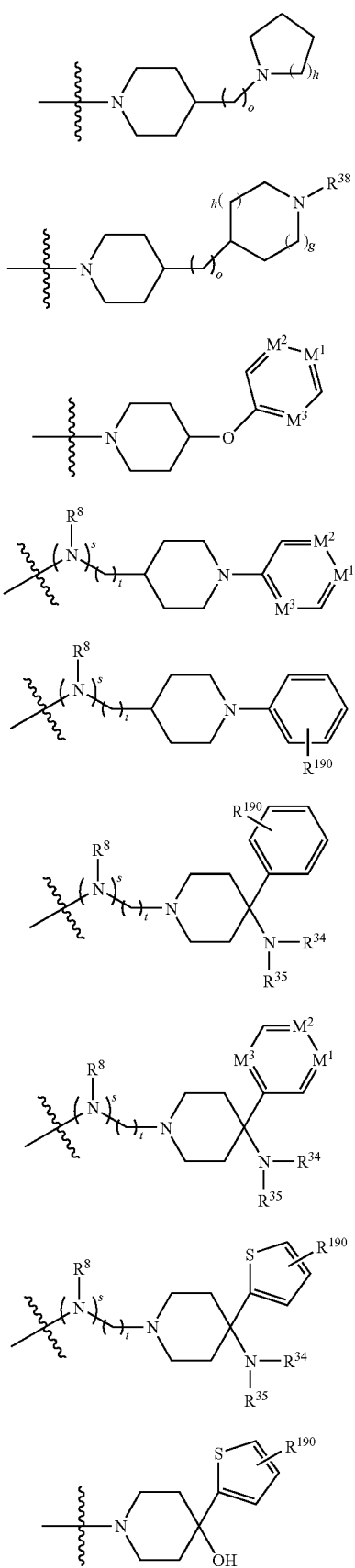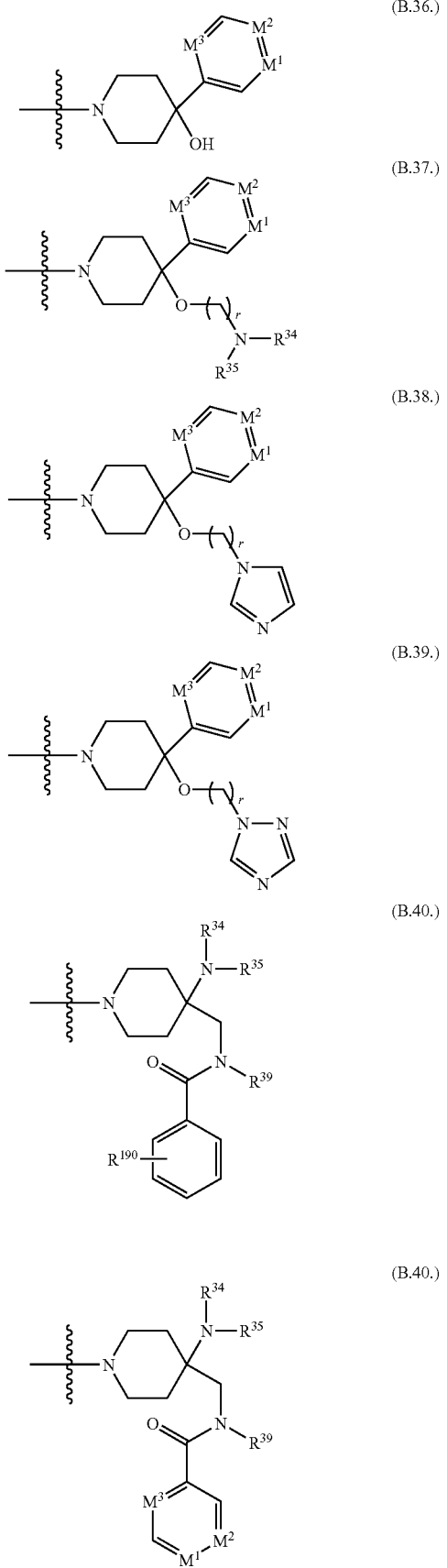

-continued

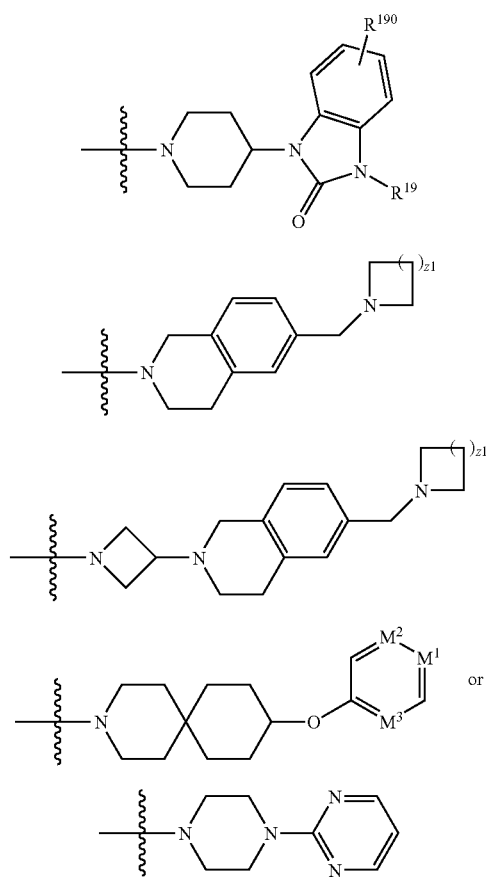

(B.41.)
(B.42.)
(B.43.)
(B.44.)
(B.45.)

wherein
h=0 or 1;
g=0 or 1;
n=0 or 1;
m=0 or 1;
o=0, 1, 2 or 3;
r=1, 2 or 3, in particular 1 or 2;
s=0 or 1;
t=0, 1, 2 or 3, in particular 0, 1 or 2, with the proviso that if s is 0, t likewise is 0;
z1=0, 1, 2 or 3, in particular 1;
$M^1$, $M^2$ and $M^3$ each represent N or CH, on condition that only one of the variables $M^1$, $M^2$ and $M^3$ represents N and the other two represent CH; (so that the heterocycle described by means of the variables $M^1$, $M^2$ and $M^3$ can represent 2-pyridinyl, 3-pyridinyl and 4-pyridinyl.);
In groups B42 and B43 shown above, z1 can in particular represent 1.
$R^8$ represents H; $C_{1-6}$-alkyl, in particular methyl, ethyl, n-propyl, isopropyl, n-butyl, sec-butyl, isobutyl and tert-butyl; $C_{3-6}$-cycloalkyl, in particular cyclopropyl; in each case unsubstituted or mono- or poly-substituted by identical or different substituents,
$R^{19}$ is selected from H; $C_{1-6}$-alkyl, in particular methyl, ethyl, n-propyl, isopropyl, n-butyl, sec-butyl, isobutyl and tert-butyl; $C_{3-6}$-cycloalkyl, in particular cyclopropyl; in each case unsubstituted or mono- or poly-substituted by identical or different substituents;
$R^{34}$ and $R^{35}$ are each independently preferably methyl or ethyl or, together with the N atom linking them, form an azetidinyl; pyrrolidinyl, piperidinyl, 4-($C_{1-6}$-alkyl)-piperazinyl group; in each case unsubstituted or mono- or poly-substituted by identical or different substituents;
$R^{38}$ represents H, $C_{1-6}$-alkyl, $C_{3-6}$-cycloalkyl or pyridinyl (pyridyl);
$R^{39}$ is selected from H; $C_{1-6}$-alkyl, in particular methyl, ethyl, n-propyl, isopropyl, n-butyl, sec-butyl, isobutyl and tert-butyl; $C_{3-6}$-cycloalkyl, in particular cyclopropyl, in each case unsubstituted or mono- or poly-substituted by identical or different substituents; and
$R^{45}$ represents H, $C_{1-6}$-alkyl, $C_{3-6}$-cycloalkyl or pyridyl;
$R^{190}$ represents from 0 to 4 substituents independently selected from F, Cl, O—$CF_3$, $CF_3$ and CN.

In specific embodiments of the compounds according to the invention which contain one of the partial structures B.1. to B.45. described above, $R^8$, $R^{9a}$, $R^{9b}$, $R^{19}$ and $R^{39}$ are each independently H or methyl.

In the partial structures B.5., B.6., B.7., B.8., B.13., B.14., B. 20., B. 21., B.24., B. 25. and B.26. shown above, o preferably represents 0 or 1, in partial structures B.5., B.6., B.7., B.8. and B.13. o preferably represents 1, and in partial structure B.26. o preferably represents 0. In partial structures B.27. and B.28. o preferably represents 1 or 2.

In partial structures B.1. to B.45. shown above, $R^{190}$, when bonded to a phenyl group, preferably represents a substituent which is selected from F and $CF_3$ and is preferably bonded in the 3- or 4-position to the phenyl ring.

Further embodiments of the compounds according to the invention are those represented by formulas C1 to C21 shown below:

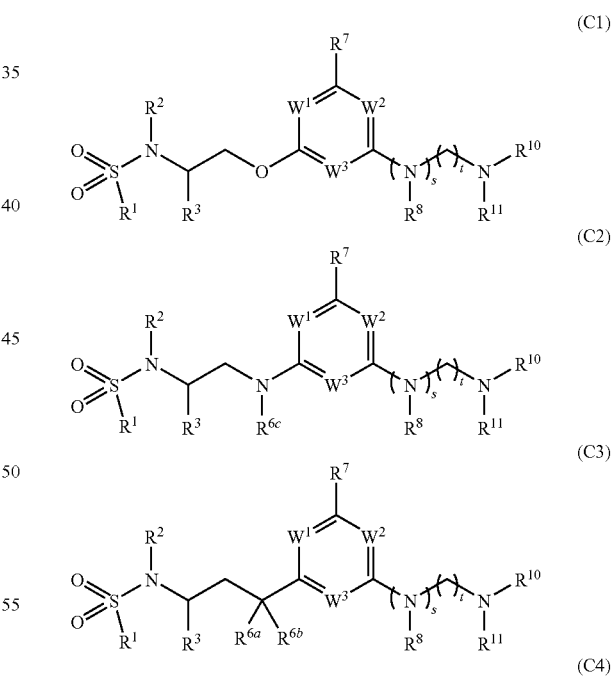

(C1)
(C2)
(C3)

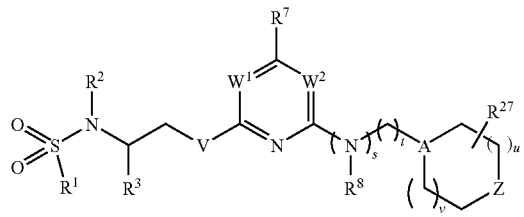

(C4)

-continued
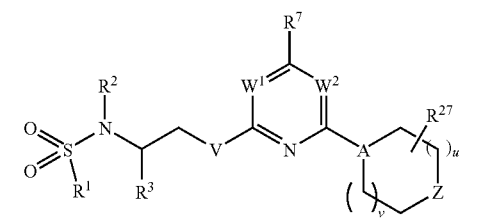
(C5)
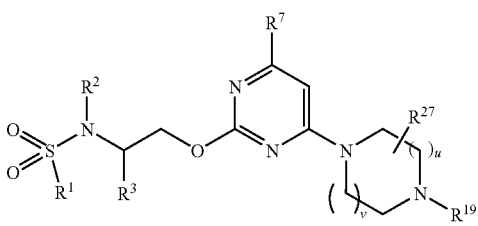
(C6)
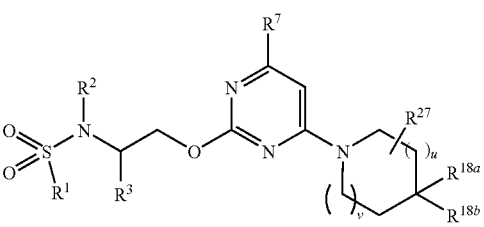
(C7)
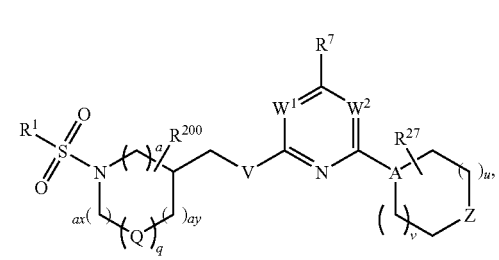
(C8)
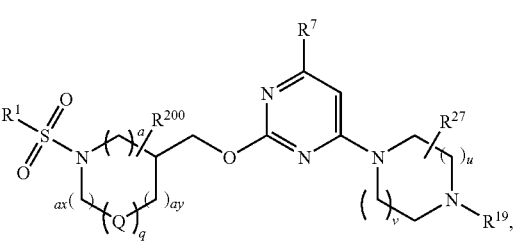
(C9)
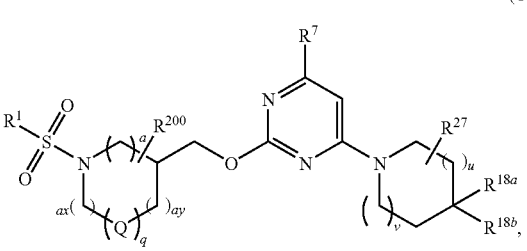
(C10)
-continued
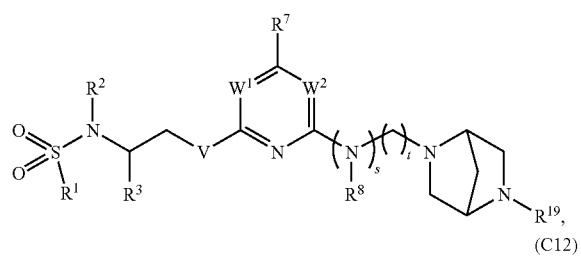
(C11)
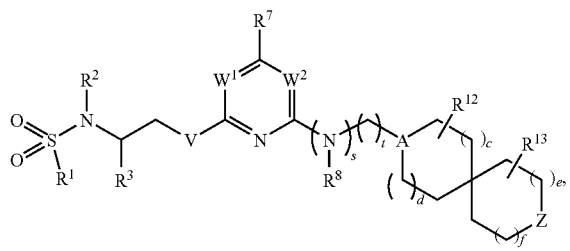
(C12)
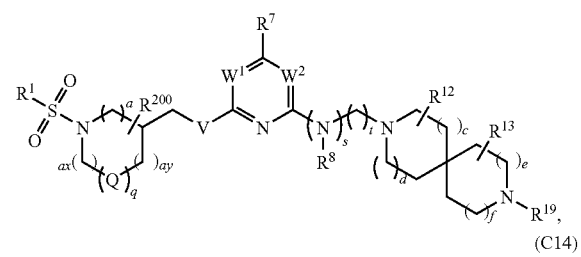
(C13)
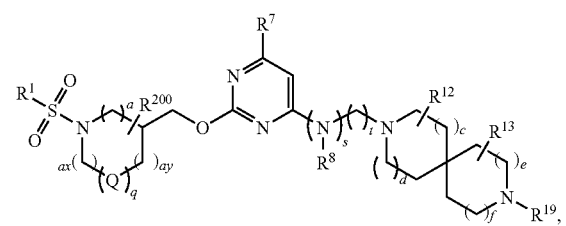
(C14)
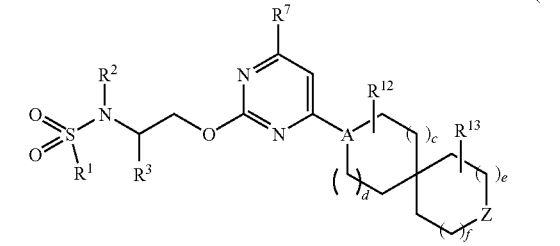
(C15)
(C16)

-continued (C17)

(C18)

(C19)

(C20)

(C21)

wherein
q represents 0 or 1,
a represents 0, 1 or 2;
ax represents 0, 1, 2 or 3;
ay represents 0, 1 or 2;
q represents 0 or 1;
with the proviso that a+ax+ay+q≧2;
Q represents $CH_2$, $NR^{50}$, O, S, S=O or S(=O)$_2$,
and all other radicals, variables and indices have the meanings described above in connection with the compounds according to the invention and preferred embodiments thereof.

In preferred embodiments of the compounds according to the invention, these are compounds of the general formulas C1 to C21 shown above wherein, where present in the general formula in question, a represents 0, 1 or 2;
ax represents 0, 1 or 2;
ay represents 0, 1 or 2,
q represents 0 or 1;
with the proviso that a+ax+ay+q≧2;
Q represents $CH_2$, $NR^{50}$ or O,
V represents O;
c, d, e and f each independently represent 0 or 1.
s represents 1,
t represents 1, 2 or 3,
u and v each independently represent 0 or 1;
$W^1$ and $W^3$ represent N and $W^2$ represents CH, or
$W^2$ and $W^3$ represent N and $W^1$ represents CH, or
$W^1$ and $W^2$ represent N and $W^3$ represents CH;
$R^1$ represents phenyl or naphthyl, wherein the phenyl or naphthyl is unsubstituted or mono- or poly-substituted, for example substituted 2, 3, 4 or 5 times, by identical or different substituents selected from methyl, methoxy, $CF_3$, $OCF_3$, F, Cl and Br;
$R^2$ represents H, $C_{1-6}$-alkyl, $C_{3-6}$-cycloalkyl, phenyl, or $C_{3-6}$-cycloalkyl or phenyl bonded via a $C_{1-3}$-alkylene group; in each case unsubstituted or mono- or poly-substituted by identical or different radicals;
$R^3$ represents H, F, Cl, —$CF_3$, OH, methoxy, methyl or phenyl or benzyl, in each case unsubstituted or mono- or poly-substituted by identical or different radicals;
$R^7$ represents H or methyl, ethyl, n-propyl, isopropyl, n-butyl, isobutyl, sec-butyl, tert-butyl, in particular H or methyl, in each case unsubstituted or mono- or poly-substituted by identical or different substituents;
$R^8$ represents H, methyl, ethyl, n-propyl, isopropyl, n-butyl, isobutyl, sec-butyl, tert-butyl; cyclopropyl, cyclobutyl, cyclopentyl, cyclohexyl, phenyl, benzyl, phenylethyl, phenylpropyl, or cyclopropyl, cyclobutyl, cyclopentyl or cyclohexyl bonded via a $C_{1-3}$-alkylene group, in each case unsubstituted or mono- or poly-substituted by identical or different substituents;
$R^{9a}$ and $R^{9b}$ each independently of the other represents H; F; cyclobutyl, cyclopentyl, cyclohexyl; methyl; methoxy; cyclopropyl; phenyl; benzyl, phenylethyl, or $C_{3-6}$-cycloalkyl bonded via a $C_{1-3}$-alkylene group, in each case unsubstituted or mono- or poly-substituted by identical or different substituents;
$R^{12}$ is absent or represents from 0 to 4-F or methyl;
$R^{13}$ and $R^{27}$ are absent or represent from 1 to 4-F or methyl or represent a fused benzo group that is unsubstituted or mono- or poly-substituted by identical or different substituents;
$R^{18a}$ represents H; $C_{1-6}$-alkyl; $C_{3-8}$-cycloalkyl, N($C_{1-6}$-alkyl)$_2$; NH($C_{1-6}$-alkyl), azetidinyl; pyrrolidinyl, piperidinyl, 4-($C_{1-6}$-alkyl)piperazinyl; phenyl, pyridyl, pyrimidyl, imidazolyl, triazolyl, thiazolyl or thienyl, in each case unsubstituted or mono- or poly-substituted; N($C_{1-6}$-alkyl)$_2$; NH($C_{1-6}$-alkyl), azetidinyl; pyrrolidinyl, piperidinyl, 4-($C_{1-6}$-alkyl)piperazinyl; phenyl, pyridyl, pyrimidyl, imidazolyl, triazolyl, thiazolyl or thienyl bonded via a —(O)$_{0/1}$—$C_{1-6}$-alkylene group and in each case unsubstituted or mono- or poly-substituted;
$R^{18b}$ represents H; OH; $C_{1-6}$-alkyl; phenyl, pyridyl, pyrimidyl, imidazolyl, triazolyl, thiazolyl or thienyl, in each case unsubstituted or mono- or poly-substituted; phenyl, pyridyl, pyrimidyl, imidazolyl, triazolyl, thiazolyl or thienyl, O-phenyl or O-pyridyl bonded via a $C_{1-6}$-alkylene group and in each case unsubstituted or mono- or poly-substituted; phenyl, pyridyl, pyrimidyl, imidazolyl, triazolyl, thiazolyl or thienyl bridged via $C_{1-6}$-alkylene-NH (C=O) and in each case unsubstituted or mono- or poly-substituted;

$R^{19}$ represents H; $C_{1-6}$-alkyl; $C_{3-8}$-cycloalkyl, or $C_{1-6}$-alkyl bonded via $(C=O)_{0-1}$; phenyl, pyridyl, pyrimidyl, imidazolyl, triazolyl, thiazolyl or thienyl; in each case unsubstituted or mono- or poly-substituted; phenyl, pyridyl, pyrimidyl, imidazolyl, triazolyl, thiazolyl or thienyl bonded via a $C_{1-6}$-alkylene group and in each case unsubstituted or mono- or poly-substituted.

In embodiments of the compounds according to the invention that are likewise preferred, the following combinations are met in the compounds of formulas C1 to C21, namely:

a represents 0, ax represents 2, q represents 1, ay represents 1 and Q represents $CH_2$;
a represents 0, ax represents 2, q represents 1, ay represents 1 and Q represents 0;
a represents 0, ax represents 2, q represents 1, ay represents 1 and Q represents $NR^{50}$;
a represents 1, ax represents 1, q represents 1, ay represents 1 and Q represents $CH_2$;
a represents 2, ax represents 1, q represents 1, ay represents 0 and Q represents $CH_2$;
a represents 0, ax represents 1, q represents 1, ay represents 1 and Q represents $CH_2$;
a represents 1, ax represents 1, q represents 0; and ay represents 1;
a represents 0, ax represents 0, q represents 1, ay represents 2 and Q represents O;
a represents 1, ax represents 0, q represents 1, ay represents 1 and Q represents O;
a represents 1; ax represents 0, q represents 1, ay represents 0 and Q represents $CH_2$; or
a represents 0, ax represents 0, q represents 1, ay represents 1 and Q represents $CH_2$.

Embodiments of the compounds according to the invention that are likewise preferred are compounds selected from the group consisting of:

[G-001] 4-methoxy-N,2,6-trimethyl-N-[2-[[4-[4-(2-1-pyrrolidinylethyl)-1-piperidinyl]-2-pyrimidinyl]oxy]ethyl]benzenesulfonamide
[G-002] 4-methoxy-N,2,6-trimethyl-N-[2-[[4-[4-(4-pyridyl)-1-piperazinyl]-2-pyrimidinyl]oxy]ethyl]benzenesulfonamide
[G-003] N-[2-[[4-[2-(4-dimethylamino-4-phenyl-1-piperidinyl)ethyl-methylamino]-2-pyrimidinyl]oxy]ethyl]-4-methoxy-N,2,6-trimethylbenzenesulfonamide
[G-004] 2-[[1-(4-methoxy-2,6-dimethylphenyl)sulfonyl-2-piperidinyl]methoxy]-4-[4-(3-pyridyl)-4-(2-1-pyrrolidinylethoxy)-1-piperidinyl]pyrimidine
[G-005] N-cyclopropyl-4-methoxy-2,6-dimethyl-N-[2-[[4-[9-(4-pyridyl)-3,9-diazaspiro[5.5]undecan-3-yl]-2-pyrimidinyl]oxy]ethyl]benzenesulfonamide hydrochloride
[G-006] N-cyclopropyl-4-methoxy-2,6-dimethyl-N-[2-[[4-[2-[1-(4-pyridyl)-4-piperidinyl]ethylamino]-2-pyrimidinyl]oxy]ethyl]benzenesulfonamide
[G-007] N-cyclopropyl-4-methoxy-2,6-dimethyl-N-[2-[[4-[4-(3-pyridyl)-4-(2-1-pyrrolidinylethoxy)-1-piperidinyl]-2-pyrimidinyl]oxy]ethyl]benzenesulfonamide
[G-008] N-cyclopropyl-N-[2-[[4-[4-hydroxy-4-(3-pyridyl)-1-piperidinyl]-2-pyrimidinyl]oxy]ethyl]-4-methoxy-2,6-dimethylbenzenesulfonamide
[G-009] 2-chloro-N-cyclopropyl-6-methyl-N-[2-[[4-[9-(4-pyridyl)-3,9-diazaspiro[5.5]undecan-3-yl]-2-pyrimidinyl]oxy]ethyl]benzenesulfonamide
[G-010] N-cyclopropyl-N-[2-[[4-[9-(4-pyridyl)-3,9-diazaspiro[5.5]undecan-3-yl]-2-pyrimidinyl]oxy]ethyl]-2-(trifluoromethyl)benzenesulfonamide
[G-011] 3-[2-[[(2S,4R)-4-fluoro-1-(4-methoxy-2,6-dimethylphenyl)sulfonyl-2-pyrrolidinyl]methoxy]-4-pyrimidinyl]-9-(4-pyridyl)-3,9-diazaspiro[5.5]undecane
[G-012] N-cyclopropyl-4-methoxy-2,6-dimethyl-N-[2-[[4-[4-(4-pyridyloxy)-1-piperidinyl]-2-pyrimidinyl]oxy]ethyl]benzenesulfonamide
[G-013] N-[2-[[4-[6-(1-azetidinylmethyl)-3,4-dihydro-1H-isoquinolin-2-yl]-2-pyrimidinyl]oxy]ethyl]-N-cyclopropyl-4-methoxy-2,6-dimethylbenzenesulfonamide
[G-014] N-cyclopropyl-4-methoxy-2,6-dimethyl-N-[2-[[4-[8-(4-pyridyl)-3,8-diazaspiro[4.4]nonan-3-yl]-2-pyrimidinyl]oxy]ethyl]benzenesulfonamide
[G-015] N-[2-[[4-[9-(1-azetidinyl)-3-azaspiro[5.5]undecan-3-yl]-2-pyrimidinyl]oxy]ethyl]-N-cyclopropyl-4-methoxy-2,6-dimethylbenzenesulfonamide hydrochloride
[G-016] N-cyclopropyl-4-methoxy-2,6-dimethyl-N-[2-[[4-[9-(4-pyridyloxy)-3-azaspiro[5.5]undecan-3-yl]-2-pyrimidinyl]oxy]ethyl]benzenesulfonamide
[G-017] N-cyclopropyl-N-[2-[[4-[9-(3,3-difluoro-1-azetidinyl)-3-azaspiro[5.5]undecan-3-yl]-2-pyrimidinyl]oxy]ethyl]-4-methoxy-2,6-dimethylbenzenesulfonamide
[G-018] 3-[2-[[1-(4-methoxy-2,6-dimethylphenyl)sulfonyl-3-azetidinyl]oxy]-4-pyrimidinyl]-9-(4-pyridyl)-3,9-diazaspiro[5.5]undecane
[G-019] N-cyclopropyl-4-methoxy-2,6-dimethyl-N-[2-[[4-[8-(4-pyridyl)-3,8-diazaspiro[4.5]decan-3-yl]-2-pyrimidinyl]oxy]ethyl]benzenesulfonamide
[G-020] N-[2-[[4-[3-[6-(1-azetidinylmethyl)-3,4-dihydro-1H-isoquinolin-2-yl]-1-azetidinyl]-2-pyrimidinyl]oxy]ethyl]-N-cyclopropyl-4-methoxy-2,6-dimethylbenzenesulfonamide
G-021 2,6-dichloro-N-cyclopropyl-3-methyl-N-[2-[4-(9-pyridin-4-yl-3,9-diazaspiro[5.5]undecan-3-yl)-pyrimidin-2-yl]oxy-ethyl]-benzenesulfonic acid amide
G-022 4-methoxy-2,6-dimethyl-N-[1-[[4-(9-pyridin-4-yl-3,9-diazaspiro[5.5]undecan-3-yl)-pyrimidin-2-yl]oxy-methyl]-cyclobutyl]-benzenesulfonic acid amide
G-023 N-cyclopropyl-4-methoxy-2,6-dimethyl-N-[2-[4-[9-pyridin-3-yl-9-(2-pyrrolidin-1-yl-ethoxy)-3-azaspiro[5.5]undecan-3-yl]-pyrimidin-2-yl]oxy-ethyl]-benzenesulfonic acid amide
G-024 N-[1,1-dimethyl-2-[4-(9-pyridin-4-yl-3,9-diazaspiro[5.5]undecan-3-yl)-pyrimidin-2-yl]oxy-ethyl]-4-methoxy-2,6-dimethyl-benzenesulfonic acid amide
G-025 N-cyclopropyl-4-methoxy-2,6-dimethyl-N-[3-[4-(9-pyridin-4-yl-3,9-diazaspiro[5.5]undecan-3-yl)-pyrimidin-2-yl]oxy-propyl]-benzenesulfonic acid amide
G-026 3-[2-[[(2S)-1-[(4-methoxy-2,6-dimethyl-phenyl)sulfonyl]-piperidin-2-yl]-methoxy]-pyrimidin-4-yl]-9-pyridin-4-yl-3,9-diazaspiro[5.5]undecane
[H-001] 4-methoxy-N,2,6-trimethyl-N-[2-[[2-[4-(2-1-pyrrolidinylethyl)-1-piperidinyl]-4-pyrimidinyl]oxy]ethyl]benzenesulfonamide
[H-002] 4-methoxy-N,2,6-trimethyl-N-[2-[2-[4-(4-pyridyl)-1-piperazinyl]-4-pyrimidinyl]oxy]ethyl]benzenesulfonamide
[H-003] N-[2-[[2-[2-(4-dimethylamino-4-phenyl-1-piperidinyl)ethyl-methylamino]-4-pyrimidinyl]oxy]ethyl]-4-methoxy-N,2,6-trimethylbenzenesulfonamide
[H-004] N-[2-(4-dimethylamino-4-phenyl-1-piperidinylethyl]-4-[[1-(4-methoxy-2,6-dimethylphenyl)sulfonyl-2-piperidinyl]methoxy]-N-methyl-2-pyrimidineamine

[H-005] N-cyclopropyl-4-methoxy-2,6-dimethyl-N-[2-[[2-[4-(4-pyridyloxy)-1-piperidinyl]-4-pyrimidinyl]oxy]ethyl]benzenesulfonamide

[H-006] 2-chloro-N-cyclopropyl-6-methyl-N-[2-[[2-[9-(4-pyridyl)-3,9-diazaspiro[5.5]undecan-3-yl]-4-pyrimidinyl]oxy]ethyl]benzenesulfonamide

[H-007] 3-[4-[[1-(4-methoxy-2,6-dimethylphenyl)sulfonyl-3-azetidinyl]oxy]-2-pyrimidinyl]-9-(4-pyridyl)-3,9-diazaspiro[5.5]undecane

[I-001] N-cyclopropyl-4-methoxy-2,6-dimethyl-N-[2-[[6-[9-(4-pyridyl)-3,9-diazaspiro[5.5]undecan-3-yl]-4-pyrimidinyl]oxy]ethyl]benzenesulfonamide I-002 N-cyclopropyl-4-methoxy-2,6-dimethyl-N-[2-[methyl-[6-(9-pyridin-4-yl-3,9-diazaspiro[5.5]undecan-3-yl)-pyrazin-2-yl]-amino]-ethyl]-benzenesulfonic acid amide I-003 N-cyclopropyl-4-methoxy-2,6-dimethyl-N-[2-[methyl-[6-(9-pyridin-4-yl-3,9-diazaspiro[5.5]undecan-3-yl)-pyrimidin-4-yl]-amino]-ethyl]-benzenesulfonic acid amide I-004 N-cyclopropyl-4-methoxy-2,6-dimethyl-N-[2-[methyl-[2-(9-pyridin-4-yl-3,9-diazaspiro[5.5]undecan-3-yl)-pyrimidin-4-yl]-amino]-ethyl]-benzenesulfonic acid amide I-005 N-cyclopropyl-4-methoxy-2,6-dimethyl-N-[2-[methyl-[4-(9-pyridin-4-yl-3,9-diazaspiro[5.5]undecan-3-yl)-pyrimidin-2-yl]-amino]-ethyl]-benzenesulfonic acid amide I-006 N-cyclopropyl-4-methoxy-2,6-dimethyl-N-[3-[6-(9-pyridin-4-yl-3,9-diazaspiro[5.5]undecan-3-yl)-pyrazin-2-yl]-propyl]-benzenesulfonic acid amide I-007 N-cyclopropyl-4-methoxy-2,6-dimethyl-N-[3-[2-(9-pyridin-4-yl-3,9-diazaspiro[5.5]undecan-3-yl)-pyrimidin-4-yl]-propyl]-benzenesulfonic acid amide I-008 N-cyclopropyl-N-[3-[2-(9-pyridin-4-yl-3,9-diazaspiro[5.5]undecan-3-yl)-pyrimidin-4-yl]-propyl]-3-(trifluoromethyl)-benzenesulfonic acid amide

[G_CC-001] 4-methoxy-N,2,6-trimethyl-N-[2-[[4-[4-(1-methyl-4-piperidinyl)-1-piperazinyl]-2-pyrimidinyl]oxy]ethyl]benzenesulfonamide

[G_CC-002] 2-[[1-(4-methoxy-2,6-dimethylphenyl)sulfonyl-2-piperidinyl]methoxy]-4-[4-(1-methyl-4-piperidinyl)-1-piperazinyl]pyrimidine

[G_CC-003] 2-[[1-(4-methoxy-2,6-dimethylphenyl)sulfonyl-2-piperidinyl]methoxy]-4-[4-(2-1-pyrrolidinylethyl)-1-piperidinyl]pyrimidine

[G_CC-004] N-[2-(4-dimethylamino-4-phenyl-1-piperidinyl)ethyl]-2-[[1-(4-methoxy-2,6-dimethylphenyl)sulfonyl-2-piperidinyl]methoxy]-N-methyl-4-pyrimidineamine

[G_CC-005] N-[2-[[4-[4-(4-fluorophenyl)-1-piperazinyl]-2-pyrimidinyl]oxy]ethyl]-4-methoxy-N,2,6-trimethylbenzenesulfonamide

[G_CC-006] 4-methoxy-N,2,6-trimethyl-N-[2-[[4-[4-(4-methyl-1-piperazinyl)-1-piperidinyl]-2-pyrimidinyl]oxy]ethyl]benzenesulfonamide

[G_CC-007] 4-methoxy-N,2,6-trimethyl-N-[2-[[4-[4-[(1-methyl-4-piperidinyl)methyl]-1-piperazin]-2-pyrimidinyl]oxy]ethyl]benzenesulfonamide

[G_CC-008] N-[2-[[4-[4-hydroxy-4-(3-pyridyl)-1-piperidinyl]-2-pyrimidinyl]oxy]ethyl]-4-methoxy-N,2,6-trimethylbenzenesulfonamide

[G_CC-009] 2-[[1-(4-methoxy-2,6-dimethylphenyl)sulfonyl-2-piperidinyl]methoxy]-4-(4-methyl-1-piperazinyl)pyrimidine

[G_CC-010] 4-[4-(4-fluorophenyl)-1-piperazinyl]-2-[[1-(4-methoxy-2,6-dimethylphenyl)sulfonyl-2-piperidinyl]methoxy]pyrimidine

[G_CC-011] 2-[[1-(4-methoxy-2,6-dimethylphenyl)sulfonyl-2-piperidinyl]methoxy]-4-[4-(4-methyl-1-piperazinyl)-1-piperidinyl]pyrimidine

[G_CC-012] 2-[[1-(4-methoxy-2,6-dimethylphenyl)sulfonyl-2-piperidinyl]methoxy]-4-[4-(2-pyrimidinyl)-1-piperazinyl]pyrimidine

[G_CC-013] 2-[[1-(4-methoxy-2,6-dimethylphenyl)sulfonyl-2-piperidinyl]methoxy]-4-[4-(4-pyridyl)-1-piperazinyl]pyrimidine

[G_CC-014] 2-[[1-(4-methoxy-2,6-dimethylphenyl)sulfonyl-2-piperidinyl]methoxy]-4-[4-[(1-methyl-4-piperidinyl)methyl]-1-piperazinyl]pyrimidine

[G_CC-015] 2-[[(2S)-1-(4-methoxy-2,6-dimethylphenyl)sulfonyl-2-pyrrolidinyl]methoxy]-4-(4-methyl-1-piperazinyl)pyrimidine

[G_CC-016] 2-[[(2S)-1-(4-methoxy-2,6-dimethylphenyl)sulfonyl-2-pyrrolidinyl]methoxy]-4-[4-(2-1-pyrrolidinylethyl)-1-piperidinyl]pyrimidine

[G_CC-017] 2-[[(2S)-1-(4-methoxy-2,6-dimethylphenyl)sulfonyl-2-pyrrolidinyl]methoxy]-4-[4-(4-methyl-1-piperazinyl)-1-piperidinyl]pyrimidine

[G_CC-018] 2-[[(2S)-1-(4-methoxy-2,6-dimethylphenyl)sulfonyl-2-pyrrolidinyl]methoxy]-4-[4-(2-pyrimidinyl)-1-piperazinyl]pyrimidine

[G_CC-019] 2-[[(2S)-1-(4-methoxy-2,6-dimethylphenyl)sulfonyl-2-pyrrolidinyl]methoxy]-4-[4-(4-pyridyl)-1-piperazinyl]pyrimidine

[G_CC-020] 1-[2-[[(2S)-1-(4-methoxy-2,6-dimethylphenyl)sulfonyl-2-pyrrolidinyl]methoxy]-4-pyrimidinyl]-4-(3-pyridyl)-4-piperidinol

[G_CC-021] 1-[2-[[(2S)-1-(4-methoxy-2,6-dimethylphenyl)sulfonyl-2-pyrrolidinyl]methoxy]-4-pyrimidinyl]-4-(2-thienyl)-4-piperidinol

[G_CC-022] 3-benzyl-7-[2-[[1-(4-methoxy-2,6-dimethylphenyl)sulfonyl-2-piperidinyl]methoxy]-4-pyrimidinyl]-3,7-diazaspiro[4.4]nonane

[G_CC-023] 1'-[2-[[1-(4-methoxy-2,6-dimethylphenyl)sulfonyl-2-piperidinyl]methoxy]-4-pyrimidinyl]spiro[1H-isobenzofuran-3,4'-piperidine]

[G_CC-024] 6-chloro-3-[1-[2-[[1-(4-methoxy-2,6-dimethylphenyl)sulfonyl-2-piperidinyl]methoxy]-4-pyrimidinyl]-4-piperidinyl]-1H-benzimidazol-2-one

[G_CC-025] 8-[2-[[1-(4-methoxy-2,6-dimethylphenyl)sulfonyl-2-piperidinyl]methoxy]-4-pyrimidinyl]-4-phenyl-2,4,8-triazaspiro[4.5]decan-1-one

[G_CC-026] 2-[[1-(4-methoxy-2,6-dimethylphenyl)sulfonyl-2-piperidinyl]methoxy]-4-[4-[2-(1-pipendypethyl]-1-piperidinyl]pyrimidine

[G_CC-027] 2-[[1-(4-methoxy-2,6-dimethylphenyl)sulfonyl-3-piperidinyl]oxy]-4-[4-[2-(1-piperidypethyl]-1-piperidinyl]pyrimidine

[G_CC-028] N-[2-[[4-(3-benzyl-3,7-diazaspiro[4.4]nonan-7-yl)-2-pyrimidinyl]oxy]ethyl]-4-methoxy-N,2,6-trimethylbenzenesulfonamide

[G_CC-029] 4-methoxy-N,2,6-trimethyl-N-[2-[[4-(1'-spiro[1H-isobenzofuran-3,4'-piperidin]yl)-2-pyrimidinyl]oxy]ethyl]benzenesulfonamide

[G_CC-030] 4-methoxy-N,2,6-trimethyl-N-[2-[[4-(1-oxo-4-phenyl-2,4,8-triazaspiro[4.5]decan-8-yl)-2-pyrimidinyl]oxy]ethyl]benzenesulfonamide

[G_CC-031] 4-methoxy-N,2,6-trimethyl-N-[2-[[4-[4-[2-(1-pipendypethyl]-1-piperidinyl]-2-pyrimidinyl]oxy]ethyl]benzenesulfonamide

[G_CC-032] 3-benzyl-7-[2-[[(2S)-1-(4-methoxy-2,6-dimethylphenyl)sulfonyl-2-pyrrolidinyl]methoxy]-4-pyrimidinyl]-3,7-diazaspiro[4.4]nonane

[G_CC-033] 1'-[2-[[(2S)-1-(4-methoxy-2,6-dimethylphenyl)sulfonyl-2-pyrrolidinyl]methoxy]-4-pyrimidinyl]spiro[1H-isobenzofuran-3,4'-piperidine]

[G_CC-034] 6-chloro-3-[1-[2-[[(2S)-1-(4-methoxy-2,6-dimethylphenyl)sulfonyl-2-pyrrolidinyl]methoxy]-4-pyrimidinyl]-4-piperidinyl]-1H-benzimidazol-2-one

[G_CC-035] 8-[2-[[(2S)-1-(4-methoxy-2,6-dimethylphenyl)sulfonyl-2-pyrrolidinyl]methoxy]-4-pyrimidinyl]-4-phenyl-2,4,8-triazaspiro[4.5]decan-1-one

[G_CC-036] 2-[[(2S)-1-(4-methoxy-2,6-dimethylphenyl)sulfonyl-2-pyrrolidinyl]methoxy]-4-[4-(1-methyl-4-piperidinyl)-1-piperazinyl]pyrimidine

[G_CC-037] 2-[[(2S)-1-(4-methoxy-2,6-dimethylphenyl)sulfonyl-2-pyrrolidinyl]methoxy]-4-[4-[2-(1-piperidypethyl]-1-piperidinyl]pyrimidine

[G_CC-038] 3-(4-fluorophenyl)-8-[2-[[1-(4-methoxy-2,6-dimethylphenyl)sulfonyl-2-piperidinyl]methoxy]-4-pyrimidinyl]-3,8-diazaspiro[4.5]decan-4-one

[G_CC-039] 3-[(4-fluorophenyl)methyl]-8-[2-[[1-(4-methoxy-2,6-dimethylphenyl)sulfonyl-2-piperidinyl]methoxy]-4-pyrimidinyl]-3,8-diazaspiro[4.5]decan-4-one

[G_CC-040] 3-benzyl-8-[2-[[1-(4-methoxy-2,6-dimethylphenyl)sulfonyl-2-piperidinyl]methoxy]-4-pyrimidinyl]-3,8-diazaspiro[4.5]decan-4-one

[G_CC-041] 9-[2-[[1-(4-methoxy-2,6-dimethylphenyl)sulfonyl-3-piperidinyl]oxy]-4-pyrimidinyl]-3-(4-pyridyl)-3,9-diazaspiro[5.5]undecane

[G_CC-042] N-[2-[[4-[3-(4-fluorophenyl)-4-oxo-3,8-diazaspiro[4.5]decan-8-yl]-2-pyrimidinyl]oxy]ethyl]-4-methoxy-N,2,6-trimethylbenzenesulfonamide

[G_CC-043] 4-methoxy-N,2,6-trimethyl-N-[2-[[4-[4-oxo-1-[3-(trifluoromethyl)phenyl]-3,8-diazaspiro[4.5]decan-8-yl]-2-pyrimidinyl]oxy]ethyl]benzenesulfonamide

[G_CC-044] N-[2-[[4-[1-(4-fluorophenyl)-3-methyl-4-oxo-3,8-diazaspiro[4.5]decan-8-yl]-2-pyrimidinyl]oxy]ethyl]-4-methoxy-N,2,6-trimethylbenzenesulfonamide

[G_CC-045] N-[2-[[4-[3-[(4-fluorophenyl)methyl]-4-oxo-3,8-diazaspiro[4.5]decan-8-yl]-2-pyrimidinyl]oxy]ethyl]-4-methoxy-N,2,6-trimethylbenzenesulfonamide

[G_CC-046] N-[2-[[4-(3-benzyl-4-oxo-3,8-diazaspiro[4.5]decan-8-yl)-2-pyrimidinyl]oxy]ethyl]-4-methoxy-N,2,6-trimethylbenzenesulfonamide

[G_CC-047] 4-methoxy-N,2,6-trimethyl-N-[2-[[4-[3-(4-pyridyl)-3,9-diazaspiro[5.5]undecan-9-yl]-2-pyrimidinyl]oxy]ethyl]benzenesulfonamide

[G_CC-048] 3-(4-fluorophenyl)-8-[2-[[(2S)-1-(4-methoxy-2,6-dimethylphenyl)sulfonyl-2-pyrrolidinyl]methoxy]-4-pyrimidinyl]-3,8-diazaspiro[4.5]decan-4-one

[G_CC-049] 8-[2-[[(2S)-1-(4-methoxy-2,6-dimethylphenyl)sulfonyl-2-pyrrolidinyl]methoxy]-4-pyrimidinyl]-1-[3-(trifluoromethyl)phenyl]-3,8-diazaspiro[4.5]decan-4-one

[G_CC-050] 1-(4-fluorophenyl)-8-[2-[[(2S)-1-(4-methoxy-2,6-dimethylphenyl)sulfonyl-2-pyrrolidinyl]methoxy]-4-pyrimidinyl]-3-methyl-3,8-diazaspiro[4.5]decan-4-one

[G_CC-051] 3-[(4-fluorophenyl)methyl]-8-[2-[[(2S)-1-(4-methoxy-2,6-dimethylphenyl)sulfonyl-2-pyrrolidinyl]methoxy]-4-pyrimidinyl]-3,8-diazaspiro[4.5]decan-4-one

[G_CC-052] 2-[[(2S)-1-(4-methoxy-2,6-dimethylphenyl)sulfonyl-2-pyrrlidinyl]methoxy]-4-[4-(4-pyridyloxy)-1-piperidinyl]pyrimidine

[G_CC-053] 3-benzyl-8-[2-[[(2S)-1-(4-methoxy-2,6-dimethylphenyl)sulfonyl-2-pyrrolidinyl]methoxy]-4-pyrimidinyl]-3,8-diazaspiro[4.5]decan-4-one

[G_CC-054] N-[[1-[2-[[(2R)-1-(4-methoxy-2,6-dimethylphenyl)sulfonyl-2-pyrrolidinyl]methoxy]-4-pyrimidinyl]-(4-methyl-1-piperazinyl)-4-pipendinyl]methyl]-pyridinecarboxamide

[G_CC-055] 9-[2-[[(2S)-1-(4-methoxy-2,6-dimethylphenyl)sulfonyl-2-pyrrolidinyl)methoxy]-4-pyrimidinyl]-3-(4-pyridyl)-3,9-diazaspiro[5.5]undecane

[G_CC-056] 5-[2-[[1-(4-methoxy-2,6-dimethylphenyl)sulfonyl-2-piperidinyl]methoxy]-4-pyrimidinyl]-2-(4-pyridylmethyl)-2,5-diazabicyclo[2.2.1]heptane

[G_CC-057] 5-[2-[[1-(4-methoxy-2,6-dimethylphenyl)sulfonyl-3-piperidinyl]oxy]-4-pyrimidinyl]-2-(4-pyridylmethyl)-2,5-diazabicyclo[2.2.1]heptane

[G_CC-058] 5-[2-[[(2S)-1-(4-methoxy-2,6-dimethylphenyl)sulfonyl-2-pyrrolidinyl)methoxy]-4-pyrimidinyl]-2-(4-pyridylmethyl)-2,5-diazabicyclo[2.2.1]heptane

[G_CC-059] 4-methoxy-N,2,6-trimethyl-N-[2-[[4-[4-(1-methyl-4-pipendinyl)-1-piperazinyl]-2-pyrimidinyl]oxy]-1-phenylethyl]benzenesulfonamide

[G_CC-060] N-[2-[[4-[3-[(4-fluorophenyl)methyl]-4-oxo-3,8-diazaspiro[4.5]decan-8-yl]-2-pyrimidinyl]oxy]-1-phenylethyl]-4-methoxy-N,2,6-trimethylbenzenesulfonamide

[G_CC-061] N-[2-[[4-(3-benzyl-4-oxo-3,8-diazaspiro[4.5]decan-8-yl)-2-pyrimidinyl]oxy]-1-phenylethyl]-4-methoxy-N,2,6-trimethylbenzenesulfonamide

[G_CC-062] 4-methoxy-N,2,6-trimethyl-N-[1-phenyl-2-[[4-[4-(3-pyridyl)-4-(2-1-pyrrolidinylethoxy)-1-piperidinyl]-2-pyrimidinyl]oxy]ethyl]benzenesulfonamide

[G_CC-063] 4-methoxy-N,2,6-trimethyl-N-[1-phenyl-2-[[4-[4-(4-pyridyloxy)-1-piperidinyl]-2-pyrimidinyl]oxy]ethyl]benzenesulfonamide

[G_CC-064] 4-methoxy-N,2,6-trimethyl-N-[2-[[4-[4-[oxo-(3-pyridyl)methyl]-1-piperazinyl]-2-pyrimidinyl]oxy]-1-phenylethyl]benzenesulfonamide

[G_CC-065] N-[2-[[4-[2-[(4-fluorophenyl)methyl]-2,5-diazabicyclo[2.2.1]heptan-5-yl]-2-pyrimidinyl]oxy]-1-phenylethyl]-4-methoxy-N,2,6-trimethylbenzenesulfonamide

[G_CC-066] 2-[[1-(4-methoxy-2,6-dimethylphenyl)sulfonyl-2-pipendinyl]methoxy]-4-[4-(4-pyridyl)-1-piperazinyl]pyrimidine

[G_CC-067] 1-[2-[[1-(4-methoxy-2,6-dimethylphenyl)sulfonyl-2-piperidinyl]methoxy]-4-pyrimidinyl]-4-(3-pyridyl)-4-piperidinol

[G_CC-068] N-[2-[[4-(3-benzyl-3,7-diazaspiro[4.4]nonan-7-yl)-2-pyrimidinyl]oxy]-1-phenylethyl]-4-methoxy-N,2,6-trimethylbenzenesulfonamide G_CC-069 [4-butyl-1-[2-[[1-[(4-methoxy-2,6-dimethylphenyl)sulfonyl]-piperidin-2-yl]-methoxy]-pyrimidin-4-yl]-piperidin-4-yl]-dimethyl-amine G_CC-070 [1-[2-[[1-[(4-methoxy-2,6-dimethyl-phenyl)sulfonyl]-piperidin-2-yl]-methoxy]-pyrimidin-4-yl]-4-thiophen-2-yl-pipendin-4-yl]-dimethyl-amine G_CC-073 [2-[[1-[(4-methoxy-2,6-dimethyl-phenyl)sulfonyl]-piperidin-2-yl]-methoxy]-pyrimidin-4-yl]-methyl-[2-(4-phenyl-4-pyrrolidin-1-yl-piperidin-1-yl)-ethyl]-amine G_CC-074 2-(4-butyl-4-dimethylamino-piperidin-1-yl)-ethyl-[2-[[1-[(4-methoxy-2,6-dimethyl-phenyl)sulfonyl]-piperidin-2-yl]-methoxy]-pyrimidin-4-yl]-methyl-amine G_CC-075 3-(4-dimethylamino-4-phenyl-piperidin-1-yl)-propyl-[2-[[(2S)-1-[(4-methoxy-2,6-dimethyl-phenyl)sulfonyl]-pyrrolidin-2-yl]-methoxy]-pyrimidin-4-yl]-methyl-amine G_CC-076 3-(4-dimethylamino-4-phenyl-piperidin-1-yl)-propyl-[2-[[(2S)-1-[(4-methoxy-2,6-dimethyl-phenyl)sulfonyl]-2,3-dihydro-1H-indol-2-yl]-methoxy]-pyrimidin-4-yl]-methyl-amine G_CC-077 2-[1-[(4-methoxy-2,6-dimethyl-phenyl)sulfonyl]-azetidin-3-yl]oxy-4-[4-[(1-methyl-piperidin-4-yl)methyl]-piperazin-1-yl]-pyrimidine G_CC-078 2-[[1-[(4-methoxy-2,6-dimethyl-phenyl)sulfonyl]-piperidin-2-yl]-methoxy]-4-(4-pyridin-2-yloxy-piperidin-1-yl)-pyrimidine G_CC-079 2-[[1-[(4-methoxy-2,6-dimethyl-phenyl)sulfonyl]-piperidin-2-yl]-methoxy]-4-(4-pyrazin-2-yloxy-piperidin-1-yl)-pyrimidine G_CC-080 2-[[1-[(4-methoxy-2,6-dimethyl-phenyl)sulfonyl]-piperidin-2-yl]-methoxy]-4-[4-pyridin-3-yl-4-(3-pyrrolidin-1-yl-propyl)-piperidin-1-yl]-pyrimidine G_CC-081 2-[[1-[(4-methoxy-2,6-dimethyl-phenyl)sulfonyl]-piperidin-2-yl]-methoxy]-4-[2-(pyridin-2-yl-methyl)-pyrrolidin-1-yl]-pyrimidine G_CC-082 1-[2-[[1-[(4-methoxy-2,6-dimethyl-phenyl)sulfonyl]-piperidin-2-yl]-methoxy]-pyrimidin-4-yl]-4-pyridin-2-yl-piperidin-4-ol G_CC-083 1-[2-[[(2S)-1-[(4-methoxy-2,6-dimethyl-phenyl)sulfonyl]-pyrrolidin-2-yl]-methoxy]-pyrimidin-4-yl]-4-pyridin-2-yl-piperidin-4-ol G_CC-084 2-[[(2R)-1-[(4-methoxy-2,6-dimethyl-phenyl)sulfonyl]-pyrrolidin-2-yl]-methoxy]-4-[2-(pyridin-2-yl-methyl)-pyrrolidin-1-yl]-pyrimidine G_CC-085 5-[1-[2-[[(2S)-1-[(4-methoxy-2,6-dimethyl-phenyl)sulfonyl]-pyrrolidin-2-yl]-methoxy]-pyrimidin-4-yl]-piperidin-4-yl]-3-pyridin-4-yl-[1,2,4]oxadiazole G_CC-086 4-[4-(3-fluorophenyl)-4-(2-pyrrolidin-1-yl-ethoxy)-piperidin-1-yl]-2-[[(2S)-1-[(4-methoxy-2,6-dimethyl-phenyl)sulfonyl]-pyrrolidin-2-yl]-methoxy]-pyrimidine G_CC-087 [4-butyl-1-[2-[[(2S)-1-[(4-methoxy-2,6-dimethyl-phenyl)sulfonyl]-pyrrolidin-2-yl]-methoxy]-pyrimidin-4-yl]-piperidin-4-yl]-dimethyl-amine G_CC-088 2-(4-dimethylamino-4-phenyl-piperidin-1-yl)-ethyl-[2-[[(2S)-1-[(4-methoxy-2,6-dimethyl-phenyl)sulfonyl]-pyrrolidin-2-yl]-methoxy]-pyrimidin-4-yl]-methyl-amine G_CC-089 N-[2-[4-(4-butyl-4-dimethylamino-piperidin-1-yl)-pyrimidin-2-yl]oxy-ethyl]-4-methoxy-N,2,6-trimethyl-benzenesulfonic acid amide G_CC-091 [2-[[(2S)-1-[(4-methoxy-2,6-dimethyl-phenyl)sulfonyl]-pyrrolidin-2-yl]-methoxy]-pyrimidin-4-yl]-methyl-[2-(4-phenyl-4-pyrrolidin-1-yl-piperidin-1-yl)-ethyl]-amine G_CC-092 (2S)-1-[(4-methoxy-2,6-dimethyl-phenyl)sulfonyl]-2-[[4-(4-pyrazin-2-yloxy-piperidin-1-yl)-pyrimidin-2-yl]oxy-methyl]-2,3-dihydro-1H-indole G_CC-093 [4-butyl-1-[2-[[(2S)-1-[(4-methoxy-2,6-dimethyl-phenyl)sulfonyl]-2,3-dihydro-1H-indol-2-yl]-methoxy]-pyrimidin-4-yl]-piperidin-4-yl]-dimethyl-amine G_CC-094 2-(4-dimethylamino-4-phenyl-piperidin-1-yl)-ethyl-[2-[[(2S)-1-[(4-methoxy-2,6-dimethyl-phenyl)sulfonyl]-2,3-dihydro-1H-indol-2-yl]-methoxy]-pyrimidin-4-yl]-methyl-amine G_CC-096 [2-[[(2S)-1-[(4-methoxy-2,6-dimethyl-phenyl)sulfonyl]-2,3-dihydro-1H-indol-2-yl]-methoxy]-pyrimidin-4-yl]-methyl-[2-(4-phenyl-4-pyrrolidin-1-yl-piperidin-1-yl)-ethyl]-amine G_CC-097 2-(4-butyl-4-dimethylamino-piperidin-1-yl)-ethyl-[2-[[(2S)-1-[(4-methoxy-2,6-dimethyl-phenyl)sulfonyl]-2,3-dihydro-1H-indol-2-yl]-methoxy]-pyrimidin-4-yl]-methyl-amine G_CC-098 N-[2-[4-[2-(4-dimethylamino-4-phenyl-piperidin-1-yl)-ethyl-methyl-amino]-pyrimidin-2-yl]oxy-ethyl]-4-methoxy-N,2,6-trimethyl-benzenesulfonic acid amide G_CC-100 N-[2-[4-[3-(4-dimethylamino-4-phenyl-piperidin-1-yl)-propyl-methyl-amino]-pyrimidin-2-yl]oxy-ethyl]-4-methoxy-N,2,6-trimethyl-benzenesulfonic acid amide G_CC-101 3-(4-dimethylamino-4-phenyl-piperidin-1-yl)-propyl-[2-[[1-[(4-methoxy-2,6-dimethyl-phenyl)sulfonyl]-piperidin-2-yl]-methoxy]-pyrimidin-4-yl]-methyl-amine G_CC-103 5-[1-[2-[[1-[(4-methoxy-2,6-dimethyl-phenyl)sulfonyl]-piperidin-2-yl]-methoxy]-pyrimidin-4-yl]-piperidin-4-yl]-3-pyridin-4-yl-[1,2,4]oxadiazole G_CC-104 4-[4-(3-fluorophenyl)-4-(4-methyl-piperazin-1-yl)-piperidin-1-yl]-2-[[1-[(4-methoxy-2,6-dimethyl-phenyl)sulfonyl]-piperidin-2-yl]-methoxy]-pyrimidine G_CC-105 (1S,5R)-8-[2-[[1-[(4-methoxy-2,6-dimethyl-phenyl)sulfonyl]-piperidin-2-yl]-methoxy]-pyrimidin-4-yl]-3-pyridin-3-yloxy-8-azabicyclo[3.2.1]octane G_CC-106 1-[2-[[2-[[1-[(4-methoxy-2,6-dimethyl-phenyl)sulfonyl]-piperidin-2-yl]-methoxy]-pyrimidin-4-yl]-methyl-amino]ethyl]-4-pyridin-3-yl-piperidin-4-ol G_CC-107 4-methoxy-N,2,6-trimethyl-N-[1-phenyl-2-[4-[(1S,5R)-3-pyridin-3-yloxy-8-azabicyclo[3.2.1]octan-8-yl]-pyrimidin-2-yl]oxy-ethyl]-benzenesulfonic acid amide G_CC-108 4-methoxy-N,2,6-trimethyl-N-[1-phenyl-2-[4-[4-pyridin-3-yl-4-(3-pyrrolidin-1-yl-propyl)-piperidin-1-yl]-pyrimidin-2-yl]oxy-ethyl]-benzenesulfonic acid amide G_CC-109 7-[2-[[(2S)-1-[(4-methoxy-2,6-dimethyl-phenyl)sulfonyl]-pyrrolidin-2-yl]-methoxy]-pyrimidin-4-yl]-2-(piperidin-1-yl-methyl)-5,6,7,8-tetrahydro-imidazo[1,2-a]pyrazine G_CC-111 1-[2-[[1-[(4-methoxy-2,6-dimethyl-phenyl)sulfonyl]-piperidin-2-yl]-methoxy]-pyrimidin-4-yl]-4-pyridin-4-yl-piperidin-4-ol G_CC-112 N-[2-[4-(4-hydroxy-4-pyridin-4-yl-piperidin-1-yl)-pyrimidin-2-yl]oxy-1-phenyl-ethyl]-4-methoxy-N,2,6-trimethyl-benzenesulfonic acid amide G_CC-113 [1-[2-[[1-[(4-methoxy-2,6-dimethyl-phenyl)sulfonyl]-piperidin-2-yl]-methoxy]-pyrimidin-4-yl]-4-phenyl-piperidin-4-yl]-dimethyl-amine G_CC-114 2-[1-[(4-methoxy-2,6-dimethyl-phenyl)sulfonyl]-piperidin-3-yl]oxy-4-(4-phenyl-4-pyrrolidin-1-yl-piperidin-1-yl)-pyrimidine G_CC-115 2-[[(2S)-1-[(4-methoxy-2,6-dimethyl-phenyl)sulfonyl]-pyrrolidin-2-yl]-methoxy]-4-(4-phenyl-4-pyrrolidin-1-yl-piperidin-1-yl)-pyrimidine G_CC-116 4-methoxy-N,2,6-trimethyl-N-[2-[4-(4-phenyl-4-pyrrolidin-1-yl-piperidin-1-yl)-pyrimidin-2-yl]oxy-ethyl]benzenesulfonic acid amide G_CC-117 N-[2-[4-(4-dimethylamino-4-phenyl-piperidin-1-yl)-pyrimidin-2-yl]oxy-ethyl]-4-methoxy-N,2,6-trimethyl-benzenesulfonic acid amide G_CC-118 N-[2-[4-(4-dimethylamino-4-thiophen-2-yl-piperidin-1-yl)-pyrimidin-2-yl]oxy-ethyl]-4-methoxy-N,2,6-trimethyl-benzenesulfonic acid amide G_CC-119 4-methoxy-N,2,6-trimethyl-N-[2-[4-[methyl-[2-(4-phenyl-4-pyrrolidin-1-yl-piperidin-1-yl)-ethyl]-amino]-pyrimidin-2-yl]oxy-ethyl]benzenesulfonic acid amide G_CC-120 N-[2-[4-[2-(4-butyl-4-dimethylamino-piperidin-1-yl)-ethyl-methyl-amino]-pyrimidin-2-yl]oxy-ethyl]-4-methoxy-N,2,6-trimethyl-benzenesulfonic acid amide G_CC-121 2-[[1-[(4-methoxy-2,6-dimethyl-phenyl)sulfonyl]-piperidin-2-yl]-methoxy]-4-(4-phenyl-4-pyrrolidin-1-yl-piperidin-1-yl)-pyrimidine G_CC-122 2-[1-[(4-methoxy-2,6-dimethyl-phenyl)sulfonyl]-azetidin-3-yl]oxy-4-(4-phenyl-4-pyrrolidin-1-yl-piperidin-1-yl)-pyrimidine G_CC-123 2-(4-dimethylamino-4-phenyl-piperidin-1-yl)-ethyl-[2-[1-[(4-methoxy-2,6-dimethyl-phenyl)sulfonyl]-azetidin-3-yl]oxy-pyrimidin-4-yl]-methyl-amine G_CC-124 [2-[1-[(4-methoxy-2,6-dimethyl-phenyl)sulfonyl]-azetidin-3-yl]oxy-pyrimidin-4-yl]-methyl-[2-(4-phenyl-4-pyrrolidin-1-yl-piperidin-1-yl)-ethyl]amine G_CC-125 [1-[2-[[(2S)-1-[(4-methoxy-2,6-dimethyl-phenyl)sulfonyl]-2,3-dihydro-1H-indol-2-yl]-methoxy]-pyrimidin-4-yl]-4-thiophen-2-yl-piperidin-4-yl]-dimethyl-amine G_CC-126 3-(4-dimethylamino-4-phenyl-piperidin-1-yl)-propyl-[2-[1-[(4-methoxy-2,6-dimethyl-phenyl)sulfonyl]-azetidin-3-yl]oxy-pyrimidin-4-yl]-methyl-amine G_CC-127 3-[4-[2-[1-[(4-methoxy-2,6-dimethyl-phenyl)sulfonyl]-azetidin-3-yl]oxy-pyrimidin-4-yl]-piperazin-1-yl]-propyl-dimethyl-amine G_CC-128 1-[2-[1-[(4-methoxy-2,6-dimethyl-phenyl)sulfonyl]-azetidin-3-yl]oxy-pyrimidin-4-yl]-4-pyridin-3-yl-piperidin-4-ol G_CC-129 2-[1-[(4-methoxy-2,6-dimethyl-phenyl)sulfonyl]-azetidin-3-yl]oxy-4-[4-(2-piperidin-1-yl-ethyl)-piperidin-1-yl]-pyrimidine G_CC-130 (2S)-2-[[4-[2-[(4-fluorophenyl)-methyl]-2,5-diazabicyclo[2.2.1]heptan-5-yl]-pyrimidin-2-yl]oxy-methyl]-1-[(4-methoxy-2,6-dimethyl-phenyl)sulfonyl]-2,3-dihydro-1H-indole G_CC-131 4-[1-[2-[[1-[(4-methoxy-2,6-dimethyl-phenyl)sulfonyl]-piperidin-2-yl]-methoxy]-pyrimidin-4-yl]-4-methyl-piperidin-4-yl]-morpholine G_CC-133 4-methoxy-N,2,6-trimethyl-N-[1-phenyl-2-[4-[2-(pyridin-2-yl-methyl)-pyrrolidin-1-yl]-pyrimidin-2-yl]oxy-ethyl]benzenesulfonic acid amide G_CC-134 4-methoxy-N,2,6-trimethyl-N-[1-phenyl-2-[4-]4-(3-pyridin-4-yl-[1,2,4]oxadiazol-5-yl)-piperidin-1-yl]-pyrimidin-2-yl]oxy-ethyl]benzenesulfonic acid amide G_CC-135 N-[2-[4-[4-(3-fluorophenyl)-4-(4-methyl-piperazin-1-yl)-piperidin-1-yl]-pyrimidin-2-yl]oxy-1-phenyl-ethyl]-4-methoxy-N,2,6-trimethyl-benzenesulfonic acid amide G_CC-136 4-methoxy-N,2,6-trimethyl-N-[1-phenyl-2-[4-(4-pyridin-2-yloxy-piperidin-1-yl)-pyrimidin-2-yl]oxy-ethyl]benzenesulfonic acid amide G_CC-137 4-methoxy-N,2,6-trimethyl-N-[2-[4-(4-methyl-4-morpholin-4-yl-piperidin-1-yl)-pyrimidin-2-yl]oxy-1-phenyl-ethyl]benzenesulfonic acid amide G_CC-138 N-[2-[4-[2-(4-hydroxy-4-pyridin-3-yl-piperidin-1-yl)-ethyl-methyl-amino]-pyrimidin-2-yl]oxy-1-phenyl-ethyl]-4-methoxy-N,2,6-trimethyl-benzenesulfonic acid amide

[H_CC-001] 4-[[1-(4-methoxy-2,6-dimethylphenyl)sulfonyl-2-piperidinyl]methoxy]-2-[4-(1-methyl-4-piperidinyl)-1-piperazinyl]pyrimidine

[H_CC-002] 4-[[1-(4-methoxy-2,6-dimethylphenyl)sulfonyl-2-piperidinyl]methoxy]-2-[4-(2-1-pyrrolidinylethyl)-1-piperidinyl]pyrimidine

[H_CC-003] 4-[[1-(4-methoxy-2,6-dimethylphenyl)sulfonyl-2-piperidinyl]methoxy]-2-(4-methyl-1-piperazinyl)pyrimidine

[H_CC-004] 4-[[1-(4-methoxy-2,6-dimethylphenyl)sulfonyl-2-pipendinyl]methoxy]-2-[4-(2-pyrimidinyl)-1-piperazinyl]pyrimidine

[H_CC-005] 4-[[1-(4-methoxy-2,6-dimethylphenyl)sulfonyl-2-pipendinyl]methoxy]-2-[4-(4-pyridyl)-1-piperazinyl]pyrimidine

[H_CC-006] 4-[[1-(4-methoxy-2,6-dimethylphenyl)sulfonyl-2-pipendinyl]methoxy]-2-[4-[(1-methyl-4-pipendinyl)methyl]-1-piperazinyl]pyrimidine

[H_CC-007] 1-[4-[[1-(4-methoxy-2,6-dimethylphenyl)sulfonyl-2-piperidinyl]methoxy]-2-pyrimidinyl]-4-(3-pyridyl)-4-piperidinol

[H_CC-008] 4-[[(2S)-1-(4-methoxy-2,6-dimethylphenyl)sulfonyl-2-pyrrolidinyl]methoxy]-2-(4-methyl-1-piperazinyl)pyrimidine

[H_CC-009] 4-[[(2S)-1-(4-methoxy-2,6-dimethylphenyl)sulfonyl-2-pyrrolidinyl]methoxy]-2-[4-(2-1-pyrrolidinylethyl)-1-piperidinyl]pyrimidine

[H_CC-010] 4-[[(2S)-1-(4-methoxy-2,6-dimethylphenyl)sulfonyl-2-pyrrolidinyl]methoxy]-2-[4-(4-methyl-1-piperazinyl)-1-piperidinyl]pyrimidine

[H_CC-011] 4-[[(2S)-1-(4-methoxy-2,6-dimethylphenyl)sulfonyl-2-pyrrolidinyl]methoxy]-2-[4-(2-pyrimidinyl)-1-piperazinyl]pyrimidine

[H_CC-012] 4-[[(2S)-1-(4-methoxy-2,6-dimethylphenyl)sulfonyl-2-pyrrolidinyl]methoxy]-2-[4-[(1-methyl-4-pipendinyl)methyl]-1-piperazinyl]pyrimidine

[H_CC-013] 1-[4-[[(2S)-1-(4-methoxy-2,6-dimethylphenyl)sulfonyl-2-pyrrolidinyl]methoxy]-2-pyrimidinyl]-4-(3-pyridyl)-4-piperidinol

[H_CC-014] 4-[[1-(4-methoxy-2,6-dimethylphenyl)sulfonyl-3-azetidinyl]oxy]-2-[4-(2-1-pyrrolidinylethyl)-1-piperidinyl]pyrimidine

[H_CC-015] 4-[[1-(4-methoxy-2,6-dimethylphenyl)sulfonyl-3-azetidinyl]oxy]-2-[4-(4-methyl-1-piperazinyl)-1-piperidinyl]pyrimidine

[H_CC-016] (2S)-1-(4-methoxy-2,6-dimethylphenyl)sulfonyl-2-[[2-(4-methyl-1-piperazinyl)-4-pyrimidinyl]oxymethyl]indoline

[H_CC-017] (2S)-1-(4-methoxy-2,6-dimethylphenyl)sulfonyl-2-[[2-[4-(2-1-pyrrolidinylethyl)-1-pipendinyl]-4-pyrimidinyl]oxymethyl]indoline

[H_CC-018] (2S)-1-(4-methoxy-2,6-dimethylphenyl)sulfonyl-2-[[2-[4-(4-methyl-1-piperazinyl)-1-pipendinyl]-4-pyrimidinyl]oxymethyl]indoline

[H_CC-019] (2S)-1-(4-methoxy-2,6-dimethylphenyl)sulfonyl-2-[[2-[4-(4-pyridyl)-1-piperazinyl]-4-pyrimidinyl]oxymethyl]indoline

[H_CC-020] (2S)-1-(4-methoxy-2,6-dimethylphenyl)sulfonyl-2-[[2-[4-[(1-methyl-4-pipendinyl)methyl]-1-piperazinyl]-4-pyrimidinyl]oxymethyl]indoline

[H_CC-021] 3-benzyl-7-[4-[[1-(4-methoxy-2,6-dimethylphenyl)sulfonyl-2-piperidinyl]methoxy]-2-pyrimidinyl]-3,7-diazaspiro[4.4]nonane

[H_CC-022] 4-[[1-(4-methoxy-2,6-dimethylphenyl)sulfonyl-2-pipendinyl]methoxy]-2-[4-[2-(1-pipendypethyl]-1-piperidinyl]pyrimidine

[H_CC-023] 3-benzyl-7-[4-[[(2S)-1-(4-methoxy-2,6-dimethylphenyl)sulfonyl-2-pyrrolidinyl]methoxy]-2-pyrimidinyl]-3,7-diazaspiro[4.4]nonane

[H_CC-024] 8-[4-[[(2S)-1-(4-methoxy-2,6-dimethylphenyl)sulfonyl-2-pyrrlidinyl]methoxy]-2-pyrimidinyl]-4-phenyl-2,4,8-triazaspiro[4.5]decan-1-one

[H_CC-025] 4-[[(2S)-1-(4-methoxy-2,6-dimethylphenyl)sulfonyl-2-pyrrlidinyl]methoxy]-2-[4-(1-methyl-4-piperidinyl)-1-piperazinyl]pyrimidine

[H_CC-026] 4-[[(2S)-1-(4-methoxy-2,6-dimethylphenyl)sulfonyl-2-pyrrlidinyl]methoxy]-2-[4-[2-(1-piperidyl)ethyl]-1-piperidinyl]pyrimidine

[H_CC-027] (2S)-1-(4-methoxy-2,6-dimethylphenyl)sulfonyl-2-[[2-[4-(1-methyl-4-piperidinyl)-1-piperazinyl]-4-pyrimidinyl]oxymethyl]indoline

[H_CC-028] (2S)-1-(4-methoxy-2,6-dimethylphenyl)sulfonyl-2-[[2-[4-[2-(1-piperidyl)ethyl]-1-piperidinyl]-4-pyrimidinyl]oxymethyl]indoline

[H_CC-029] 4-methoxy-N,2,6-trimethyl-N-[2-[[2-[3-(4-pyridyl)-3,9-diazaspiro[5.5]undecan-9-yl]-4-pyrimidinyl]oxy]ethyl]benzenesulfonamide

[H_CC-030] 3-[(4-fluorophenyl)methyl]-8-[4-[[1-(4-methoxy-2,6-dimethylphenyl)sulfonyl-2-piperidinyl]methoxy]-2-pyrimidinyl]-3,8-diazaspiro[4.5]decan-4-one

[H_CC-031] N-[[1-[4-[[1-(4-methoxy-2,6-dimethylphenyl)sulfonyl-2-piperidinyl]methoxy]-2-pyrimidinyl]-4-(4-methyl-1-piperazinyl)-4-piperidinyl]methyl]-4-pyridinecarboxamide

[H_CC-032] 9-[4-[[1-(4-methoxy-2,6-dimethylphenyl)sulfonyl-2-piperidinyl]methoxy]-2-pyrimidinyl]-3-(4-]pyridyl)-3,9-diazaspiro[5.5]undecane

[H_CC-033] 4-methoxy-N,2,6-trimethyl-N-[2-[[2-[4-(3-pyridyl)-4-(2-1-pyrrolidinylethoxy)-1-piperidinyl]-4-pyrimidinyl]oxy]ethyl]benzenesulfonamide

[H_CC-034] 4-methoxy-N,2,6-trimethyl-N-[2-[[2-[2-(4-pyridylmethyl)-2,5-diazabicyclo[2.2.1]heptan-5-yl]-4-pyrimidinyl]oxy]ethyl]benzenesulfonamide

[H_CC-035] 4-[[1-(4-methoxy-2,6-dimethylphenyl)sulfonyl-2-piperidinyl]methoxy]-2-[4-(3-pyridyl)-4-(2-1-pyrrolidinylethoxy)-1-piperidinyl]pyrimidine

[H_CC-036] 4-methoxy-N,2,6-trimethyl-N-[1-phenyl-2-[[2-[4-(4-pyridyl)-1-piperazinyl]-4-pyrimidinyl]oxy]ethyl]benzenesulfonamide

[H_CC-037] 4-methoxy-N,2,6-trimethyl-N-[1-phenyl-2-[[2-[3-(4-pyridyl)-3,9-diazaspiro[5.5]undecan-9-yl]-4-pyrimidinyl]oxy]ethyl]benzenesulfonamide

[H_CC-038] N-methyl-N-[1-phenyl-2-[[2-[4-(3-pyridyl)-4-(2-1-pyrrolidinylethoxy)-1-piperidinyl]-4-pyrimidinyl]oxy]ethyl]-2-naphthalenesulfonamide

[H_CC-039] N-[2-[[2-[3-[(4-fluorophenyl)methyl]-4-oxo-3,8-diazaspiro[4.5]decan-8-yl]-4-pyrimidinyl]oxy]ethyl]-4-methoxy-N,2,6-trimethylbenzenesulfonamide

[H_CC-040] 4-[[(2S)-1-(4-methoxy-2,6-dimethylphenyl)sulfonyl-2-pyrrolidinyl]methoxy]-2-[4-(3-pyridyl)-4-(2-1-pyrrolidinylethoxy)-1-piperidinyl]pyrimidine

[H_CC-041] 4-[[1-(4-methoxy-2,6-dimethylphenyl)sulfonyl-3-piperidinyl]oxy]-2-[4-[2-(1-piperidyl)ethyl]-1-piperidinyl]pyrimidine H_CC-042 1-[4-[[1-[(4-methoxy-2,6-dimethyl-phenyl)sulfonyl]-piperidin-2-yl]-methoxy-pyrimidin-2-yl]-4-(pyridin-2-yl-methyl)-[1,4]diazepan H_CC-043 1-[4-[[(2R)-1-[(4-methoxy-2,6-dimethyl-phenyl)sulfonyl]-pyrrolidin-2-yl]-methoxy]-pyrimidin-2-yl]-4-(pyridin-2-yl-methyl)-[1,4]diazepam H_CC-044 2-(4-dimethylamino-4-phenyl-piperidin-1-yl)-ethyl-[4-[[1-[(4-methoxy-2,6-dimethyl-phenyl)sulfonyl]-piperidin-2-yl]-methoxy-pyrimidin-2-yl]-methyl-amine H_CC-045 2-(4-butyl-4-dimethylamino-piperidin-1-yl)-ethyl-[4-[[1-[(4-methoxy-2,6-dimethyl-phenyl)sulfonyl]-piperidin-2-yl]-methoxy-pyrimidin-2-yl]-methyl-amine H_CC-046 3-(4-dimethylamino-4-phenyl-piperidin-1-yl)-propyl-[4-[[(2S)-1-[(4-methoxy-2,6-dimethyl-phenyl)sulfonyl]-pyrrolidin-2-yl]-methoxy]-pyrimidin-2-yl]-methyl-amine H_CC-047 1-[4-[[(2S)-1-[(4-methoxy-2,6-dimethyl-phenyl)sulfonyl]-pyrrolidin-2-yl]-methoxy]-pyrimidin-2-yl]-4-pyridin-4-yl-piperidin-4-ol H_CC-048 5-[1-[4-[[(2S)-1-[(4-methoxy-2,6-dimethyl-phenyl)sulfonyl]-pyrrolidin-2-yl]-methoxy]-pyrimidin-2-yl]-piperidin-4-yl]-3-pyridin-4-yl-]1,2,4]oxadiazole H_CC-049 4-[[1-[(4-methoxy-2,6-dimethyl-phenyl)sulfonyl]-piperidin-2-yl]-methoxy]-pyrimidin-2-yl]-methyl-[2-(4-pyridin-4-yloxy-piperidin-1-yl)-ethyl]amine H_CC-050 (1S,5R)-8-[4-[[1-[(4-methoxy-2,6-dimethyl-phenyl)sulfonyl]-piperidin-2-yl]-methoxy]-pyrimidin-2-yl]-3-pyridin-4-yloxy-8-azabicyclo[3.2.1]octane H_CC-051 [4-[[(2S)-1-[(4-methoxy-2,6-dimethyl-phenyl)sulfonyl]-pyrrolidin-2-yl]-methoxy]-pyrimidin-2-yl]-methyl-[2-(4-pyridin-4-yloxy-piperidin-1-yl)-ethyl]amine H_CC-052 (1S,5R)-8-[4-[[(2S)-1-[(4-methoxy-2,6-dimethyl-phenyl)sulfonyl]-pyrrolidin-2-yl]-methoxy]-pyrimidin-2-yl]-3-pyridin-4-yloxy-8-azabicyclo[3.2.1]octane H_CC-053 2-(4-butyl-4-dimethylamino-piperidin-1-yl)-ethyl-[4-1-[(4-methoxy-2,6-dimethyl-phenyl)sulfonyl]-piperidin-3-yl]oxy-pyrimidin-2-yl]-methyl-amine H_CC-054 2-(4-dimethylamino-4-phenyl-piperidin-1-yl)-ethyl-[4-[[(2S)-1-[(4-methoxy-2,6-dimethyl-phenyl)sulfonyl]-pyrrolidin-2-yl]-methoxy]-pyrimidin-2-yl]-methyl-amine H_CC-055 [4-[[(2S)-1-[(4-methoxy-2,6-dimethyl-phenyl)sulfonyl]-pyrrolidin-2-yl]-methoxy]-pyrimidin-2-yl]-methyl-[2-(4-phenyl-4-pyrrolidin-1-yl-piperidin-1-yl)-ethyl]-amine H_CC-056 2-(4-butyl-4-dimethylamino-piperidin-1-yl)-ethyl-[4-[[(2S)-1-[(4-methoxy-2,6-dimethyl-phenyl)sulfonyl]-pyrrolidin-2-yl]-methoxy]-pyrimidin-2-yl]-methyl-amine H_CC-057 2-(4-dimethylamino-4-phenyl-piperidin-1-yl)-ethyl-[4-[[(2S)-1-[(4-methoxy-2,6-dimethyl-phenyl)sulfonyl]-2,3-dihydro-1H-indol-2-yl]-methoxy]-pyrimidin-2-yl]-methyl-amine H_CC-058 2-(4-butyl-4-dimethylamino-piperidin-1-yl)-ethyl-[4-[[(2S)-1-[(4-methoxy-2,6-dimethyl-phenyl)sulfonyl]-2,3-dihydro-1H-indol-2-yl]-methoxy]-pyrimidin-2-yl]-methyl-amine H_CC-059 4-methoxy-N,2,6-trimethyl-N-[2-[2-[methyl-[2-(4-phenyl-4-pyrrolidin-1-yl-piperidin-1-yl)-ethyl]-amino]-pyrimidin-4-yl]oxy-ethyl]-benzenesulfonic acid amide H_CC-060 N-[2-[2-[2-(4-butyl-4-dimethylamino-piperidin-1-yl)-ethyl-methyl-amino]pyrimidin-4-yl]oxy-ethyl]-4-methoxy-N,2,6-trimethyl-benzenesulfonic acid amide H_CC-061 3-(4-dimethylamino-4-phenyl-piperidin-1-yl)-propyl-[4-[[1-[(4-methoxy-2,6-dimethyl-phenyl)sulfonyl]-piperidin-2-yl]-methoxy]-pyrimidin-2-yl]-methyl-amine H_CC-062 [4-butyl-1-[4-[[1-[(4-methoxy-2,6-dimethyl-phenyl)sulfonyl]-piperidin-2-yl]-methoxy]-pyrimidin-2-yl]-piperidin-4-yl]-dimethyl-amine H_CC-063 [4-[[1-[(4-methoxy-2,6-dimethyl-phenyl)sulfonyl]-piperidin-2-yl]-methoxy]-pyrimidin-2-yl]-methyl-[2-(4-phenyl-4-pyrrolidin-1-yl-piperidin-1-yl)-ethyl]-amine H_CC-064 [1-[4-[1-[(4-methoxy-2,6-dimethyl-phenyl)sulfonyl]-piperidin-3-yl]oxy-pyrimidin-2-yl]-4-phenyl-piperidin-4-yl]-dimethyl-amine H_CC-065 2-(4-dimethylamino-4-phenyl-piperidin-1-yl)-ethyl-[4-[1-[(4-methoxy-2,6-dimethyl-phenyl)sulfonyl]-piperidin-3-yl]oxy-pyrimidin-2-yl]-methyl-amine H_CC-066 [4-1-[(4-methoxy-2,6-dimethyl-phenyl)sulfonyl]-piperidin-3-yl]oxy-pyrimidin-2-yl]-methyl-[2-(4-phenyl-4-pyrrolidin-1-yl-piperidin-1-yl)-ethyl]amine H_CC-067 N-[2-[2-[2-(4-dimethylamino-4-phenyl-piperidin-1-yl)-ethyl-methyl-amino]-pyrimidin-4-yl]oxy-ethyl]-4-methoxy-N,2,6-trimethyl-benzenesulfonic acid amide H_CC-068 [4-butyl-1-[4-[[(2S)-1-[(4-methoxy-2,6-dimethyl-phenyl)sulfonyl]-pyrrolidin-2-yl]-methoxy]-pyrimidin-2-yl]-piperidin-4-yl]-dimethyl-amine H_CC-069 2-(4-dimethylamino-4-phenyl-piperidin-1-yl)-ethyl-[4-[1-[(4-methoxy-2,6-dimethyl-phenyl)sulfonyl]-azetidin-3-yl]oxy-pyrimidin-2-yl]-methyl-amine H_CC-070 [4-[1-[(4-methoxy-2,6-dimethyl-phenyl)sulfonyl-[azetidin-3-yl]oxy-pyrimidin-2-yl]-methyl-[2-(4-phenyl-4-pyrrolidin-1-yl-piperidin-1-yl)-ethyl]amine H_CC-071 2-(4-butyl-4-dimethylamino-piperidin-1-yl)-ethyl-[4-[1-[(4-methoxy-2,6-dimethyl-phenyl)sulfonyl]-azetidin-3-yl]oxy-pyrimidin-2-yl]-methyl-amine H_CC-072 [4-[[(2S)-1-[(4-methoxy-2,6-dimethyl-phenyl)sulfonyl]-2,3-dihydro-1H-indol-2-yl]-methoxy]-pyrimidin-2-yl]-methyl-[2-(4-phenyl-4-pyrrolidin-1-yl-piperidin-1-yl)-ethyl]-amine H_CC-073 3-(4-dimethylamino-4-phenyl-piperidin-1-yl)-propyl-[4-[1-[(4-methoxy-2,6-dimethyl-phenyl)sulfonyl]-piperidin-3-yl]oxy-pyrimidin-2-yl]-methyl-amine H_CC-074 3-(4-dimethylamino-4-phenyl-piperidin-1-yl)-propyl-[4-[1-[(4-methoxy-2,6-dimethyl-phenyl)sulfonyl]-azetidin-3-yl]oxy-pyrimidin-2-yl]-methyl-amine H_CC-075 3-(4-dimethylamino-4-phenyl-piperidin-1-yl)-propyl-[4-[[(2S)-1-[(4-methoxy-2,6-dimethyl-phenyl)sulfonyl]-2,3-dihydro-1H-indol-2-yl]-methoxy]-pyrimidin-2-yl]-methyl-amine H_CC-076 1-[4-[1-[(4-methoxy-2,6-dimethyl-phenyl)sulfonyl]-azetidin-3-yl]oxy-pyrimidin-2-yl]-4-pyridin-3-yl-piperidin-4-ol H_CC-077 1-[4-[1-[(4-methoxy-2,6-dimethyl-phenyl)sulfonyl]-azetidin-3-yl]oxy-pyrimidin-2-yl]-4-(pyridin-2-yl-methyl)-[1,4]diazepan H_CC-078 4-[[1-[(4-methoxy-2,6-dimethyl-phenyl)sulfonyl]-piperidin-2-yl]-methoxy]-2-[2-(pyridin-2-yl-methyl)-pyrrolidin-1-yl]-pyrimidine H_CC-079 4-[[1-[(4-methoxy-2,6-dimethyl-phenyl)sulfonyl]-piperidin-2-yl]-methoxy]-2-(4-pyridin-2-yloxy-piperidin-1-yl)-pyrimidine H_CC-080 4-[[1-[(4-methoxy-2,6-dimethyl-phenyl)sulfonyl]-piperidin-2-yl]-methoxy]-2-(4-pyrazin-2-yloxy-piperidin-1-yl)-pyrimidine H_CC-081 4-[1-[4-[[1-[(4-methoxy-2,6-dimethyl-phenyl)sulfonyl]-piperidin-2-yl]-methoxy]-pyrimidin-2-yl]-4-methyl-piperidin-4-yl]-morpholine H_CC-082 4-[[1-[(4-methoxy-2,6-dimethyl-phenyl)sulfonyl]-piperidin-2-yl]-methoxy]-2-[4-pyridin-3-yl-4-(3-pyrrolidin-1-yl-propyl)piperidin-1-yl]-pyrimidine H_CC-083 1-[4-[[1-[(4-methoxy-2,6-dimethyl-phenyl)sulfonyl]-piperidin-2-yl]-methoxy]-pyrimidin-2-yl]-4-pyridin-2-yl-piperidin-4-ol H_CC-084 4-[[(2R)-1-[(4-methoxy-2,6-dimethyl-phenyl)sulfonyl]-pyrrolidin-2-yl]-methoxy]-2-[2-(pyridin-2-yl-methyl)-pyrrolidin-1-yl]-pyrimidine H_CC-085 [1-[4-[[(2S)-1-[(4-methoxy-2,6-dimethyl-phenyl)sulfonyl]-pyrrolidin-2-yl]-methoxy]-pyrimidin-2-yl]-4-phenyl-piperidin-4-yl]-dimethyl-amine H_CC-086 [1-[4-[[(2S)-1-[(4-methoxy-2,6-dimethyl-phenyl)sulfonyl]-pyrrolidin-2-yl]-methoxy]-pyrimidin-2-yl]-4-thiophen-2-yl-piperidin-4-yl]-dimethyl-amine H_CC-087 4-methoxy-N,2,6-trimethyl-N-[2-[2-[2-(pyridin-2-yl-methyl)-pyrrolidin-1-yl]-pyrimidin-4-yl]oxy-ethyl]-benzenesulfonic acid amide H_CC-088 4-[[(2S)-1-[(4-methoxy-2,6-dimethyl-phenyl)sulfonyl]-pyrrolidin-2-yl]-methoxy]-2-[2-(pyridin-2-yl-methyl)-pyrrolidin-1-yl]-pyrimidine H_CC-089 4-methoxy-N,2,6-trimethyl-N-[2-[2-[methyl-[2-(4-pyridin-4-yloxy-piperidin-1-yl)-ethyl]-amino]-pyrimidin-4-yl]oxy-ethyl]benzenesulfonic acid amide H_CC-090 N-[2-[2-[4-(3-fluorophenyl)-4-(2-pyrrolidin-1-yl-ethoxy)-piperidin-1-yl]-pyrimidin-4-yl]oxy-ethyl]-4-methoxy-N,2,6-trimethyl-benzenesulfonic acid amide H_CC-091 2-[4-(3-fluorophenyl)-4-(4-methyl-piperazin-1-yl)-piperidin-1-yl]-4-[[1-[(4-methoxy-2,6-dimethyl-phenyl)sulfonyl]-piperidin-2-yl]-methoxy]-pyrimidine H_CC-092 2-[4-(3-fluorophenyl)-4-(2-pyrrolidin-1-yl-ethoxy)-piperidin-1-yl]-4-[[(2S)-1-[(4-methoxy-2,6-dimethyl-phenyl)sulfonyl]-pyrrolidin-2-yl]-methoxy]-pyrimidine H_CC-093 4-methoxy-N,2,6-trimethyl-N-[1-phenyl-2-[2-[(1S,5R)-3-pyridin-4-yloxy-8-azabicyclo[3.2.1]octan-8-yl]-pyrimidin-4-yl]oxy-ethyl]-benzenesulfonic acid amide The numbering of the individual embodiments of the compounds according to the invention that has been used above is retained in the explanations of the present invention given hereinbelow, in particular in the description of the examples.

According to one aspect of the present invention, the compounds according to the invention preferably exhibit an antagonistic activity on the human B1R receptor or the B1R receptor of the rat. In a preferred embodiment of the invention, the compounds according to the invention exhibit an antagonistic activity both on the human B1R receptor (hB1R) and on the B1R receptor of the rat (rB1R).

In a preferred embodiment of the present invention, the compounds according to the invention exhibit an inhibition of at least 15%, 25%, 50%, 70%, 80% or 90% on the human B1R receptor and/or on the B1R receptor of the rat in the FLIPR assay at a concentration of 10 µM. Most particular preference is given to compounds that exhibit an inhibition of at least 70%, in particular of at least 80% and particularly preferably of at least 90%, on the human B1R receptor and on the B1R receptor of the rat at a concentration of 10 µM.

The agonistic or antagonistic activity of substances can be quantified on the bradykinin receptor 1 (B1R) of the species human and rat using ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-Arg$^9$-bradykinin (0.5 nM) or Des-Arg$^9$-bradykinin (100 nM). Antagonists lead to suppression of the $Ca^{2+}$ influx after the addition of the agonist. % Inhibition compared with the maximum achievable inhibition is indicated.

The substances according to the invention act especially, for example, on B1R, which is relevant in connection with various diseases, so that they are suitable as a pharmaceutical active ingredient in medicaments. The invention accordingly further provides medicaments comprising at least one substituted pyrimidine and/or triazine derivative according to the invention as well as, optionally, suitable additives and/or auxiliary substances and/or optionally further active ingredients.

The pharmaceutical compositions according to the invention optionally comprise, in addition to at least one substituted pyrimidine and/or triazine compound according to the invention, suitable additives and/or auxiliary substances, that is to say also carriers, fillers, solvents, diluents, colourings and/or binders, and can be administered as liquid medicament forms in the form of injection solutions, drops or juices, or as semi-solid medicament forms in the form of granules, tablets, pellets, patches, capsules, plasters/spray-on plasters or aerosols. The choice of the auxiliary substances etc. and the amounts thereof to be employed depend on whether the medicament is to be administered orally, perorally, parenterally, intravenously, intraperitoneally, intradermally, intramuscularly, nasally, buccally, rectally or topically, for example to the skin, the mucous membranes or into the eyes. Preparations in the form of tablets, dragées, capsules, granules, drops, juices and syrups are suitable for oral administration, and solutions, suspensions, readily reconstitutable dry formulations and sprays are suitable for parenteral, topical and inhalatory administration. Substituted pyrimidine and/or triazine derivatives according to the invention in a depot, in dissolved form or in a plaster, optionally with the addition of agents which promote penetration through the skin, are suitable formulations for percutaneous administration. Forms of preparation which can be used orally or percutaneously can release the substituted pyrimidine and/or triazine derivatives according to the invention in a delayed manner. The substituted pyrimidine and/or triazine derivatives according to the invention can also be used in parenteral long-term depot forms, such as, for example, implants or implanted pumps. In principle, other further active ingredients known to the person skilled in the art can be added to the medicaments according to the invention.

The amount of active ingredient to be administered to the patient varies according to the weight of the patient, the manner of administration, the indication and the severity of the disease. From 0.00005 to 50 mg/kg, preferably from 0.01 to 5 mg/kg, of at least one substituted pyrimidine and/or triazine derivative according to the invention are conventionally administered. In a preferred form of the pharmaceutical composition, a substituted pyrimidine and/or triazine derivative according to the invention that is present is in the form of a pure diastereoisomer and/or enantiomer, in the form of the racemate or in the form of a non-equimolar or equimolar mixture of the diastereoisomers and/or enantiomers.

B1R is involved in particular in the occurrence of pain. Accordingly, the substituted pyrimidine and/or triazine derivatives according to the invention can be used in the preparation of a medicament for the treatment of pain, in particular of acute, visceral, neuropathic or chronic pain.

The invention further provides a pharmaceutical composition comprising at least one of the substituted pyrimidine and/or triazine derivatives of the invention.

The invention also relates to the use of the substituted pyrimidine and/or triazine compounds according to the invention as a medicament.

Accordingly, the invention further relates to the use of a substituted pyrimidine and/or triazine compound according to the invention in the preparation of a medicament for the treatment of pain, in particular of acute, visceral, neuropathic or chronic pain. A specific embodiment of the present invention is the use of at least one of the substituted pyrimidine and/or triazine compounds according to the invention in the preparation of a medicament for the treatment of inflammatory pain.

The invention further relates to the use of a substituted pyrimidine and/or triazine compound according to the invention in the preparation of a medicament for the treatment of diabetes, respiratory diseases, for example Asthma bronchiale, allergies, COPD/chronic-obstructive pulmonary disease or cystic fibrosis; inflammatory intestinal diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; spetic shock; reperfusion syndrome, for example following heart attack or stroke, obesity; and as an angiogenesis inhibitor.

It can be preferred in one of the above uses for a substituted pyrimidine and/or triazine derivative that is used to be in the form of a pure diastereoisomer and/or enantiomer, in the form of the racemate or in the form of a non-equimolar or equimolar mixture of the diastereoisomers and/or enantiomers.

The invention further relates to a method of treating, in particular in one of the above-mentioned indications, a non-human mammal or a human being requiring treatment of pain, in particular chronic pain, by administration of a therapeutically effective dose of a substituted pyrimidine and/or triazine derivative according to the invention, or of a medicament according to the invention.

The invention further provides a process for the preparation of the substituted pyrimidine and/or triazine derivatives according to the invention, in particular as specified in the following description, examples and claims.

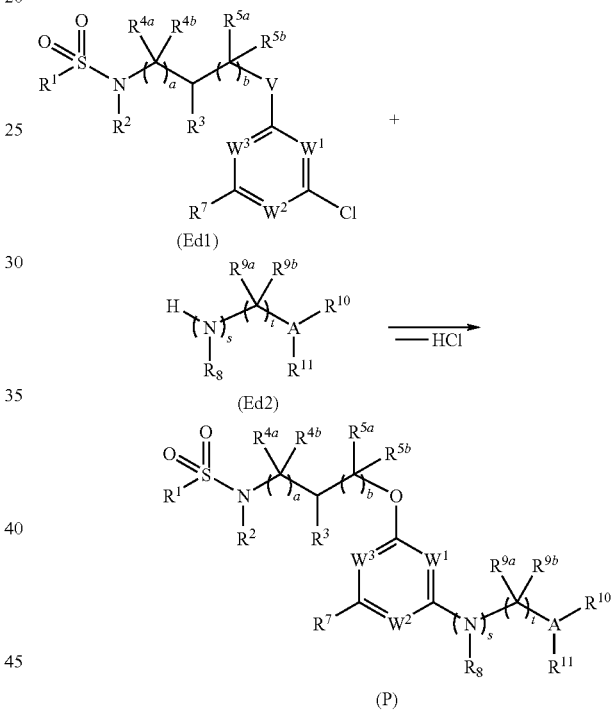

Scheme 1

The process according to the invention is shown in Scheme 1. In the process, at least one compound of the general structure Ed1 is reacted in the presence of a solvent and of a base with a compound of the general structure Ed2 to give the products P according to the invention. Particularly suitable solvents, bases and other reaction conditions are described hereinbelow in connection with step 3 of the particular embodiment of the process according to the invention shown in Scheme 2.

The invention is explained in further detail hereinafter with reference to examples, which are merely illustrative and do not limit the overall scope of the invention.

General Synthesis Processes

The following abbreviations are used in the examples below:
GWP=general working procedure
equiv.=equivalent
Boc=tert-butyloxycarbonyl
Bu=butyl Cbz=benzyloxycarbonyl
TLC=thin-layer chromatography
DCM=dichloromethane
Et=ethyl
EtOAc=ethyl acetate
IPA=isopropylamine
LAH=lithium aluminium hydride
LC=liquid chromatography
LC-Ms=liquid chromatograhy-mass spectrometry
Me=methyl
THF=tetrahydrofuran It will be apparent to persons skilled in the art that the sequence of the reaction steps can optionally be changed in some cases.

The separation of diastereoisomers and/or enantiomers is carried out by conventional methods known to the person skilled in the art, for example by recrystallization, chromatography or, in particular, HPLC chromatography or crystallization with an optionally chiral acid or base and separation of the salts or chiral HPLC chromatography (Fogassy et al., Optical Resolution Methods, Org. Biol. Chem 2006, 4, 3011-3030).

The chemicals and solvents used were obtained commercially from the usual suppliers (e.g. Acros, Avocado, Aldrich, Bachem, Fluke, Lancaster, Maybridge, Merck, Sigma, TCI, etc.) or were synthesized by the methods known to the person skilled in the art or the processes described hereinbelow. Commercially available materials, for example $Al_2O_3$ or silica gel [for example from E. Merck, Darmstadt, Germany], were used as the stationary phase for column chromatography. Thin-layer chromatography investigations were carried out with commercially available HPTLC pre-coated plates (for example silica gel 60 F 254 from E. Merck, Darmstadt). The mixing ratios of solvents, eluants or for chromatographic investigations are always given in volume/volume, unless indicated otherwise. Unless indicated otherwise, analysis was carried out by mass spectroscopy (ESI-MS).

General Process for the Preparation of Target Structures G, H, I and J

A preferred process for the preparation of the compounds according to the invention is shown in the following Scheme 2:

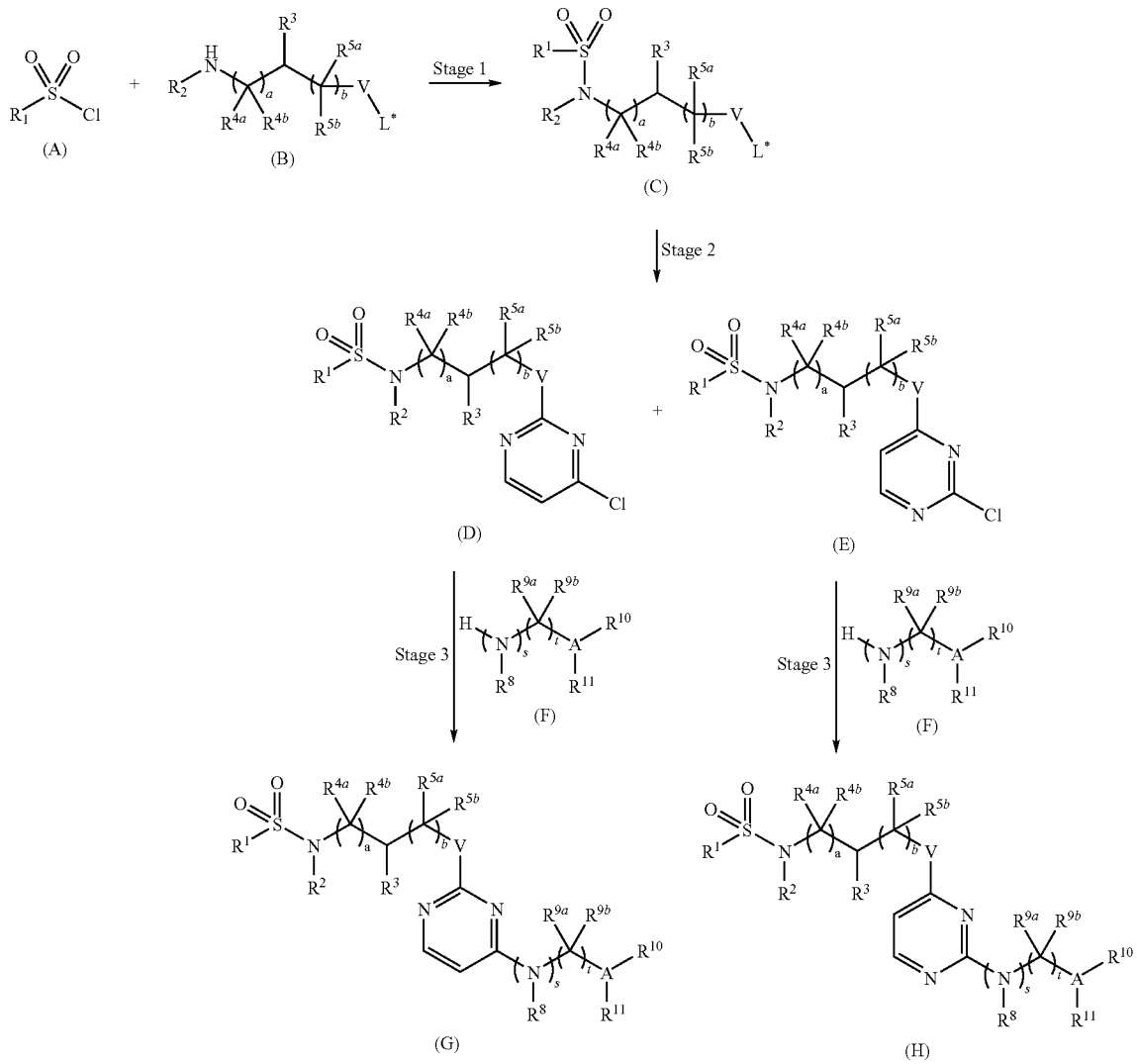

From compounds of the general formulas (A) and (B) it is possible, as shown in Scheme 2, to prepare compounds of formulas (G) and (H). The radicals, variables and indices used in Scheme 2 to describe the respective chemical compounds have the same meaning as described hereinbefore in connection with the compounds according to the invention. The group L* represents a reactive group which is cleaved in the course of the bond linkage at the heteroaromatic nucleus. In the case where V represents O or $NR^{6c}$, L* can represent H or a metal ion, in particular H.

In stage 1, sulfonyl chloride of the general formula (A) is reacted in at least one solvent, preferably selected from the group consisting of dichloromethane, acetonitrile, dimethylformamide, diethyl ether, dioxane, tetrahydrofuran, methanol, ethanol and isopropanol, with compound (B), for example an amino alcohol, in the presence of at least one inorganic base, preferably selected from the group consisting of potassium carbonate and caesium carbonate, or of an organic base, preferably selected from the group consisting of triethylamine, diisopropylethylamine and pyridine, and optionally with the addition of 4-(dimethylamino)pyridine or 1-hydroxybenzotriazole, at temperatures of preferably from −15° C. to 50° C., to give compounds of the general formula (C).

In stage 2, the compounds of the general formula (C), for example sulfonylated amino alcohols, are reacted in at least one solvent, preferably selected from the group consisting of dichloromethane, acetonitrile, dimethylformamide, diethyl ether, dioxane and tetrahydrofuran, with 2,4-dichloropyrimidine, in the presence of at least one inorganic base, preferably selected from the group consisting of potassium hydride, sodium hydride, potassium carbonate and caesium carbonate, or of an organic base, preferably selected from the group consisting of 2,3,4,6,7,8,9,10-octahydropyrimido[1,2-a]azepine, 1,8-bis(dimethylamino)naphthalene, triethylamine, diisopropylethyl-amine, pyridine and dimethylaminopyridine, at temperatures of preferably from −25° C. to 100° C., to give compounds of the general formulas (D) and (E). The compounds of the general formulas (D) and (E) can be used in the further synthesis in the form of a mixture or, for example after separation by column chromatography, individually.

In stage 3, pyrimidine structural units of the general formulas (D) and (E) are reacted in at least one solvent, preferably selected from the group consisting of dichloromethane, acetonitrile, dimethylformamide, diethyl ether, dioxane, tetrahydrofuran, methanol, ethanol and isopropanol, with amine (F), in the presence of at least one inorganic base, preferably selected from the group consisting of potassium carbonate and caesium carbonate, or of an organic base, preferably selected from the group consisting of 2,3,4,6,7,8,9,10-octahydro-pyrimido[1,2-a]azepine, 1,8-bis(dimethylamino)naphthalene, triethylamine, diisopropylethylamine and pyridine, and optionally with the addition of 4-(dimethylamino)pyridine or 1-hydroxybenzotriazole, at temperatures of preferably from 0° C. to 100° C., to give compounds of the general formulas (G) and (H).

In order to obtain 4-,6-substituted pyrimidine derivatives of type (I) shown below, 4-,6-dichloropyrimidine can be used in stage 2 instead of 2-,4-dichloropyrimidine. In an analogous manner, the triazine derivatives (J) can be obtained if 2-,4-dichloro-1,3,5-triazine is used in stage 2 instead of 2-,4-dichloropyrimidine.

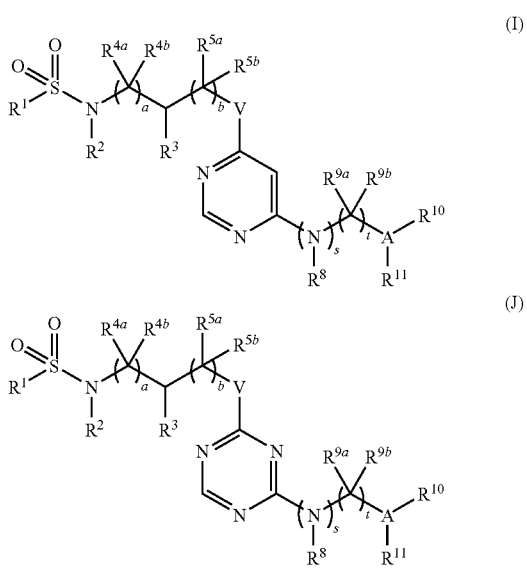

In order to obtain compounds of type (G), (H), (I) or (J) in which V represents a $CR^{6a}R^{6b}$ group, bonding at the heteroaromatic nucleus can be effected by means of a Grignard reaction, analogous to the processes described by B. Scheiper et al. in J. Org. Chem. 2004, 69, 3943-3949. L* in this case represents a halogen atom that is cleaved from compound (C) in the course of the Grignard reaction.

SYNTHESIS OF STRUCTURAL UNITS

1) Synthesis of the Sulfonyl Chlorides A

Sulfonyl chloride A-01: 4-Methoxy-2,6-dimethylphenyl-1-sulfonyl chloride Chlorosulfonic acid (1.83 ml, 2.3 equiv.) in dichloromethane (10 ml) was added dropwise at 0° C., in the course of 20 minutes, to a solution of 3,5-dimethylanisole (1.632 g, 11.982 mmol) in dichloromethane (15 ml). The reaction mixture was then stirred for 10 minutes at room temperature. The reaction mixture was added to ice-water (3 ml, 5 equiv. based on chlorosulfonic acid) and the aqueous phase was extracted with dichloromethane (3×100 ml). The organic phase was dried ($Na_2SO_4$) and concentrated in vacuo. Yield: 2.6 g (92%)

Sulfonyl chloride A-03: Naphthalene-2-sulfonyl chloride [93-11-8] available commercially from, for example, Aldrich.

Sulfonyl chloride A-04: 2-(Trifluoromethyl)phenyl-1-sulfonyl chloride [776-04-5] available commercially from, for example, Aldrich.

Sulfonyl chloride A-05: 2-Chloro-6-methylphenyl-1-sulfonyl chloride [25300-37-2] available commercially from, for example, Fluorochem.

Sulfonyl chloride A-06: 2,6-Dichloro-3-methylbenzene-1-sulfonyl chloride 2,6-Dichloro-3-methylaniline (10.56 mmol, 1 equiv.) was added to a solution of hydrochloric acid (240 mmol, 4 equiv.) and glacial acetic acid (10.8 mmol, 1.8 equiv.). The suspension was cooled to −10° C., and aqueous sodium nitrite solution (65 mmol, 1.08 equiv., water 360 mmol, 6 equiv.) was added dropwise over a period of 30 minutes. Stirring was carried out for a further 45 minutes at a constant temperature. The reaction mixture was added in portions to acetic acid saturated with sulfur dioxide (1080 mmol, 18 equiv.), and the mixture was stirred for 30 minutes at 0° C. The reaction mixture was poured onto ice/distilled water (200 ml) and the resulting oil was separated off. The aqueous phase was washed with ether (3×20 ml). The combined organic phases were washed with distilled water (1×50 ml), with saturated sodium hydrogen carbonate solution (1×50 ml) and again with distilled water (1×50 ml), dried over magnesium sulfate and concentrated. The crude substance was purified by column chromatography (hexane/ethyl acetate 10:1). Yield: 9.1 g (58%)

2) Synthesis of the Amino Alcohols B

Amino alcohol B-01: 2-(Methylamino)ethanol [109-83-1] available commercially from, for example, Aldrich.

Amino alcohol B-02: Piperidin-2-ylmethanol [3433-37-2] available commercially from, for example, ABCR.

Amino alcohol B-03: Piperidin-3-ol [6859-99-0] available commercially from, for example, Acros.

Amino alcohol B-04: (S)-Pyrrolidin-2-ylmethanol [23356-96-9] available commercially from, for example, ACROS.

Amino alcohol B-05: Azetidin-3-ol [18621-18-6] available commercially from, for example, Aldrich.

Amino alcohol B-06: (S)-Indolin-2-ylmethanol [27640-33-1] available commercially from, for example, Aldrich.

Amino alcohol B-07: 2-(Methylamino)-2-phenylethanol (i) Sodium carbonate (66 mmol, 0.5 equiv.) was added to a solution, at 0° C., of phenylglycine (132 mmol, 1 equiv.) in 1N sodium hydroxide solution, and stirring was carried out for 30 minutes. Ethyl chloroformate (132 mmol, 1 equiv.) was added, the reaction mixture was stirred for 1 hour at room temperature, dichloromethane was added and stirring was continued for a further hour at room temperature. Phases were separated, and the aqueous phase was neutralized with dilute hydrochloric acid and extracted with dichloromethane. The combined organic phases were washed with saturated sodium hydrogen carbonate solution and with water, dried over sodium sulfate and concentrated under reduced pressure. The desired product was obtained in a yield of 71%.

(ii) The product so obtained (89.6 mmol), dissolved in THF, was added dropwise to a solution, at 0° C., of lithium aluminium hydride (358 mmol, 4 equiv.) in THF and a reaction temperature of 0-5° C. was thereby maintained. The reaction mixture was stirred for 15 minutes at room temperature and then for 12 hours under reflux. For working up, the mixture was cooled to 0° C., and 15% NaOH solution (~40 ml) was added. After addition of about 20 ml of the sodium hydroxide solution, the mixture was diluted with 250 ml of THF, and the remaining 20 ml of sodium hydroxide solution was added, with gentle agitation. After stirring for one hour at room temperature, the precipitate was filtered off and then washed with ethyl acetate. The solvent was concentrated under reduced pressure and the desired product was obtained in the form of a yellow oil in a yield of 88%.

Amino alcohol B-08: 2-(Cyclopropylamino)ethanol hydrobromide

Cyclopropylamine (7 ml, 100.8 mmol) and 2-bromoethanol (5 g, 40.32 mmol) were stirred for 16 hours at 50° C. in ethanol (47 ml). The solvent was removed in vacuo and the residue was taken up in toluene (3×40 ml) and dried in vacuo. Yield: 6.99 g (95%).

Amino alcohol B-09: ((2S,4R)-4-Fluoropyrrolidin-2-yl) methanol hydrochloride (i) (2S,4R)—N-Boc-4-fluoropyrrolidine-2-carboxylic acid (2 g, 8.58 mmol) was dissolved in tetrahydrofuran (31 ml) and cooled, and boron hydride-tetrahydrofuran complex (1 mol/l, 12.87 ml) was added slowly at 0° C. The reaction mixture slowly warmed to room temperature, and after 30 minutes' stirring it was cooled to 0° C. again. Water (3.9 ml) was slowly added dropwise; potassium carbonate (2 g, 14.59 mmol) was then added slowly and stirring was carried out for 30 minutes at RT. The mixture was diluted with water (10 ml) and the phases were separated. The aqueous phase was extracted with ethyl acetate (3×20 ml), and the combined organic phases were dried over sodium sulfate and concentrated in vacuo. The crude product was purified by column chromatography (silica gel, diethyl ether/dichloromethane/hexane, 2:1:1). Yield: 1.5 g (80%).

(ii) Hydrogen chloride in methanol (27 ml, 1.25 mol/l) was added to the (2S,4R)—N-Boc-4-fluoropyrrolidin-2-ylmethanol (1.5 g, 6.845 mmol) so obtained, and refluxing was carried out. After 30 minutes, the mixture was cooled to RT and concentrated in vacuo. The residue was taken up in ethanol (10 ml); acetone (20 ml) was added and stirring was carried out for 30 minutes in an ice bath. The precipitate was filtered off with suction, washed with diethyl ether and dried in vacuo to give the desired target compound. Yield: 0.93 g (87%).

Amino alcohol B-10: 2-Amino-2-methyl-propan-1-ol [124-68-5] available commercially, for example, from Aldrich.

Amino alcohol B-11: 3-(Cyclopropylamino)propan-1-ol

3-Bromopropanol (26.26 mmol, 1.0 equiv.) was added to a solution of cyclopropyl-amine (52.53 mmol, 2.0 equiv.) in ethanol (150 ml), and the mixture was refluxed for 14 hours. The solvent was concentrated under reduced pressure, and the crude product so obtained was used in the next step without further purification.

Amino alcohol B-12: (S)-Piperidin-2-ylmethanol $BH_3$-DMS (62.0 mmol, 4.0 equiv.) and $BF_3$-$Et_2O$ (15.5 mmol, 1.0 equiv.) were added at 0° C. to a solution of (2S)-piperidine-2-carboxylic acid (15.5 mmol, 1.0 equiv.) in THF (50 ml), and the mixture was refluxed for 14 hours. The solvent was concentrated under reduced pressure, and then MeOH (40 ml) was added dropwise at 0° C. Concentrated HCl (5 ml) was added to the reaction mixture, and refluxing was carried out for a further 2 hours. The solvent was concentrated, and the residue was stirred for 15 minutes in 10% isopropanol in DCM and filtered. The filtrate was concentrated to dryness, and a white solid was obtained. Yield: 80%.

3) Synthesis of the Sulfonylated Amino Alcohols C

General Method for the Synthesis of the Sulfonylated Amino Alcohols C

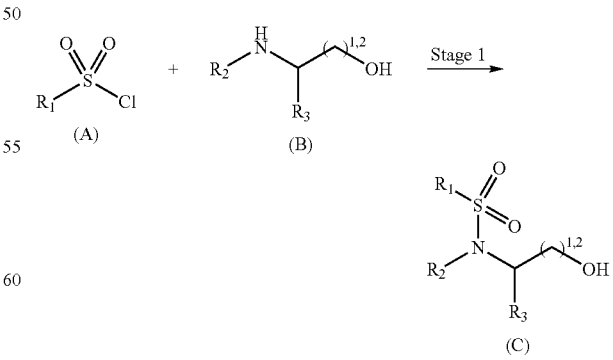

FIG. 1: Synthesis of the Sulfonylated Amino Alcohols C

General working procedure GWP I: A solution of sulfonyl chloride (A) (1 equiv.) in dichloromethane was added at room temperature to a solution of amino alcohol (B) (5 equiv.) in dichloromethane. The resulting reaction mixture was stirred for 12 hours at room temperature and then washed 3× with a 5% HCl solution. The organic phase was dried over magnesium sulfate and concentrated under reduced pressure. The sulfonylated amino alcohol (C) so obtained was used in the next stage without further purification.

General working procedure GWP II: A solution of sulfonyl chloride (A) (1 equiv.) in dichloromethane was added after 30 minutes to a solution, at 0° C., of amino alcohol (B) (1 equiv.) and triethylamine (2.5 equiv.) in dichloromethane. The resulting reaction mixture was stirred for 1-6 hours at room temperature, diluted with dichloromethane and then washed with 1N HCl solution and water. The organic phase was dried over sodium sulfate and concentrated under reduced pressure. The resulting sulfonylated amino alcohol (C) was purified by column chromatography.

General working procedure GWP V: The hydrochloride or hydrobromide of amino alcohol (B) (1 equiv.) was dissolved in dichloromethane and triethylamine (2 equiv.) and stirred for 15 minutes, during which cooling with an ice bath was carried out. Sulfonyl chloride (A) (1.5 equiv.), dissolved in dichloromethane, was then added slowly at 0° C. The cooling bath was removed and the reaction mixture was stirred for 15 hours. Saturated sodium hydrogen carbonate solution was added to the mixture, and the phases were separated. The aqueous phase was extracted with dichloromethane, and the combined organic phases were washed with saturated sodium chloride solution, dried over sodium sulfate and concentrated in vacuo. The resulting sulfonylated amino alcohol (C) was optionally purified by column chromatography (silica gel). The sulfonated amino alcohols (C) synthesized by these general working procedures are listed in Table 1 below.

Synthesis of amino alcohol C-15: N-(1-(Hydroxymethyl)cyclobutyl)-4-methoxy-2,6-dimethylbenzene-sulfonamide Stage 1: Methyl 1-aminocyclobutanecarboxylate Concentrated $H_2SO_4$ (10 ml) was added at 0° C. to a solution of 1-(tert-butoxy-carbonylamino)-cyclobutane-1-carboxylic acid (9.29 mmol, 1 equiv.) in MeOH (30 ml), and the reaction was refluxed for 2 hours at 0° C. The solvent was removed under reduced pressure. The residue was taken up in distilled water, adjusted to pH 8-9 with saturated sodium hydrogen carbonate solution and extracted with ethyl acetate (2×200 ml). The combined organic phases were washed with distilled water (2×150 ml) and saturated NaCl solution (2×50 ml) and dried over sodium sulfate. The solvent was concentrated under reduced pressure to yield the desired product in the form of a white solid. Yield: 75%

Stage 2: Methyl 1-(4-methoxy-2,6-dimethylphenyl-sulfonamido)cyclobutane-carboxylate Triethylamine (13.9 mmol, 2.0 equiv.) was added at 0° C. to a solution of methyl 1-aminocyclobutanecarboxylate (6.97 mmol, 1 equiv.) in dichloromethane p.a. (20 ml), and the mixture was stirred for 10 minutes. 4-Methoxy-2,6-dimethylphenylsulfonyl chloride (8.36 mmol, 1.2 equiv.), dissolved in DCM (5 ml), was slowly added dropwise at the same temperature, and the mixture was stirred for 4 hours at 25° C. The reaction mixture was diluted with dichloromethane (100 ml), washed with distilled water (2×50 ml) and saturated sodium chloride solution (2×50 ml) and dried over sodium sulfate. The solvent was concentrated and the crude product was purified by column chromatography (15% ethyl acetate in hexane) to yield the desired product in the form of a white solid. Yield: 66%

Stage 3: N-(1-(Hydroxymethyl)cyclobutyl)-4-methoxy-2,6-dimethylbenzene-sulfonamide (C-15)

Methyl 1-(4-methoxy-2,6-dimethylphenylsulfonamido) cyclobutanecarboxylate (4.58 mmol, 1.0 equiv.) was dissolved in THF p.a. (40 ml) and slowly added dropwise, under nitrogen, at 0° C., to a suspension of $LiAlH_4$ (11.4 mmol, 2.5 equiv.) in THF p.a. (20 ml). The reaction mixture was stirred for 1 hour at 25° C., then saturated $Na_2SO_4$ solution was added and the mixture was filtered off over Celite. The filtrate was concentrated and the desired product was precipitated in the form of a white solid from hexane. Yield: 92%

TABLE 1

Synthesis of the sulfonylated amino alcohols C

| Alcohol No. | Structure | Name | Sulfonyl chloride (A) | Alcohol (B) | Synthesis according to | Yield |
|---|---|---|---|---|---|---|
| C-01 | 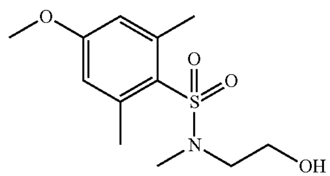 | N-(2-Hydroxyethyl)-4-methoxy-N,2,6-trimethylphenylsulfonamide (C-01) | 4-Methoxy-2,6-dimethylphenyl-1-sulfonyl chloride (A-01) | 2-(Methylamino)ethanol (B-01) | GWP I | 91%, (30.36 mmol) |
| C-02 | 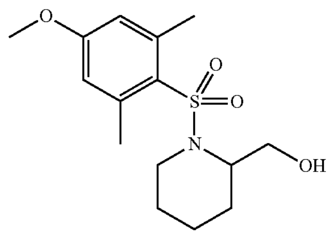 | (1-(4-Methoxy-2,6-dimethylphenylsulfonyl)-piperidin-2-yl)methanol (C-02) | 4-Methoxy-2,6-dimethylphenyl-1-sulfony chloride (A-01) | Piperidin-2-ylmethanol (B-02) | GWP I | 63%, (21.1 mmol) |
| C-03 | 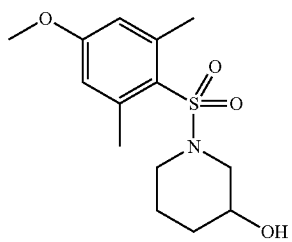 | 1-(4-Methoxy-2,6-dimethylphenylsulfonyl)-piperidin-3-ol (C-03) | 4-Methoxy-2,6-dimethylphenyl-1-sulfonyl chloride (A-01) | Piperidin-3-ol (B-03) | GWP I | 99%, (56.45 mmol) |
| C-04[a] | | (S)-2-(4-Methoxy-2,6-dimethylphenylsulfonyl)-pyrrolidin-2-yl)methanol (C-04) | 4-Methoxy-2,6-dimethylphenyl-1-sulfonyl chloride (A-01) | (S)-Pyrrolidin-2-ylmethanol (B-04) | GWP I | 100%, (35.4 mmol) |

TABLE 1-continued

Synthesis of the sulfonylated amino alcohols C

| Alcohol No. | Structure | Name | Sulfonyl chloride (A) | Alcohol (B) | Synthesis according to | Yield |
|---|---|---|---|---|---|---|
| C-06 | 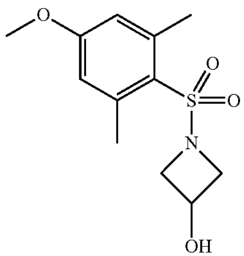 | 1-(4-Methoxy-2,6-dimethylphenylsulfonyl)-azetidin-3-ol (C-06) | 4-Methoxy-2,6-dimethylphenyl-1-sulfonyl chloride (A-01) | Azetidin-3-ol (B-05) | GWP I | 94%, (14.26 mmol) |
| C-07[b] | RAC | (S)-(1-(4-Methoxy-2,6-dimethylphenylsulfonyl)-indolin-2-yl)methanol (C-07) | 4-Methoxy-2,6-dimethylphenyl-1-sulfonyl chloride (A-01) | (S)-Indolin-2-ylmethanol (B-06) | GWP I | 86%, (9.6 mmol) |
| C-08 | 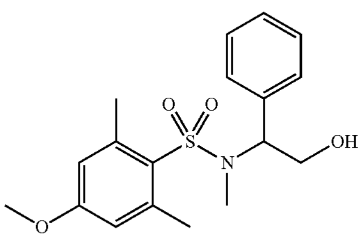 | N-(4-Hydroxy-1-phenylethyl)-4-methoxy-N,2,6-trimethylphenylsulfonamide (C-08) | 4-Methoxy-2,6-dimethylphenyl-1-sulfonyl chloride (A-01) | 2-(Methylamino)-2-phenylethanol (B-07) | GWP II | 71% (93 mmol) |

TABLE 1-continued

Synthesis of the sulfonylated amino alcohols C

| Alcohol No. | Structure | Name | Sulfonyl chloride (A) | Alcohol (B) | Synthesis according to | Yield |
|---|---|---|---|---|---|---|
| C-09 | 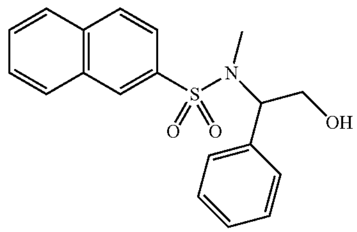 | N-(4-Hydroxy-1-phenylethyl)-N-methylnaphthalene-2-sulfonamide (C-09) | Naphthalene-2-sulfonyl chloride (A-03) | 2-(Methylamino)-2-phenylethanol (B-07) | GWP II | 58% (46 mmol) |
| C-10 | 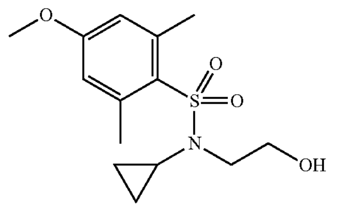 | N-Cyclopropyl-N-(2-hydroxyethyl)-4-methoxy-2,6-dimethylphenyl-sulfonamide (C-10) | 4-Methoxy-2,6-dimethylphenyl-1-sulfonyl chloride (A-01) | 2-(Cyclopropylamino)-ethanol hydrobromide (B-08) | GWP III | 51% (2.53 g) |
| C-11 | 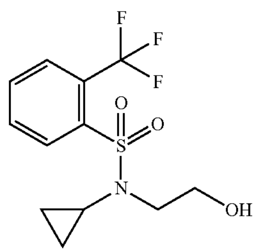 | N-Cyclopropyl-N-(2-hydroxyethyl)-2-(trifluoromethyl)phenyl-sulfonamide (C-11) | 2-(Trifluoromethyl)phenyl-1-sulfonyl chloride (A-04) | 2-(Cyclopropylamino)-ethanol hydrobromide (B-08) | GWP III | 31% (0.91 g) |
| C-12 | 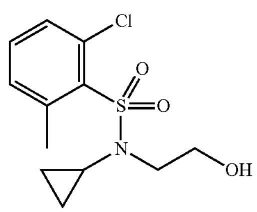 | 2-Chloro-N-cyclopropyl-N-(2-hydroxyethyl)-6-methylphenylsulfonamide (C-12) | 2-Chloro-6-methylphenyl-1-sulfonyl chloride (A-05) | 2-(Cyclopropylamino)-ethanol hydrobromide (B-06) | GWP III | 36% (1.17 g) |

TABLE 1-continued

Synthesis of the sulfonylated amino alcohols C

| Alcohol No. | Structure | Name | Sulfonyl chloride (A) | Alcohol (B) | Synthesis according to | Yield |
|---|---|---|---|---|---|---|
| C-13 ABS | | ((2S,4R)-4-Fluoro-1-(4-methoxy-2,6-dimethyl-phenylsulfonyl)pyrrolidin-2-yl)methanol (C-13) | 4-Methoxy-2,6-dimethylphenyl-1-sulfonyl chloride (A-01) | ((2S,4R)-4-Fluoropyrrolidin-2-yl)methanol hydrochloride (B-09) | GWP III | 91% (1.71 g) |
| C-14 | 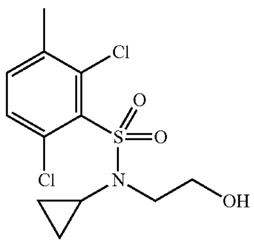 | 2,6-Dichloro-N-cyclopropyl-N-(2-hydroxy-ethyl)-3-methyl-benzene-sulfonamide (C-14) | 2,6-Dichloro-3-methylbenzene-1-sulfonyl chloride (A-06) | (Cyclopropylamino)-ethanol hydrobromide (B-08) | GWP III | 46% (1.05 g) |
| C-15(e) | | N-{1-(Hydroxymethyl)-cyclobutyl}-4-methoxy-2,6-dimethyl-benzenesulfonamide (C-15) | 4-Methoxy-2,6-dimethylphenyl-1-sulfonyl chloride (A-01) | | | |
| C-16 | 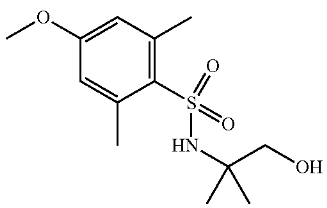 | N-(2-Hydroxy-1,1-dimethyl-ethyl)-4-methoxy-2,6-dimethyl-benzene-sulfonamide (C-16) | 4-Methoxy-2,6-dimethylphenyl-1-sulfonyl chloride (A-01) | 2-Amino-2-methyl-propan-1-ol (B-10) | GWP II | 26% |

TABLE 1-continued

Synthesis of the sulfonylated amino alcohols C

| Alcohol No. | Structure | Name | Sulfonyl chloride (A) | Alcohol (B) | Synthesis according to | Yield |
|---|---|---|---|---|---|---|
| C-17 | 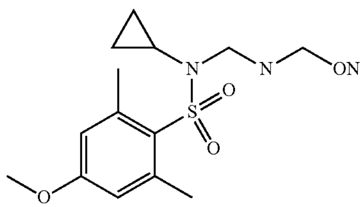 | N-Cyclopropyl-N-(3-hydroxy-propyl)-4-methoxy-2,6-dimethyl-benzenesulfonamide (C-17) | 4-Methoxy-2,6-dimethylphenyl-1-sulfonyl chloride (A-01) | 3-(Cyclopropylamino)-propan-1-ol (B-11) | GWP II | 34% |
| C-18 | 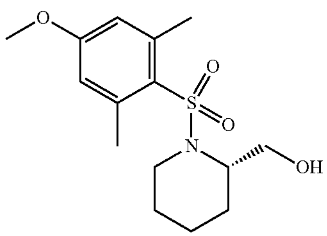 | [(2S)-1-[(4-Methoxy-2,6-dimethyl-phenyl)sulfonyl]-piperidin-2-yl]-methanol (C-18) | 4-Methoxy-2,6-dimethylphenyl-1-sulfonyl chloride (A-01) | (S)-Piperidin-2-ylmethanol (B-12) | GWP II | 30% |

(a) Synthesized according to GWP (I) using 3 equiv. of L-prolinol
(b) Purified by column chromatography (silica, EtOAc/hexane)

4) Synthesis of the Pyrimidine Structural Units D & E

General Method for the Synthesis of the Pyrimidine Structural Units D & E

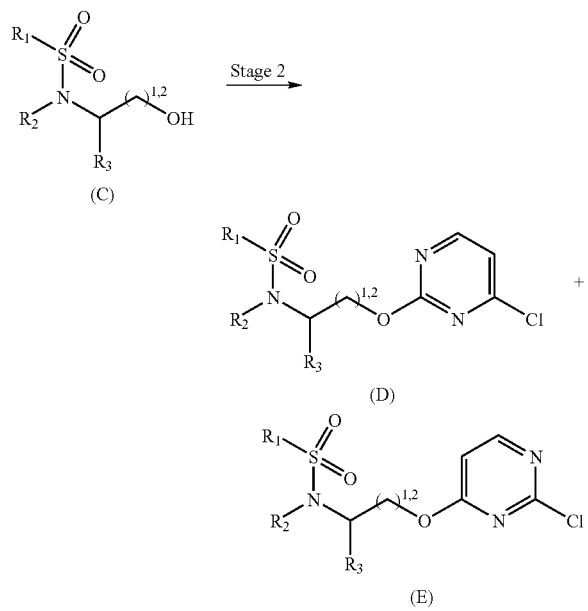

FIG. 2: Synthesis of the Pyrimidine Structural Units D & E

General working procedure GWP IVa: Sodium hydride (1.1 equiv.) was added at 0° C. to a solution of the sulfonylated amino alcohol (C) (1 equiv.) in tetrahydrofuran, and stirring was carried out for 30 minutes at 0° C. A solution of 2,4-dichloropyrimidine (1 equiv.) in tetrahydrofuran was then added to the reaction mixture, and stirring was carried out for 2-6 hours at room temperature. For working up, the reaction solution was poured into water and extracted 3× with ethyl acetate, and the combined organic phases were dried over magnesium sulfate and concentrated under reduced pressure. After purification by column chromatography (silica; ethyl acetate/hexane), the two regioisomers (D & E) were obtained in sufficiently pure form.

General working procedure GWP IVb: The sulfonylated amino alcohol (C) (1 equiv.) was dissolved, under a protecting gas, in tetrahydrofuran and cooled. Sodium hydride (1.1 equiv.) was added at 0° C., stirring was carried out for 30 minutes at the same temperature, and then 2,4-dichloropyrimidine (1 equiv.), dissolved in tetrahydrofuran, was slowly added dropwise. The reaction mixture was stirred for 15 hours and thereby warmed to room temperature. After monitoring by thin-layer chromatography, stirring was optionally continued for a further 2 hours at 40° C. and then optionally for a further 22 hours at room temperature. Saturated sodium hydrogen carbonate solution and ethyl acetate were added, the phases were separated, and the aqueous phase was extracted with ethyl acetate. The combined organic phases were dried over magnesium sulfate and concentrated in vacuo. The crude product was purified by column chromatography (silica gel), the two regioisomers (D & E) of the pyrimidine structural unit, where both were obtained, thereby being separated at least partly. The pyrimidine structural units prepared by the above-described general working procedures are listed in Table 2 below.

General working procedure GWP Va: The sulfonylated amino alcohol (C) (1 equiv.) was dissolved under protecting gas in dry tetrahydrofuran and cooled. At 0° C., sodium hydride (2 equiv.) was added, stirring was carried out for 30 minutes at the same 25° C., and then the mixture was cooled to −78° C. 4-Chloro-2-(methylsulfonyl)pyrimidine (1 equiv.), dissolved in tetrahydrofuran, was slowly added dropwise over a period of 1 hour. The reaction mixture was warmed to 25° C. and quenched with water. Extraction with ethyl acetate was carried out 2×, and the combined organic phases were extracted with water (2×) and saturated NaCl solution (2×). Drying over sodium sulfate and concentration in vacuo were then carried out. The crude product of the pyrimidine structural unit (D) was used directly in the next stage.

General working procedure GWP Vb: The sulfonylated amino alcohol (C) (1 equiv.) was dissolved under protecting gas in dry tetrahydrofuran and cooled. At 0° C., sodium hydride (2 equiv.) was added, stirring was carried out for 30 minutes to 1 hour at 25° C., and then the mixture was cooled to −78° C. 4-Chloro-2-(methylsulfonyl)pyrimidine (1 equiv.), dissolved in tetrahydrofuran, was slowly added dropwise over a period of 45 minutes. The reaction mixture was then quenched with water, warmed to 25° C. and then extracted with ethyl acetate. The combined organic phases were dried over sodium sulfate and concentrated in vacuo. After purification by column chromatography, the pyrimidine structural unit (D) was obtained in sufficiently pure form.

General working procedure GWP Vc: The sulfonylated amino alcohol (C) (1 equiv.) was dissolved under protecting gas in dry tetrahydrofuran and cooled. At 0° C., sodium hydride (2 equiv.) was added, stirring was carried out for 30 minutes at 25° C., and then the mixture was cooled to −78° C. 4-Chloro-2-(methylsulfonyl)pyrimidine (1 equiv.), dissolved in tetrahydrofuran, was slowly added dropwise. The reaction mixture was stirred for 1 hour at the same temperature. Then the reaction mixture was quenched with water and then extracted with ethyl acetate. The combined organic phases were dried over sodium sulfate and concentrated in vacuo. After purification by column chromatography, the pyrimidine structural unit (D) was obtained in sufficiently pure form.

General working procedure GWP Vd: The sulfonylated amino alcohol (C) (1 equiv.) was dissolved under protecting gas in dry tetrahydrofuran and cooled. At 0° C., sodium hydride (2 equiv.) was added, stirring was carried out for 1 hour at 25° C., and then the mixture was cooled to −78° C. 4-Chloro-2-(methylsulfonyl)-pyrimidine (1 equiv.), dissolved in tetrahydrofuran, was slowly added dropwise. The mixture was stirred for 1 hour at −30° C. Then the reaction mixture was quenched with ice and then extracted with ethyl acetate. The combined organic phases were dried over sodium sulfate and concentrated in vacuo. After purification by column chromatography, the pyrimidine structural unit (D) was obtained in sufficiently pure form.

The pyrimidine structural units prepared by the above-described general working procedures are listed in the following Table 2:

TABLE 2

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| E-01 | | N-(2-(2-Chloropyrimidin-4-yloxy)ethyl)-4-methoxy-N,2,6-trimethylphenylsulfonamide (E-01) | N-(2-Hydroxyethyl)-4-methoxy-N,2,6-Trimethylphenylsulfonamide (C-01) | GWP IVa | 46%, (7.07 mmol) |
| D-01 | | N-(2-(4-Chloropyrimidin-2-yloxy)ethyl)-4-methoxy-N,2,6-trimethylphenylsulfonamide (D-01) | N-(2-Hydroxyethyl)-4-methoxy-N,2,6-trimethylphenylsulfonamide (C-01) | GWP IVa | 23%, (3.5 mmmol) |
| E-02 | | 2-Chloro-4-((1-(4-methoxy-2,6-dimethylphenylsulfonyl)piperidin-2-yl)methoxy)pyrimidine (E-02) | (1-(4-Methoxy-2,6-dimethylphenylsulfonyl)piperidin-2-yl)methanol (C-02) | GWP IVa | 42%, (8.87 mmol) |
| D-02 | | 4-Chloro-2-((1-(4-methoxy-2,6-dimethylphenylsulfonyl)piperidin-2-yl)methoxy)pyrimidine (D-02) | (1-(4-Methoxy-2,6-dimethylphenylsulfonyl)piperidin-2-yl)methanol (C-02) | GWP IVa | 49%, (10.33 mmol) |

TABLE 2-continued

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| E-03 | | 2-Chloro-4-(1-(4-methoxy-2,6-dimethylphenylsulfonyl)piperidin-3-yloxy)pyrimidine (E-03) | 1-(4-Methoxy-2,6-dimethylphenylsulfonyl)piperidin-3-ol (C-03) | GWP IVa | 36%, (6.04 mmol) |
| D-03 | | 4-Chloro-2-(1-(4-methoxy-2,6-dimethylphenylsulfonyl)piperidin-3-yloxy)pyrimidine (D-03) | 1-(4-Methoxy-2,6-dimethylphenylsulfonyl)piperidin-3-ol (C-03) | GWP IVa | 18%, (3.01 mmol) |
| E-04 | | (S)-2-Chloro-4-((1-(4-methoxy-2,6-dimethylphenylsulfonyl)pyrrolidin-2-yl)methoxy)pyrimidine (E-04) | (S)-1-(4-Methoxy-2,6-dimethylphenylsulfonyl)pyrrolidin-2-yl)methanol (C-04) | GWP IVa | 57%, (8.67 mmol) |
| D-04 | | (S)-4-Chloro-2-((1-(4-methoxy-2,6-dimethylphenylsulfonyl)pyrrolidin-2-yl)methoxy)pyrimidine (D-04) | (S)-(1-(4-Methoxy-2,6-dimethylphenylsulfonyl)pyrrolidin-2-yl)methanol (C-04) | GWP IVa | 43%, (6.5 mmol) |

TABLE 2-continued

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| E-06 | (structure) | 2-Chloro-4-(1-(4-methoxy-2,6-dimethylphenylsulfonyl)azetidin-3-yloxy)pyrimidine (E-06) | 1-(4-Methoxy-2,6-dimethylphenylsulfonyl)azetidin-3-ol (C-06) | GWP IVa | 0.12%, (1.69 mmol) |
| D-06/E-06[e] | (structure) (structure) | 4-Chloro-2-(1-(4-methoxy-2,6-dimethylphenylsulfonyl)azetidin-3-yloxy)pyrimidine (D-06)/2-Chloro-4-(1-(4-methoxy-2,6-dimethylphenylsulfonyl)azetidin-3-yloxy)pyrimidine (E-06) | 1-(4-Methoxy-2,6-dimethylphenylsulfonyl)azetidin-3-ol (C-06) | GWP IVa | 69% (9.9 mmol) |

TABLE 2-continued

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| E-07[a] | RAC | (S)-2-((2-Chloropyrimidin-4-yloxy)methyl)-1-(4-methoxy-2,6-dimethylphenylsulfonyl)indoline (E-07) | (S)-(1-(4-Methoxy-2,6-dimethylphenylsulfonyl)indolin-2-yl)methanol (C-07) | GWP IVa | 28%, (2.7 mmol) |
| E-08[b] | | N-(2-(2-Chloropyrimidin-4-yloxy)-1-phenylethyl)-4-methoxy-N,2,6-trimethylphenylsulfonamide (E-08) | N-(2-Hydroxy-1-phenylethyl)-4-methoxy-N,2,6-trimethylphenylsulfonamide (C-08) | GWP IVa | 15%, (1.5 mmol) |
| D-06[b] | | N-(2-(4-Chloropyrimidin-2-yloxy)-1-phenylethyl)-4-methoxy-N,2,6-trimethylphenylsulfonamide (D-08) | N-(2-Hydroxy-1-phenylethyl)-4-methoxy-N,2,6-trimethylphenylsulfonamide (C-06) | GWP IVa | 25%, (2.5 mmol) |
| E-09[b] | | N-(2-(2-Chloropyrimidin-4-yloxy)-1-phenylethyl)-N-methylnaphthalene-2-sulfonamide (E-09) | N-(2-Hydroxy-1-phenylethyl)-N-methylnaphthalene-2-sulfonamide (C-09) | GWP IVa | 15%, (3.45 mmol) |

TABLE 2-continued

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| D-09[b] | | N-(2-(4-Chloropyrimidin-2-yloxy)-1-phenylethyl)-N-methylnaphthalene-2-sulfonamide (D-09) | N-(2-Hydroxy-1-phenylethyl)-N-methylnaphthalene-2-sulfonamide (C-09) | GWP IVa | 20%, (4.6 mmol) |
| D-10[c] | | N-(2-(4-Chloropyrimidin-2-yloxy)ethyl)-N-cyclopropyl-4-methoxy-2,6-dimethylphenylsulfonamide (D-10) | N-Cyclopropyl-N-(2-hydroxyethyl)-4-methoxy-2,6-dimethylphenylsulfonamide (C-10) | GWP IVb | 7% (0.38 g (D-10) (plus 1.94 g (D & E)) |
| E-10[c] | | N-(2-(2-chloropyrimidin-4-yloxy)ethyl)-N-cyclopropyl-4-methoxy-2,6-dimethylphenylsulfonamide (E-10) | N-Cyclopropyl-N-(2-hydroxyethyl)-4-methoxy-2,6-dimethylphenylsulfonamide (C-10) | GWP IVb | 23% (1.21 g (E-10) (plus 1.94 g (D & E)) |
| D-11[c] | | N-(2-(4-Chloropyrimidin-2-yloxy)ethyl)-N-cyclopropyl-2-(trifluoromethyl)phenylsulfonamide (D-11) | N-Cyclopropyl-N-(2-hydroxyethyl)-2-(trifluoromethyl)phenylsulfonamide (C-11) | GWP IVb | 9% (0.11 g (D-11)) (plus 0.49 g (E-11) and 0.45 g (D & E)) |

TABLE 2-continued

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| D-12[a],[d] | | 2-Chloro-N-(2-(4-chloropyrimidin-2-yloxy)ethyl)-N-cyclopropyl-6-methylphenylsulfonamide (D-12) | 2-Chloro-N-cyclopropyl-N-(2-hydroxyethyl)-6-methylphenylsulfonamide (C-12) | GWP IVb | 16% (0.19 g (D-12)) (plus 0.31 g (D & E)) |
| E-12[c],[e] | | 2-Chloro-N-(2-(2-Chloropyrimidin-4-yloxy)ethyl)-N-cyclopropyl-6-methylphenylsulfonamide (E-12) | 2-Chloro-N-cyclopropyl-N-(2-hydroxyethyl)-6-methylphenylsulfonamide (C-12) | GWP IVb | 35% (0.41 g (E-12)) (plus 0.31 g (D & E)) |
| D-13[c] | | 4-Chloro-2-((2S,4R)-4-fluoro-1-(4-methoxy-2,6-dimethylphenylsulfonyl)pyrrolidin-2-yl)methoxy)pyrimidine (D-13) | ((2S,4R)-4-Fluoro-1-(4-methoxy-2,6-dimethylphenylsulfonyl)pyrrolidin-2-yl)methanol (C-13) | GWP IVb | 7% (0.15 g (D-13)) (plus 1.88 g (D & E)) |
| D-14[c] | | 2,6-Dichloro-N-[2-(4-chloropyrimidin-2-yl)oxy-ethyl]-N-cyclopropyl-3-methyl-benzenesulfonamide (D-14) | 2,6-Dichloro-N-cyclopropyl-N-(2-hydroxy-ethyl)-3-methyl-benzenesulfonamide (C-14) | GWP IVb | 16% (0.22 g) (D-14) |

TABLE 2-continued

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| D-15 | | N-{1-[(4-Chloro-pyrimidin-2-yl)oxy-methyl]-cyclobutyl}-4-methoxy-2,6-dimethyl-benzenesulfonamide (D-15) | N-[1-(Hydroxymethyl)-cyclobutyl]-4-methoxy-2,6-dimethyl-benzenesulfonamide (C-15) | GWP Va | 84% (D-15) |
| D-16 | | N-[2-(4-Chloro-pyrimidin-2-yl)oxy-1,1-dimethyl-ethyl]-4-methoxy-2,6-dimethyl-benzenesulfonamide (D-16) | N-(2-Hydroxy-1,1-dimethyl-ethyl)-4-methoxy-2,6-dimethyl-benzenesulfonamide (C-16) | GWP Vb | 27% (D-16) |
| D-17 | | N-[3-(4-Chloro-pyrimidin-2-yl)oxy-propyl]-N-cyclopropyl-4-methoxy-2,6-dimethyl-benzenesulfonamide (D-17) | N-Cyclopropyl-N-(3-hydroxy-propyl)-4-methoxy-2,6-dimethyl-benzenesulfonamide (C-17) | GWP Vc | 10% (D-17) |

TABLE 2-continued

Synthesis of pyrimidine structural units D & E

| Pyrimidine No. | Pyrimidine structure | Pyrimidine | Sulfonylated amino alcohol | Synthesis according to | Yield |
|---|---|---|---|---|---|
| D-18 | (structure shown) | 4-Chloro-2-{[(2S)-1-[(4-methoxy-2,6-dimethyl-phenyl)sulfonyl]-pipridin-2-yl]-methoxy}-pyrimidine (D-18) | [(2S)-1-[(4-Methoxy-2,6-dimethyl-phenyl)sulfonyl]-piperidin-2-yl]-methanol (C-18) | GWP Vd | 43% (D-18) |

(a) The reaction mixture was stirred for 12 hours at room temperature. Because the reaction was incomplete, heating was carried out for 12 hours at 50° C.
(b) The synthesis was carried out using 2.5 equiv. of NaH.
(c) The regiochemistry was assigned in this and/or the subsequent synthesis stage by 1H NMR.
(d) 1H NMR (400 MHz, DMSO-$d_6$) d ppm 0.26-0.34(m, 2 H) 0.53-0.62(m, 2 H) 2.64(s, 3H) 3.81(t, J = 5.52 Hz, 2 H) 4.58(t, J = 5.52 Hz, 2 H) 7.35(d, J = 5.02 Hz, 2 H) 7.47-7.52(m, 1 H) 7.37-7.42(m, 1 H) 8.60(d, J = 5.02 Hz, 1 H)
(e) 1H NMR (400 MHz, DMSO-$d_6$) d ppm 0.20-0.34(m, 2 H) 0.59(dd, J = 7.03, 2.01 Hz, 2 H) 2.56-2.63(m, 1 H) 2.64(s, 3 H) 3.80(t, J = 5.52 Hz, 2 H) 4.61(t, J = 5.52 Hz, 2 H) 6.95(d, J = 5.52 Hz, 2 H) 7.33-7.44(m, 1 H) 7.45-7.56(m, 2 H) 8.48(d, J = 5.52 Hz, 1 H)
(f) Products D-06 and E-06 could not be separated by column chromatography.

5) Synthesis of the Amine Structural Units F

The amine structural units F used in the synthesis of the specific embodiments of the compounds according to the invention are listed below in Table 3 and, where they are not available commercially, their preparation is described.

TABLE 3

| Example No. | Structure | Name |
|---|---|---|
| F-01 | 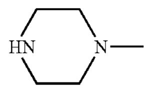 | 1-Methylpiperazine (F-01) |
| F-02 | 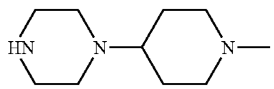 | 1-(1-Methylpiperidin-4-yl)piperazine (F-02) |
| F-03 | 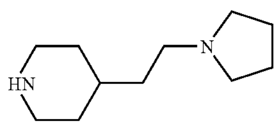 | 4-(2-(Pyrrolidin-1-yl)ethyl)piperidine (F-03) |
| F-04 | 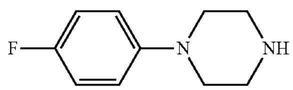 | 1-(4-Fluorophenyl)piperazine (F-04) |
| F-05 | 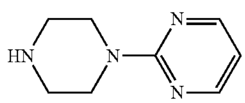 | 2-(Piperazin-1-yl)pyrimidine (F-05) |
| F-06 | 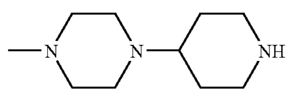 | 1-Methyl-4-(piperidin-4-yl)piperazine (F-06) |
| F-07 | 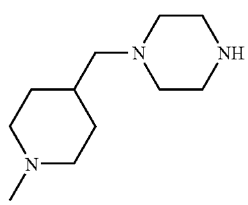 | 1-((1-Methylpiperidin-4-yl)methyl)piperazine (F-07) |
| F-08 | 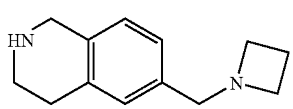 | 6-(Azetidin-1-ylmethyl)-1,2,3,4-tetrahydroisoquinoline dihydrochloride (F-08) |
| F-09 | 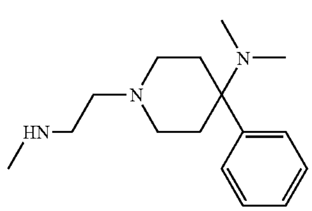 | N,N-Dimethyl-1-(2-(methylamino)ethyl)-4-phenylpiperidine-4-amine (F-09) |
| F-10 | 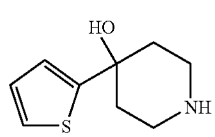 | 4-(Thiophen-2-yl)piperidin-4-ol (F-10) |

TABLE 3-continued

Amine structural units F

| Example No. | Structure | Name |
|---|---|---|
| F-11 | 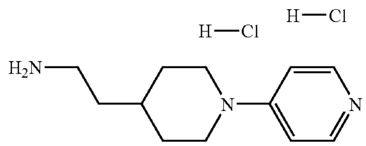 | 2-(1-(Pyridin-4-yl)piperidin-4-yl)ethanamine dihydrochloride (F-11) |
| F-12 | 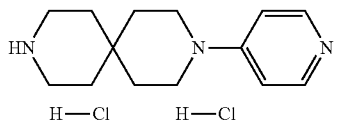 | 3-(Pyridin-4-yl)-3,9-diazaspiro[5.5]undecane dihydrochloride (F-12) |
| F-13 | 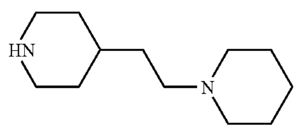 | 1,4'-(Ethane-1,2-diyl)dipiperidine (F-13) |
| F-14 | 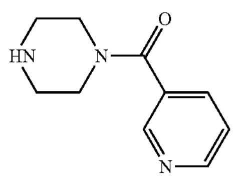 | Piperazin-1-yl(pyridin-3-yl)methanon (F-14) |
| F-15 | 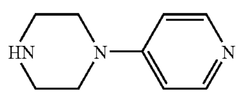 | 1-(Pyridin-4-yl)piperazine (F-15) |
| F-16 | 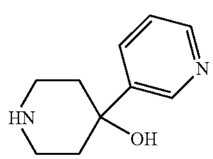 | 4-(Pyridin-3-yl)piperidin-4-ol (F-16) |
| F-17 | 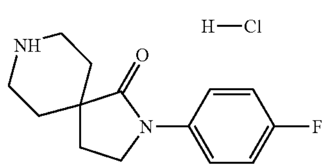 | 2-(4-Fluorophenyl)-2,8-diazaspiro[4.5]decan-1-one hydrochloride (F-17) |
| F-18 | 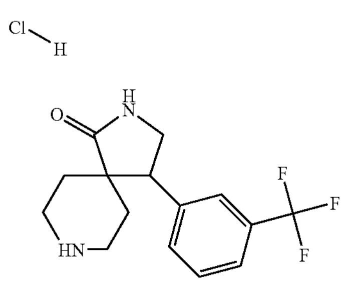 | 4-(3-(Trifluoromethyl)phenyl)-2,8-diazaspiro[4.5]decan-1-one hydrochloride (F-18) |
| F-19 | 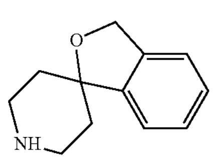 | 3H-Spiro[isobenzofuran-1,4'-piperidine] (F-19) |

TABLE 3-continued

| Amine structural units F | | |
|---|---|---|
| Example No. | Structure | Name |
| F-20 | | 5-Chloro-1-(piperidin-4-yl)-1H-benzo[d]imidazol-2(3H)-one (F-20) |
| F-21 | | 1-Phenyl-1,3,8-triazaspiro[4.5]decan-4-one (F-21) |
| F-22 | | 4-(4-Fluorophenyl)-2-methyl-2,8-diazaspiro[4.5]decan-1-one hydrochloride (F-22) |
| F-23 | | 2-(4-Fluorobenzyl)-2,8-diazaspiro[4.5]decan-1-one hydrochloride (F-23) |
| F-24 | | 2-Benzyl-2,8-diazaspiro[4.5]decan-1-one hydrochloride (F-24) |
| F-25 | | 2-Benzyl-2,7-diazaspiro[4.4]nonane (F-25) |
| F-26 | | 2-(Pyridin-4-ylmethyl)-2,5-diazabicyclo[2.2.1]heptane dihydrochloride (F-26) |

TABLE 3-continued

Amine structural units F

| Example No. | Structure | Name |
|---|---|---|
| F-27 | 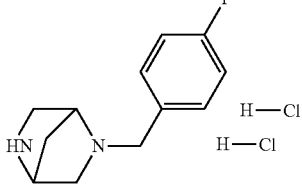 | 2-(4-Fluorobenzyl)-2,5-diazabicyclo[2.2.1]heptane dihydrochloride (F-27) |
| F-28 | 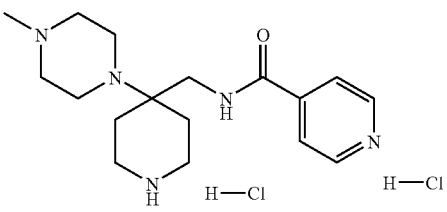 | N-((4-(4-Methylpiperazin-1-yl)piperidin-4-yl)methyl)isonicotinamide dihydrochloride (F-28) |
| F-31 | 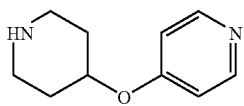 | 4-(Piperidin-4-yloxy)pyridine dihydrochloride (F-31) |
| F-37 | 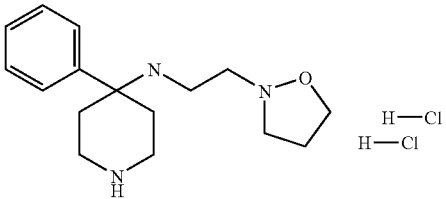 | 3-(4-(2-(Pyrrolidin-1-yl)ethoxy)piperidin-4-yl)pyridine dihydrochloride (F-37) |
| F-38 | 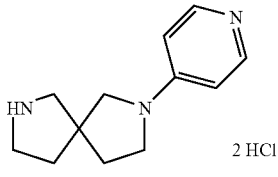 | 2-(Pyridin-4-yl)-2,7-diazaspiro[4.4]nonane dihydrochloride (F-38) |
| F-39 | 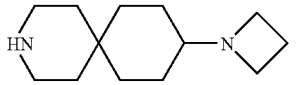 | 9-(Azetidin-1-yl)-3-azaspiro[5.5]undecane dihydrochloride (F-39) |
| F-40 | 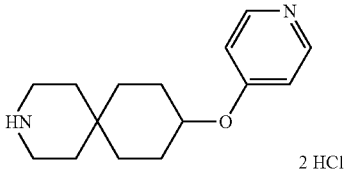 | 9-(Pyridin-4-yloxy)-3-azaspiro[5.5]undecane dihydrochloride (F-40) |
| F-41 | 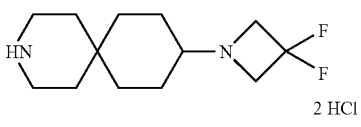 | 9-(3,3-Difluoroazetidin-1-yl)-3-azaspiro[5.5]undecane dihydrochloride (F-41) |

TABLE 3-continued

| Amine structural units F | | |
|---|---|---|
| Example No. | Structure | Name |
| F-42 | 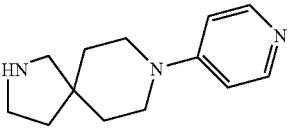 2 HCl | 8-(Pyridin-4-yl)-2,8-diazaspiro[4.5]decane dihydrochloride (F-42) |
| F-43 | 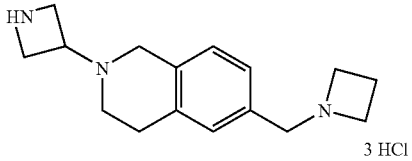 3 HCl | 6-(Azetidin-1-ylmethyl)-2-(azetidin-3-yl)-1,2,3,4-tetrahydroisoquinoline trifhydrochloride (F-43) |
| F-44 | 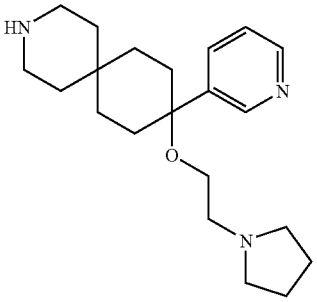 | 3-Pyridin-3-yl-3-(2-pyrrolidin-1-yl-ethoxy)-9-azaspiro[5.5]undecane (F-44) |
| F-45 | 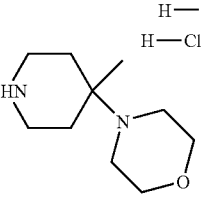 H—Cl H—Cl | 4-(4-Methyl-piperidin-4-yl)-morpholine dihydrochloride (F-45) |
| F-46 | 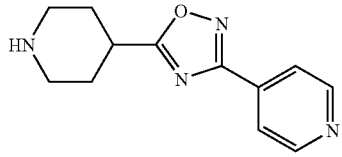 | 5-Piperidin-4-yl-3-pyridin-4-yl-[1,2,4]oxadiazole (F-46) |
| F-47 | 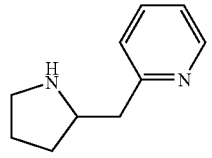 | 2-(Pyrrolidin-2-yl-methyl)-pyridine (F-47) |
| F-48 | 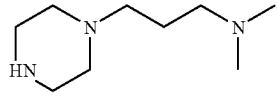 | Dimethyl-(3-piperazin-1-yl-propyl)-amine (F-48) |
| F-49 | 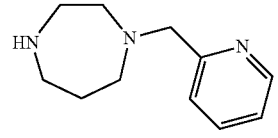 | 1-(Pyridin-2-yl-methyl)-[1,4]diazepan (F-49) |

TABLE 3-continued

| | Amine structural units F | |
|---|---|---|
| Example No. | Structure | Name |
| F-50 | | 2-Piperidin-4-yloxy-pyridine dihydrochloride (F-50) |
| F-51 | | 2-Piperidin-4-yloxy-pyrazine dihydrochloride (F-51) |
| F-52 | RAC | (1S,5R)-3-Pyridin-4-yloxy-8-azabicyclo[3.2.1]octane hydrochloride (F-52) |
| F-53 | RAC | (1S,5R)-3-Pyridin-3-yloxy-8-azabicyclo[3.2.1]octane hydrochloride (F-53) |
| F-54 | | Methyl-[2-(4-pyridin-4-yloxy-piperidin-1-yl)-ethyl]-amine dihydrochloride (F-54) |
| F-55 | | 4-Pyridin-4-yl-piperidin-4-ol (F-55) |
| F-56 | | 4-Pyridin-2-yl-piperidin-4-ol (F-56) |
| F-57 | | 1-(2-Methylamino-ethyl)-4-pyridin-3-yl-piperidin-4-ol hydrochloride (F-57) |

TABLE 3-continued

| | Amine structural units F | |
|---|---|---|
| Example No. | Structure | Name |
| F-58 | 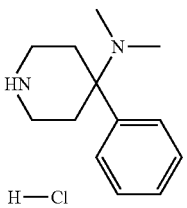 | Dimethyl-(4-phenyl-piperidin-4-yl)-amine dihydrochloride (F-58) |
| F-59 | 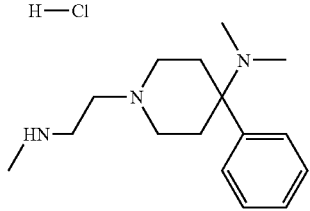 | Dimethyl-[1-(2-methylamino-ethyl)-4-phenyl-piperidin-4-yl]-amine trihydrochloride (F-59) |
| F-60 | 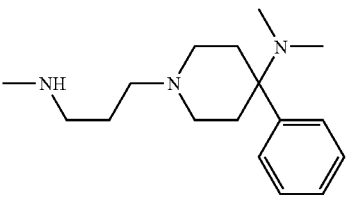 | Dimethyl-[1-(3-methylamino-propyl)-4-phenyl-piperidin-4-yl]-amine trihydrochloride (F-60) |
| F-61 | 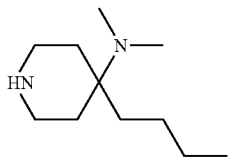 | (4-Butyl-piperidin-4-yl)-dimethyl-amine (F-61) |
| F-62 | 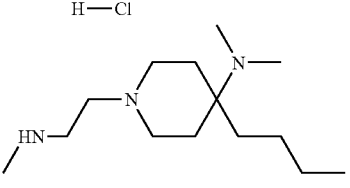 | [4-Butyl-1-(2-methylamino-ethyl)-piperidin-4-yl]-dimethyl-amine trihydrochloride (F-62) |
| F-63 | 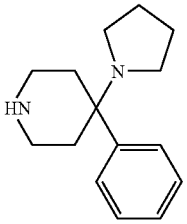 | 4-Phenyl-4-pyrrolidin-1-yl-piperidine (F-63) |

TABLE 3-continued

| | Amine structural units F | |
|---|---|---|
| Example No. | Structure | Name |
| F-64 | 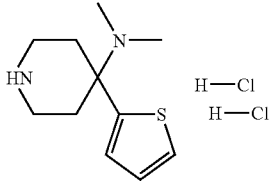 | Dimethyl-(4-thiophen-2-yl-piperidin-4-yl)-amine dihydrochloride (F-64) |
| F-65 | 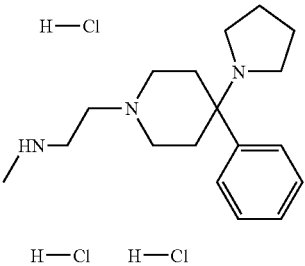 | Methyl-[2-(4-phenyl-4-pyrrolidin-1-yl-piperidin-1-yl)-ethyl]-amine trihydrochloride (F-65) |
| F-66 | 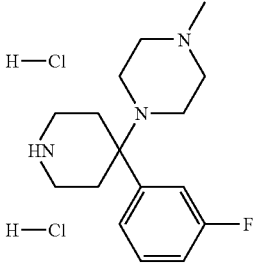 | 1-[4-(3-Fluorophenyl)-piperidin-4-yl]-4-methyl-piperazine dihydrochloride (F-66) |
| F-67 | 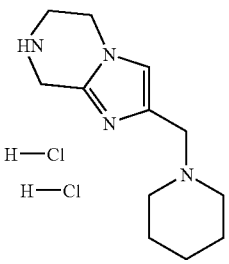 | 2-(Piperidin-1-yl-methyl)-5,6,7,8-tetrahydro-imidazo[1,2-a]pyrazine dihydrochloride (F-67) |
| F-68 | 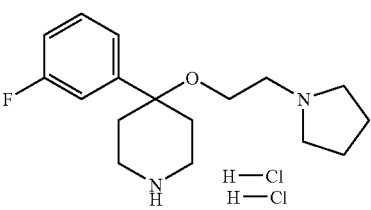 | 4-(3-Fluorophenyl)-4-(2-pyrrolidin-1-yl-ethoxy)-piperidine dihydrochloride (F-68) |

TABLE 3-continued

Amine structural units F

| Example No. | Structure | Name |
|---|---|---|
| F-69 | 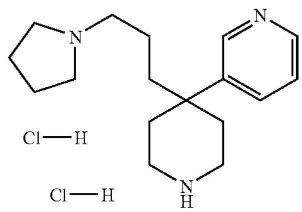 | 3-[4-(3-Pyrrolidin-1-yl-propyl)-piperidin-4-yl]-pyridine dihydrochloride (F-69) |

Amine F-01: 1-Methylpiperazine [109-01-3] available commercially from, for example, Aldrich.
Amine F-02: 1-(1-Methylpiperidin-4-yl)piperazine [23995-88-2] available commercially from, for example, Fluka.
Amine F-03: 4-(2-(Pyrrolidin-1-yl)ethyl)piperidine [14759-08-1] available commercially from, for example, ABCR.
Amine F-04: 1-(4-Fluorophenyl)piperazine [16141-90-5] available commercially from, for example, Aldrich.
Amine F-05: 2-(Piperazin-1-yl)pyrimidine [20980-22-7] available commercially from, for example, Aldrich.
Amine F-06: 1-Methyl-4-(piperidin-4-yl)piperazine [436099-90-0] available commercially from, for example, ABCR.
Amine F-07: 1 1-((1-Methylpiperidin-4-yl)methyl)piperazine [735262-46-1] available commercially from, for example, Otava.
Amine F-08: 6-(Azetidin-1-ylmethyl)-1,2,3,4-tetrahydroisoquinoline dihydrochloride (i): 2-(2,2,2-Trifluoroacetyl)-1,2,3,4-tetrahydroisoquinoline-6-carbaldehyde (2 g, 7.78 mmol) and azetidine (532 mg, 9.33 mmol) were placed in 1,2-dichloroethane (37 ml), and sodium triacetoxyborohydride (2.31 g, 10.89 mmol) was added. The reaction mixture was stirred for 15 hours, then diluted with dichloromethane, and saturated sodium hydrogen carbonate solution (100 ml) was added. After phase separation, the aqueous phase was extracted with dichloromethane (3×100 ml). The combined organic phases were washed with saturated sodium chloride solution (50 ml), dried over magnesium sulfate and concentrated in vacuo. The crude product was purified by column chromatography (silica gel, ethyl acetate/dichloromethane/methanol/hexane, 300:100:20:10).

Yield: 1.55 g (66%).

(ii): 1-(6-(Azetidin-1-ylmethyl)-3,4-dihydroisoquinolin-2(1H)-yl)-2,2,2-trifluoroethanone (1.54 g, 5.162 mmol) was placed in methanol (21 ml); potassium carbonate (1.42 g, 10.32 mmol) was added and the reaction mixture was stirred for 15 hours at room temperature. The solvent was then removed in vacuo and the residue was taken up in dichloromethane and washed with water. The aqueous phase was extracted with dichloromethane and the combined organic phases were dried over sodium sulfate and concentrated in vacuo. The residue was taken up in an ethanol/diethyl ether mixture, and the hydrochloride was precipitated with hydrogen chloride in diethyl ether (4 equiv., 2 mol/l) and then filtered out with suction and dried in vacuo. Yield: 1.03 g (72%).

Amine F-09: N,N-Dimethyl-1-(2-(methylamino)ethyl)-4-phenylpiperidine-4-amine

Stage 1: tert-Butyl 2-(4-(dimethylamino)-4-phenylpiperidin-1-yl)ethyl(methyl)-carbamate 7 g (1 equiv.) of N,N-dimethyl-4-phenylpiperidine-4-amine were added in portions to a solution of 6.5 g (1.5 equiv.) of tert-butyl methyl(2-oxoethyl)carbamate in 60 ml of methanol. The reaction mixture was cooled to 0° C., 3.97 g (2.5 equiv.) of sodium cyanoborohydride were added in portions, and stirring was then carried out for 10 minutes at room temperature. The resulting reaction mixture was adjusted to a pH of ~5 by means of acetic acid and was stirred for 12 hours at room temperature. The progress of the reaction was monitored by means of thin-layer chromatography (20% MeOH/CHCl₃). Because the reaction was not yet complete, 1.5 g of sodium cyanoborohydride and acetic acid were added and the reaction mixture was stirred for a further 35-40 minutes.

When the reaction was complete, the methanol was distilled off, 100 ml of saturated NaHCO₃ solution were added, the resulting mixture was extracted with chloroform (2×200 ml), and the combined organic phases were dried over Na₂SO₄. After removal of the solvent under reduced pressure, the product was purified by column chromatography (silica gel; 5% MeOH/CHCl₃). 8 g (64%) of product were obtained in the form of an oil.

Stage 2: N,N-Dimethyl-1-(2-(methylamino)ethyl)-4-phenylpiperidine-4-amine tris-hydrochloride HCl gas was passed for 30 minutes through a solution of 9 g (1 equiv.) of tert-butyl 2-(4-(dimethylamino)-4-phenylpiperidin-1-yl)ethyl(methyl)carbamate in 600 ml of CH₃Cl. The progress of the reaction was monitored by means of thin-layer chromatography (20% MeOH/CHCl₃). When the reaction was complete, HCl gas was passed through for a further 30 minutes and the complete reaction was again monitored by means of thin-layer chromatography (20% MeOH/CHCl₃). When the reaction was complete, the solvent was removed under reduced pressure and 7.2 g (96%) of the desired product were obtained in the form of a white solid. The free base was obtained by dissolving the hydrochloride in aqueous sodium hydroxide solution and extracting with dichloromethane.

Amine F-10: 4-(Thiophen-2-yl)piperidin-4-ol (i) Thiopene (10 g) was dissolved in dry THF (500 ml); the solution was cooled to −78° C., and n-BuLi (66 ml) was added slowly at −78° C. The reaction mixture was stirred for one hour, and then N-Cbz-4-piperidone (25 g) in 50 ml of THF was added. The resulting reaction mixture was stirred for one hour, warmed to room temperature and quenched with saturated NH₄Cl (250 ml). The phases were separated, the aqueous phase was extracted 3× with ethyl acetate and the combined organic phases were dried over sodium sulfate and concentrated under reduced pressure. The residue was recrystallized from EtOAc/n-hexane. The resulting solid was filtered off and washed with EtOAc/n-hexane. 22.4 g (66%) of product in the form of a colourless solid were obtained.

(ii) A solution of KOH (2.7 g) in water (10 ml) was added to a solution of the solid (10 g) so obtained in ethanol (100 ml), and the resulting reaction mixture was heated for 24 hours at reflux. When the reaction was complete, the reaction mixture was concentrated under reduced pressure, 30 ml of water were added, and the mixture was extracted 4× with IPA/CHCl$_3$. The combined organic phases were dried over sodium sulfate and concentrated under reduced pressure. The residue was recrystallized from EtOAc/n-hexane. 3.2 g (55%) of product in the form of a pale-brown solid were obtained.

Amine F-11: 2-(1-(Pyridin-4-yl)piperidin-4-yl)ethanamine dihydrochioride (i): Tert-butyl 2-(piperidin-4-yl)ethylcarbamate (0.2 g, 0.876 mmol), 4-chloro-pyridinium chloride (0.197 g, 1.314 mmol) and N-ethyl-diisopropylamine (0.37 ml, 2.19 mmol) were refluxed for 15 hours in 2-propanol (10 ml). Saturated sodium hydrogen carbonate solution (20 ml) and ethyl acetate (50 ml) were added, the phases were separated, and the aqueous phase was extracted with ethyl acetate (2×50 ml). The combined organic phases were dried over magnesium sulfate and concentrated in vacuo. The crude product was purified by column chromatography (silica gel, ethyl acetate/dichloromethane/methanol/ammonia (25% aq.), 400:100:50:1). Yield: 80 mg (30%).

(ii): Hydrogen chloride (1.25 M solution in methanol, 1.25 ml) was added at room temperature to a solution of tert-butyl 2-(1-(pyridin-4-yl)piperidin-4-yl)ethylcarbamate (0.12 g, 0.393 mmol) in methanol (3 ml), and the reaction mixture was refluxed for one hour. The solvent was removed in vacuo and the residue was dried. Yield: quantitative.

Amine F-12: 3-(Pyridin-4-yl)-3,9-diazaspiro[5.5]undecane dihydrochioride (i): Tert-butyl 3,9-diazaspiro[5.5]undecane-3-carboxylate (1 g, 3.931 mmol), 4-chloropyridinium chloride (1.765 g, 11.794 mmol) and triethylamine (2.2 ml, 15.725 mmol) were refluxed for 15 hours in 1-butanol (50 ml). Saturated sodium hydrogen carbonate solution (30 ml) and ethyl acetate (80 ml) were added, the phases were separated, and the aqueous phase was extracted with ethyl acetate (2×80 ml). The combined organic phases were dried over magnesium sulfate and concentrated in vacuo. The crude product was purified by column chromatography (silica gel, ethyl acetate/hexane/methanol/ammonia (25% aq.), 400:40:40:1). Yield: 0.52 g (39%).

[This reaction was in some cases carried out in 2-propanol instead of 1-butanol as solvent, and stirring was carried out for 15 hours at 90° C.]

(ii): Hydrogen chloride in methanol (1.25 mol/l, 6.3 ml) was added to tert-butyl 9-(pyridin-4-yl)-3,9-diazaspiro[5.5]undecane-3-carboxylate (0.52 g, 1.569 mmol), and the mixture was refluxed for one hour. The solvent was removed in vacuo, and the residue was taken up in ethanol (3 ml) and cooled. Acetone (80 ml) was added, and stirring was carried out for 30 minutes in an ice bath. The precipitate was filtered off with suction, washed with diethyl ether and dried in vacuo. Yield: 0.4 g (83%).

Amine F-13: 1,4'-(Ethane-1,2-diyl)dipiperidine [14759-09-2] available commercially from, for example, Fluorochem.

Amine F-14: Piperazin-1-yl(pyridin-3-yl)methanone [39640-08-9] available commercially from, for example, Fluorochem.

Amine F-15: 1-(Pyridin-4-yl)piperazine [1008-91-9] available commercially from, for example, ABCR.

Amine F-16: 4-(Pyridin-3-yl)piperidin-4-ol (i) (Apparatus: 1-litre three-necked flask with nitrogen flask). Magnesium (5.7 g) was placed in anhydrous ether (125 ml); 1,1-dibromoethane (0.5 g) and isopropyl chloride (17.3 ml) were added dropwise, and stirring was carried out for 15 minutes in order to initiate the magnesium. A solution of 3-bromopyridine (25 g) in anhydrous tetrahydrofuran (400 ml) was added dropwise over a period of 20 minutes at 40° C., and the mixture was then refluxed for 2 hours. Finally, a solution of 1-benzylpiperidin-4-one (30 g) in anhydrous tetrahydrofuran (100 ml) was added dropwise over a period of 20 minutes at 40° C., and stirring was carried out overnight at room temperature. Monitoring by thin-layer chromatography: 10% methanol in chloroform. The reaction mixture was hydrolyzed at 0° C. with water (50 ml) and filtered over Celite. Extraction with dichloromethane (2×100 ml) was carried out, and the combined organic phases were washed with water (50 ml), dried over sodium sulfate and concentrated in vacuo. The crude product was purified by column chromatography (Alox neutral) with 5% methanol in chloroform. Yield: 8.2 g (19.3%).

(ii) (Apparatus: 1-litre three-necked flask with cooler). To a solution of 1-benzyl-4-(pyridin-3-yl)piperidin-4-ol (32 g) in methanol (220 ml) there was added palladium-on-carbon (10%, catalytic amount), followed by ammonium formate solution (22.7 g in 50 ml of water). The reaction mixture was refluxed overnight at 68° C. Monitoring by thin-layer chromatography: 20% methanol in chloroform. The mixture was filtered over Celite, and the filtrate was concentrated in vacuo. The residue was washed with acetone (100 ml) to give the desired compound in clean form. Yield: 17.3 g (81.3%).

Amine F-17: 2-(4-Fluorophenyl)-2,8-diazaspiro[4.5]decan-1-one hydrochloride (MDL No.: MFCD05861564) available commercially from, for example, ASW MedChem.

Amine F-18: 4-(3-(Trifluoromethyl)phenyl)-2,8-diazaspiro[4.5]decan-1-one hydrochloride available commercially from, for example, ASW MedChem.

Amine F-19: 3H-Spiro[isobenzofuran-1,4'-piperidine] [38309-60-3] available commercially from, for example, Chem Impex.

Amine F-20: 3H 5-Chloro-1-(piperidin-4-yl)-1H-benzo[d]imidazol-2(3H)-one [53786-28-0] available commercially from, for example, Aldrich.

Amine F-21: 1-Phenyl-1,3,8-triazaspiro[4.5]decan-4-one [1021-25-6] available commercially from, for example, ABCR.

Amine F-22: 4-(4-Fluorophenyl)-2-methyl-2,8-diazaspiro[4.5]decan-1-one hydrochloride (MDL No: MFCD08460813) available commercially from, for example, ASW MedChem.

Amine F-23: 2-(4-Fluorobenzyl)-2,8-diazaspiro[4.5]decan-1-one hydrochloride (MDL No: MFCD08461093) available commercially from, for example, ASW MedChem.

Amine F-24: 2-Benzyl-2,8-diazaspiro[4.5]decan-1-one hydrochloride (MDL No: MFCD02179153) available commercially from, for example, ASW MedChem.

Amine F-25: 2-Benzyl-2,7-diazaspiro[4.4]nonane (MDL No: MFCD04115133) available commercially from, for example, Tyger.

Amine F-26: 2-(Pyridin-4-ylmethyl)-2,5-diazabicyclo[2.2.1]heptane dihydrochloride (i): Tert-butyl 2,5-diazabicyclo[2.2.1]heptane-2-carboxylate (5 g, 25.214 mmol) and pyridine-4-carbaldehyde (2.97 g, 27.74 mmol) were placed in dichloromethane (650 ml); sodium triacetoxyborohydride (10.6 g, 50.43 mmol) and glacial acetic acid (0.14 ml, 2.521 mmol) were added, and the reaction mixture was stirred for 15 hours at room temperature. Hydrolysis was then carried out with saturated sodium hydrogen carbonate solution, the phases were separated, and the aqueous phase was extracted 2× with diethyl ether. The combined organic phases were washed with saturated sodium chloride solution, dried over magnesium sulfate and concentrated under reduced pressure. The crude product was purified by column chromatography (silica gel; dichloromethane/methanol).

Yield: 5.8 g, 79%.

(ii): Tert-butyl 5-(pyridin-4-ylmethyl)-2,5-diazabicyclo[2.2.1]heptane-2-carboxylate (5.8 g, 20.0 mmol) was dissolved in methanol (50 ml); the solution was cooled in an ice bath, and acetyl chloride (7.1 ml) was added. The reaction mixture was stirred for 15 hours at room temperature and then concentrated under reduced pressure. The residue was taken up in water, the aqueous phase was washed 2× with dichloromethane and frozen, and the water was removed by lyophilization.

Yield: 5.2 g, 99%.

The amine F-27 listed in the following table was prepared analogously to amine F-38 from tert-butyl 2,5-diazabicyclo[2.2.1]heptane-2-carboxylate by reaction with the appropriate aldehyde followed by protecting group cleavage.

| Amine | Aldehyde | Yield (after 2 stages) |
|---|---|---|
| 2-(4-Fluorobenzyl)-2,5-diazabicyclo[2.2.1]heptane dihydrochloride (F-27) | 4-Fluoro-benzaldehyde | 77% |

Amine F-28: N-((4-(4-Methylpiperazin-1-yl)piperidin-4-yl)methyl)isonicotinamide dihydrochloride (i) A mixture of N-Boc-piperidone (10.0 g, 50.2 mmol), 1-methylpiperazine (5.57 ml, 50.2 mmol), water (1.18 ml, 65.2 mmol) and acetic acid (3.18 ml, 55.2 mmol) in methanol (20 ml) was stirred at RT under a nitrogen atmosphere. KCN (3.44 g, 52.8 mmol) was added and the reaction mixture was stirred at RT. After 30 minutes, a solid precipitated. Aqueous $NH_4OH$ solution (35%, 300 ml) and ice (100 g) were added to the reaction mixture. The solid was filtered off, dried and used further without further purification.

(ii) A LAH solution (1.0 M in diethyl ether, 34.6 ml, 34.6 mmol) was cooled to 0° C., and the product from stage (i), dissolved in diethyl ether (150 ml), was added dropwise. Stirring was then carried out for 2 hours at 0° C. $Na_2SO_4.10 H_2O$ was then added at 0° C. until no further evolution of gas could be detected. The reaction mixture was filtered and washed with DCM. The solvent was removed and the crude product was used further without further purification.

(iii) Triethylamine (4.2 ml, 29.7 mmol) and isonicotinoyl chloride hydrochloride (1.20 g, 6.74 mmol) were added at RT to a solution of the crude product from step (ii) (max. 9.89 mmol) in DCM (125 ml). The reaction mixture was stirred for 3 hours at RT and then concentrated to dryness. The crude product was purified by column chromatography (silica gel, DCM, 7 M $NH_3$ in methanol, 95:5).

(iv) HCl (4 M in dioxane, 2.35 ml, 9.4 mmol) was added to a solution of the product from stage (iii) (490 mg, 1.17 mmol) in dioxane (10 ml), and stirring was carried out for 3 hours at RT. The solvent was removed and the crude product was used further without being worked up further.

Amine F-31: 4-(Piperidin-4-yloxy)pyridine dihydrochloride (i) Tert-butyl-4-hydroxypiperidine-1-carboxylate (6.348 g, 31.546 mmol) and triphenylphosphine (10.256 g, 39.432 mmol) were added at room temperature to a solution of 4-hydroxypyridine (3 g, 31.546 mmol) in tetrahydrofuran (50 ml). Diisopropyl-azodicarboxylate (7.66 ml, 39.432 mmol) was then added dropwise, and the mixture was then stirred for 15 hours at 55° C. Saturated sodium hydrogen carbonate solution (50 ml) was added to the reaction mixture, and extraction with ethyl acetate (4×80 ml) was carried out. The combined organic phases were washed with saturated sodium chloride solution (20 ml), dried ($Na_2SO_4$) and concentrated in vacuo. The crude product was then purified by column chromatography (silica gel, ethyl acetate/hexane, 4:1). Yield: 4.11 g (46%).

(ii) Hydrogen chloride (47 ml, 59 mmol, 1.25 M solution in methanol) was added at room temperature to a solution of tert-butyl 4-(pyridin-3-yloxy)piperidine-1-carboxylate (4.1 g, 14.727 mmol) in methanol (10 ml), and the reaction mixture was refluxed for 30 minutes. The solvent was removed in vacuo, the residue was taken up in a small amount of ethanol, and diethyl ether was added. The mixture was then cooled for 30 minutes in an ice bath, and the resulting solid was filtered off and dried. Yield: 3.46 g (93%).

Amine F-37: 3-(4-(2-(Pyrrolidin-1-yl)ethoxy)piperidin-4-yl)pyridine dihydrochloride (i) n-Butyllithium (2 equiv.) was added at −70° C. to a solution of 3-bromopyridine (7.94 g, 1 equiv.) in dry THF (1600 ml), and stirring was carried out for one hour at that temperature. A solution of N-Boc-piperidone (10 g, 1 equiv.) in THF (400 ml) was then added at −70° C., and stirring was carried out for 2 hours at that temperature (TLC monitoring). When the reaction had ended, the mixture was hydrolyzed with saturated ammonium chloride solution and then slowly warmed to RT. Dilution with ethyl acetate was carried out. The organic phase was washed with sodium chloride solution and dried over sodium sulfate. The solvent was removed using a rotary evaporator and the resulting crude product was purified by column chromatography (silica gel, DCM/methanol, 9:1).

(ii) The alcohol (2 g) was dissolved in benzene (20 ml); sodium amide (10 equiv.) was added at 25° C., and stirring was carried out for 15 minutes at that temperature. 1-(2-Chloroethyl)pyrrolidine (1.2 equiv.) was then added and the mixture was heated for 16 hours under reflux. When the reaction had ended (TLC monitoring), the mixture was cooled to 0° C. and hydrolyzed with ice. The aqueous phase was extracted with ethyl acetate. The organic phase was washed with water and saturated NaCl solution and dried over $Na_2SO_4$. The solvent was removed using a rotary evaporator and the resulting crude product was purified by column chromtography (silica gel, DCM/methanol, 95:5).

(iii) Tert-butyl 4-(pyridin-3-yl)-4-(2-(pyrrolidin-1-yl)ethoxy)piperidine-1-carboxylate (12.7 g, 33.82 mmol) was dissolved in methanol (80 ml) and cooled in an ice bath; acetyl chloride (12 ml, 169.1 mmol) was added. After 3 hours, the reaction had ended according to TLC monitoring (dichloromethane/methanol, 9:1), the solvent was removed in vacuo, and the residue was taken up in water/dichloromethane. The phases were separated, and the aqueous phase was washed (twice) with dichloromethane and dried by lyophilization. Yield: quantitative.

Amine F-38: 2-(Pyridin-4-yl)-2,7-diazaspiro[4.4]nonane

The preparation was carried out in two stages, analogously to the synthesis of amine F-12, from tert-butyl 2,7-diazaspiro[4.4]nonane-2-carboxylate and 4-chloropyridinium chloride.

Amine F-39: 9-(Azetidin-1-yl)-3-azaspiro[5.5]undecane dihydrochloride (i): Tert-butyl 9-oxo-3-azaspiro[5.5]undecane-3-carboxylate (1 g, 3.74 mmol) and azetidine (0.25 ml, 3.74 mmol) were placed in 1,2-dichloroethane (15 ml), and sodium triacetoxyborohydride (1.1 g, 5.23 mmol) was added. The reaction mixture was stirred for 3 days at room temperature, and then saturated sodium hydrogen carbonate solution was added. After phase separation, the aqueous phase was extracted (2×)

with dichloromethane. The combined organic phases were washed (1×) with saturated sodium chloride solution, dried over magnesium sulfate and concentrated in vacuo. The crude product was purified by column chromatography (silica gel, ethyl acetate/methanol/ammonia (25% aq.), 100:10:1). Yield: 1 g (89%).

(ii): Hydrogen chloride in methanol (1.25 mol/l, 15.5 ml) was added to tert-butyl 9-(azetidin-1-yl)-3-azaspiro[5.5]undecane-3-carboxylate (1 g, 3.24 mmol), and the mixture was refluxed for 45 minutes. The solvent was removed in vacuo and the residue was dissolved in a small amount of ethanol. A solid was then precipitated by addition of acetone. Finally, diethyl ether was added and the resulting precipitate was filtered off with suction. Yield: 0.87 g (95%).

Amine F-40: 9-(Pyridin-4-yloxy)-3-azaspiro[5.5]undecane dihydrochloride

Stage (i):
1-(Benzyloxycarbonyl)piperidine-4-carboxylic acid

To piperidine-4-carboxylic acid (25 g) in THF (75 ml) there was added water (75 ml) followed by sodium bicarbonate (30.8 g). The mixture was cooled to 0° C., and Cbz chloride (38.9 ml) was added dropwise. The reaction mixture was then stirred for 5 hours at room temperature (TLC monitoring). When the reaction was complete, the organic solvent was distilled off and the residue was taken up in water (200 ml) and washed with ethyl acetate (2×150 ml). The aqueous phase was acidified with dilute aqueous HCl solution and extracted with ethyl acetate. The organic phase was dried ($Na_2SO_4$) and concentrated in vacuo.
Yield: 48.5 g (96%)

Stage (ii): 1-Benzyl 4-methyl piperidine-1,4-dicarboxylate 1-(Benzyloxycarbonyl)piperidine-4-carboxylic acid (48.5 g) in methanol (485 ml) was cooled to 0° C., and thionyl chloride (13.34 ml) was added dropwise. The mixture was then refluxed for 20 minutes (TLC monitoring). When the reaction was complete, the methanol was distilled off and the residue was taken up in water (15 ml) and with ethyl acetate (2×150 ml). The combined organic phases were extracted with water and saturated sodium chloride solution, dried ($Na_2SO_4$) and concentrated in vacuo. Yield: 38 g (67%)

Stage (iii): Benzyl 4-formylpiperidine-1-carboxylate

A solution of 1-benzyl 4-methylpiperidine-1,4-dicarboxylate (10 g) in toluene (100 ml) under nitrogen was cooled to −78° C. DIBAL-H (60.9 ml) was then added dropwise at −78° C., and the mixture was stirred for one hour at that temperature (TLC monitoring). Because the reaction was incomplete, a further 0.2 eq. of DIBAL-H were added and stirring was carried out for a further 30 minutes (TLC monitoring: some starting material and the corresponding alcohol were detectable). Methanol (40 ml) followed by saturated sodium chloride solution (40 ml) were added slowly to the reaction mixture at −78° C. The mixture was filtered over Celite and the solvent was removed in vacuo. The residue was extracted with ethyl acetate (3×75 ml), dried ($Na_2SO_4$) and concentrated in vacuo. The crude product so obtained was purified by column chromatography (silica gel, 20% ethyl acetate/hexane). Yield: 4.3 g (49%)

Stage (iv): Benzyl 9-oxo-3-azaspiro[5.5]undec-7-ene-carboxylate

Methyl vinyl ketone (1.64 ml), ethanol (5 ml) and water (5 ml) were added to benzyl 4-formylpiperidine-1-carboxylate (5 g). The mixture was then added to a boiling solution of potassium hydroxide (0.22 g) in ethanol (10 ml), and the resulting reaction mixture was refluxed for 1 hour (TLC monitoring). When the reaction was complete, the mixture was added to water (25 ml) and extracted with ethyl acetate (2×50 ml). The combined organic phases were dried ($Na_2SO_4$) and concentrated in vacuo. The crude product so obtained was purified by column chromatography (silica gel, 25% ethyl acetate/hexane). Yield: 2.8 g (46%)

Stage (v): tert-Butyl 9-oxo-3-azaspiro[5.5]undecane-3-carboxylate

Boc anhydride (9.4 ml) and potassium carbonate (7.56 g) were added to benzyl 9-oxo-3-azaspiro[5.5]undec-7-ene-3-carboxylate (8.2 g) in EtOH/water (9:1) (200 ml). Pd/C (1 g) was then added, and hydrolysis was carried out for 4 hours at 80 psi (TLC monitoring). When the reaction was complete, the mixture was filtered over Celite and then rinsed with ethanol and ethyl acetate. The filtrate was dried ($Na_2SO_4$) and concentrated in vacuo. The residue was taken up in ethyl acetate and water, and the aqueous phase was extracted with ethyl acetate. The combined organic phases were dried ($Na_2SO_4$) and concentrated in vacuo. The crude product so obtained was purified by column chromatography (silica gel, 20% ethyl acetate/hexane). Yield: 2.92 g (40%)

Stage (vi): tert-Butyl 9-hydroxy-3-azaspiro[5.5]undecan-3-carboxylate tert-Butyl 9-oxo-3-azaspiro[5.5]undecane-3-carboxylate (1.5 g) was dissolved in THF (7.5 ml) and cooled to −5° C. $NaBH_4$ (0.212 g) was then added and the mixture was stirred for 1 hour at room temperature (TLC monitoring). When the reaction was complete, acetic acid was added to the mixture and the methanol was then distilled off. The residue was taken up in water (50 ml) and extracted with ethyl acetate (2×50 ml). The combined organic phases were dried ($Na_2SO_4$) and concentrated in vacuo. The crude product so obtained was purified by column chromatography (silica gel, 30% ethyl acetate/hexane). Yield: 1.2 g (80%)

Stage (vii): tert-Butyl 9-(pyridin-4-yloxy)-3-azaspiro[5.5]undecane-3-carboxylate 4-Chloropyridine hydrochloride (1.3 g) was added to sodium hydride (0.89 g) in DMSO (20 ml), and the mixture was stirred for 10 minutes. tert-Butyl 9-hydroxy-3-azaspiro[5.5]undecane-3-carboxylate (2.0 g) in DMSO (20 ml) was then added slowly, and the mixture was stirred overnight (TLC control, conversion about 30-35%). A catalytic amount of sodium iodide was added, and the reaction mixture was stirred for 8 hours at 80° C. (TLC monitoring). Methanol and $NaHCO_3$ solution were added to the reaction mixture, and stirring was carried out for 20 minutes. The mixture was then extracted with ethyl acetate and washed again with $NaHCO_3$ solution and cold water. The organic phase was dried ($Na_2SO_4$) and concentrated in vacuo. The crude product so obtained was purified by column chromatography (silica gel, 70% ethyl acetate/hexane). Yield: 1.0 g (40%)

Stage (viii):
9-Pyridin-4-yloxy-3-azaspiro[5.5]undecane dihydrochloride tert-Butyl 9-(pyridin-4-yloxy)-3-azaspiro[5.5]undecane-3-carboxylate (1 g, 2.886 mmol) was dissolved in methanol (2 ml); hydrogen chloride in methanol (1.25 mol/l, 11.5 ml) was added, and the mixture was refluxed for 30 minutes. The solvent was removed in vacuo and the residue was dissolved in a small amount of ethanol. Acetone (about 25 ml) was then added, the mixture was stirred for 30 minutes at 0° C. and finally the resulting solid was filtered off with suction.

Yield: 0.96 g (>99%)

Amine F-41: 9-(3,3-Difluoroazetidin-1-yl)-3-azaspiro[5.5]undecane dihydrochloride The preparation was carried out in two stages, analogously to the synthesis of amine F-39, from tert-butyl 9-oxo-3-azaspiro[5.5]undecane-3-carboxylate and 3,3-difluoroazetidine hydrochloride with the addition of triethylamine (1 equiv.), or as follows:

Stage (i): tert-Butyl 9-(3,3-difluorazetidin-1-yl)-3-azaspiro[5.5]undecane-3-carboxylate tert-Butyl 9-oxo-3-azaspiro[5.5]undecane-3-carboxylate (stage (iv) Amine F-40) (1 g, 3.74 mmol) was added to 3,3-difluoroazetidine hydrochloride (0.484 g, 3.74 mmol) and triethylamine (0.52 ml, 3.74 mmol) in 1,2-dichloroethane (15 ml). The mixture was stirred for 5 minutes, and then sodium triacetoxyborohydride (1.1 g, 5.23 mmol) was added and stirring was carried out for 3 days at room temperature. Saturated sodium hydrogen carbonate solution was added and, after phase separation, the aqueous phase was extracted with dichloromethane (2×). The combined organic phases were washed with saturated sodium chloride solution (1×), dried over magnesium sulfate and concentrated in vacuo.

Yield: 1.26 g (98%)

Stage (ii): 9-(3,3-Difluoro-azetidin-1-yl)-3-azaspiro[5.5]undecane dihydrochloride tert-Butyl 9-(3,3-difluoroazetidin-1-yl)-3-azaspiro[5.5]undecane-3-carboxylate (1.26 g, 3.66 mmol) was dissolved in hydrogen chloride in methanol (1.25 mol/l, 29 ml) and refluxed for 45 minutes. The solvent was removed in vacuo and the residue was dissolved in a small amount of ethanol. A solid was then precipitated by addition of acetone. The mixture was stirred for 10 minutes at room temperature, then diethyl ether was added and stirring was carried out for a further 30 minutes at room temperature. The resulting precipitate was filtered off with suction, washed with diethyl ether and dried in vacuo. Yield: 1.1 g (95%)

Amine F-42: 8-(Pyridin-4-yl)-2,8-diazaspiro[4.5]decane dihydrochloride

The preparation was carried out in two stages, analogously to the synthesis of amine F-12, from tert-butyl 2,8-diazaspiro[4.5]decane-2-carboxylate and 4-chloro-pyridinium chloride, or as follows:

Stage (I): tert-Butyl 8-(pyridin-4-yl)-2,8-diazaspiro[4,5]decane-2-carboxylate tert-Butyl-2,8-diazaspiro[4.5]decane-2-carboxylate (10.403 mmol, 1 equiv.) and N-ethyl-diisopropylamine (41.608 mmol, 4 equiv.) were placed in 2-propanol (20 ml). 4-Chloropyridine (31.206 mmol, 3 equiv.) was added, and the mixture was heated for 16 hours at 90° C. Saturated sodium hydrogen carbonate solution (50 ml) was then added, and the phases were separated. The aqueous phase was extracted with ethyl acetate (4×50 ml), and the combined organic phases were washed with saturated NaCl solution (50 ml) and dried over magnesium sulfate. After purification by column chromatography (ethyl acetate/DCM/methanol/ammonia (25% aq), 100:100:25:1), the desired product was obtained in the form of a yellow oil. Yield: 1.8 g (55%)

Stage (II): 8-(Pyridin-4-yl)-2,8-diazaspiro[4.5]decane dihydrochloride tert-Butyl 8-(pyridin-4-yl)-2,8-diazaspiro[4.5]decane-2-carboxylate (5.671 mmol, 1 equiv.) was placed in ethanol p.a. (20 ml). Acetyl chloride (28.355 mmol, 3 equiv.) was then added at 0° C., and the resulting mixture was stirred for 16 hours at 25° C. The solvent was concentrated in vacuo and the residue was dried under a high vacuum to yield the desired product. Yield: 1.48 g (90%)

Amine F-43: 6-(Azetidin-1-ylmethyl)-2-(azetidin-3-yl)-1,2,3,4-tetrahydro-isoquinoline trihydrochloride (i): 6-(Azetidin-1-ylmethyl)-1,2,3,4-tetrahydroisoquinoline dihydrochloride (F-08) (0.7 g, 2.54 mmol), triethylamine (0.7 ml, 5.09 mmol) and 1-Boc-3-azetidinone (433 mg, 2.54 mmol) were placed in 1,2-dichloroethane (10 ml), and sodium triacetoxyborohydride (747 mg, 3.56 mmol) was added. The reaction mixture was stirred for 15 hours, and then saturated sodium hydrogen carbonate solution was added. After phase separation, the aqueous phase was extracted (2×) with dichloromethane. The combined organic phases were washed (1×) with saturated sodium chloride solution, dried over magnesium sulfate and concentrated in vacuo. The crude product was purified by column chromatography (silica gel, ethyl acetate/hexane/methanol/ammonia (25% aq.), 600:100:100:5). Yield: 0.74 g (81%).

(ii): Hydrogen chloride in methanol (1.25 mol/l, 16 ml) was added to tert-butyl 3-(6-(azetidin-1-ylmethyl)-3,4-dihydroisoquinolin-2(1H)-yl)azetidine-1-carboxylate (0.73 g, 2.04 mmol), and the mixture was refluxed for 30 minutes. The solvent was removed in vacuo and the residue was taken up in ethanol/acetone (20 ml). Diethyl ether (20 ml) was then added, and the resulting precipitate was filtered off with suction. Yield: 0.76 g (>99%).

Alternatively, the preparation can be carried out as follows:

Stage (i): 1-[6-(Azetidin-1-yl-methyl)-1,2,3,4-tetrahydro-isoquinolin-2-yl]-2,2,2-trifluoro-ethanone 2-(2,2,2-Trifluoro-acetyl)-1,2,3,4-tetrahydro-isoquinoline-6-carbaldehyde (7.776 mmol, 1 equiv.) and azetidine (9.331 mmol, 1.2 equiv.) were dissolved in 1,2-dichloroethane (37 ml), and the mixture was stirred for 10 minutes at 25° C. Sodium triacetoxyborohydride (10.89 mmol, 1.4 equiv.) was added, and the reaction mixture was stirred for 16 hours at 25° C. Saturated sodium hydrogen carbonate solution (50 ml) was then added, the phases were separated, and the aqueous phase was extracted with dichloromethane (4×20 ml). The combined organic phases were washed with saturated NaCl solution (1×50 ml), dried over sodium sulfate and concentrated in vacuo. The crude product was purified by column chromatography (ethyl acetate/dichloromethane/hexane/methanol/-ammonia (25% aq), 30:10:10:2:0.02). Yield: 1.55 g (67%)

Stage (ii): 6-(Azetidin-1-yl-methyl)-1,2,3,4-tetrahydro-isoquinoline dihydrochloride 1-[6-(Azetidin-1-yl-methyl)-1,2,3,4-tetrahydro-isoquinolin-2-yl]-2,2,2-trifluoro-ethanone (5.162 mmol, 1 equiv.) was dissolved in methanol (20 ml); $K_2CO_3$ (10.32 mmol, 2 equiv.) was added, and the mixture was stirred for 1 hour at 25° C. Methanol was concentrated in vacuo, and the residue was taken up in dichloromethane (30 ml) and washed with distilled water (5 ml). The aqueous phase was extracted with DCM (20 ml), and the combined organic phases were dried over sodium sulfate and concentrated in vacuo. For purification, the crude product was dissolved in diethyl ether (50 ml), and a hydrochloride was precipitated with 2 M HCl in diethyl ether solution (3 equiv.). The hydrochloride was filtered off, washed with diethyl ether and dried in vacuo to yield the desired product. Yield: 1.03 g (73%)

Stage (iii): 3-[6-(Azetidin-1-yl-methyl)-1,2,3,4-tetrahydro-isoquinolin-2-yl]-azetidine-1-carboxylic acid tert-butyl ester 6-(Azetidin-1-yl-methyl)-1,2,3,4-tetrahydro-isoqinoline dihydrochloride (2.455 mmol, 1 equiv.) was dissolved in 1,2-dichloroethane (10 ml) and triethylamine (5.088 mmol, 2 equiv.), and 1-Boc-3-azetidine (2.544 mmol, 1 equiv.) was added. After 5 minutes, sodium triacetoxyborohydride (2.652 mmol, 1.4 equiv.) was added, and the reaction mixture was stirred for 16 hours at RT under nitrogen. Saturated sodium hydrogen carbonate solution was added to the reaction mixture, and extraction with dichloromethane (2×50 ml) was carried out. The combined organic phases were washed with saturated NaCl solution, dried over magnesium sulfate and concentrated under reduced pressure. The crude product was purified by column chromatography (ethyl acetate/hexane/methanol/ammonia (25% aq) 60:10:10:0.1). Yield: 81%

Stage (iv): 6-(Azetidin-1-ylmethyl)-2-(azetidin-3-yl)-1,2,3,4-tetrahydro-isoquinoline trihydrochloride 3-[6-(Azetidin-1-yl-methyl)-1,2,3,4-tetrahydro-isoquinolin-2-yl]-azetidine-1-carboxylic acid tert-butyl ester (2.042 mmol, 2 equiv.) was dissolved in hydrogen chloride in methanol (1.25 M, 10 equiv., 16 ml) and stirred for 30 minutes at boiling temperature. After monitoring by thin-layer chromatography, the methanol was removed and the residue was dissolved in ethanol/acetone (1:5, 20 ml). The hydrochloride was precipitated with diethyl ether (50 ml), filtered, washed with diethyl ether and dried in vacuo to yield the desired product. Yield: 100%

Amine F-44: 3-Pyridin-3-yl-3-(2-pyrrolidin-1-yl-ethoxy)-9-azaspiro[5.5]-undecane Stage 1: 3-Hydroxy-3-pyridin-3-yl-9-azaspiro[5.5]undecane-9-carboxylic acid tert-butyl ester 3-Bromopyridine (14.9 mmol, 1 equiv.) was dissolved in ether (50 ml) and added dropwise at −78° C. to a solution of n-BuLi (16.5 mmol, 1.17 M solution in ether, 1.1 equiv.). The mixture was stirred for 20 minutes. tert-Butyl 9-oxo-3-azaspiro[5.5]undecane-3-carboxylate (stage (iv) Amine F-40) (7.49 mmol) was then dissolved in ether (90 ml) and added slowly. The reaction mixture was stirred for a further hour at −78° C. Distilled water was added and the mixture was thawed to 25° C. The phases were separated, and the organic phase was washed with saturated NaCl solution (30 ml), dried over $Na_2SO_4$ and concentrated. The crude product was taken up in ethyl acetate (10 ml) and a solid was precipitated with hexane (30 ml). The solid was filtered off and dried under a high vacuum to yield the desired product. Yield: 50%

Stage 2: 3-Pyridin-3-yl-3-(2-pyrrolidin-1-yl-ethoxy)-9-azaspiro[5.5]undecane-9-carboxylic acid tert-butyl ester A mixture of 3-hydroxy-3-pyridin-3-yl-9-azaspiro[5.5]undecane-9-carboxylic acid tert-butyl ester (0.867 mmol), 1-(2-chloro-ethyl)-pyrrolidine hydrochloride (1.3 mmol, 1.5 equiv.), dry KOH powder (4.33 mmol, 5 equiv.) and catalytic amounts of 18-Crown-6 in toluene (20 ml) was heated for 16 hours at boiling temperature. The reaction mixture was diluted with ethyl acetate (25 ml) and washed with distilled water (10 ml) and saturated sodium chloride solution (10 ml). The organic phase was dried over sodium sulfate and concentrated. The crude product was then purified by column chromatography (5% MeOH in DCM). Yield: 34%

Stage 3: 3-Pyridin-3-yl-3-(2-pyrrolidin-1-yl-ethoxy)-9-azaspiro[5.5]undecane

3-Pyridin-3-yl-3-(2-pyrrolidin-1-yl-ethoxy)-9-azaspiro[5.5]undecane-9-carboxylic acid tert-butyl ester (0.282 mmol, 1 equiv.) was dissolved in DCM (3 ml). At 0° C., trifluoroacetic acid (1.5 ml) was added, and the mixture was stirred for 2 hours at 25° C. The solvent was concentrated under reduced pressure and the residue was taken up in DCM (2×10 ml) and dried to yield the desired product.

Amine F-45: 4-(4-Methyl-piperidin-4-yl)-morpholine dihydrochloride, [MFCD09743690] available commercially from SynChem Inc.

Amine F-46: 5-Piperidin-4-yl-3-pyridin-4-yl-[1,2,4]oxadiazole, [276237-03-7] available commercially from Fluorochem.

Amine F-47: 2-(Pyrrolidin-2-yl-methyl)-pyridine, [MFCD04966889] available commercially from ACB Blocks.

Amine F-48: Dimethyl-(3-piperazin-1-yl-propyl)-amine, [877-96-3] available commercially from ABCR.

Amine F-49: 1-(Pyridin-2-yl-methyl)-[1,4]diazepan, [247118-06-5] available commercially from Matrix.

Amine F-50: 2-Piperidin-4-yloxy-pyridine dihydrochloride, [28033-37-6] available commercially from Interchim BB.

Amine F-51: 2-Piperidin-4-yloxy-pyrazine dihydrochloride, [MFCD03840122] available commercially from Interchim BB.

Amine F-52: (1S,5R)-3-Pyridin-4-yloxy-8-azabicyclo[3.2.1]octane hydrochloride

Stage 1: (1R,3r,5S)-tert-Butyl 3-hydroxy-8-azabicyclo[3.2.1]octane-8-carboxylate Nortropin (9.099 g, 71.541 mmol) was placed in dichloromethane (140 ml) and the solution was cooled to 0° C. At that temperature, triethylamine (19.82 ml, 143.08 mmol) and di-tert-butyl dicarbonate (18.73 g, 85.85 mmol) were added. The reaction mixture was slowly warmed to room temperature and was stirred for 15 hours. After hydrolysis with water, the phases were separated and the organic phase was washed with saturated citric acid solution, water and saturated sodium chloride solution, dried over sodium sulfate and concentrated in vacuo. The crude product was used without further purification. Yield: 14.36 g, 88%

Stage 2: (1R,3r,5S)-tert-Butyl 3-(pyridin-4-yloxy)-8-azabicyclo[3.2.1]octane-8-carboxylate (1R,3r,5S)-tert-Butyl 3-hydroxy-8-azabicyclo[3.2.1]octane-8-carboxylate (0.61 g, 2.685 mmol), 4-hydroxypyridine (255 mg, 2.685 mmol) and triphenylphosphine (873 mg, 3.357 mmol) were placed in tetrahydrofuran (11 ml), and diisopropyl azodicarboxylate (0.65 ml, 3.357 mmol) was added. The reaction mixture was warmed to 55° C. and stirred for 15 hours at that temperature. Tetrahydrofuran was removed in vacuo, and the residue was dissolved in ethyl acetate (50 ml) and washed with hydrogen chloride solution (1 mol/l, 2×30 ml). The aqueous phase was rendered alkaline (pH=8) with dilute sodium hydroxide solution and extracted with ethyl acetate (3×70 ml). The organic phases were combined, dried over sodium sulfate and concentrated in vacuo. The crude product was purified by column chromatography (silica gel) with ethyl acetate/hexane 3/1. Yield: 0.45 g, 55%

Stage 3: (1S,5R)-3-Pyridin-4-yloxy-8-azabicyclo [3.2.1]octane hydrochloride (1R,3r,5S)-tert-Butyl 3-(pyridin-4-yloxy)-8-azabicyclo [3.2.1]octane-8-carboxylate (4.6 g, 15.123 mmol) was dissolved in methanol (37 ml) and cooled in an ice bath, and acetyl chloride (5.36 ml) was added. The reaction mixture was stirred for 15 hours at room temperature and then concentrated in vacuo. The residue was taken up in water and dichloromethane, the phases were separated and the aqueous phase was washed (twice) with dichloromethane and dried by freeze-drying. Yield: 3.47 g, 95%

Amine F-53: (1S,5R)-3-Pyridin-3-yloxy-8-azabicyclo [3.2.1]octane hydrochloride

The synthesis was carried out analogously to F-52 using 3-pyridinol.

Amine F-54: (Methyl-[2-(4-pyridin-4-yloxy-piperidin-1-yl)-ethyl]amine dihydrochloride Stage 1: N-Boc-4-hydroxy-piperidine (5.0 g, 24.8 mmol) was added at room temperature to a solution of 4-hydroxy-pyridine (1.89 g, 19.8 mmol) in 70 ml of dry THF. Triphenylphosphine (6.49 g, 24.77 mmol) and diisopropyl azodicarboxylate (DIAD, 4.91 ml) were added, and the reaction mixture was heated for 12 hours at 55° C. and finally concentrated under reduced pressure. 30 ml of 1M HCl were added to the residue, and the mixture was washed with dichloromethane. The combined organic phases were washed with 1M HCl and water. The combined aqueous phases were adjusted to pH 12 with 1M NaOH solution and extracted with dichloromethane. The combined organic phases were washed with saturated NaCl solution, dried over sodium sulfate and concentrated under reduced pressure. The residue was recrystallized from pentane/ether 3:1. Yield: 50%.

Stage 2: 100 ml of TFA were added at 0° C. to a solution of the product obtained in stage 1 (50 g) in 400 ml of dichloromethane, and the reaction mixture was stirred for 3 hours at RT. The solvent was then distilled off, the residue was taken up in ethanol, and Amberlyst A21 resin (25 g) was added. The resin was filtered out and the solvent was removed under reduced pressure to yield the desired amine.

Stage 3: Methyl-(2-oxo-ethyl)-carbamic acid tert-butyl ester (2 equiv.), acetic acid (3 equiv.) and triacetoxy borohydride (3 equiv.) were added to a solution of the amine obtained above in dichloromethane (5 ml/mmol); the mixture was stirred for 12 hours at RT and then diluted with dichloromethane. the reaction mixture was washed with saturated sodium hydrogen carbonate solution and saturated NaCl solution, dried over sodium sulfate and concentrated under reduced pressure. The residue was purified by column chromatography (10% MeOH in dichloromethane).

Stage 4: 10 equiv. of acetyl chloride were added at 0° C. to a solution of the product obtained above in methanol. The progress of the reaction was monitored by thin-layer chromatography (10% MeOH/CHCl₃). When the reaction was complete, the solvent was removed under reduced pressure and the desired product was obtained in the form of a solid.

Amine F-55: 4-Pyridin-4-yl-piperidin-4-ol, [233261-75-1] available commercially from ABCR.

Amine F-56: 4-Pyridin-2-yl-piperidin-4-ol, [50461-56-8] available commercially from Apollo.

Amine F-57: 1-(2-Methylamino-ethyl)-4-pyridin-3-yl-piperidin-4-ol hydrochloride

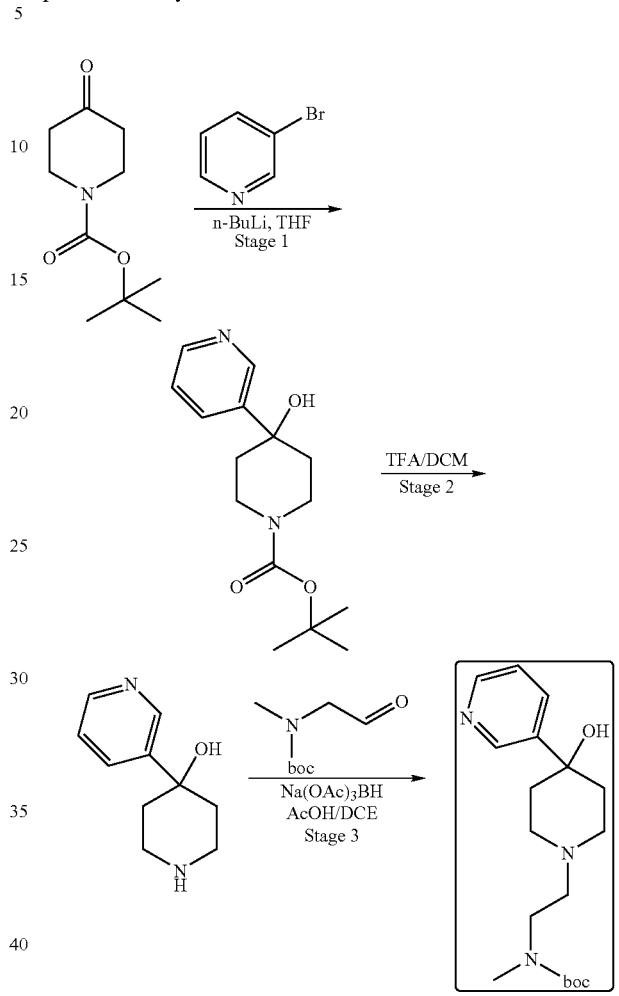

Stage 1: Methyl-(2-oxo-ethyl)-carbamic acid tert-butyl ester (2 equiv.), acetic acid (3 equiv.) and triacetoxy borohydride (3 equiv.) were added to a solution of F-16 in dichloromethane (5 ml/mmol); the mixture was stirred for 12 hours at room temperature and then diluted with dichloromethane. The reaction mixture was washed with saturated sodium hydrogen carbonate solution and saturated NaCl solution, dried over sodium sulfate and concentrated under reduced pressure. The residue was purified by column chromatography (10% methanol in dichloromethane).

Stage 2: 10 equiv. of acetyl chloride were added at 0° C. to a solution of the product obtained above in methanol. The progress of the reaction was monitored by thin-layer chromatography (10% MeOH/CHCl₃). When the reaction was complete, the solvent was removed under reduced pressure and the desired product was obtained in the form of a solid.

Amine F-58: Dimethyl-(4-phenyl-piperidin-4-yl)-amine dihydrochloride

Stage 1:
1-Benzyl-N,N-dimethyl-4-phenylpiperidine-4-amine

To a mixture of 34.5 g (3.5 equiv.) of magnesium and 100 ml of dry diethyl ether there were added first a small amount of iodine and then, over a period of 10 minutes, 10 g (0.15 equiv.) of bromobenzene, and stirring was carried out for a further 10 minutes. When the reaction had started, 183 g (2.85 equiv.) of bromobenzene dissolved in 500 ml of diethyl ether were added dropwise over a period of 2 hours, and stirring was continued for 15 minutes. 100 g (1 equiv.) of 1-benzyl-4-(dimethylamino)piperidine-4-carbonitrile dissolved in 900 ml of diethyl ether were added over a period of 2 hours to the Grignard reagent prepared above, and finally the mixture was heated for 12 hours at 80° C. The progress of the reaction was monitored by thin-layer chromatography (10% MeOH/CHCl$_3$). When the reaction was complete, the reaction solution was cooled to 0° C.; saturated NH$_4$Cl solution was added, the mixture was extracted with ethyl acetate (3×300 ml) and the combined organic phases were dried with Na$_2$SO$_4$. After removal of the solvent under reduced pressure, purification was carried out by column chromatography (silica gel; 1% MeOH/CHCl$_3$). 30 g (35%) of product were obtained in the form of a yellow solid.

Stage 2: Benzyloxycarbonyl-4-(dimethylamino)-4-phenylpiperidine 500 ml (10 equiv.) of Cbz chloride were added dropwise, over a period of 1 hour, to 50 g (1 equiv.) of 1-benzyl-N,N-dimethyl-4-phenylpiperidine-4-amine, and the resulting reaction mixture was stirred for 2 hours at room temperature. The progress of the reaction was monitored by thin-layer chromatography (10% MeOH/CHCl$_3$). When the reaction was complete, the mixture was cooled to 0° C. and rendered basic with saturated sodium hydrogen carbonate solution, and the reaction mixture was extracted 3× with 300 ml of EtOAc. The combined organic phases were dried with Na$_2$SO$_4$. After removal of the solvent under reduced pressure, purification was carried out by column chromatography (silica gel; 50% EtOAc/heptane). 12 g (21%) of product were obtained in the form of an oil.

Stage 3: tert-Butyloxycarbonyl-4-(dimethylamino)-4-phenylpiperidine 12.2 g of KOH were added to a solution of 12 g (1 equiv.) of benzyloxycarbonyl-4-(dimethylamino)-4-phenylpiperidine in 120 ml of ethanol, and the reaction mixture was heated for 48 hours at reflux. The progress of the reaction was monitored by thin-layer chromatography (20% MeOH/CHCl$_3$). When the reaction was complete, the solvent was distilled off, the residue was suspended in ethyl acetate and filtered, and the organic phase was dried over sodium sulfate. After removal of the solvent under reduced pressure, the crude product was dissolved in dioxane; saturated sodium hydrogen carbonate solution and 11.9 g (1.5 equiv.) of Boc anhydride were added, and stirring was carried out for 30 minutes at room temperature. When the reaction was complete, the reaction mixture was extracted with 3×200 ml of ethyl acetate and the combined organic phases were dried over Na$_2$SO$_4$. After removal of the solvent under reduced pressure, 8.5 g (77%) of crude product were obtained in the form of a colorless solid.

Stage 4: Dimethyl-(4-phenyl-piperidin-4-yl)-amine dihydrochloride 10 equiv. of acetyl chloride were added at 0° C. to a solution of tert-butyloxy-carbonyl-4-(dimethylamino)-4-phenylpiperidine in methanol. The progress of the reaction was monitored by thin-layer chromatography (10% MeOH/CHCl$_3$). When the reaction was complete, the solvent was removed under reduced pressure and the product was obtained in the form of a solid.

Amine F-59: Dimethyl-[1-(2-methylamino-ethyl)-4-phenyl-piperidin-4-yl]-amine trihydrochloride. See AMN-09.

Amine F-60: Dimethyl-[1-(3-methylamino-propyl)-4-phenyl-piperidin-4-yl]-amine trihydrochloride Stage 1: tert-Butyl 3-(4-(dimethylamino)-4-phenylpiperidin-1-yl)propyl-(methyl)carbamate 11.1 g (1.3 equiv.) of tert-butylmethyl (3-oxopropyl)carbamate were added at 0° C. to a solution of 11 g (1 equiv.) of N,N-dimethyl-4-phenylpiperidine-4-amine dihydrochloride in 110 ml of methanol, and the reaction mixture was stirred for 15 minutes at 0° C. 6.2 g (3 equiv.) of sodium cyanoborohydride were then added in portions and stirring was carried out for 30 minutes at room temperature. The resulting reaction mixture was adjusted to pH 5-6 with acetic acid and stirred for 12 hours at room temperature. The progress of the reaction was monitored by thin-layer chromatography (20% MeOH/CHCl$_3$). Because the reaction was not yet complete, 2.4 g of sodium cyanoborohydride were added and the resulting reaction mixture was adjusted to pH 5-6 with acetic acid and stirred for 60 minutes at room temperature. When the reaction was complete, the methanol was distilled off, the mixture was rendered basic with saturated NaHCO$_3$ solution, the resulting mixture was extracted with chloroform (3×100 ml), and the combined organic phases were dried over Na$_2$SO$_4$. After removal of the solvent under reduced pressure, purification was carried out by column chromatography (silica gel; 5% MeOH/CHCl$_3$). 9 g (60%) of product were obtained.

Stage 2: Dimethyl-[1-(3-methylamino-propyl)-4-phenyl-piperidin-4-yl]-amine trihydrochloride HCl gas was passed for 1 hour through a solution at 0° C. of 9 g (1 equiv.) of tert-butyl 3-(4-dimethylamino)-4-phenylpiperidin-1-yl)propyl(methyl)carbamate in 100 ml of chloroform. The progress of the reaction was monitored by thin-layer chromatography (20% MeOH/CHCl$_3$). When the reaction was complete, the solvent was removed under reduced pressure and, after trituration with diethyl ether, 10 g (100%) of product were obtained in the form of a white solid.

Amine F-61: (4-Butyl-piperidin-4-yl)-dimethyl-amine

Stage 1: 1-Benzyl-4-(dimethylamino)piperidine-4-carbonitrile 208 g (3 equiv.) of N,N-dimethylamine hydrochloride, 154 g (3 equiv.) of potassium cyanide in 154 ml of water and 1050 ml (7 equiv.) of a 40% aqueous dimethylamine solution were added to a solution of 150 g (1 equiv.) of 1-benzyl-piperidin-4-one in 300 ml of methanol, and the mixture was cooled to 0° C. 75 ml (0.5 equiv.) of concentrated hydrochloric acid were then added at 0° C. and the reaction mixture was stirred for 24 hours at room temperature. The progress of the reaction was monitored by thin-layer chromatography (20% EtOAc/hexane). When the reaction was complete, the solid that had formed was filtered off and washed with ice-water (4 l). The resulting solid was then dissolved in ethyl acetate and dried with Na$_2$SO$_4$. After removal of the solvent under reduced pressure, 165 g (85%) of crude product were obtained in the form of a solid.

Stage 2:
1-Benzyl-4-butyl-N,N-dimethylpiperidine-4-amine

To a mixture of 17.7 g (6 equiv.) of magnesium and 50 ml of dry ether there were added first a small amount of iodine and then, over a period of 1 hour, 100 g (6 equiv.) of bromobutane dissolved in 100 ml of dry ether. This reaction mixture was stirred for 1 hour at room temperature. The Grignard reagent prepared above was added over a period of 20 minutes to a solution of 30 g (1 equiv.) of 1-benzyl-4-(dimethylamino) piperidine-4-carbonitrile dissolved in 210 ml of dry THF, and the resulting reaction mixture was then stirred for 12 hours at room temperature. The progress of the reaction was monitored by thin-layer chromatography (10% MeOH/CHCl$_3$). When the reaction was complete, the reaction solution was cooled to 0° C.; saturated NH$_4$Cl solution was added, the mixture was filtered over Celite and extracted with ethyl acetate (3×200 ml), and the combined organic phases were dried over Na$_2$SO$_4$. After removal of the solvent under reduced pressure, purification was carried out by column chromatography (aluminium oxide neutral; hexane). 18.2 g (53%) of product were obtained in the form of an oil.

Stage 3: 4-Butyl-N,N-dimethylpiperidine-4-amine bis hydrochloride 1.5 g of 20% Pd(OH)$_2$/C and 6.95 g (3 equiv.) of ammonium formate were added to a solution of 10 g (1 equiv.) of 1-benzyl-4-butyl-N,N-dimethylpiperidine-4-amine in 100 ml of MeOH. The resulting reaction mixture was heated for 30 minutes at reflux. The progress of the reaction was monitored by thin-layer chromatography (20% MeOH/CHCl$_3$). When the reaction was complete, the reaction solution was cooled to room temperature, filtered over Celite and then washed with methanol. The methanol was distilled off, the residue was taken up in ethyl acetate/hexane, the solvent was decanted off and toluene was added. The organic phase so obtained was concentrated under reduced pressure and the residue was taken up in 150 ml of dichloromethane. HCl gas was passed for 20 minutes through the dichloromethane solution, the solvent was distilled off, and 7 g (74%) of product were thus obtained in the form of a white solid. The free base was obtained after dissolving the hydrochloride in aqueous sodium hydroxide solution and extracting it with dichloromethane.

Amine F-62: [4-Butyl-1-(2-methylamino-ethyl)-piperidin-4-yl]-dimethyl-amine trihydrochloride

Stage 1: tert-Butyl 2-(4-butyl-4-(dimethylamino) piperidin-1-yl)ethyl(methyl)-carbamate A solution of 4.73 g (1 equiv.) of tert-butyl methyl(2-oxoethyl)carbamate in 20 ml of methanol was added at room temperature to a solution of 7 g (1 equiv.) of 4-butyl-N,N-dimethylpiperidine-4-amine bis hydrochloride in 50 ml of methanol, and the resulting reaction mixture was stirred for 50 minutes at room temperature. 3.43 g (2 equiv.) of sodium cyanoborohydride were added in portions to this reaction mixture, and stirring was then carried out for 12 hours at room temperature. The progress of the reaction was monitored by thin-layer chromatography (20% MeOH/CHCl$_3$). When the reaction was complete, the reaction mixture was cooled to 0° C. and adjusted to a pH of ~5 with acetic acid. 2 g of tert-butyl formylmethyl-methylcarbamate and 1.7 g of sodium cyanoborohydride were then added, and the reaction mixture was stirred for a further 60 minutes at room temperature. Finally, the methanol was distilled off, 100 ml of saturated NaHCO$_3$ solution were added, the resulting mixture was extracted with ethyl acetate (2×200 ml), and the combined organic phases were dried over Na$_2$SO$_4$. After removal of the solvent under reduced pressure, 10.5 g of crude product were obtained in the form of a pale yellow oil.

Stage 2: 4-Butyl-N,N-dimethyl-1-(2-(methylamino) ethyl)piperidine-4-amine tris hydrochloride HCl gas was passed for approximately 1 hour through a solution at 0° C. of 10.5 g (1 equiv.) of tert-butyl 2-(4-butyl-4-(dimethylamino)piperidin-1-yl)ethyl(methyl)-carbamate in 1000 ml of chloroform. The reaction mixture was then stirred for 12 hours at room temperature. The progress of the reaction was monitored by thin-layer chromatography (20% MeOH/CHCl$_3$). When the reaction was complete, the solvent was removed under reduced pressure and the residue was washed with hexane (3×50 ml) and ethyl acetate (3×50 ml) and dried. 9 g (87%) of product were obtained in the form of a white solid.

Amine F-63: 4-Phenyl-4-pyrrolidin-1-yl-piperidine

Stage 1: 1-Benzyl-4-(pyrrolidin-1-yl)piperidine-4-carbonitrile 100 g (5 equiv.) of pyrrolidine were added to a solution of 50 g (1 equiv.) of 1-benzylpiperidin-4-one in 250 ml of ethanol, and stirring was carried out for 10 minutes at room temperature. 25 ml (0.5 equiv.) of hydrochloric acid were then added dropwise, over a period of 10 minutes, to the reaction mixture, and stirring was carried out for 30 minutes at room temperature. 55 g (3 equiv.) of potassium cyanide dissolved in 250 ml of water were added to this reaction mixture, and stirring was carried out for three days at room temperature. The progress of the reaction was monitored by thin-layer chromatography (50% EtOAc/heptane). When the reaction was complete, the solid that had formed was filtered off and washed with ice-water (3×150 ml). The resulting solid was then suspended in ethyl acetate and dried with Na$_2$SO$_4$. After removal of the solvent under reduced pressure, 70 g of crude product were obtained in the form of a solid.

Stage 2: 1-Benzyl-4-phenyl-4-(pyrrolidin-1-yl)piperidine

To a mixture of 31.2 g (5 equiv.) of magnesium and 100 ml of dry THF there were added first a small amount of iodine and then, over a period of 10 minutes, 10 g (0.25 equiv.) of bromobenzene, and stirring was carried out for a further 10 minutes. When the reaction had started, 194.2 g (4.75 equiv.) of bromobenzene dissolved in 500 ml of THF were added dropwise over a period of 2 hours, and stirring was then carried out for 15 minutes. 70 g (1 equiv.) of 1-benzyl-4-(pyrrolidin-1-yl)piperidine-4-carbonitrile dissolved in 450 ml of THF were added over a period of 2 hours to the Grignard reagent prepared above, and finally the mixture was heated for 12 hours at 80° C. The progress of the reaction was monitored by thin-layer chromatography (10% MeOH/CHCl$_3$). When the reaction was complete, the reaction solution was cooled to 0° C., saturated NH$_4$Cl solution was added, extraction with ethyl acetate (3×200 ml) was carried out, and the combined organic phases were dried with Na$_2$SO$_4$. After removal of the solvent under reduced pressure, 33 g (40%) of crude product were obtained in the form of an oil.

Stage 3: Benzyloxycarbonyl-4-phenyl-4-(pyrrolidin-1-yl)piperidine 60 g (3.5 equiv.) of Cbz chloride were added dropwise over a period of 10 minutes to a solution of 33 g (1 equiv.) of 1-benzyl-4-phenyl-4-(pyrrolidin-1-yl)piperidine in 330 ml of chloroform, and the resulting reaction mixture was stirred for 30 minutes at room temperature. The progress of the reaction was monitored by thin-layer chromatography (ethyl acetate). When the reaction was complete, the solvent was distilled off completely and the residue was adjusted to ~pH 6 with 10% HCl solution and washed 3× with 100 ml of EtOAc. In an ice bath, the aqueous solution was adjusted to ~pH 9 with NaOH solution and then extracted 3× with 100 ml of chloroform. The combined organic phases were dried with $Na_2SO_4$. After removal of the solvent under reduced pressure, purification was carried out by column chromatography (silica gel; 20% EtOAc/heptane). 11 g (29%) of product were obtained in the form of a yellow solid.

Stage 4: 4-Phenyl-4-(pyrrolidin-1-yl)piperidine 11 g of KOH were added to a solution of 7.3 g (1 equiv.) of benzyloxycarbonyl-4-phenyl-4-(pyrrolidin-1-yl)piperidine in 100 ml of ethanol, and the reaction mixture was heated for 24 hours at reflux. The progress of the reaction was monitored by thin-layer chromatography (20% $MeOH/CHCl_3$). When the reaction was complete, the solvent was distilled off completely, 100 ml of water were added to the residue, and extraction was carried out 3× with 100 ml of $CHCl_3$. The combined organic phases were dried with $Na_2SO_4$. After removal of the solvent under reduced pressure, 7 g of crude product were obtained in the form of an oil.

Stage 5: 4-Phenyl-4-(pyrrolidin-1-yl)piperidine bishydrochloride

HCl gas was passed for ~30 minutes through a solution of 9 g (1 equiv.) of 4-phenyl-4-(pyrrolidin-1-yl)piperidine in 180 ml of chloroform, until the reaction mixture reached a pH of ~2. The progress of the reaction was monitored by thin-layer chromatography (10% $MeOH/CHCl_3$). When the reaction was complete, the solvent was removed under reduced pressure and the residue was washed with ethyl acetate (3×100 ml) and dried. 9 g (76%) of product were obtained in the form of a solid.

Amine F-64: Dimethyl-(4-thiophen-2-yl-piperidin-4-yl)-amine dihydrochloride

Stage 1: tert-Butyloxycarbonyl-4-cyano-4-(dimethylamino)piperidine 500 ml (10 equiv.) of dimethylamine solution and 109.9 g (5 equiv.) of dimethylamine hydrochloride were added to a solution of 50 g (1 equiv.) of tert-butyloxycarbonyl-4-oxopiperidine in 100 ml of methanol, and the mixture was cooled to 5° C. 5 ml (0.1 equiv.) of hydrochloric acid were then added dropwise, over a period of 10 minutes, to the reaction mixture, and stirring was carried out for 60 minutes at room temperature. 48.9 g (3 equiv.) of potassium cyanide were added in portions to the reaction mixture, and stirring was carried out for 24 hours at room temperature. The progress of the reaction was monitored by thin-layer chromatography (50% EtOAc/hexane). When the reaction was complete, 150 ml of water were added to the reaction mixture, and extraction was carried out 3× with 100 ml of ethyl acetate. The combined organic phases were dried with $Na_2SO_4$. After removal of the solvent under reduced pressure, crude product was obtained and was recrystallized from hexane. 57 g (90%) of product were obtained in the form of a colourless solid.

Stage 2: tert-Butyloxycarbonyl-4-(dimethylamino)-4-(thiophen-2-yl)piperidine

To a mixture of 5.6 g (3 equiv.) of magnesium and 20 ml of dry diethyl ether there were added first a small amount of iodine and then, over a period of 10 minutes, 5 g of 2-bromothiophene, and stirring was carried out for a further 10 minutes. When the reaction had started, 33.5 g (2.6 equiv.) of 2-bromothiophene dissolved in 80 ml of diethyl ether were added dropwise, and stirring was carried out over a period of 2 hours at room temperature. The Grignard reagent prepared above was added dropwise to a solution of 20 g (1 equiv.) of tert-butyloxycarbonyl-4-cyano-4-(dimethylamino)piperidine dissolved in 200 ml of THF, and stirring was carried out overnight at room temperature. The progress of the reaction was monitored by thin-layer chromatography (50% EtOAc/hexane). When the reaction was complete, the reaction solution was cooled to 0° C., saturated $NH_4Cl$ solution was added, extraction with ethyl acetate (3×100 ml) was carried out, and the combined organic phases were dried with $Na_2SO_4$. After removal of the solvent under reduced pressure, purification was carried out by column chromatography (Alox Neutral; 30% EtOAc/hexane). 6.1 g (25%) of product were obtained in the form of a white solid.

Stage 3: N,N-Dimethyl-4-(thiophen-2-yl)piperidine-4-amine

HCl gas was passed for ~1 hour through a solution at 0° C. of 10 g (1 equiv.) of tert-butyloxycarbonyl-4-(dimethylamino)-4-(thiophen-2-yl)piperidine in chloroform. The progress of the reaction was monitored by thin-layer chromatography (75% EtOAc/hexane). When the reaction was complete, 200 ml of water were added to the reaction mixture, the pH was adjusted to ~8 with $Na_2CO_3$, and finally extraction with 15% $IPA/CHCl_3$ was carried out. The combined organic phases were dried over $Na_2SO_4$. After removal of the solvent under reduced pressure, 6 g (89%) of product were obtained in the form of a white solid.

Amine F-65: Methyl-[2-(4-phenyl-4-pyrrolidin-1-yl-piperidin-1-yl)-ethyl]-amine trihydrochloride Stage 1: tert-Butyl methyl(2-(4-phenyl-4-(pyrrolidin-1-yl)piperidin-1-yl)ethyl)-carbamate 7 g (1 equiv.) of 4-phenyl-4-(pyrrolidin-1-yl)piperidine bishydrochloride were added, under a nitrogen atmosphere, to a solution of 4.4 g (1.1 equiv.) of tert-butyl-methyl(2-oxoethyl))carbamate in 70 ml of methanol, and the reaction mixture was stirred for 10 minutes at 0° C. 3.62 g (2.5 equiv.) of sodium cyanoborohydride were then added and stirring was carried out for 30 minutes at room temperature. The resulting reaction mixture was adjusted to a pH 5-6 with acetic acid and stirred for 14 hours at room temperature. The progress of the reaction was monitored by thin-layer chromatography (10% $MeOH/CHCl_3$). When the reaction was complete, the methanol was distilled off, saturated $NaHCO_3$ solution was added, the resulting mixture was extracted with chloroform (3×50 ml), and the combined organic phases were dried over $Na_2SO_4$. After removal of the solvent under reduced pressure, purification was carried out by column chromatography (silica gel; 50% EtOAc/heptane). 8 g (89%) of product were obtained in the form of a red oil.

Stage 2: tert-Butyl methyl(2-(4-phenyl-4-(pyrrolidin-1-yl)piperidin-1-yl)ethyl)-carbamate tris hydrochloride HCl gas was passed for ~30 minutes through a solution at 0° C. of 8 g (1 equiv.) of tert-butyl methyl(2-(4-phenyl-4-

(pyrrolidin-1-yl)piperidin-1-yl)ethyl)carbamate in 160 ml of chloroform, until the reaction mixture reached a pH of ~2. The reaction mixture was then stirred for 4 hours at room temperature. The progress of the reaction was monitored by thin-layer chromatography (10% MeOH/CHCl₃). When the reaction was complete, the solvent was removed under reduced pressure and 8 g (97%) of product were obtained in the form of a white solid.

Amine F-66: 1-[4-(3-Fluorophenyl)-piperidin-4-yl]-4-methyl-piperazine dihydrochloride

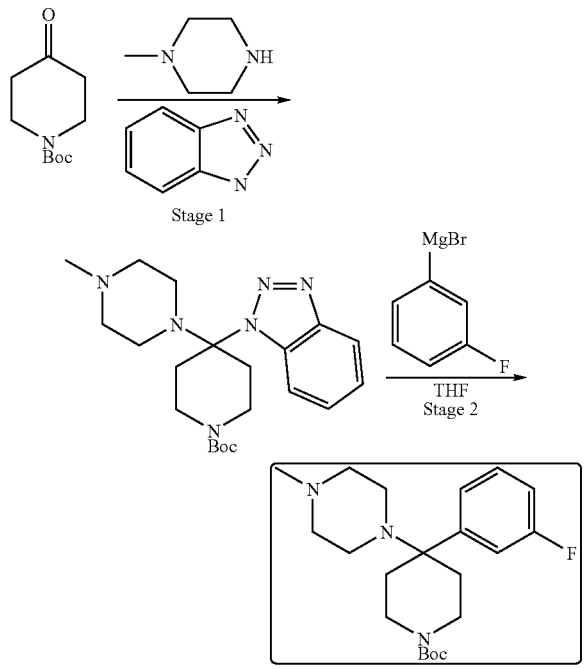

Stage 1: The benzotriazole adduct obtained in stage 1, dissolved in dry THF, was added at 0° C. to a THF solution of the corresponding Grignard reagent (60 mmol), and the resulting reaction mixture was stirred for 16 hours at 25° C. The mixture was then cooled to 0° C., quenched with saturated ammonium chloride solution and extracted with ethyl acetate. The combined organic phases were washed with water and saturated sodium chloride solution, dried over sodium sulfate and concentrated under reduced pressure. The residue was purified by column chromatography (2% methanol in dichloromethane).

Stage 2: 10 equiv. of acetyl chloride were added at 0° C. to a solution of the product obtained above in methanol. The progress of the reaction was monitored by thin-layer chromatography (10% MeOH/CHCl₃). When the reaction was complete, the solvent was removed under reduced pressure and the desired product was obtained in the form of a solid.

Amine F-67: 2-(Piperidin-1-yl-methyl)-5,6,7,8-tetrahydro-imidazo[1,2-a]-pyrazine dihydrochloride Stage 1: To a solution of ethyl 5,6,7,8-tetrahydroimidazo[1,2-a]pyrazine-2-carboxylate hydrochloride (1.09 g, 4.70 mmol) in DCM (100 ml) there were added first DMAP (0.75 g, 6.12 mmol) and then Boc₂O (1.34 g, 6.12 mmol). The reaction mixture was stirred for 18 hours at RT. Because the reaction was not yet complete, further Boc₂O (0.12 g, 0.53 mmol) was added and stirring was again carried out overnight. When the reaction was complete, the mixture was washed with aqueous HCl solution (1 M, 100 ml), and the organic phase was dried over sodium sulfate and concentrated in vacuo. The crude product was purified by column chromatography (silica gel, ethyl acetate). Yield: 300 mg, 21%

Stage 2: A solution of 7-tert-butyl 2-ethyl 5,6-dihydroimidazo[1,2-a]pyrazine-2,7(8H)-dicarboxylate (300 mg, 1.02 mmol) in THF (15 ml) was cooled to −78° C., and DIBAL-H (1 M in hexane, 2.0 ml, 2.0 mmol) was added slowly under an N₂ atmosphere. The reaction mixture was stirred for 1 hour at that temperature and then Na₂SO₄×10H₂O was added until no further evolution of gas was observed. Further sodium sulfate was added, the solution was filtered, and the residue was washed with DCM (25 ml). The filtrate was concentrated and the resulting crude product (450 mg) was used in the next stage without further purification.

Stage 3: tert-Butyl 2-formyl-5,6-dihydroimidazo[1,2-a]pyrazine-7(8H)-carboxylate (400 mg, max. 0.91 mmol) and piperidine (158 μl, 1.59 mmol) were dissolved in DCM (8 ml), and NaBH(OAc)₃ (506 mg, 2.39 mmol) was added in portions. The reaction mixture was stirred for 2 hours at RT and then hydrolyzed with saturated sodium hydrogen carbonate solution (25 ml). The phases were separated and the aqueous phase was extracted again with DCM (25 ml). The combined organic phases were washed with saturated sodium chloride solution and dried over sodium sulfate and concentrated in vacuo. Yield: 260 mg, 90% over 2 stages.

Stage 4: TFA (2.83 ml, 36.7 mmol) was added to a solution of tert-butyl 2-(piperidin-1-ylmethyl)-5,6-dihydroimidazo[1,2-a]pyrazine-7(8H)-carboxylate (235 mg, 0.73 mmol) in DCM (10 ml), and stirring was carried out for 3-4 hours at RT (TLC monitoring). When the reaction was complete, the solvent was first removed, DCM was added, and concentration to dryness was carried out again. The product was used for further reactions without further purification.

Amine F-68: 4-(3-Fluorophenyl)-4-(2-pyrrolidin-1-yl-ethoxy)-piperidine dihydrochloride Stage 1: A solution of N-boc piperidone (10.05 mmol) in THF (10 mmol) was added at 0° C. to a solution of 3-fluorophenylmagnesium bromide (15.075 mmol, 0.5 M) in THF. When the addition was complete, the reaction was stirred for 2 hours at the same temperature (TLC monitoring). Quenching with saturated aqueous NH₄Cl solution was then carried out, the reaction mixture was diluted with ethyl acetate, and the organic phase was washed in succession with water and saturated NaCl solution. The organic phase was dried over Na₂SO₄ and finally concentrated in vacuo to yield the crude product, which was purified by column chromatography (50% ethyl acetate in hexane). Yield: 40%.

Stage 2: Dry powdered KOH (9.9 g), 18-Crown-6 (1.06 g) and 2-chloroethylpyrrolidine hydrochloride (1.5 eq.) were added to a benzene solution (200 ml) of the pyridine derivative obtained in stage 1 (9.84 g, 35.3 mmol), and the resulting mixture was refluxed for 16 hours. It was then cooled to 25° C. and diluted with ethyl acetate, and the organic phase was washed in succession with water and saturated NaCl solution and finally was dried over Na₂SO₄. Concentration of the organic phase in vacuo yielded the crude product, which was purified by column chromatography (5% methanol in dichloromethane). Yield: 50%.

Stage 3: The product obtained above was dissolved in methanol; acetyl chloride (3 eq.) was added at 0° C., and stirring was carried out for 16 hours at 25° C. The solvent was then removed under reduced pressure and the residue was dried under a high vacuum.

Amine F-69: 3-[4-(3-Pyrrolidin-1-yl-propyl)-piperidin-4-yl]-pyridine dihydrochloride Stage 1: bis-(2-Chloro-ethyl)-carbamic acid tert-butyl ester (1.5 eq.), NaH (3 eq.), 18-Crown-6 (0.2 eq.) and DMF (2 ml) were added at 25° C. to a solution of 3-pyridyl acetate (2 g) in THF (36 ml), and the resulting reaction mixture was stirred for 4 hours at that temperature (TLC monitoring). The reaction was cooled to 0° C., quenched with crushed ice and diluted with ethyl acetate. The organic phase was washed in succession with water and saturated NaCl solution and finally was dried over Na₂SO₄. Concentration of the organic phase in vacuo yielded the crude product, which was purified by column chromatography. Yield: 25%.

Stage 2: A solution of the ester (1 eq.) from stage 1 in THF (2 ml/mmol) was added dropwise to a cold (0° C.) suspension of LAH (1.2 eq.) in THF (3 ml/mmol). When the addition was complete, the reaction mixture was stirred at that temperature for 2 hours, after which time the starting material had reacted completely (TLC monitoring). The reaction was quenched carefully with saturated aqueous $Na_2SO_4$ solution and filtered over Celite. The residue was washed with ethyl acetate, and the combined organic phases were dried over $Na_2SO_4$ and concentrated in vacuo to yield the crude alcohol, which was used directly in the next stage without further purification. Yield: 90%.

Stage 3: DMSO (2 eq.) was added at −78° C., under an argon atmosphere, to a solution of oxalyl chloride (1.1 eq.) in dichloromethane (3 ml/mmol), and the resulting reaction mixture was stirred at that temperature for 15 minutes. The alcohol obtained in stage 2, dissolved in dichloromethane (3 ml/mmol), was added dropwise to this cold reaction mixture, and stirring was carried out for a further hour at that temperature. Triethylamine (5 eq.) was then added to the reaction, and the mixture was brought slowly to room temperature and stirred for 1 hour at that temperature. The reaction mixture was diluted with dichloromethane, and the organic phase was washed in succession with saturated aqueous $NH_4Cl$ solution, water and saturated NaCl solution and finally dried over $Na_2SO_4$. Concentration of the organic phase in vacuo yielded the crude product, which was used directly in the next stage without further purification. Yield: 90% (crude).

Stage 4: A solution of triethyl phosphonoacetate (1.1 eq.) in THF (5 ml/mmol) was added slowly to a cold suspension (0° C.) of 60% NaH (1.1 eq.) in abs. THF (5 ml/mmol), and the resulting reaction mixture was stirred for 30 minutes at 25° C. It was then cooled to 0° C., and the aldehyde from stage 3, dissolved in abs. THF (5 ml/mmol), was added dropwise, while keeping the temperature constant, and the reaction mixture was then stirred for 16 hours at 25° C. (after that time the starting materials had reacted completely). Quenching was carried out with ice and saturated NaCl solution, the aqueous phase was extracted with ethyl acetate, and the organic phase was washed in succession with water and saturated NaCl solution. The organic phase was dried over $Na_2SO_4$ and concentrated in vacuo to yield the crude product, which was purified by column chromatography (50% ethyl acetate in hexane). Yield: 50%.

Stage 5: A solution of the ester (1 eq.) obtained in stage 4 in methanol (5 ml/mmol) was degassed for 15 minutes with argon, and then 10% Pd/C (50% by weight) was added, and the resulting reaction mixture was hydrogenated for 1 hour under atmospheric pressure (monitoring by LCMS). The reaction mixture was filtered over Celite, the residue was washed with methanol and the combined organic phases were concentrated completely to yield the crude product, which was used directly in the next stage without further purification. Yield: 95% (crude).

Stage 6: The ester obtained in stage 5, dissolved in THF (2 ml/mmol), was added dropwise under an argon atmosphere to a cold (0° C.) suspension of LAH (1.2 eq.) in THF (3 ml/mmol). When the addition was complete, the reaction mixture was stirred for 2 hours at that temperature (after which time the starting materials had reacted completely→TLC monitoring). The reaction was quenched carefully with saturated aqueous $Na_2SO_4$ solution and filtered over Celite. The residue was washed with ethyl acetate, and the combined organic phases were dried over $Na_2SO_4$ and concentrated in vacuo to yield the crude alcohol, which was used directly in the next stage without further purification. Yield: 90%.

Stage 7: TEA (21.2 mmol) and methane sulfonyl chloride (7.95 mmol) were added at 0° C. to a solution of the alcohol from stage 6 (5.3 mmol) in dichloromethane (22 ml), and the resulting reaction mixture was stirred for 2 hours at that temperature (TLC monitoring). The reaction was diluted with dichloromethane, washed in succession with water and saturated NaCl and finally dried over $Na_2SO_4$. Concentration of the organic phase in vacuo yielded the crude product, which was used directly in the next stage. Yield: quantitative.

Stage 8: Potassium carbonate (26.5 mmol) and pyrrolidine (6.36 mmol) were added to a solution of the mesyl derivative from stage 7 in toluene (30 ml), and the resulting reaction mixture was refluxed for 16 hours. It was then cooled to 25° C. and diluted with ethyl acetate, and the organic phase was washed in succession with water and saturated NaCl solution. After drying over $Na_2SO_4$, the organic phase was concentrated in vacuo to yield the crude product, which was purified by column chromatography (5% methanol in dichloromethane). Yield: 50%.

Syntheses of Individual Substances

6a) Synthesis of the Pyrimidine Derivatives G & H

General Method for the Synthesis of the Pyrimidine Derivatives G & H

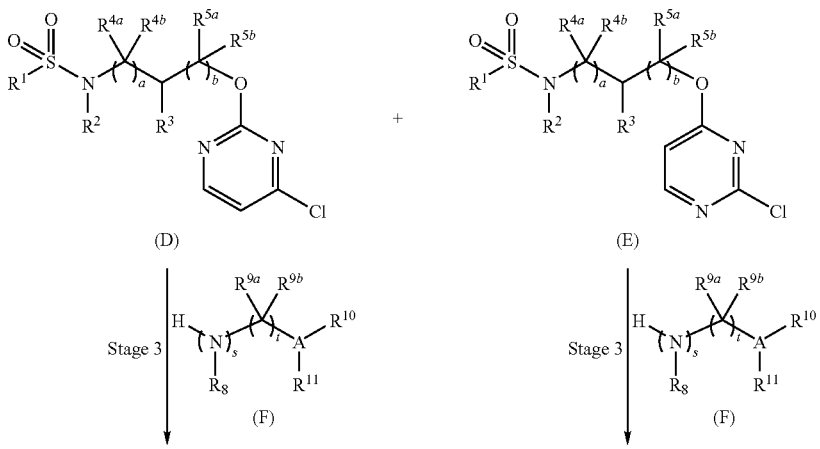

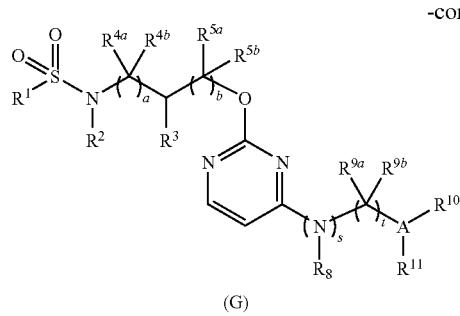
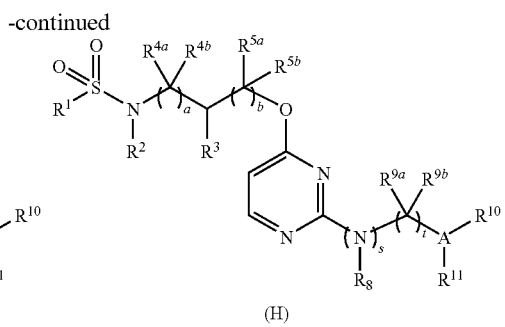

(G)           (H)

FIG. 3: Synthesis of the Pyrimidine Derivatives G & H

General working procedure GWP VI: To a solution of the pyrimidine structural unit (D or E) (1 equiv.) and diisopropylethylamine (1.5 equiv.) in isopropanol there was added the appropriate amine (F) (1.5 equiv.), and the mixture was heated for 2-5 hours at reflux. For working up, saturated sodium hydrogen carbonate solution was added to the reaction mixture, extraction was carried out 3× with ethyl acetate, and the combined organic phases were dried over magnesium sulfate and concentrated under reduced pressure. After purification by column chromatography (Alox Neutral; ethyl acetate/hexane), the desired end product (G or H) was obtained. When amine hydrochloride (F+n HCl) was used, the amount of diisopropylamine was increased to 1.5 equiv.+n equiv.

General working procedure GWP VII: The pyrimidine structural unit (D or E) (1 equiv.) was dissolved in 2-propanol; N-ethyl-diisopropylamine (1.5-4 equiv.) and the amine (F) (1.5 equiv.), optionally in the form of the corresponding hydrochloride (xHCl), were added and the mixture was refluxed for 15 hours. The reaction mixture was then cooled to room temperature, saturated sodium hydrogen carbonate solution and ethyl acetate were added, and the phases were separated. The aqueous phase was extracted with ethyl acetate, and the combined organic phases were dried over magnesium sulfate and concentrated in vacuo. The crude product was purified by column chromatography (silica gel), and the compounds according to the invention (G or H) were obtained.

General working procedure GWP VIII: The pyrimidine structural unit ((D or E) (1 equiv.) was dissolved in 1,4-dioxane; $Cs_2CO_3$ (2 equiv.) and the amine (F) (1.5 equiv.), optionally in the form of the corresponding hydrochloride (xHCl), were added and the mixture was refluxed for 16 hours. The reaction mixture was then cooled to room temperature, saturated sodium hydrogen carbonate solution and ethyl acetate were added, and the phases were separated. The aqueous phase was extracted with ethyl acetate. The combined organic phases were washed with water and saturated NaCl solution, dried over sodium sulfate and concentrated in vacuo. The crude product was purified by column chromatography (silica gel), and the compounds according to the invention (G or H) were obtained.

Specific embodiments of the compounds according to the invention prepared by these general working procedures are listed in Tables 4 and 5 shown below. The corresponding data for the compounds of type (I) are given in Table 6.

TABLE 4

Synthesis of the pyrimidine derivatives G

| Ex. No. | Structure | Name | Pyrimidine (D or E) | Amine (F) |
|---|---|---|---|---|
| G-001 | 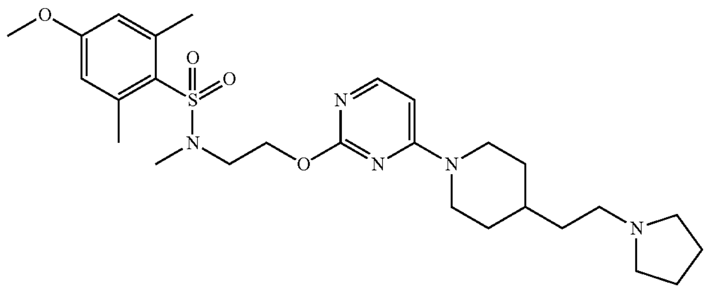 | 4-Methoxy-N,2,6-trimethyl-N-(2-(4-(4-(2-(pyrrolidin-1-yl)ethyl)piperidin-1-yl)pyrimidin-2-yloxy)ethyl)phenylsulfonamide (G-001) | N-(2-(4-Chloropyrimidin-2-yloxy)ethyl)-4-methoxy-N,2,6-trimethylphenylsulfonamide (D-01) | 4-(2-(Pyrrolidin-1-yl)ethyl)piperidine (F-03) |
| G-002 | 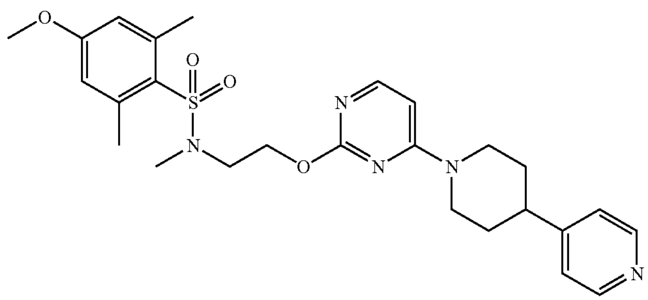 | 4-Methoxy-N,2,6-trimethyl-N-(2-(4-(pyridin-4-yl)piperazin-1-yl)pyrimidin-2-yloxy)ethyl)phenylsulfonamide (G-002) | N-(2-(4-Chloropyrimidin-2-yloxy)ethyl)-4-methoxy-N,2,6-trimethylphenylsulfonamide (D-01) | 1-(Pyridin-4-yl)piperazine (F-15) |
| G-003 | 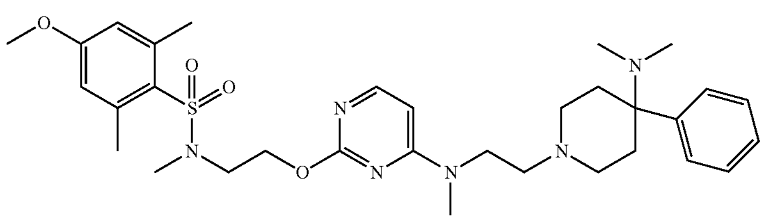 | N-(2-(4-((2-(4-(Dimethylamino)-4-phenylpiperidin-1-yl)ethyl)(methyl)amino)pyrimidin-2-yloxy)ethyl)-4-methoxy-N,2,6-trimethylphenylsulfonamide (G-003) | N-(2-(4-Chloropyrimidin-2-yloxy)ethyl)-4-methoxy-N,2,6-trimethylphenylsulfonamide (D-01) | N,N-Dimethyl-1-(2-(methylamino)ethyl)-4-phenylpiperidine-4-amine (F-09) |

TABLE 4-continued

| | | | |
|---|---|---|---|
| G-004 |  2-((1-(4-Methoxy-2,6-dimethylphenyl)sulfonyl)piperidin-2-yl)methoxy)-4-(4-(pyridin-3-yl)-4-(2-(pyrrolidin-1-yl)ethoxy)piperidin-1-yl)pyrimidine (G-004) | 4-Chloro-2-((1-(4-methoxy-2,6-dimethylphenyl)sulfonyl)-piperidin-2-yl)methoxy)-pyrimidine (D-02) | 3-(4-(2-(Pyrrolidin-1-yl)ethoxy)piperidin-4-yl)pyridine dihydrochloride (F-37) |
| G-005 |  N-Cyclopropyl-4-methoxy-2,6-dimethyl-N-(2-(4-(9-(pyridin-4-yl)-3,9-diazaspiro[5.5]undecan-3-yl)pyrimidin-2-yloxy)ethyl)phenylsulfonamide hydrochloride (G-005) | N-(2-(4-Chloropyrimidin-2-yloxy)ethyl)-N-cyclopropyl-4-methoxy-2,6-dimethylphenylsulfonamide (D-10) | 3-(Pyridin-4-yl)-3,9-diazaspiro[5.5]-undecane dihydrochloride (F-12) |
| G-006 |  N-Cyclopropyl-4-methoxy-2,6-dimethyl-N-(2-(4-(2-(1-(pyridin-4-yl)piperidin-4-yl)ethylamino)pyrimidin-2-yloxy)ethyl)phenylsulfonamide (G-006) | N-(2-(4-Chloropyrimidin-2-yloxy)ethyl)-N-cyclopropyl-4-methoxy-2,6-dimethylphenylsulfonamide (D-10) | 2-(1-(Pyridin-4-yl)-piperidin-4-yl)-ethanamine dihydrochloride (F-11) |

TABLE 4-continued

| | | | |
|---|---|---|---|
| G-007 |  | N-Cyclopropyl-4-methoxy-2,6-dimethyl-N-(2-(4-(4-(pyridin-3-yl)-4-(2-(pyrrolidin-1-yl)ethoxy)piperidin-1-yl)pyrimidin-2-yloxy)ethyl)phenylsulfonamide (G-007) | N-(2-(4-Chloropyrimidin-2-yloxy)ethyl)-N-cyclopropyl-4-methoxy-2,6-dimethylphenylsulfonamide (D-10) | 3-(4-(2-(Pyrrolidin-1-yl)ethoxy)piperidin-4-yl)pyridine dihydrochloride (F-37) |
| G-008 |  | N-Cyclopropyl-N-(2-(4-(4-hydroxy-4-(pyridin-3-yl)piperidin-1-yl)pyrimidin-2-yloxy)ethyl)-4-methoxy-2,6-dimethylphenylsulfonamide (G-008) | N-(2-(4-Chloropyrimidin-2-yloxy)ethyl)-N-cyclopropyl-4-methoxy-2,6-dimethylphenylsulfonamide (D-10) | 4-(Pyridin-3-yl)piperidin-4-ol (F-16) |
| G-009 |  | 2-Chloro-N-cyclopropyl-6-methyl-N-(2-(4-(9-(pyridin-4-yl)-3,9-diazaspiro[5.5]undecan-3-yl)pyrimidin-2-yloxy)ethyl)phenylsulfonamide (G-009) | 2-Chloro-N-(2-(4-chloropyrimidin-2-yloxy)ethyl)-N-cyclopropyl-6-methylphenylsulfonamide (D-12) | 3-(Pyridin-4-yl)-3,9-diazaspiro[5.5]-undecane dihydrochloride (F-12) |

TABLE 4-continued

| | | | |
|---|---|---|---|
| G-010 |  | N-Cyclopropyl-N-(2-(4-(9-(pyridin-4-yl)-3,9-diazaspiro[5.5]undecan-3-yl)pyrimidin-2-yloxy)ethyl)-2-(trifluoromethyl)phenylsulfonamide (G-010) | N-(2-(4-Chloropyrimidin-2-yloxy)ethyl)-N-cyclopropyl-2-(trifluoromethyl)phenylsulfonamide (D-11) | 3-(Pyridin-4-yl)-3,9-diazaspiro[5.5]undecane dihydrochloride (F-12) |
| G-011 |  ABS | 3-(2-((2S,4R)-4-Fluoro-1-(4-methoxy-2,6-dimethylphenylsulfonyl)pyrrolidin-2-yl)methoxy)pyrimidin-4-yl)-9-(pyridin-4-yl)-3,9-diazaspiro[5.5]undecane (G-011) | 4-Chloro-2-(((2S,4R)-4-fluoro-1-(4-methoxy-2,6-dimethylphenylsulfonyl)pyrrolidin-2-yl)methoxy)pyrimidine (D-13) | 3-(Pyridin-4-yl)-3,9-diazaspiro[5.5]undecane dihydrochloride (F-12) |
| G-012 |  | N-Cyclopropyl-4-methoxy-2,6-dimethyl-N-(2-(4-(4-(pyridin-4-yloxy)piperidin-1-yl)pyrimidin-2-yloxy)ethyl)phenylsulfonamide (G-012) | N-(2-(4-Chloropyrimidin-2-yloxy)ethyl)-N-cyclopropyl-4-methoxy-2,6-dimethylphenylsulfonamide (D-10) | 4-(Piperidin-4-yloxy)pyridine dihydrochloride (F-31) |

TABLE 4-continued

| | | | |
|---|---|---|---|
| G-013 | N-(2-(4-(6-(Azetidin-1-ylmethyl)-3,4-dihydroisoquinolin-2(1H)-yl)pyrimidin-2-yloxy)ethyl)-N-cyclopropyl-4-methoxy-2,6-dimethylphenylsulfonamide (G-013) | N-(2-(4-Chloropyrimidin-2-yloxy)ethyl)-N-cylcopropyl-4-methoxy-2,6-dimethylphenylsulfonamide (D-10) | 6-(Azetidin-1-ylmethyl)-1,2,3,4-tetrahydroisoquinoline dihydrochloride (F-08) |
| G-014 | N-Cyclopropyl-4-methoxy-2,6-dimethyl-N-(2-(4-(7-(pyridin-4-yl)-2,7-diazaspiro[4.4]nonan-2-yl)pyrimidin-2-yloxy)ethyl)benzenesulfonamide (G-014) | N-(2-(4-Chloropyrimidin-2-yloxy)ethyl)-N-cyclopropyl-4-methoxy-2,6-dimethylbenzenesulfonamide (D-10) | 2-(Pyridin-4-yl)-2,7-diazaspiro[4.4]nonane dihydrochloride (F-38) |
| G-015 | N-(2-(4-(9-(Azetidin-1-yl)-3-azaspiro[5.5]undecan-3-yl)pyrimidin-2-yloxy)ethyl)-N-cyclopropyl-4-methoxy-2,6-dimethylbenzenesulfonamide hydrochloride (G-015) | N-(2-(4-Chloropyrimidin-2-yloxy)ethyl)-N-cyclopropyl-4-methoxy-2,6-dimethylbenzenesulfonamide (D-10) | 9-(Azetidin-1-yl)-3-azaspiro[5.5]undecane dihydrochloride (F-39) |
| G-016 | N-Cyclopropyl-4-methoxy-2,6-dimethyl-N-(2-(4-(9-(pyridin-4-yloxy)-3-azaspiro[5.5]undecan-3-yl)pyrimidin-2-yloxy)ethyl)benzenesulfonamide (G-016) | N-(2-(4-Chloropyrimidin-2-yloxy)ethyl)-N-cyclopropyl-4-methoxy-2,6-dimethylbenzenesulfonamide (D-10) | 9-(Pyridin-4-yloxy)-3-azaspiro[5.5]undecane dihydrochloride (F-40) |

TABLE 4-continued

| | | | |
|---|---|---|---|
| G-017 | N-Cyclopropyl-N-(2-(4-(9-(3,3-difluoroazetidin-1-yl)-3-azaspiro[5.5]undecane-3-yl]pyrimidin-2-yloxy)ethyl)-4-methoxy-2,6-dimethylbenzenesulfonamide (-017) | N-(2-(4-Chloropyrimidin-2-yloxy)ethyl)-N-cyclopropyl-4-methoxy-2,6-dimethylbenzenesulfonamide (D-10) | 9-(3,3-Difluoroazetidin-1-yl)-3-azaspiro[5.5]undecane dihydrochloride (F-41) |
| G-018 | 3-(2-(1-(4-Methoxy-2,6-dimethylphenylsulfonyl)azetidin-3-yloxy)pyrimidin-4-yl)-9-(pyridin-4-yl)-3,9-diazaspiro[5.5]undecane (G-018) | 4-Chloro-2-(1-(4-methoxy-2,6-dimethylphenylsulfonyl)-azetidin-3-yloxy)pyrimidine (D-06)2-Chloro-4-(1-(4-methoxyphenylsulfonyl)-azetidin-3-yloxy)pyrimidine (E-06) | 3-(Pyridin-4-yl)-3,9-diazaspiro[5.5]-undecane dihydrochloride (F-12) |
| G-019 | N-Cyclopropyl-4-methoxy-2,6-dimethyl-N-(2-(4-(8-(pyridin-4-yl)-2,8-diazaspiro[4.5]decan-2-yl)pyrimidin-2-yloxy)ethyl)-benzenesulfonamide (G-019) | N-(2-(4-Chloropyrimidin-2-yloxy)ethyl)-N-cyclopropyl-4-methoxy-2,6-dimethylbenzenesulfonamide (D-10) | 8-(Pyridin-4-yl)-2,8-diazaspiro[4.5]decane dihydrochloride (F-42) |

TABLE 4-continued

| | Structure | Name |
|---|---|---|
| G-020 | | N-(2-(4-(3-(6-(Azetidin-1-ylmethyl)-3,4-dihydroisoquinolin-2(1H)-yl)azetidin-1-yl)pyrimidin-2-yloxy)ethyl)-N-cyclopropyl-4-methoxy-2,6-dimethyl-benzenesulfonamide (G-020) | N-(2-(4-Chloropyrimidin-2-yl)oxy)ethyl)-N-cyclopropyl-4-methoxy-2,6-dimethylbenzenesulfonamide (D-10) | 6-(Azetidin-1-ylmethyl)-2-(azetidin-3-yl)-1,2,3,4-tetrahydroisoquinoline trihydrochloride (F-43) |
| G-021 | | 2,6-Dichloro-N-cyclopropyl-3-methyl-N-[2-[4-(9-pyridin-4-yl-3,9-diazaspiro[5.5]undecan-3-yl)-pyrimidin-2-yl]oxy-ethyl]-benzenesulfonamide (G-021) | 2,6-Dichloro-N-[2-(4-chloro-pyrimidin-2-yl)oxy-ethyl]-N-cyclopropyl-3-methyl-benzenesulfonamide (D-14) | 3-(Pyridin-4-yl)-3,9-diazaspiro[5.5]-undecane dihydrochloride (F-12) |
| G-022 | | 4-Methoxy-2,6-dimethyl-N-[1-[[4-(9-pyridin-4-yl-3,9-diazaspiro[5.5]undecan-3-yl)-pyrimidin-2-yl]oxy-methyl]cyclobutyl]-benzenesulfonamide (G-022) | N-{1-[((4-Chloro-pyrimidin-2-yl)oxy-methyl]-cyclobutyl}-4-methoxy-2,6-dimethyl-benzenesulfonamide (D-15) | 3-(Pyridin-4-yl)-3,9-diazaspiro[5.5]-undecane dihydrochloride (F-12) |

TABLE 4-continued

| | | | |
|---|---|---|---|
| G-023 | N-Cyclopropyl-4-methoxy-2,6-dimethyl-N-[2-[9-pyridin-3-yl-9-(2-pyrrolidin-1-yl-ethoxy)-3-azaspiro[5.5]undecan-3-yl]-pyrimidin-2-yl)oxy-ethyl]-benzenesulfonamide (G-023) | N-(2-(4-Chloropyrimidin-2-yl)oxy)ethyl)-N-cyclopropyl-4-methoxy-2,6-dimethylphenylsulfonamide (D-10) | 3-Pyridin-3-yl-3-(2-pyrrolidin-1-yl-ethoxy)-9-azaspiro[5.5]undecane (F-44) |
| G-024 | N-[1,1-Dimethyl-2-[4-(9-pyridin-4-yl-3,9-diazaspiro[5.5]undecan-3-yl)-pyrimidin-2-yl)oxy-ethyl]-4-methoxy-2,6-dimethyl-benzenesulfonamide (G-024) | N-[2-(4-Chloropyrimidin-2-yl)oxy-1,1-dimethyl-ethyl]-4-methoxy-2,6-dimethyl-benzenesulfonamide (D-16) | 3-(Pyridin-4-yl)-3,9-diazaspiro[5.5]-undecane dihydrochloride (F-12) |
| G-025 | N-Cyclopropyl-4-methoxy-2,6-dimethyl-N-[3-[4-(9-pyridin-4-yl-3,9-diazaspiro[5.5]undecan-3-yl)-pyrimidin-2-yl)oxy-propyl]-benzenesulfonamide (G-025) | N-{3-[(4-Chloro-pyrimidin-2-yl)oxy-N-cyclopropyl-4-methoxy-2,6-dimethyl-benzenesulfonamide (D-17) | 3-(Pyridin-4-yl)-3,9-diazaspiro[5.5]-undecane dihydrochloride (F-12) |

TABLE 4-continued

| | 3-[2-[[(2S)-1-[(4-Methoxy-2,6-dimethyl-phenyl)sulfonyl]-piperidin-2-yl]-methoxy]-pyrimidin-4-yl]-9-pyridin-4-yl-3,9-diazaspiro[5.5]undecane (G-026) | 4-Chloro-2-[[(2S)-1-[(4-methoxy-2,6-dimethyl-phenyl)sulfonyl]-piperidin-2-yl]-methoxy]-pyrimidine (D-18) | 3-(Pyridin-4-yl)-3,9-diazaspiro[5.5]-undecane dihydrochloride (F-12) |
|---|---|---|---|
| G-026 | | | |

| Ex. No. | Yield | Analysis (LC/MS) | Synthesized according to |
|---|---|---|---|
| G-001 | 61%, (0.17 mmol) | R$_t$ = 2.0 min; Purity (UV 200-400 nm) 93%; m/z = 532.2 [MH]$^+$ | GWP VI |
| G-002 | 81%; (0.31 mmol) | R$_t$ = 2.1 min; Purity (UV 200-400 nm) 99%; m/z = 513.2 [MH]$^+$ | GWP VI |
| G-003 | 88%; (0.34 mmol) | R$_t$ = 1.9 min; Purity (UV 200-400 nm) 97%; m/z = 611.2 [MH]$^+$ | GWP VI |
| G-004 | 23%, (0.11 mmol) | R$_t$ = 2.1 min; Purity (UV 200-400 nm) 91%; m/z = 665.2 [MH]$^+$ | GWP VI[a] |
| G-005 | 51% (0.08 g) | R$_t$ = 2.5 min; m/z = 607.1 [MH]$^+$ | GWP VII[b] |
| G-006 | 24% (0.04 g) | R$_t$ = 2.6 min; m/z = 581.1 [MH]$^+$ | GWP VII |
| G-007 | 80% (0.24 g) | R$_t$ = 2.2 min; m/z = 651.1 [MH]$^+$ | GWP VII |
| G-008 | 74% (0.18 g) | R$_t$ = 2.3 min; m/z = 554.0 [MH]$^+$ | GWP VII |
| G-009 | 71% (0.19 g) | R$_t$ = 2.6 min; m/z = 597.2 [MH]$^+$ | GWP VII[c] |
| G-010 | 99% (0.16 g) | R$_t$ = 2.5 min; m/z = 617.4 [MH]$^+$ | GWP VII |

TABLE 4-continued

| | | | |
|---|---|---|---|
| G-011 | 79% (0.16 g) | $R_t$ = 2.5 min; m/z = 625.4 $[MH]^+$ | GWP VII |
| G-012 | 64% (0.18 g) | $R_t$ = 2.2 min; m/z = 554.0 $[MH]^+$ | GWP VII |
| G-013 | 51% (0.05 g) | $R_t$ = 2.5 min; m/z = 578.4 $[MH]^+$ | GWP VII |
| G-014 | 91% (0.09 g) | $R_s$ = 2.5 min; m/z = 579.4 $[MH]^+$ | GWP VII |
| G-015 | 88% (0.1 g) | $R_t$ = 2.5 min; m/z = 584.4 $[MH]^+$ | GWP VII[b] |
| G-016 | >99% (0.12 g) | $R_t$ = 2.8 min; m/z = 622.4 $[MH]^+$ | GWP VII |
| G-017 | 62% (0.07 g) | $R_t$ = 2.7 min; m/z = 620.5 $[MH]^+$ | GWP VII |
| G-018 | 15% (0.11 g) | $R_t$ = 2.7 min; m/z = 579.4 $[MH]^+$ | GWP VII[d] |
| G-019 | 79% (0.08 g) | $R_t$ = 2.6 min; m/z = 593.4 $[MH]^+$ | GWP VII |
| G-020 | 74% (0.08 g) | $R_t$ = 2.3 min; m/z = 633.5 $[MH]^+$ | GWP VII |
| G-021 | 61% (0.15 g) | $R_t$ = 3.7 min; m/z = 631.2 $[MH]^+$ | GWP VII |
| G-022 | 23% | $R_t$ = 2.5 min; m/z = 607.2 $[MH]^+$ | GWP VIII |
| G-023 | 49% | $R_t$ = 3.0 min; m/z = 719.5 $[MH]^+$ | GWP VIII |
| G-024 | 64% | $R_t$ = 2.7 min; m/z = 595.3 $[MH]^+$ | GWP VIII |
| G-025 | 62% | $R_t$ = 3.3 min; m/z = 621.4 $[MH]^+$ | GWP VIII |
| G-026 | 50% | $R_t$ = 3.0 min; m/z = 621.4 $[MH]^+$ | GWP VIII |

Notes on Table 4:

[a]The reaction mixture was heated for 12 hours at reflux before being worked up.

[b]The end compound (G) was converted into the corresponding hydrochloride under the action of hydrochloric acid, more preferably 2 M HCl in diethyl ether (up to 4 equiv.), in an organic solvent or solvent mixture, more preferably acetone/diethyl ether.

[c]The regiochemistry was determined by NMR: 1H NMR (600 MHz, DMSO-d$_6$) δ ppm 0.28-0.36 (m, 2 H) 0.53-0.60 (m, 2 H) 1.47-1.54 (m, 4 H) 1.53-1.60 (m, 4 H) 2.57-2.63 (m, 1 H) 2.65 (s, 3H) 3.33-3.41 (m, 4 H) 3.55-3.67 (m, 4 H) 3.71-3.77 (m, 3H) 4.44 (t, J = 6.04 Hz, 2 H) 6.47 (d, J = 6.04 Hz, 1 H) 6.77-6.84 (m, 2 H) 7.36-7.42 (m, 1 H) 7.46-7.55 (m, 1 H) 7.96 (d, J = 6.04 Hz, 1 H) 8.12 (d, J = 6.80 Hz, 2 H)

[d]A mixture of D-06/E-06 was used as starting material; the isomers were separated by column chromatography and via preparative HPLC: [15% G-018], [8% H-007] [18% G-018], [8% H-007] [contaminated with H-007].

TABLE 5

Synthesis of the pyrimidine derivatives H

| Ex. No. | Structure | Name |
|---|---|---|
| H-001 | 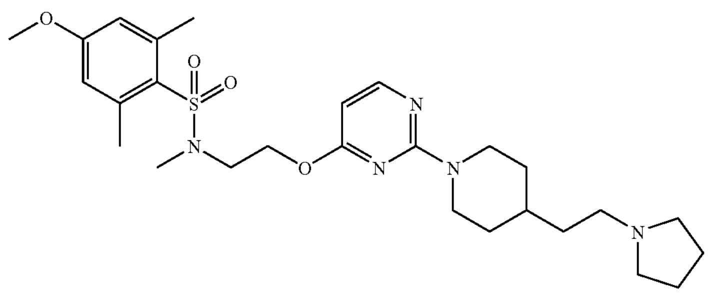 | 4-Methoxy-N-2,6-trimethyl-N-(2-{2-(4-(2-(pyrrolidin-1-yl)ethyl)piperidin-1-yl)pyrimidin-4-yl-yloxy)ethyl)phenylsulfonamide (H-001) |
| H-002 | 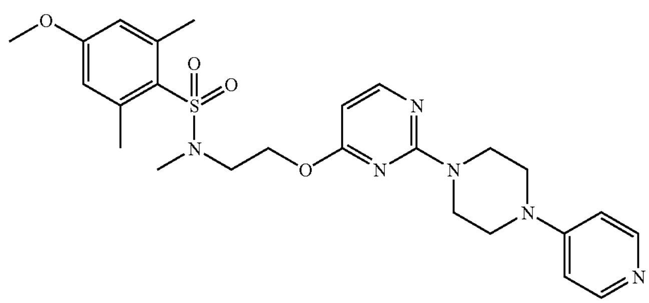 | 4-Methoxy-N,2,6-trimethyl-N-{2-(2-[4-(pyridin-4-yl)piperazin-1-yl)pyrimidin-4-yloxy)ethyl}phenylsulfonamide (H-002) |
| H-003 | 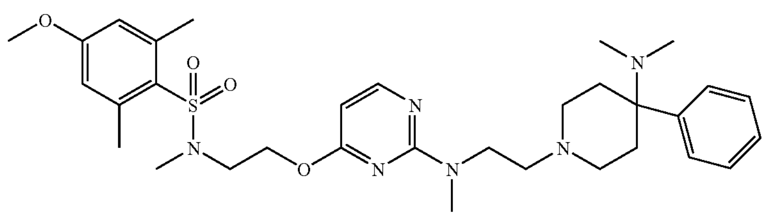 | N-(2-(2-((2-(4-(Dimethylamino)-4-phenylpiperidin-1-yl)ethyl)(methyl)amino)pyrimidin-4-yloxy)ethyl)-4-methoxy-N,2,6-trimethylphenylsulfonamide (H-003) |
| H-004 | 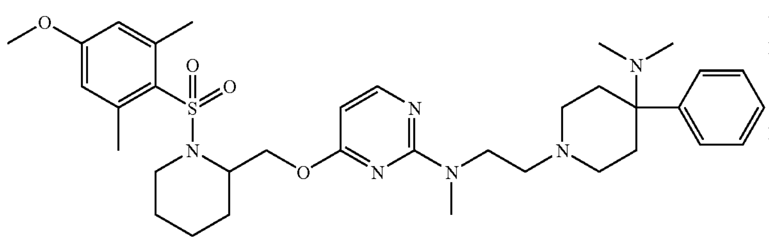 | N-(2-(4-(Dimethylamino)-4-phenylpiperidin-1-yl)ethyl)-4-((1-(4-methoxy-2,6-dimethylphenylsulfonyl)piperidin-2-yl)methoxy)-N-methyl-pyrridine-2-amine (H-004) |
| H-005 | 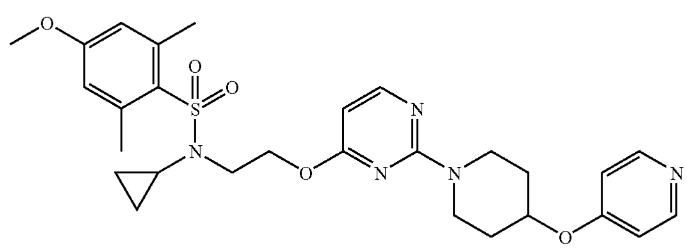 | N-Cyclopropyl-4-methoxy-2,6-dimethyl-N-(2-(2-(4-(pyridin-4-yloxy)piperidin-1-yl)pyrimidin-4-yloxy)ethyl)phenylsulfonamide (H-005) |

TABLE 5-continued

Synthesis of the pyrimidine derivatives H

H-006 — 2-Chloro-N-cyclopropyl-6-methyl-N-(2-(2-(9-(pyridin-4-yl)-3,9-diazaspiro[5.5]undecan-3-yl)pyrimidin-4-yloxy)ethyl)phenylsulfonamide (H-006)

H-007 — 3-(4-(1-(4-Methoxy-2,6-dimethylphenylsulfonyl)azetidin-3-yloxy]pyrimidin-2-yl)-9-(pyridin-4-yl)-3,9-diazaspiro[5.5]-undecane (H-007)

| Ex. No. | Pyrimidine (D or E) | Amine (F) | Yield | Analysis (LC/MS) | Synthesized according to |
|---|---|---|---|---|---|
| H-001 | N-(2-(2-Chloropyrimidin-4-yloxy)ethyl)-4-methoxy-N,2,6-trimethylphenylsulfonamide (E-01) | 4-[2-(Pyrrolidin-1-yl)ethyl]piperidine (F-03) | 61% (0.22 mmol) | $R_t$ = 2.2 min; Purity (UV 200-400 nm) 93%; m/z = 532.3 [MH]$^+$ | GWP VI |
| H-002 | N-(2-(2-Chloropyrimidine-4-yloxy)ethyl)-4-methoxy-N-2,6-trimethylphenylsulfonamide E-01 | 1-(Pyridin-4-yl)piperazine (F-15) | 58.2% (0.23 mmol) | $R_t$ = 2.8 min; Purity (UV 200-400 nm) 99%; m/z = 513.2 [MH]$^+$ | GWP VI |
| H-003 | N-(2-(2-Chloropyrimidin-4-yloxy)ethyl)-4-methoxy-N,2,6-trimethylphenylsulfonamide E-01 | N,N-Dimethyl-1-(2-(methylamino)ethyl)-4-phenylpiperidine-4-amine (F-09) | 73% (0.28 mmol) | $R_t$ = 2.5 min; Purity (UV 200-400 nm) 91%; m/z = 611.1 [MH]$^+$ | GWP VI |
| H-004 | 2-Chloro-4-((1-(4-methoxy-2,6-dimethlphenylsulfonyl)-piperidin-2-yl)methoxy)-pyrridine (E-02) | N,N-Dimethyl-1-(2-(methylamino)ethyl)-4-phenylpiperidin-4-amine (F-09) | 71.6% (0.25 mmol) | $R_t$ = 2.7 min; Purity (UV 200-400 nm) 99%; m/z = 651.3 [MH]$^+$ | GWP VI |
| H-005 | N-(2-(2-Chloropyrimidin-4-yloxy)ethyl)-N-cyclopropyl-4-methoxy-2,6-dimethylphenylsulfonamide (E-10) | 4-(Piperidin-4-yloxy)pyridine dihydrochloride (F-31) | 89% (0.18 g) | $R_t$ = 2.8 min; m/z = 554.1 [MH]$^+$ | GWP VII |
| H-006 | N-(2-(2-Chloropyrimidin-4-yloxy)ethyl)-N-cyclopropyl-4-methoxy-2,6-dimethylphenylsulfonamide (E-10) | 3-(Pyridin-4-yl)-3,9-diazaspiro[5.5]-undecane dihydrochloride (F-12) | 76% (0.17 g) | $R_t$ = 3.0 min; m/z = 597.2 [MH]$^+$ | GWP VII[a] |
| H-007 | 4-Chloro-2-(1-(4-methoxy-2,6-dimethylphenylsulfonyl)-azetidin-3-yloxy)pyrimidine (D-06)/2-Chloro-4-(1-(4-methoxy-2,6-dimethyl-phenylsulfonyl)azetidin-3-yloxy)pyrimidine (E-06) | 3-(Pyridin-4-yl)-3,9-diazaspiro[5.5]-undecane dihydrochloride (F-12) | 8% (0.06 g) | $R_t$ = 3.3 min; m/z = 579.4 [MH]$^+$ | GWP VII[b] |

[a] The regiochemistry was determined by NMR: 1H NMR (600 MHz, DMSO-$d_6$) d ppm 0.24-0.33(m, 2 H) 0.51-065(m, 2 H) 1.43-1.53(m, 4 H) 1.53-1.61(m, 4 H) 2.64(s, 1 H) 2.65(s, 3 H) 3.32-3.38(m, 4 H) 3.73-3.77(m, 6 H) 4.51(t, J = 5.67 Hz, 2 H) 5.97(d, J = 6.04 Hz, 1 H) 6.79(d, J = 6.80 Hz, 2 H) 7.37-7.41(m, 1 H) 7.45-7.54(m, 2 H) 8.07(d, J = 6.29 Hz, 1 H) 8.12(d, J = 6.04 Hz, 2 H)
[b] A mixture of D-06/E-06 was used as starting material; the isomers were separated by column chromatography and via preparative HPLC: [15% G-018], [8% H-007] [18% G-018, contaminated with H-007].

6b) Synthesis of the Pyrimidine Derivatives I

EXAMPLE I-001

N-Cyclopropyl-4-methoxy-2,6-dimethyl-N-(2-(6-(9-(pyridin-4-yl)-3,9-diazaspiro[5.5]undecan-3-yl)pyrimidin-4-yloxy)ethyl)benzenesulfonamide

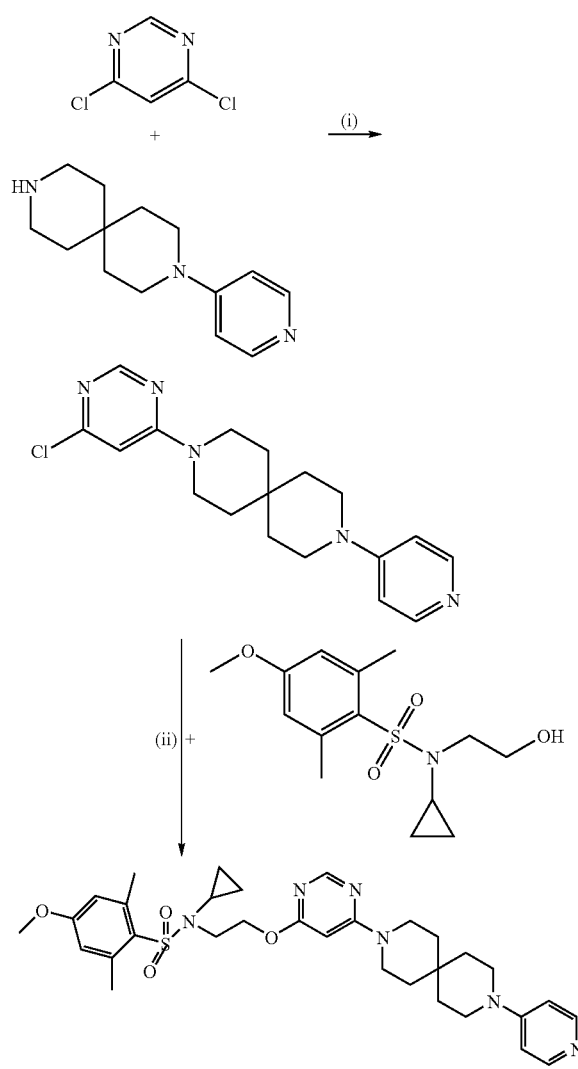

(i) To a solution of 4,6-dichloropyrimidine (1.35 mmol, 1 equiv.) in acetone there was added potassium carbonate (4 equiv.), followed by 3-(pyridin-4-yl)-3,9-diazaspiro[5.5]undecane (F-12, free base) (1 equiv.). The resulting solution was refluxed overnight and then the solvent was removed in vacuo. The residue was taken up in dichloromethane and washed with water and saturated sodium chloride solution. The organic phase was dried over magnesium sulfate and concentrated in vacuo, and the crude product was purified by column chromatography (Alox-neutral). Yield: 49%.

(ii) To a suspension of sodium hydride (7.28 mmol, 10 equiv.) in tetrahydrofuran (10 ml) there was added, at 0° C., N-cyclopropyl-N-(2-hydroxyethyl)-4-methoxy-2,6-dimethylphenylsulfonamide (C-10) (0.8 mmol, 1.1 equiv.), followed by 3-(6-chloro-pyrimidin-4-yl)-9-(pyridin-4-yl)-3,9-diazaspiro[5.5]undecane (0.73 mmol, 1 equiv.). The reaction mixture was stirrred overnight at room temperature; water was then added and the mixture was diluted with ethyl acetate. The organic phase was extracted with water and saturated sodium chloride solution, dried ($Na_2SO_4$) and concentrated in vacuo. The crude product was purified by column chromatography (Alox-neutral). Yield: 7%. $R_f$=3.4 min; m/z=607.5 $[MH]^+$

EXAMPLE I-002

N-Cyclopropyl-4-methoxy-2,6-dimethyl-N-[2-[methyl-[6-(9-pyridin-4-yl-3,9-diazaspiro[5.5]undecan-3-yl)-pyrazin-2-yl]-amino]-ethyl]-benzenesulfonic acid amide (I-002)

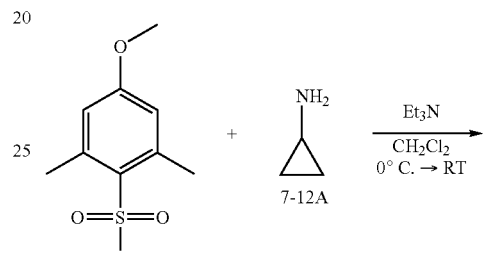

A solution of 7-12A and triethylamine (40.2 ml, 288 mmol) in dichloromethane (150 ml) was added at 0° C. to a solution of dimethylmethoxysulfonyl chloride (32.2 g; 137 mmol) in dichloromethane (150 ml) and stirring was carried out overnight at room temperature. The reaction mixture was washed with aqueous 1 M $KHSO_4$ solution and saturated NaCl solution, dried over sodium sulfate and concentrated under reduced pressure. 7-12B (33.3 g, 95%) was obtained.

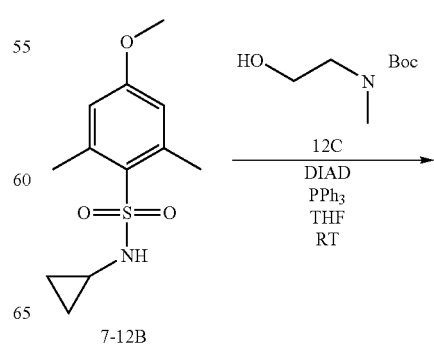

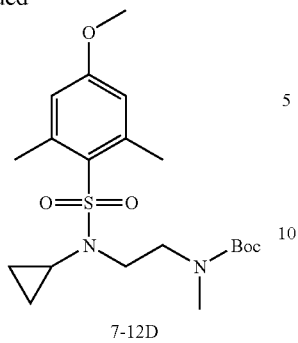

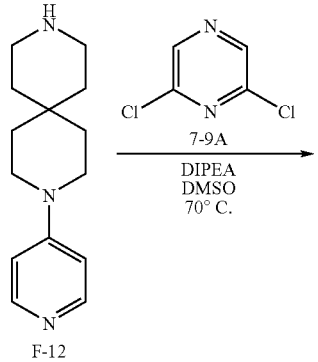

DIAD (8.22 ml, 42.3 mmol) was added to a solution of PPh₃ (12.33 g, 47.0 mmol) in THF (60 ml), and stirring was carried out for 5 minutes. 12C (4.94 g, 28.2 mmol) in THF (60 ml) and 7-12B (6.00 g, 23.5 mmol) in THF (60 ml) were then added and stirring was carried out overnight at room temperature. The reaction mixture was concentrated under reduced pressure and the crude product was purified by column chromatography (silica (~500 g); heptane/EtOAc, 4:1→3:1). Yield: 10.81 g.

F-12 (1.00 g, 4.23 mmol) and DIPEA (1.51 ml, 8.65 mmol) were added to a solution of 7-9A (0.708 g, 4.75 mmol) in DMSO (3 ml), and the mixture was heated for 5 hours at 70° C. The reaction mixture was concentrated under reduced pressure and purified by column chromatography (silica; CH₂Cl₂/(7 M NH₃ in MeOH), 98:2→9:1). Yield: 319 mg (21%).

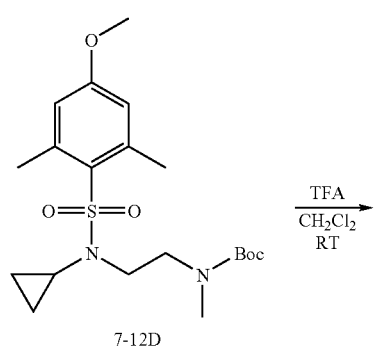

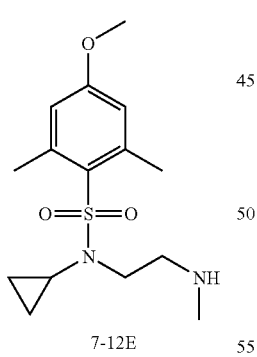

Trifluoroacetic acid (10 ml, 130 mmol) was added to a solution of 7-12D (10.81 g, 23.5 mmol) in dichloromethane (100 ml), and stirring was carried out overnight at room temperature. The reaction mixture was concentrated under reduced pressure and the crude product was purified by column chromatography (silica; CH₂Cl₂/(7 M NH₃ in MeOH), 98:2→95:5). 7-12E was obtained (6.35 g, 86%).

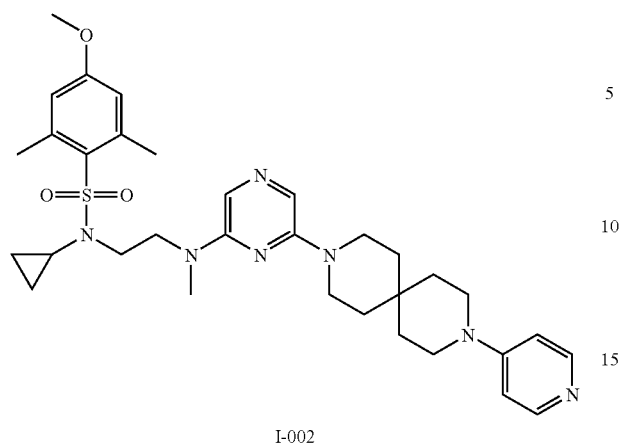

I-002

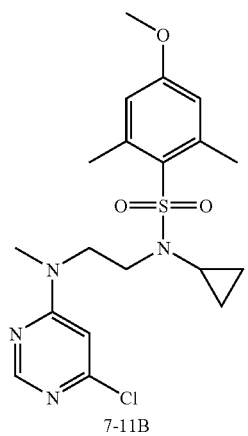

7-11B 7-9B (400 mg, 1.16 mmol) and 7-12E (400 mg, 1.28 mmol) were dissolved in toluene (5 ml); Pd$_2$(dba)$_3$ (43 mg, 0.047 mmol) and BINAP (44 mg, 0.070 mmol) were added, and the reaction mixture was flushed with argon for 10 minutes. The mixture was then heated to 100° C., stirred for 10 minutes at that temperature and cooled to room temperature; Cs$_2$CO$_3$ (57 mg, 0.17 mmol) was added and stirring was carried out for 5 hours at 100° C. After cooling to room temperature, the mixture was filtered over Celite, the filtrate was concentrated and the residue was purified by column chromatography (silica; CH$_2$Cl$_2$/(7 M NH$_3$ in MeOH), 95:5→96.5:3.5), followed by preparative LC-MS. The resulting fractions were collected, freeze-dried, taken up in DCM and concentrated (2×), taken up in DCM and dried over sodium sulfate and concentrated. Yield: 137 mg (19%).

EXAMPLE I-003

N-Cyclopropyl-4-methoxy-2,6-dimethyl-N-[2-[methyl-[6-(9-pyridin-4-yl-3,9-diazaspiro[5.5]undecan-3-yl)-pyrimidin-4-yl]amino]-ethyl]-benzenesulfonic acid amide (I-003)

DIPEA (0.839 ml, 4.80 mmol) was added to a solution of 7-11A (0.477 g, 3.20 mmol) and 7-12E (1.00 g, 3.20 mmol) in i-PrOH (2.5 ml), and stirring was carried out overnight at 70° C. The reaction mixture was cooled to room temperature, filtered, washed with 2-propanol and dried. Yield: 0.893 g (66%).

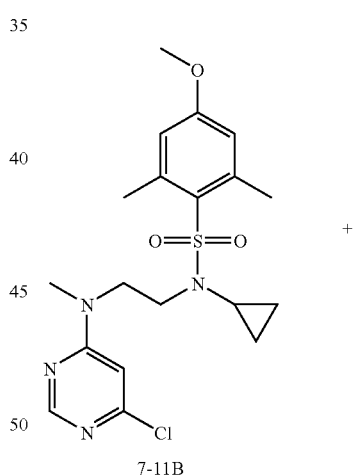

7-11B

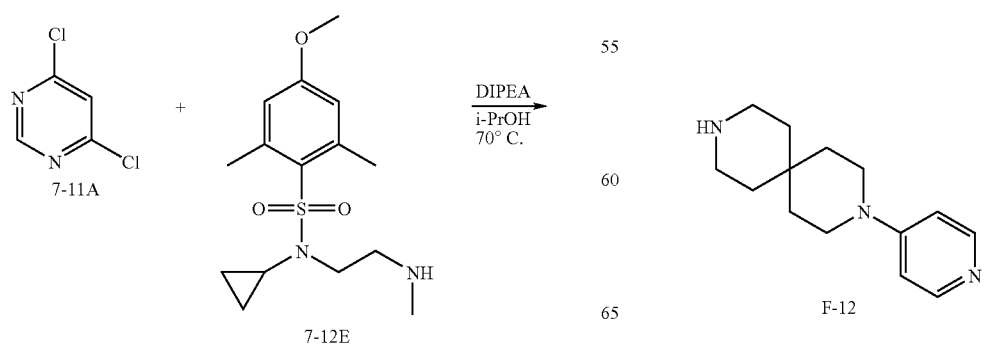

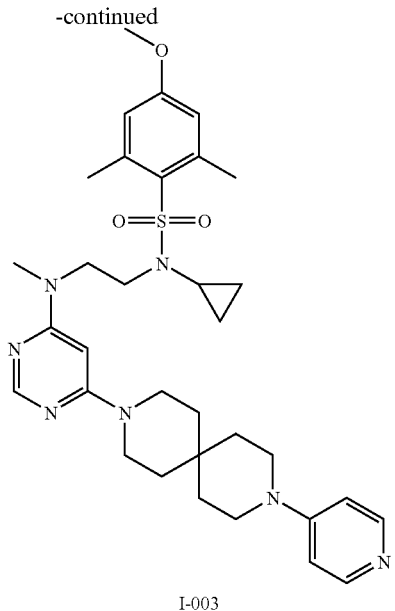

I-003

7-11B (400 mg, 0.941 mmol), F-12 (218 mg, 0.941 mmol), Pd$_2$(dba)$_3$ (35 mg, 0.038 mmol) and BINAP (35 mg, 0.056 mmol) were dissolved in succession in toluene (5 ml), and the solution was flushed with argon for 10 minutes. The reaction mixture was heated to 100° C., stirred for 10 minutes at that temperature and cooled to room temperature; Cs$_2$CO$_2$ (368 mg, 1.13 mmol) was added, and stirring was carried out overnight at 100° C. under argon. After cooling to room temperature, the mixture was concentrated under reduced pressure. The residue was purified by column chromatography (silica; CH$_2$Cl$_2$/(7 M NH$_3$ in MeOH), 98:2→95:5). Yield: 192 mg (33%).

EXAMPLE I-004

N-Cyclopropyl-4-methoxy-2,6-dimethyl-N-[2-[methyl-[2-(9-pyridin-4-yl-3,9-diazaspiro[5.5]undecan-3-yl)-pyrimidin-4-yl]-amino]-ethyl]-benzenesulfonic acid amide (I-004)

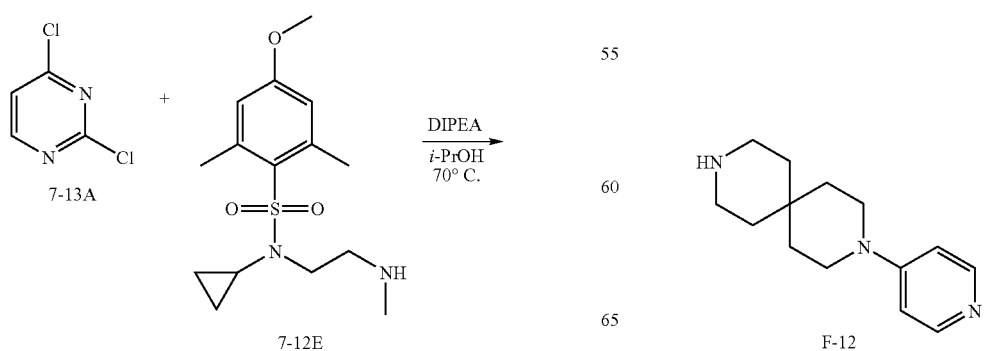

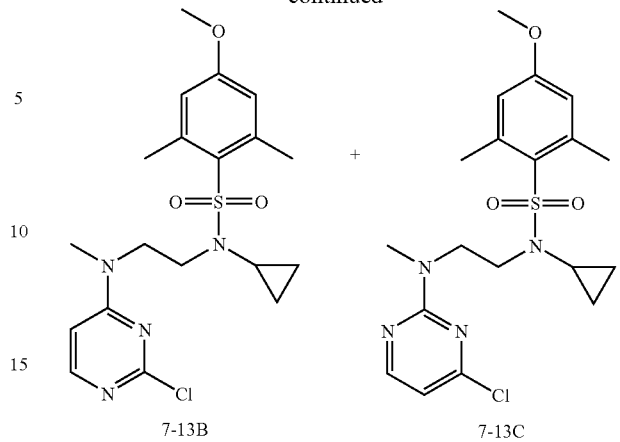

DIPEA (0.839 ml, 4.80 mmol) was added to a solution of 7-13A (0.477 g, 3.20 mmol) and 7-12E (1.00 g, 3.20 mmol) in i-PrOH (2.5 ml) (0.839 ml, 4.80 mmol), and stirring was carried out overnight at 70° C. The reaction mixture was cooled to room temperature and concentrated, and the crude product was purified by column chromatography (silica; heptane/EtOAc, 1:1) and separated into 7-13B (889 mg, 65%) and 7-13C (not pure). 7-13C was again purified by column chromatography (silica; heptane/EtOAc, 3:1) (114 mg, 8%). Yield:0.889 g; (65%); 7-13B, 0.114 g; 8%; 7-13C.

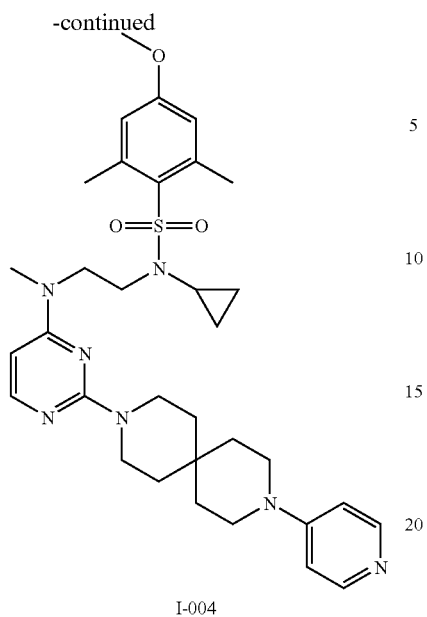

I-004

7-13B (400 mg, 0.941 mmol), F-12 (218 mg, 0.941 mmol), Pd$_2$(dba)$_3$ (35 mg, 0.038 mmol) and BINAP (35 mg, 0.056 mmol) were dissolved in succession in toluene (5 ml), and the solution was flushed for 10 minutes with argon. The reaction mixture was heated to 100° C., stirred for 10 minutes at that temperature and cooled to room temperature; Cs$_2$CO$_3$ (368 mg, 1.13 mmol) was added and stirring was carried out overnight at 100° C. under argon. After cooling to room temperature, concentration was carried out under reduced pressure. The residue was taken up in DCM/7M NH$_3$ in MeOH, filtered and concentrated. The crude product was purified by column chromatography (silica; CH$_2$Cl$_2$/(7 M NH$_3$ in MeOH), 98:2→95:5). Yield: 308 mg, (53%).

EXAMPLE I-005

N-Cyclopropyl-4-methoxy-2,6-dimethyl-N-[2-[methyl-[4-(9-pyridin-4-yl-3,9-diazaspiro[5.5]undecan-3-yl)-pyrimidin-2-yl]-amino]-ethyl]-benzenesulfonic acid amide (I-005)

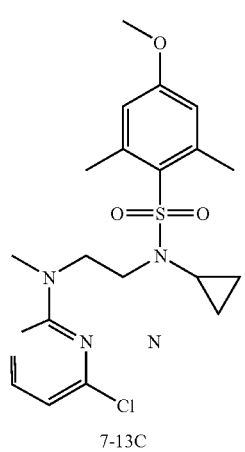

7-13C

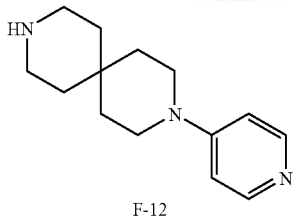

F-12

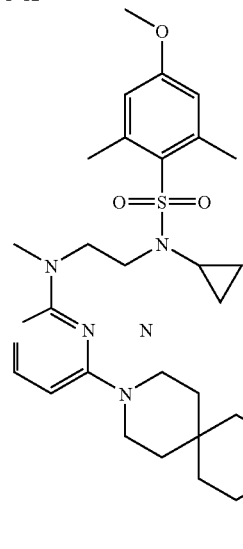

I-005

7-13C (165 mg, 0.165 mmol), F-12 (38 mg, 0.165 mmol), Pd$_2$(dba)$_3$ (6 mg, 0.07 mmol) and BINAP (6 mg, 0.07 mmol) were dissolved in succession in toluene (1 ml), and the solution was flushed for 10 minutes with argon. The reaction mixture was heated to 100° C., stirred at that temperature for 10 minutes and cooled to room temperature; Cs$_2$CO$_3$ (64 mg, 0.198 mmol) was added, and stirring was carried out overnight at 100° C. under argon. After cooling to room temperature, the mixture was concentrated under reduced pressure. The residue was purified by preparative TLC (silica; CH$_2$Cl$_2$/(7 M NH$_3$ in MeOH), 95:5).
Yield: 51 mg (50%)

EXAMPLE I-006

N-Cyclopropyl-4-methoxy-2,6-dimethyl-N-[3-[6-(9-pyridin-4-yl-3,9-diazaspiro[5.5]undecan-3-yl)-pyrazin-2-yl]-propyl]-benzenesulfonic acid amide (I-006)

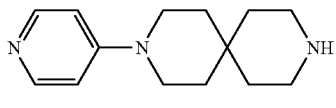

F-12

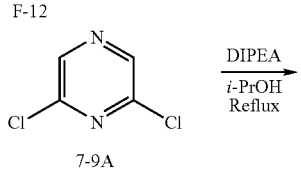

7-9A

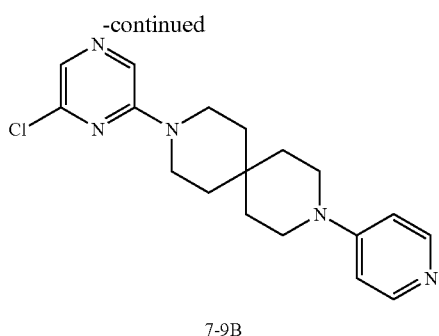

7-9B

DIPEA (5.75 ml, 32.9 mmol) and 2,6-dichloropyrazine (7-9A, 4.90 g, 32.9 mmol) were added to a solution of F-12 (7.61 g, 32.9 mmol) in i-PrOH (20 ml), and the mixture was heated overnight at reflux. Further 2,6-dichloropyrazine 7-9A (1.17 g, 7.8 mmol) and DIPEA (1.4 ml, 8.0 mmol) were then added, and refluxing was carried out for a further 4 hours. The reaction solution was concentrated to dryness under reduced pressure and purified by column chromatography (silica, $CH_2Cl_2$/(7 M $NH_3$ in MeOH, 98:2). Yield: 5.6 g (50%).

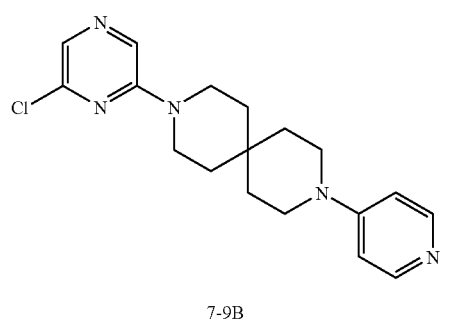

7-9B

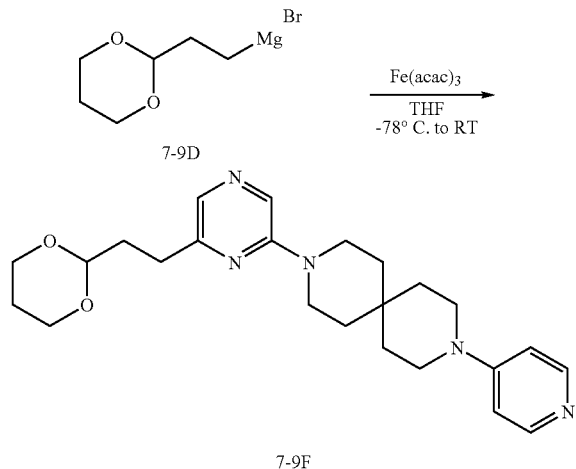

7-9F

A solution of 7-9B (4.70 g, 13.67 mmol) and Fe(acac)$_3$ (483 mg, 1.37 mmol) in THF (200 ml) was cooled to −78° C., and a solution of (2-(1,3-dioxan-2-yl)ethyl)-magnesium bromide (7-9D, 0.5 M in THF 137 ml, 68.3 mmol) was added thereto. The reaction mixture was warmed slowly to room temperature, stirred for 3 hours and cooled to −78° C. again. (2-(1,3-Dioxan-2-yl)ethyl)magnesium bromide (7-9D, 0.5 M in THF, 82 ml, 41.0 mmol) was metered in dropwise and the mixture was then warmed slowly to room temperature. Saturated $NH_4Cl$ (600 ml) was added, and the reaction mixture was extracted with dichloromethane (500 ml). The combined organic phases were washed with saturated NaCl solution and the combined aqueous phases were extracted with DCM (2×200 ml). The combined organic phases were dried over sodium sulfate, concentrated under reduced pressure and purified by column chromatography (silica, $CH_2Cl_2$/(7 M $NH_3$ in MeOH), 98:2). Yield: 4.92 g, 85% 7-9F.

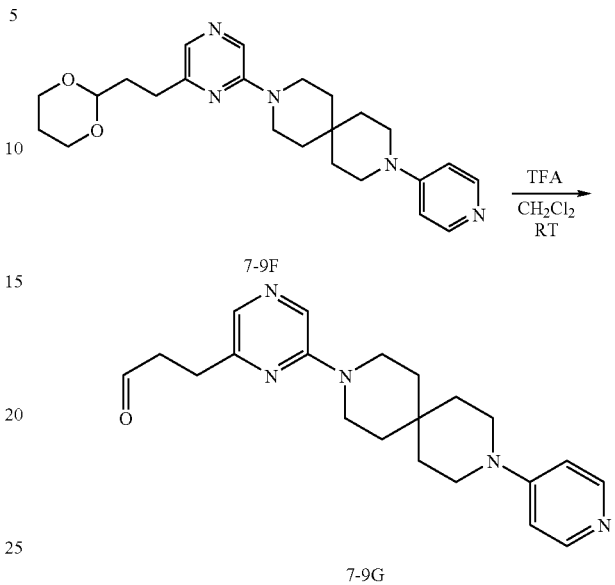

A solution of acetal 7-9F (1.0 g, 2.36 mmol) in TFA (148 g, 1.3 mol) and $H_2O$ (20 ml) was stirred for 2 hours at room temperature and then concentrated to dryness. The residue was taken up in $H_2O$ (50 ml), toluene (2×50 ml) and $CH_2Cl_2$ (3×50 ml) and concentrated again in each case. The crude product was taken up in $CH_2Cl_2$ (100 ml), washed with saturated $NaHCO_3$ solution, dried over sodium sulfate and concentrated to dryness under reduced pressure. Yield: 761 mg (88%).

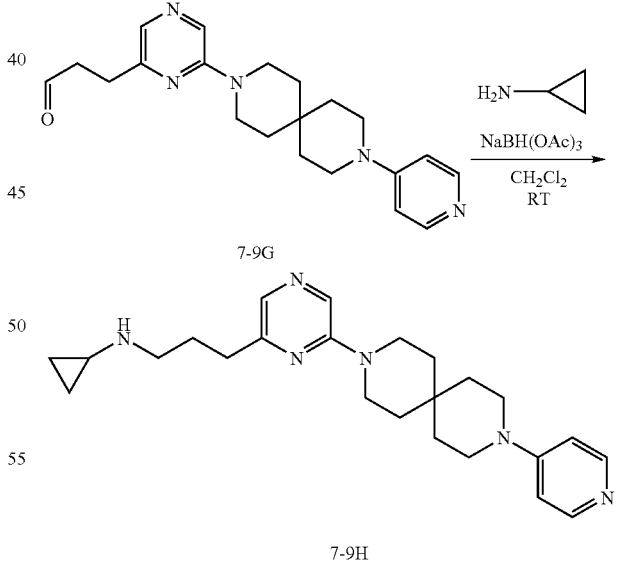

Cyclopropylamine (587 µl, 8.33 mmol) and NaBH(OAc)$_3$ (353 mg, 1.67 mmol) were added to a solution of aldehyde 7-9G (761 mg, 2.08 mmol) in $CH_2Cl_2$ (2 ml), and the mixture was stirred overnight at room temperature. The reaction mixture was concentrated to dryness under reduced pressure and the crude product was purified by column chromatography (silica, $CH_2Cl_2$/(7 M $NH_3$ in MeOH), 98:2). Yield: 313 mg (37%).

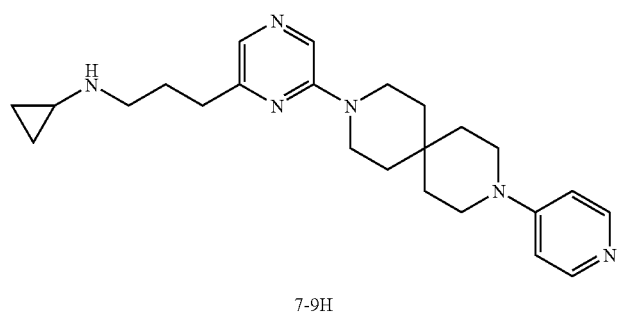

7-9H

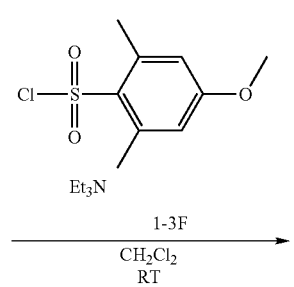

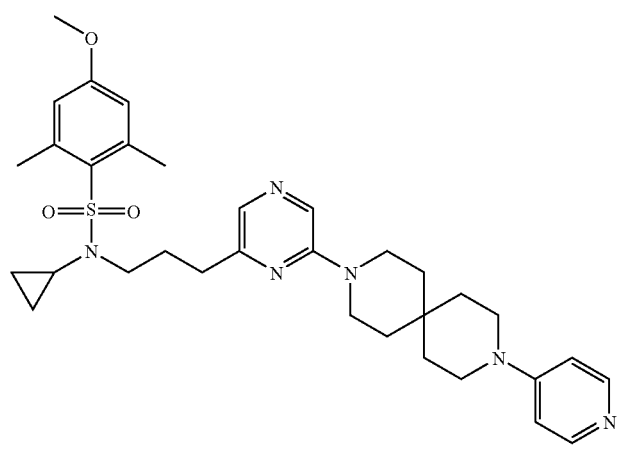

I-0006

A solution of sulfonyl chloride 1-3F (271 mg, 1.155 mmol) in CH$_2$Cl$_2$ (5 ml) was added to a solution of amine 7-9H (313 mg, 0.77 mmol) in CH$_2$Cl$_2$ (5 ml) and Et$_3$N (268 μl, 1.92 mmol), and the mixture was stirred overnight at room temperature. The reaction mixture was concentrated to dryness and purified by column chromatography (silica, CH$_2$Cl$_2$/(7 M NH$_3$ in MeOH), 99:1). Yield: 417 mg (90%).

EXAMPLE I-007

N-Cyclopropyl-4-methoxy-2,6-dimethyl-N-[3-[2-(9-pyridin-4-yl-3,9-diazaspiro[5.5]undecan-3-yl)-pyrimidin-4-yl]-propyl]-benzenesulfonic acid amide
(I-007)

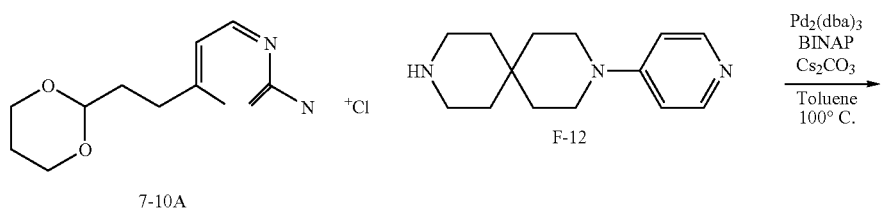

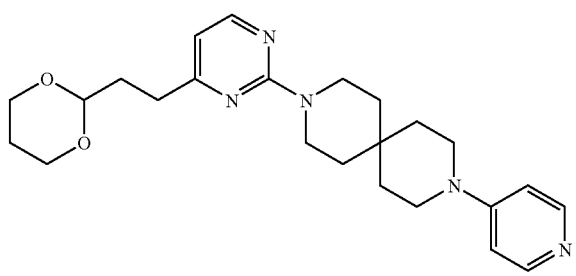

7-10C

Cs₂CO₃ (3.25 g, 9.97 mmol), BINAP (310 mg, 499 μmol) and Pd₂(dba)₃ (304 mg, 332 μmol) were added in succession to a solution of 7-10A (1.90 g, 8.31 mmol), F-12 (1.92 g, 8.31 mmol) in dry toluene (50 ml), and the solution was flushed for 15 minutes with argon. The reaction mixture was heated to 100° C., stirred for 3 hours at that temperature and cooled overnight to room temperature. The reaction mixture was filtered over sodium sulfate and washed with dichloromethane. The filtrate was washed with saturated NaHCO₃ solution and saturated NaCl solution, dried over sodium sulfate and concentrated. The crude product was purified by column chromatography (silica, CH₂Cl₂/(7 M NH₃ in MeOH), 98:2). Yield: 750 mg (21%).

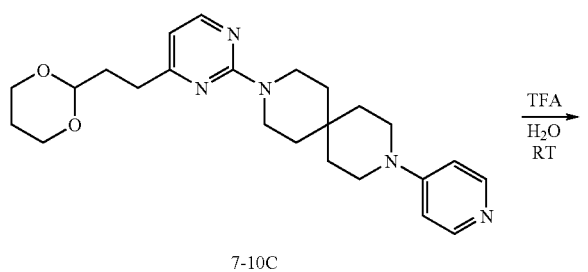

7-10C

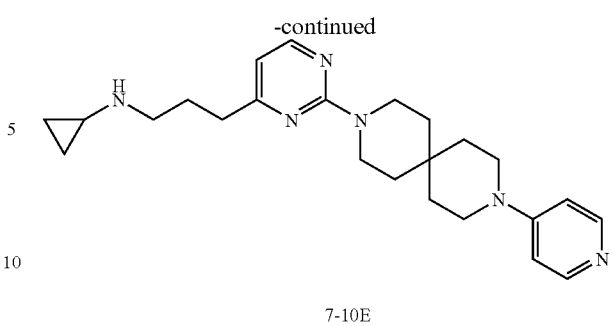

7-10E

Cyclopropylamine (1.25 ml, 17.7 mmol) and NaBH(OAc)₃ (751 mg, 3.54 mmol) were added to a solution of aldehyde 7-10D (780 mg, 1.77 mmol) in CH₂Cl₂ (10 ml) and the mixture was stirred for 2 hours at room temperature. The reaction mixture was filtered over a little sodium sulfate, the filtrate was concentrated to dryness under reduced pressure, and the crude product was purified by column chromatography (silica, CH₂Cl₂/(7 M NH₃ in MeOH), 98:2). Yield: 313 mg (37%).

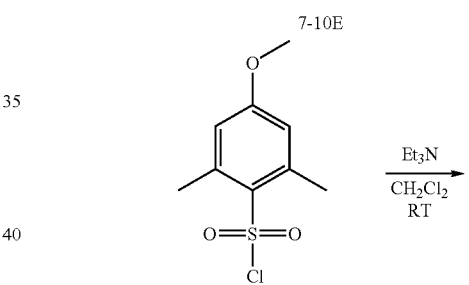

7-10E

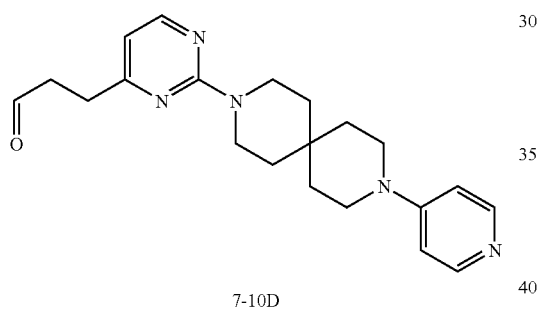

7-10D

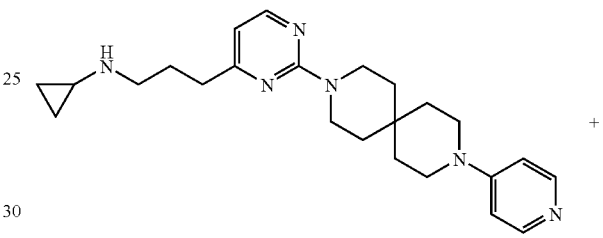

A solution of acetal 7-10C (750 mg, 1.77 mmol) in TFA (50 ml, 673 mmol) and H₂O (10 ml) was stirred for 2 hours at room temperature and then concentrated to dryness. The residue was taken up in dichloromethane (2×50 ml), toluene (50 ml) and dichloromethane (50 ml) and concentrated again in each case. The crude product was taken up in DCM (30 ml) and washed with saturated NaHCO₃ solution (100 ml), dried over sodium sulfate and concentrated to dryness under reduced pressure. Yield: 780 mg (100%).

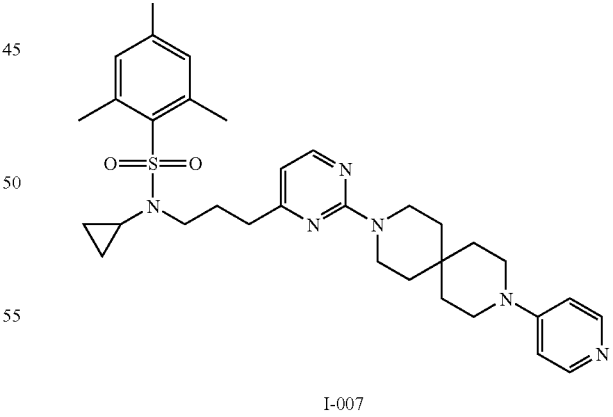

I-007

A solution of 4-methoxy-2,6-dimethylbenzenesulfonic acid chloride (398 mg, 1.70 mmol) in CH₂Cl₂ (10 ml) was added at 0° C. to a solution of amine 7-10E (460 mg, 1.13 mmol) and Et₃N (394 μl, 2.83 mmol) in CH₂Cl₂ (15 ml), and the mixture was stirred overnight at room temperature. The reaction mixture was concentrated to dryness and purified by column chromatography (silica, CH₂Cl₂/(7 M NH₃ in MeOH), 98:2). Yield: 325 mg (48%).

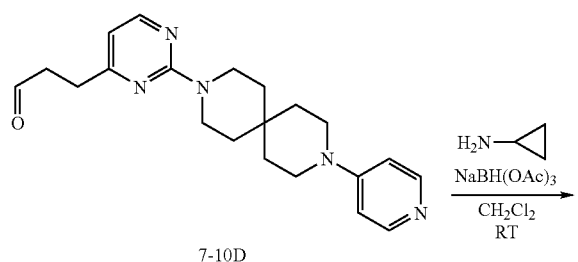

7-10D

EXAMPLE I-008

N-Cyclopropyl-N-[3-[2-(9-pyridin-4-yl-3,9-diaza-spiro[5.5]-undecan-3-yl)-pyrimidin-4-yl]-propyl]-3-(trifluoromethyl)-benzenesulfonic acid amide (I-008)

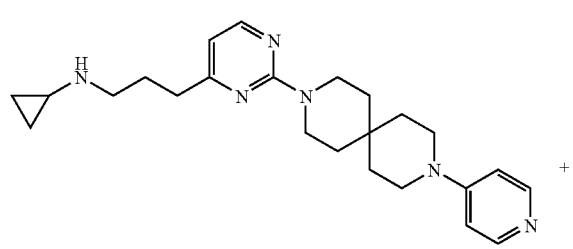

7-10E

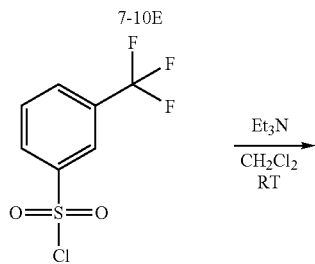

+

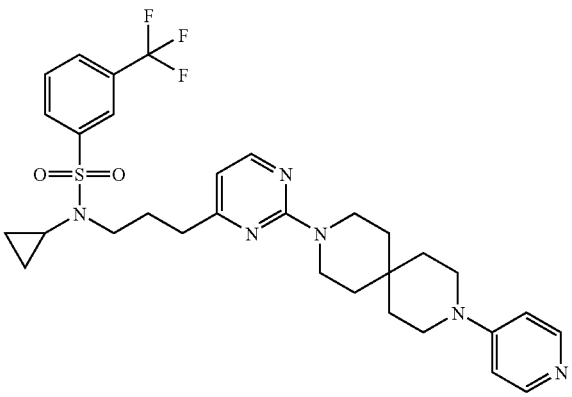

I-008

A solution of 3-(trifluoromethyl)phenyl-1-sulfonyl chloride (82 µl, 509 µmol) in $CH_2Cl_2$ (5 ml) was added at 0° C. to a solution of amine 7-10E (138 mg, 339 µmol) and $Et_3N$ (118 µl, 849 µmol) in $CH_2Cl_2$ (5 ml), and the mixture was stirred at room temperature for 2 hours. The reaction mixture was concentrated to dryness and purified by column chromatography (silica, $CH_2Cl_2$/(7 M $NH_3$ in MeOH), 99:1).

Yield: 61 mg (30%)

TABLE 6

Synthesis of derivatives I

| Ex. No. | Structure | Name | Amine (F) | Yield last stage | Analysis (LC/MS)[1] |
|---|---|---|---|---|---|
| I-001 | 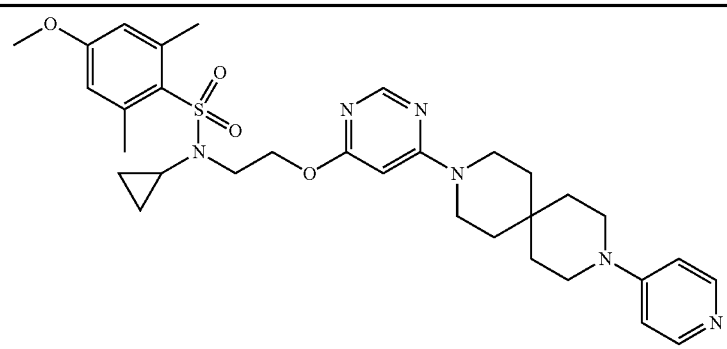 | N-Cyclopropyl-4-methoxy-2,6-dimethyl-N-[2-[[6-[9-(4-pyridyl)-3,9-diazaspiro[5.5]undecan-3-yl]-4-pyrimidinyl]oxy]ethyl]phenylsulfonamide (I-001) | 3-(Pyridin-4-yl)-3,9-diazaspiro[5.5]undecane (F-12) | 7% | $R_t = 3.4$ min; m/z = 607.5 [MH]$^+$ |
| I-002 | 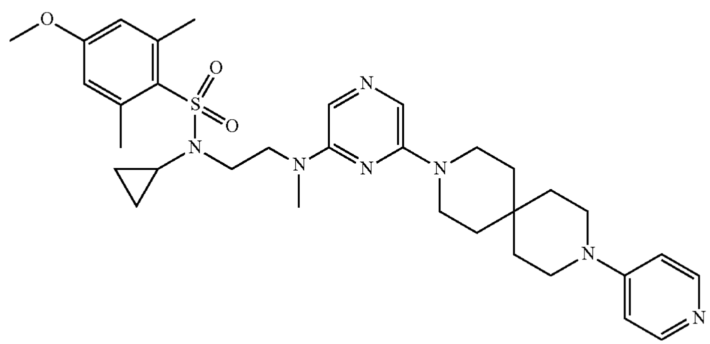 | N-Cyclopropyl-4-methoxy-2,6-dimethyl-N-[2-[methyl-[6-(9-pyridin-4-yl-3,9-diazaspiro[5.5]undecan-3-yl)-pyrazin-2-yl]-amino]-ethyl]-benzenesulfonic acid amide (I-002) | 3-(Pyridin-4-yl)-3,9-diazaspiro[5.5]undecane (F-12) | 137 mg (19%) | $R_t = 3.4$ min; m/z = 620.4 [MH]$^+$ |

TABLE 6-continued

Synthesis of derivatives I

| Ex. No. | Structure | Name | Amine (F) | Yield last stage | Analysis (LC/MS)[1] |
|---|---|---|---|---|---|
| I-003 | 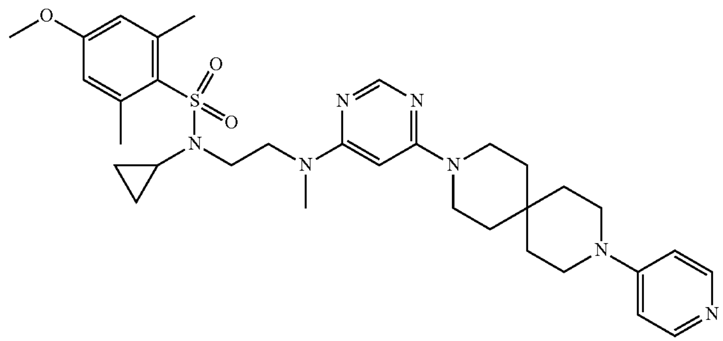 | N-Cyclopropyl-4-methoxy-2,6-dimethyl-N-[2-[methyl-[6-(9-pyridin-4-yl-3,9-diazaspiro[5.5]undecan-3-yl)-pyrimidin-4-yl]-amino]-ethyl]-benzenesulfonaic acid amide (I-003) | 3-(Pyridin-4-yl)-3,9-diazaspiro[5.5]-undecane (F-12) | 192 mg (33%) | $R_t$ = 3.3 min; m/z = 620.4 [MH]+ |
| I-004 | 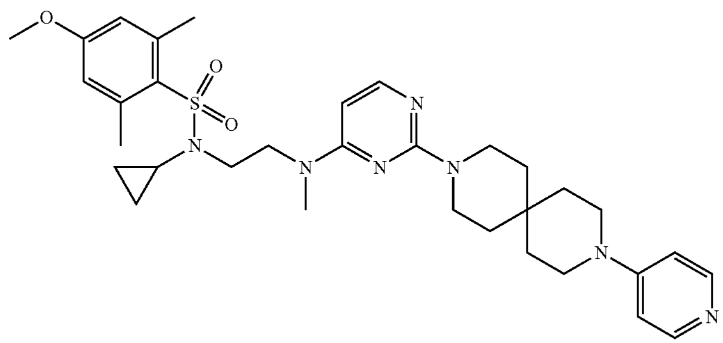 | N-Cyclopropyl-4-methoxy-2,6-dimethyl-N-[2-(9-pyridin-4-yl-3,9-diazaspiro[5.5]undecan-3-yl)-pyrimidin-4-yl]-amino]-ethyl]-benzenesulfonic acid amide (I-004) | 3-(Pyridin-4-yl)-3,9-diazaspiro[5.5]-undecane (F-12) | 308 mg (53%) | $R_t$ = 3.2 min; m/z = 620.4 [MH]+ |

TABLE 6-continued

Synthesis of derivatives I

| Ex. No. | Structure | Name | Amine (F) | Yield last stage | Analysis (LC/MS)[1] |
|---|---|---|---|---|---|
| I-005 | 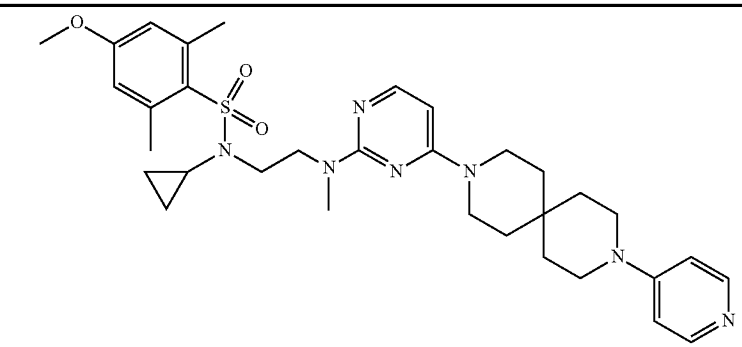 | N-Cyclopropyl-4-methoxy-2,6-dimethyl-N-[2-[methyl-[4-(9-pyridin-4-yl-3,9-diazaspiro[5.5]undecan-3-yl)-pyrimidin-2-yl]-amino]-ethyl]-benzenesulfonic acid amide (I-005) | 3-(Pyridin-4-yl)-3,9-diazaspiro[5.5]-undecane (F-12) | 51 mg (50%) | $R_t = 3.0$ min; m/z = 620.4 [MH]$^+$ |
| I-006 | 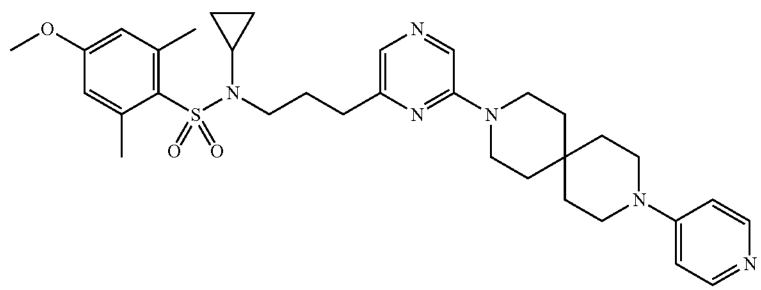 | N-Cyclopropyl-4-methoxy-2,6-dimethyl-N-[3-[6-(9-pyridin-4-yl-3,9-diazaspiro[5.5]undecan-3-yl)-pyrazin-2-yl]-propyl]-benzenesulfonic acid amide (I-006) | 3-(Pyridin-4-yl)-3,9-diazaspiro[5.5]-undecane (F-12) | 417 mg (90%) | $R_t = 3.3$ min; m/z = 605.5 [MH]$^+$ |

TABLE 6-continued

Synthesis of derivatives I

| Ex. No. | Structure | Name | Amine (F) | Yield last stage | Analysis (LC/MS)[1] |
|---|---|---|---|---|---|
| I-007 | 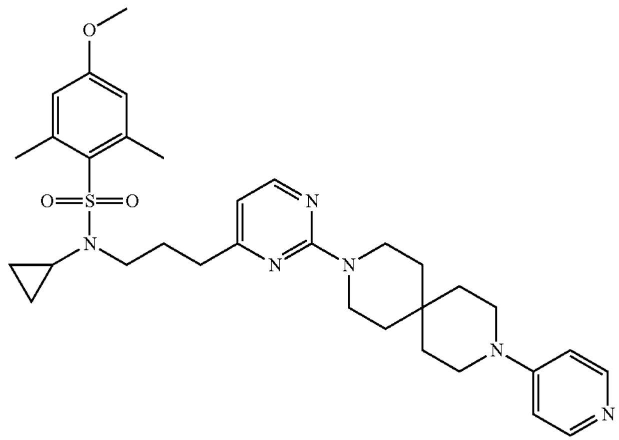 | N-Cyclopropyl-4-methoxy-2,6-dimethyl-N-[3-[2-(9-pyridin-4-yl-3,9-diazaspiro[5.5]undecan-3-yl)-pyrimidin-4-yl]-propyl]-benzenesulfonic acid amide (I-007) | 3-(Pyridin-4-yl)-3,9-diazaspiro[5.5]-undecane (F-12) | 325 mg (48%) | $R_t$ = 4.0 min; m/z = 605.5 [MH]$^+$ |
| I-008 | 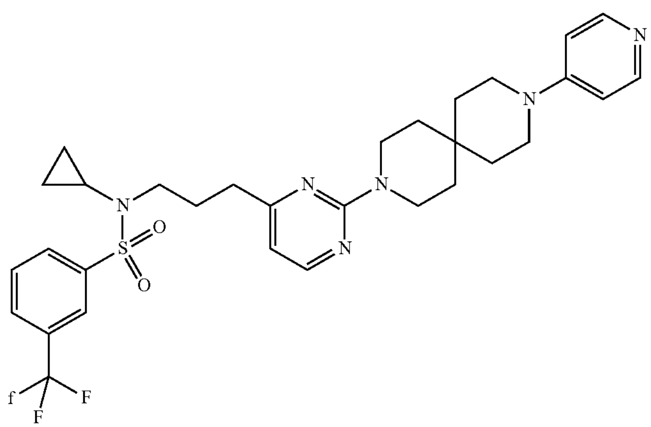 | N-Cyclopropyl-N-[3-[2-(9-pyridin-4-yl-3,9-diazaspiro[5.5]undecan-3-yl)-pyrimidin-4-yl]-propyl]-3-(trifluoromethyl)-benzenesulfonic acid amide (I-008) | 3-(Pyridin-4-yl)-3,9-diazaspiro[5.5]-undecane (F-12) | 61 mg (30%) | $R_5$ = 4.0 min; m/z = 615.4 [MH]$^+$ |

Parallel Syntheses

7) Parallel Synthesis of the Pyrimidine Derivatives G_CC & H_CC

Parallel Method for the Synthesis of the Pyrimidine Derivatives G_CC & H_CC

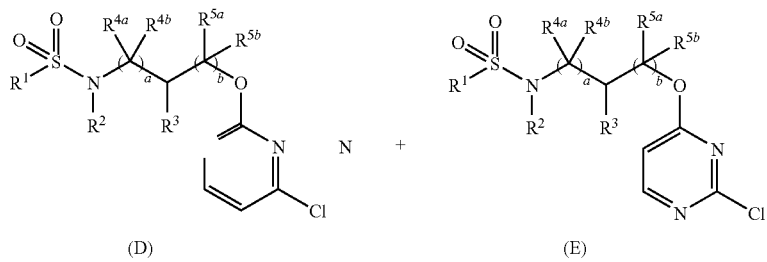

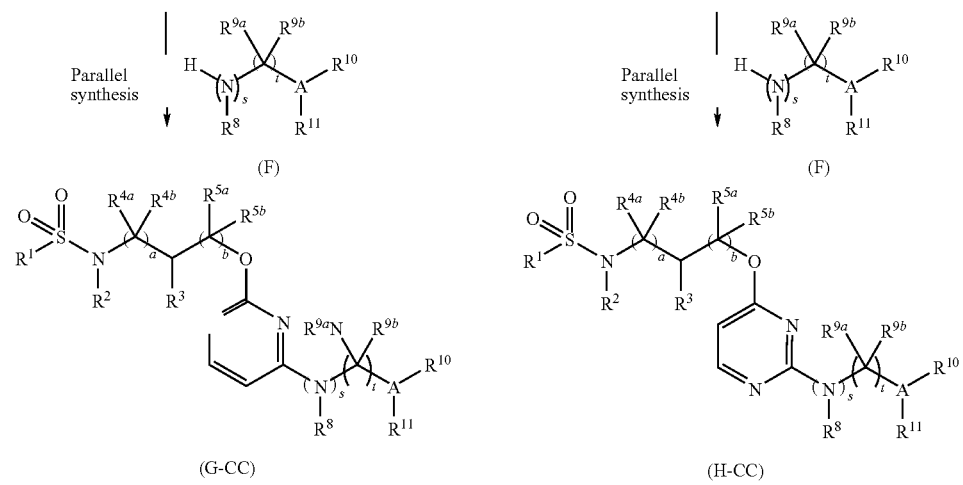

Scheme 3: Parallel synthesis of the pyrimidine derivatives G_CC & H_CC According to the above figure, both the pyrimidine structural units D and the pyrimidine structural units E were reacted in parallel synthesis with amine F to give the pyrimidine derivatives G_CC and H_CC. The correlation of product to reagent and structural units is to be found in the synthesis matrix. The crude products of the parallel synthesis were analyzed by HPLC-MS and then purified by means of reverse phase HPLC-MS. The identity of the products could be determined by analytical HPLC-MS measurements. It was supposed that the pyrimidine regioisomers G_CC are obtained from the regioisomers D after reaction with F. The same applies for the conversion of the regioisomers E into the pyrimidine regioisomers H_CC. In the case where mixtures of G_CC and H_CC were obtained in the parallel synthesis (e.g. owing to the use of D & E mixtures as starting material in the parallel synthesis), it was assumed that G_CC is always the regioisomer with the shorter retention time.

Parallel Synthesis
Synthesis Procedure for the Preparation of the Pyrimidine Derivatives G_CC & H_CC A solution of diisopropylethylamine (187 μM) in 1 ml of isopropanol is added to a solution of the chloropyrimidine D (or E) (125 μM) in 1 ml of isopropanol, and the mixture is agitated for 15 minutes at room temperature. A solution of the amine F (187 μM) in 1 ml of isopropanol is then added and the reaction mixture is agitated for from 10 hours to 15 hours at 60° C. When amine hydrochlorides (F+n HCl) were used, the amount of diisopropylamine was increased to 1.5 equiv.+n equiv. For working up, 2 ml of a 2M sodium hydroxide solution, 1 ml of a saturated sodium chloride solution and 1 ml of ethyl acetate were added to the mixtures. Further working up was carried out on a Myriad-Allex working-up system (Mettler-Toledo). After thorough mixing, the organic phase was separated off, the aqueous phase was extracted 2× with 3 ml of ethyl acetate, and the organic phases were combined. The solvent was removed in vacuo using a vacuum centrifuge (GeneVac). Final purification was carried out by HPLC-MS. Final analysis was carried out by means of LC-MS.

Devices and Methods for HPLC-MS Analysis:
Parallel synthesis method: HPLC: Waters Alliance 2795 with PDA Waters 996; MS: ZQ 2000 MassLynx Single Quadrupol MS detector;

Column: Atlantis dC18 30×2.1 mm, 3 μm; Column temperature: 40° C., Eluent A: water+0.1% formic acid; Eluent B: methanol+0.1% formic acid; Gradient: 0% B to 100% B in 2.3 min, 100% B for 0.4 min, 100% B to 0% B in 0.01 min, 0% B for 0.8 min; Flow: 1.0 mL/min; Ionization: ES+, 25V; Make up: 100 μL/min 70% methanol+0.2% formic acid; UV: 200-400 nm Devices and methods for HPLC-MS purification: Prep pump: Waters 2525; Make up pump: Waters 515; Auxiliary detector: Waters DAD 2487; MS detector: Waters Micromass ZQ; Injector/fraction collector: Waters Sample Manager 2767; Gradient: initial: 50% water/50% methanol→2-20 min: 0% water 100% methanol; Flow: 35 ml/min; Column: Phenomenex Gemini, C18, 100×21.2 mm, Axia, 110 A, 5μ.

The compounds prepared by means of the above-described parallel syntheses and the synthesis structural units used therefor are listed in Table 6 below.

TABLE 7

Compounds according to parallel synthesis

| Compound | Pyrimidine unit (D), (E) | Amine unit (F) |
|---|---|---|
| G_CC-001 | D-01 | F-02 |
| G_CC-002 | D-02 | F-02 |
| G_CC-003 | D-02 | F-03 |
| G_CC-004 | D-02 | F-09 |
| G_CC-005 | D-01 | F-04 |
| G_CC-006 | D-01 | F-06 |
| G_CC-007 | D-01 | F-07 |
| G_CC-008 | D-01 | F-16 |
| G_CC-009 | D-02 | F-01 |
| G_CC-010 | D-02 | F-04 |
| G_CC-011 | D-02 | F-06 |
| G_CC-012 | D-02 | F-05 |
| G_CC-013 | D-02 | F-15 |
| G_CC-014 | D-02 | F-07 |
| G_CC-015 | D-04 | F-01 |
| G_CC-016 | D-04 | F-03 |
| G_CC-017 | D-04 | F-06 |
| G_CC-018 | D-04 | F-05 |
| G_CC-019 | D-04 | F-15 |
| G_CC-020 | D-04 | F-16 |
| G_CC-021 | D-04 | F-10 |
| G_CC-022 | D-02 | F-25 |
| G_CC-023 | D-02 | F-19 |
| G_CC-024 | D-02 | F-20 |
| G_CC-025 | D-02 | F-21 |
| G_CC-026 | D-02 | F-13 |
| G_CC-027 | D-03 | F-13 |
| G_CC-028 | D-01 | F-25 |
| G_CC-029 | D-01 | F-19 |
| G_CC-030 | D-01 | F-21 |
| G_CC-031 | D-01 | F-13 |
| G_CC-032 | D-04 | F-25 |
| G_CC-033 | D-04 | F-19 |
| G_CC-034 | D-04 | F-20 |
| G_CC-035 | D-04 | F-21 |
| G_CC-036 | D-04 | F-02 |
| G_CC-037 | D-04 | F-13 |
| G_CC-038 | D-02 | F-17 |
| G_CC-039 | D-02 | F-23 |
| G_CC-040 | D-02 | F-24 |
| G_CC-041 | D-03 | F-12 |
| G_CC-042 | D-01 | F-17 |
| G_CC-043 | D-01 | F-18 |
| G_CC-044 | D-01 | F-22 |
| G_CC-045 | D-01 | F-23 |
| G_CC-046 | D-01 | F-24 |
| G_CC-047 | D-01 | F-12 |
| G_CC-048 | D-04 | F-17 |
| G_CC-049 | D-04 | F-18 |
| G_CC-050 | D-04 | F-22 |
| G_CC-051 | D-04 | F-23 |
| G_CC-052 | D-04 | F-31 |
| G_CC-053 | D-04 | F-24 |
| G_CC-054 | D-04 | F-28 |
| G_CC-055 | D-04 | F-12 |
| G_CC-056 | D-02 | F-26 |
| G_CC-057 | D-03 | F-26 |
| G_CC-058 | D-04 | F-26 |
| G_CC-059 | D-08 | F-02 |
| G_CC-060 | D-08 | F-23 |
| G_CC-061 | D-08 | F-24 |
| G_CC-062 | D-08 | F-37 |
| G_CC-063 | D-08 | F-31 |
| G_CC-064 | D-08 | F-14 |
| G_CC-065 | D-08 | F-27 |
| G_CC-067 | D-02 | F-16 |
| G_CC-068 | D-08 | F-25 |
| G_CC-069 | E-02 | F-61 |
| G_CC-070 | E-02 | F-64 |
| G_CC-073 | E-02 | F-65 |
| G_CC-074 | E-02 | F-62 |
| G_CC-075 | E-04 | F-60 |
| G_CC-076 | E-07 | F-60 |
| G_CC-077 | E-06 | F-07 |
| G_CC-078 | D-02 | F-50 |
| G_CC-079 | D-02 | F-51 |
| G_CC-080 | D-02 | F-69 |
| G_CC-081 | E-02 | F-47 |
| G_CC-082 | E-02 | F-56 |
| G_CC-083 | E-04 | F-56 |
| G_CC-084 | D-04 | F-47 |
| G_CC-085 | D-04 | F-46 |
| G_CC-086 | D-04 | F-68 |
| G_CC-087 | E-04 | F-61 |
| G_CC-088 | E-04 | F-59 |
| G_CC-089 | E-01 | F-61 |
| G_CC-091 | E-04 | F-65 |
| G_CC-092 | E-07 | F-51 |
| G_CC-093 | E-07 | F-61 |
| G_CC-094 | E-07 | F-59 |
| G_CC-096 | E-07 | F-65 |
| G_CC-097 | E-07 | F-62 |
| G_CC-098 | E-01 | F-59 |
| G_CC-100 | E-01 | F-60 |
| G_CC-101 | E-02 | F-60 |
| G_CC-103 | D-02 | F-46 |
| G_CC-104 | D-02 | F-66 |
| G_CC-105 | D-02 | F-53 |
| G_CC-106 | D-02 | F-57 |
| G_CC-107 | D-08 | F-53 |
| G_CC-108 | D-08 | F-69 |
| G_CC-109 | D-04 | F-67 |
| G_CC-111 | D-02 | F-55 |
| G_CC-112 | D-08 | F-55 |
| G_CC-113 | E-02 | F-58 |
| G_CC-114 | E-03 | F-63 |
| G_CC-115 | E-04 | F-63 |
| G_CC-116 | E-01 | F-63 |
| G_CC-117 | E-01 | F-58 |
| G_CC-118 | E-01 | F-64 |
| G_CC-119 | E-01 | F-65 |
| G_CC-120 | E-01 | F-62 |
| G_CC-121 | E-02 | F-63 |
| G_CC-122 | E-06 | F-63 |
| G_CC-123 | E-06 | F-09 |
| G_CC-124 | E-06 | F-65 |
| G_CC-125 | E-07 | F-64 |
| G_CC-126 | E-06 | F-60 |
| G_CC-127 | E-06 | F-48 |
| G_CC-128 | E-06 | F-16 |
| G_CC-129 | E-06 | F-13 |
| G_CC-130 | E-07 | F-27 |
| G_CC-131 | D-02 | F-45 |
| G_CC-133 | D-08 | F-47 |
| G_CC-134 | D-08 | F-46 |
| G_CC-135 | D-08 | F-66 |
| G_CC-136 | D-08 | F-50 |
| G_CC-137 | D-08 | F-45 |
| G_CC-138 | D-08 | F-57 |
| H_CC-001 | E-02 | F-02 |
| H_CC-002 | E-02 | F-03 |
| H_CC-003 | E-02 | F-01 |
| H_CC-004 | E-02 | F-05 |
| H_CC-005 | E-02 | F-15 |
| H_CC-006 | E-02 | F-07 |
| H_CC-007 | E-02 | F-16 |
| H_CC-008 | E-04 | F-01 |
| H_CC-009 | E-04 | F-03 |
| H_CC-010 | E-04 | F-06 |
| H_CC-011 | E-04 | F-05 |
| H_CC-012 | E-04 | F-07 |
| H_CC-013 | E-04 | F-16 |
| H_CC-014 | E-06 | F-03 |
| H_CC-015 | E-06 | F-06 |
| H_CC-016 | E-07 | F-01 |
| H_CC-017 | E-07 | F-03 |
| H_CC-018 | E-07 | F-06 |
| H_CC-019 | E-07 | F-15 |
| H_CC-020 | E-07 | F-07 |
| H_CC-021 | E-02 | F-25 |

TABLE 7-continued

Compounds according to parallel synthesis

| Compound | Pyrimidine unit (D), (E) | Amine unit (F) |
|---|---|---|
| H_CC-022 | E-02 | F-13 |
| H_CC-023 | E-04 | F-25 |
| H_CC-024 | E-04 | F-21 |
| H_CC-025 | E-04 | F-02 |
| H_CC-026 | E-04 | F-13 |
| H_CC-027 | E-07 | F-02 |
| H_CC-028 | E-07 | F-13 |
| H_CC-029 | E-01 | F-12 |
| H_CC-030 | E-02 | F-23 |
| H_CC-031 | E-02 | F-28 |
| H_CC-032 | E-02 | F-12 |
| H_CC-033 | E-01 | F-37 |
| H_CC-034 | E-01 | F-26 |
| H_CC-035 | E-02 | F-37 |
| H_CC-036 | E-08 | F-15 |
| H_CC-037 | E-08 | F-12 |
| H_CC-038 | E-09 | F-37 |
| H_CC-039 | E-01 | F-23 |
| H_CC-040 | E-04 | F-37 |
| H_CC-041 | E-03 | F-13 |
| H_CC-042 | E-02 | F-49 |
| H_CC-043 | E-04 | F-49 |
| H_CC-044 | E-02 | F-09 |
| H_CC-045 | E-02 | F-62 |
| H_CC-046 | E-04 | F-60 |
| H_CC-047 | D-04 | F-56 |
| H_CC-048 | D-04 | F-46 |
| H_CC-049 | E-02 | F-54 |
| H_CC-050 | E-02 | F-52 |
| H_CC-051 | E-04 | F-54 |
| H_CC-052 | E-04 | F-52 |
| H_CC-053 | E-03 | F-62 |
| H_CC-054 | E-04 | F-09 |
| H_CC-055 | E-04 | F-65 |
| H_CC-056 | E-04 | F-62 |
| H_CC-057 | E-07 | F-59 |
| H_CC-058 | E-07 | F-62 |
| H_CC-059 | E-01 | F-65 |
| H_CC-060 | E-01 | F-62 |
| H_CC-061 | E-02 | F-60 |
| H_CC-062 | E-02 | F-61 |
| H_CC-063 | E-02 | F-65 |
| H_CC-064 | E-03 | F-58 |
| H_CC-065 | E-03 | F-59 |
| H_CC-066 | E-03 | F-65 |
| H_CC-067 | E-01 | F-59 |
| H_CC-068 | E-04 | F-61 |
| H_CC-069 | E-06 | F-59 |
| H_CC-070 | E-06 | F-65 |
| H_CC-071 | E-06 | F-62 |
| H_CC-072 | E-07 | F-65 |
| H_CC-073 | E-03 | F-60 |
| H_CC-074 | E-06 | F-60 |
| H_CC-075 | E-07 | F-60 |
| H_CC-076 | E-06 | F-16 |
| H_CC-077 | E-06 | F-49 |
| H_CC-078 | D-02 | F-47 |
| H_CC-079 | D-02 | F-50 |
| H_CC-080 | D-02 | F-51 |
| H_CC-081 | D-02 | F-45 |
| H_CC-082 | D-02 | F-69 |
| H_CC-083 | E-02 | F-56 |
| H_CC-084 | D-04 | F-47 |
| H_CC-085 | E-04 | F-58 |
| H_CC-086 | E-04 | F-64 |
| H_CC-087 | E-01 | F-47 |
| H_CC-088 | E-04 | F-47 |
| H_CC-089 | E-01 | F-54 |
| H_CC-090 | E-01 | F-68 |
| H_CC-091 | E-02 | F-66 |
| H_CC-092 | E-04 | F-68 |
| H_CC-093 | E-08 | F-52 |

1 Functional Study on the Bradykinin Receptor 1 (B1R)

The agonistic or antagonistic activity of substances can be determined on the bradykinin receptor 1 (B1R) of the species human and rat using the following assay. According to this assay, the $Ca^{2+}$ influx through the channel is quantified with the aid of a $Ca^{2+}$-sensitive dye (Fluo-4 type, Molecular Probes Europe BV, Leiden, Netherlands) using a Fluorescent Imaging Plate Reader (FLIPR, Molecular Devices, Sunnyvale, USA).

2 Method:

Chinese hamster ovary cells (CHO K1 cells) which have been stably transfected with the human B1R gene (hB1R cells) or with the B1R gene of the rat (rB1R cells) are used. For functional studies, the cells are plated out on black 96-well plates having a clear base (BD Biosciences, Heidelberg, Germany or Greiner, Frickenhausen, Germany) in a density of 20,000-35,000 cells/well. The cells are left overnight at 37° C. and with 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany), with 10 vol.% FBS (fetal bovine serum, Gibco Invitrogen GmbH, Karlsruhe, Germany or PAN Biotech GmbH, Aidenbach, Germany). On the following day, the cells are loaded for 60 minutes at 37° C. with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 M probenecid (Sigma-Aldrich, Taufkirchen, Germany) and 10 mM HEPES (Sigma-Aldrich, Taufkirchen, Germany). The plates are then washed twice with HBSS buffer, and HBSS buffer additionally containing 0.1% BSA (bovine serum albumin; Sigma-Aldrich, Taufkirchen, Germany), 5.6 mM glucose and 0.05% gelatin (Merck KGaA, Darmstadt, Germany) is added to the plates. After incubation for a further 20 minutes at room temperature, the plates are inserted into the FLIPR for $Ca^{2+}$ measurement. Alternatively, washing is carried out with buffer A (15 mM HEPES, 80 mM NaCl, 5 mM KCl, 1.2 mM $CaCl_2$, 0.7 mM $MgSO_4$, 2 g/l glucose, 2.5 mM probenecid) followed by loading with buffer A with added 2.5 µM Fluo-4 and 0.025% Pluronic F127 (Sigma-Aldrich, Taufkirchen, Germany). The cells are then washed twice with buffer A and incubated for 30 minutes at room temperature with buffer A additionally containing 0.05% BSA and 0.05% gelatin and are then inserted into the FLIPR for $Ca^{2+}$ measurement. The $Ca^{2+}$-dependent fluorescence is measured before and after the addition of substances ($\lambda_{ex}$=488 nm, $\lambda_{em}$=540 nm). Quantification is carried out by measuring the highest fluorescence intensity (FC, fluorescence counts) over time.

3 FLIPR Assay:

The FLIPR protocol consists of two substance additions. Test substances (10 µM) are first pipetted onto the cells and the $Ca^{2+}$ influx is compared with the control (hB1R: Lys-Des-Arg$^9$-bradykinin>=50 nM; rB1R: Des-Arg$^9$-bradykinin 10 µM). This gives the activation in %, based on the $Ca^{2+}$ signal after addition of Lys-Des-Arg$^9$-bradykinin (>=50 nM) or Des-Arg$^9$-bradykinin (10 μM). After 10-20 minutes' incubation, Lys-Des-Arg$^9$-bradykinin (hB1R) or Des-Arg$^9$-bradykinin (rB1R) is applied in the concentration of the EC$_{80}$, and the influx of Ca$^{2+}$ is likewise determined. Antagonists lead to suppression of the Ca$^{2+}$ influx. The % inhibition compared with the maximum achievable inhibition is calculated. In order to determine the IC$_{50}$ value, the substances are added in various concentrations. Duplicate or triplicate determinations (n=2 or n=3) are carried out, and these are repeated in at least one further independent experiment (N>=2). The compounds exhibit especially a B1R antagonistic activity on the human receptor and/or on the rat receptor. The following data are indicated by way of example in Table 8 below: (in the table, "% inh. (rat B1R) 10 μM" stands for "% inhibition rat B1R at 10 μM" and "% inh. (hum. B1R) 10 μM" stands for "% inhibition human B1R at 10 μM".

TABLE 8

% inhibition on the B1R of the rat and on human B1R (10 μM)

| Compound | [M+] found* | Rt [min]** | % inh. (rat B1R) 10 μM | % inh. (hum. B1R) 10 μM |
|---|---|---|---|---|
| G-001 | | | 99 | 84 |
| G-002 | | | 109 | 97 |
| G-003 | | | 112 | 101 |
| G-004 | | | 73 | 99 |
| G-005 | | | 96 | 99 |
| G-006 | | | 94 | 99 |
| G-007 | | | 97 | 100 |
| G-008 | | | 98 | 77 |
| G-009 | | | 91 | 97 |
| G-010 | | | 89 | 98 |
| G-011 | | | 99 | 99 |
| G-012 | | | 97 | 99 |
| G-013 | | | 102 | 92 |
| G-014 | | | 102 | 100 |
| G-015 | | | 95 | 99 |
| G-016 | | | 99 | 96 |
| G-017 | | | 103 | 22 |
| G-018 | | | 93 | 99 |
| G-019 | | | 102 | 100 |
| G-020 | | | 101 | 95 |
| G-021 | | | 86 | 90 |
| G-022 | | | 103 | 100 |
| G-023 | | | 107 | 94 |
| G-024 | | | 113 | 99 |
| G-025 | | | 104 | 92 |
| G-026 | | | 101 | 98 |
| H-001 | | | 99 | 44 |
| H-002 | | | 51 | 81 |
| H-003 | | | 71 | 90 |
| H-004 | | | 93 | 99 |
| H-005 | | | 97 | 98 |
| H-006 | | | 92 | 64 |
| H-007 | | | 80 | 11 |
| I-001 | | | 88 | 98 |
| I-002 | | | 109 | 94 |
| I-003 | | | 108 | 96 |
| I-004 | | | 102 | 85 |
| I-005 | | | 111 | 96 |
| I-006 | | | 97 | 94 |
| I-007 | | | | |
| I-008 | | | 94 | |
| G_CC-001 | 533.2 | 1.30 | 97 | 98 |
| G_CC-002 | 573.3 | 1.46 | 101 | 99 |
| G_CC-003 | 572.3 | 1.56 | 102 | 100 |
| G_CC-004 | 651.3 | 1.61 | 100 | 100 |
| G_CC-005 | 530.2 | 2.10 | 81 | |
| G_CC-006 | 533.3 | 1.33 | 97 | |
| G_CC-007 | 547.3 | 1.22 | 95 | |
| G_CC-008 | 528.2 | 1.50 | 59 | |
| G_CC-009 | 490.2 | 1.56 | 63 | |
| G_CC-010 | 570.2 | 2.24 | 70 | |
| G_CC-011 | 573.3 | 1.51 | 96 | 91 |
| G_CC-012 | 554.2 | 2.06 | 76 | |
| G_CC-013 | 553.2 | 1.60 | 102 | 100 |
| G_CC-014 | 587.3 | 1.42 | 105 | 94 |
| G_CC-015 | 476.1 | 1.48 | 83 | |
| G_CC-016 | 558.2 | 1.53 | 100 | 96 |
| G_CC-017 | 559.2 | 1.47 | 98 | |
| G_CC-018 | 540.1 | 2.00 | 97 | |
| G_CC-019 | 539.1 | 1.55 | 104 | 100 |
| G_CC-020 | 554.1 | 1.62 | 102 | |
| G_CC-021 | 559.1 | 1.99 | 105 | 36 |
| G_CC-022 | 606.2 | 1.72 | 104 | |
| G_CC-023 | | | 50 | |
| G_CC-024 | 641.1 | 2.17 | 73 | |
| G_CC-025 | 621.1 | 2.13 | 95 | |
| G_CC-026 | 586.2 | 1.60 | 100 | 97 |
| G_CC-027 | 572.2 | 1.49 | 63 | |
| G_CC-028 | 566.1 | 1.57 | 104 | |
| G_CC-029 | 539.1 | 2.11 | 52 | |
| G_CC-030 | 581.1 | 1.96 | 79 | |
| G_CC-031 | 546.2 | 1.49 | 104 | |
| G_CC-032 | 592.1 | 1.68 | 105 | 86 |
| G_CC-033 | 565.1 | 2.18 | 68 | |
| G_CC-034 | 627.1 | 2.15 | 93 | |
| G_CC-035 | 607.2 | 2.04 | 99 | -1 |
| G_CC-036 | 559.2 | 1.40 | 102 | 75 |
| G_CC-037 | 572.2 | 1.55 | 102 | |
| G_CC-038 | 638.2 | 2.16 | 94 | |
| G_CC-039 | 652.2 | 2.14 | 99 | 58 |
| G_CC-040 | 634.2 | 2.12 | 99 | 57 |
| G_CC-041 | 607.2 | 1.63 | 101 | 96 |
| G_CC-042 | 598.2 | 2.00 | 87 | |
| G_CC-043 | 648.2 | 2.06 | 70 | |
| G_CC-044 | 612.2 | 1.97 | 68 | |
| G_CC-045 | 612.2 | 2.01 | 96 | |
| G_CC-046 | 594.2 | 2.00 | 96 | |
| G_CC-047 | 581.2 | 1.60 | 99 | 100 |
| G_CC-048 | 624.2 | 2.10 | 96 | 28 |
| G_CC-049 | 674.2 | 2.12 | 72 | |
| G_CC-050 | 638.2 | 2.08 | 73 | |
| G_CC-051 | 638.2 | 2.12 | 98 | 38 |
| G_CC-052 | 554.2 | 1.60 | 99 | 74 |
| G_CC-053 | 620.2 | 2.10 | 96 | |
| G_CC-054 | 693.3 | 1.59 | 80 | |
| G_CC-055 | 607.2 | 1.72 | 101 | 97 |
| G_CC-056 | 579.2 | 1.66 | 98 | |
| G_CC-057 | 565.2 | 1.53 | 90 | |
| G_CC-058 | 565.2 | 1.61 | 93 | |
| G_CC-059 | 609.2 | 1.65 | 98 | |
| G_CC-060 | 688.3 | 2.25 | 88 | 17 |
| G_CC-061 | 670.3 | 2.25 | 81 | |
| G_CC-062 | 701.4 | 1.74 | 78 | |
| G_CC-063 | 604.3 | 1.72 | 101 | 28 |
| G_CC-064 | 617.3 | 2.05 | 55 | |
| G_CC-065 | 632.3 | 1.97 | 58 | |
| G_CC-067 | 568.2 | 1.69 | 104 | |
| G_CC-068 | 642.2 | 1.83 | 68 | |
| G_CC-069 | 574.5 | 1.72 | 102 | |
| G_CC-070 | 600.4 | 1.77 | 95 | |
| G_CC-073 | 677.6 | 1.66 | 101 | |
| G_CC-074 | 631.6 | 1.66 | 102 | |
| G_CC-075 | 651.5 | 1.47 | 104 | |
| G_CC-076 | 699.6 | 1.63 | 105 | |
| G_CC-077 | 545.4 | 1.53 | 92 | |
| G_CC-078 | 568.4 | 2.07 | 98 | |
| G_CC-079 | 569.4 | 2.02 | 98 | |
| G_CC-080 | 663.6 | 1.58 | 103 | |
| G_CC-081 | 552.4 | 1.96 | 88 | |
| G_CC-082 | 568.4 | 1.87 | 73 | |
| G_CC-083 | 554.4 | 1.82 | 62 | |
| G_CC-084 | 538.4 | 1.86 | 83 | |
| G_CC-085 | 606.4 | 2.03 | 101 | |
| G_CC-086 | 668.5 | 1.88 | 105 | |
| G_CC-087 | 560.4 | 1.68 | 101 | |
| G_CC-088 | 637.5 | 1.36 | 100 | |
| G_CC-089 | 534.4 | 1.58 | 93 | |

TABLE 8-continued

% inhibition on the B1R of the rat and on human B1R (10 μM)

| Compound | [M+] found* | Rt [min]** | % inh. (rat B1R) 10 μM | % inh. (hum. B1R) 10 μM |
|---|---|---|---|---|
| G_CC-091 | 663.6 | 1.57 | 101 | |
| G_CC-092 | 603.4 | 2.14 | 85 | |
| G_CC-093 | 608.5 | 1.87 | 91 | |
| G_CC-094 | 685.6 | 1.72 | 102 | |
| G_CC-096 | 711.6 | 1.75 | 101 | |
| G_CC-097 | 665.6 | 1.74 | 101 | |
| G_CC-098 | 611.5 | 1.47 | 79 | |
| G_CC-100 | 625.5 | 1.37 | 89 | |
| G_CC-101 | 665.6 | 1.52 | 105 | |
| G_CC-103 | 620.4 | 2.08 | 93 | |
| G_CC-104 | 667.5 | 1.85 | 101 | |
| G_CC-105 | 594.4 | 1.87 | 101 | |
| G_CC-106 | 625.5 | 1.61 | 95 | |
| G_CC-107 | 630.4 | 1.98 | 94 | |
| G_CC-108 | 699.6 | 1.75 | 102 | |
| G_CC-109 | 596.5 | 1.66 | 98 | |
| G_CC-111 | 568.4 | 1.64 | 90 | |
| G_CC-112 | 604.4 | 1.77 | 88 | |
| G_CC-113 | 594.5 | 1.78 | 79 | |
| G_CC-114 | 606.5 | 1.66 | 54 | |
| G_CC-115 | 606.4 | 1.75 | 81 | |
| G_CC-116 | 580.4 | 1.62 | 64 | |
| G_CC-117 | 554.4 | 1.61 | 56 | |
| G_CC-118 | 560.4 | 1.60 | 86 | |
| G_CC-119 | 637.5 | 1.54 | 79 | |
| G_CC-120 | 591.5 | 1.49 | 86 | |
| G_CC-121 | 620.5 | 1.79 | 75 | |
| G_CC-122 | 578.4 | 1.95 | 51 | |
| G_CC-123 | 609.5 | 1.66 | 81 | |
| G_CC-124 | 635.5 | 1.69 | 57 | |
| G_CC-125 | 634.4 | 1.92 | 58 | |
| G_CC-126 | 623.5 | 1.55 | 77 | |
| G_CC-127 | 519.4 | 1.55 | 54 | |
| G_CC-128 | 526.3 | 1.72 | 57 | |
| G_CC-129 | 544.4 | 1.65 | 73 | |
| G_CC-130 | 630.4 | 1.91 | 61 | |
| G_CC-131 | 574.4 | 1.54 | 88 | |
| G_CC-133 | 588.4 | 2.02 | 78 | |
| G_CC-134 | 656.4 | 2.14 | 88 | |
| G_CC-135 | 703.6 | 1.89 | 53 | |
| G_CC-136 | 604.4 | 2.16 | 81 | |
| G_CC-137 | 610.5 | 1.67 | 77 | |
| G_CC-138 | 661.5 | 1.75 | 56 | |
| H_CC-001 | 573.3 | 1.75 | 65 | |
| H_CC-002 | 572.3 | 1.82 | 77 | |
| H_CC-003 | 490.2 | 1.97 | 58 | |
| H_CC-004 | 554.2 | 2.54 | 57 | |
| H_CC-005 | 553.2 | 2.00 | 94 | |
| H_CC-006 | 587.3 | 1.74 | 61 | |
| H_CC-007 | 568.2 | 2.01 | 71 | |
| H_CC-008 | 476.1 | 1.87 | 95 | |
| H_CC-009 | 558.2 | 1.75 | 85 | |
| H_CC-010 | 559.2 | 1.75 | 100 | |
| H_CC-011 | 540.1 | 2.39 | 56 | |
| H_CC-012 | 573.2 | 1.70 | 93 | |
| H_CC-013 | 554.1 | 1.87 | 79 | |
| H_CC-014 | 530.2 | 1.91 | 53 | |
| H_CC-015 | 531.2 | 1.89 | 56 | |
| H_CC-016 | 524.1 | 2.08 | 67 | |
| H_CC-017 | 606.2 | 2.00 | 93 | |
| H_CC-018 | 607.2 | 2.03 | 91 | |
| H_CC-019 | 587.1 | 2.16 | 98 | |
| H_CC-020 | 621.2 | 1.87 | 93 | |
| H_CC-021 | 606.2 | 1.96 | 62 | |
| H_CC-022 | 586.2 | 1.83 | 77 | |
| H_CC-023 | 592.1 | 1.89 | 76 | |
| H_CC-024 | 607.1 | 2.35 | 97 | |
| H_CC-025 | 559.2 | 1.72 | 65 | |
| H_CC-026 | 572.2 | 1.78 | 75 | |
| H_CC-027 | 607.2 | 1.91 | 91 | |
| H_CC-028 | 620.2 | 2.02 | 83 | |
| H_CC-029 | 581.2 | 1.79 | 101 | 92 |
| H_CC-030 | | | 49 | |
| H_CC-031 | 707.3 | 1.91 | 56 | |
| H_CC-032 | 621.2 | 1.96 | 101 | 77 |
| H_CC-033 | 625.2 | 1.80 | 82 | |
| H_CC-034 | 539.2 | 1.79 | 74 | |
| H_CC-035 | 665.3 | 2.01 | 86 | |
| H_CC-036 | 589.2 | 2.12 | 71 | |
| H_CC-037 | 657.3 | 2.08 | 102 | 54 |
| H_CC-038 | 693.4 | 2.12 | 70 | |
| H_CC-039 | 612.2 | 2.23 | 50 | |
| H_CC-040 | 651.3 | 1.95 | 51 | |
| H_CC-041 | | | 48 | |
| H_CC-042 | 581.2 | 2.03 | 61 | |
| H_CC-043 | 567.2 | 1.98 | 80 | |
| H_CC-044 | 651.5 | 1.85 | 102 | |
| H_CC-045 | 631.6 | 1.86 | 96 | |
| H_CC-046 | 651.5 | 1.67 | 89 | |
| H_CC-047 | 554.4 | 1.97 | 85 | |
| H_CC-048 | 606.4 | 2.38 | 63 | |
| H_CC-049 | 625.5 | 1.81 | 94 | |
| H_CC-050 | 594.4 | 1.99 | 74 | |
| H_CC-051 | 611.5 | 1.74 | 99 | |
| H_CC-052 | 653.5 | 2.09 | 72 | |
| H_CC-053 | 617.5 | 1.77 | 95 | |
| H_CC-054 | 637.9 | 1.79 | 83 | |
| H_CC-055 | 663.6 | 1.80 | 92 | |
| H_CC-056 | 617.5 | 1.78 | 98 | |
| H_CC-057 | 685.6 | 1.92 | 98 | |
| H_CC-058 | 665.6 | 1.93 | 97 | |
| H_CC-059 | 637.5 | 1.72 | 91 | |
| H_CC-060 | 591.5 | 1.66 | 102 | |
| H_CC-061 | 665.6 | 1.76 | 105 | |
| H_CC-062 | 574.5 | 2.12 | 73 | |
| H_CC-063 | 677.6 | 1.85 | 82 | |
| H_CC-064 | 580.4 | 2.03 | 61 | |
| H_CC-065 | 637.5 | 1.75 | 52 | |
| H_CC-066 | 663.6 | 1.77 | 56 | |
| H_CC-067 | 611.5 | 1.65 | 59 | |
| H_CC-068 | 560.4 | 2.05 | 65 | |
| H_CC-069 | 609.5 | 1.79 | 52 | |
| H_CC-070 | 635.5 | 1.80 | 53 | |
| H_CC-071 | 589.5 | 1.80 | 55 | |
| H_CC-072 | 711.6 | 1.96 | 83 | |
| H_CC-073 | 651.5 | 1.68 | 55 | |
| H_CC-074 | 623.5 | 1.75 | 59 | |
| H_CC-075 | 699.6 | 1.85 | 75 | |
| H_CC-076 | 526.3 | 1.99 | 69 | |
| H_CC-077 | 539.4 | 2.00 | 58 | |
| H_CC-078 | 552.4 | 2.09 | 77 | |
| H_CC-079 | 568.4 | 2.38 | 73 | |
| H_CC-080 | 604.4 | 1.96 | 59 | |
| H_CC-081 | 574.4 | 1.96 | 61 | |
| H_CC-082 | 663.5 | 1.94 | 72 | |
| H_CC-083 | 568.4 | 2.03 | 59 | |
| H_CC-084 | 538.4 | 2.01 | 55 | |
| H_CC-085 | 580.4 | 2.10 | 70 | |
| H_CC-086 | 586.4 | 2.11 | 66 | |
| H_CC-087 | 512.4 | 1.85 | 57 | |
| H_CC-088 | 538.4 | 2.00 | 67 | |
| H_CC-089 | 585.4 | 1.61 | 58 | |
| H_CC-090 | 642.5 | 2.02 | 83 | |
| H_CC-091 | 667.5 | 2.12 | 73 | |
| H_CC-092 | 668.5 | 2.16 | 50 | |
| H_CC-093 | 630.4 | 2.10 | 63 | |

[*] and [**]: Only the data for compounds from the parallel synthesis are listed in this table. For the compounds from the individual syntheses, these data are listed in Tables 4, 5 and 6.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A compound corresponding to formula I:

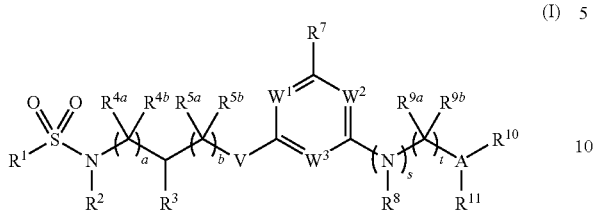

wherein
a represents 0, 1 or 2;
b represents 0, 1 or 2;
$R^1$ represents aryl, heteroaryl CH(aryl)$_2$, or an aryl or heteroaryl bonded via a $C_{1-3}$-alkylene group;
$R^2$ and $R^3$ are defined as described under (i) or (ii):
(i) $R^2$ represents H, $C_{1-6}$-alkyl, $C_{3-8}$-cycloalkyl, aryl or heteroaryl; or $R^2$ denotes a $C_{3-8}$-cycloalkyl, aryl or heteroaryl bonded via a $C_{1-6}$-alkylene group, $C_{2-6}$-alkenylene group or $C_{2-6}$-alkynylene group;
$R^3$ represents H, F, Cl, Br, I, —CF$_3$, —OCF$_3$, OH, O—C$_{1-6}$-alkyl, C$_{1-6}$-alkyl, C$_{3-8}$-cycloalkyl, aryl, heteroaryl; or $R^3$ denotes a $C_{3-8}$-cycloalkyl, aryl or heteroaryl bonded via a $C_{1-6}$-alkylene group, $C_{2-6}$-alkenylene group or $C_{2-6}$-alkynylene group; or
(ii) $R^2$ and $R^3$, together with the group —N—(CR$^{4a}$R$^{4b}$)$_a$—CH— linking them, form a heterocycle which optionally may be substituted on one or more of its carbon ring members by one or more substituents independently selected from the group consisting of F, Cl, Br, I, —CF$_3$, =O, —O—CF$_3$, —OH, —SH, —O—C$_{1-6}$-alkyl, C$_{1-6}$-alkyl, C$_{3-8}$cycloalkyl, aryl and heteroaryl and/or optionally may be fused to an aryl or heteroaryl group and/or two of its carbon ring members optionally may be linked together via a C$_{1-3}$-alkylene bridge, wherein said heterocycle may be saturated or mono- or polyunsaturated but not aromatic, is 4-, 5-, 6- or 7-membered, and optionally may contain, in addition to the N heteroatom to which $R^2$ is bonded, one or more heteroatoms or heteroatom groups independently selected from the group consisting of N, NR$^{50}$, O, S, S=O and S(=O)$_2$;
wherein R$^{50}$ denotes H, —C(=O)—R$^{51}$, C$_{3-8}$-cycloalkyl, aryl, heteroaryl, or a C$_{3-8}$-cycloalkyl, aryl or heteroaryl bonded via a C$_{1-3}$-alkylene group, and R$^{51}$ denotes C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group;
V represents C(R$^{6a}$)(R$^{6b}$), NR$^{6c}$, O or a single bond,
wherein R$^{6c}$ represents a group from the group H, C$_{1-6}$-alkyl, C$_{3-8}$-cycloalkyl, aryl, heteroaryl, or represents a C$_{3-8}$-cycloalkyl, C$_{3-8}$-cyclalkyl, aryl or heteroaryl group bonded via a C$_{1-6}$-alkylene group, C$_{2-6}$-alkenylene group or C$_{2-6}$-alkynylene group;
R$^{4a}$, R$^{4b}$, R$^{5a}$, R$^{5b}$, R$^{6a}$, R$^{6b}$ each independently represent H, F, Cl, Br, I, —CF$_3$, —OCF$_3$, OH, SH, O—C$_{1-6}$-alkyl, C$_{1-6}$-alkyl, C$_{3-8}$-cycloalkyl, aryl or heteroaryl; or represent a C$_{3-8}$-cycloalkyl, aryl or heteroaryl group bonded via a C$_{1-6}$-alkylene group or C$_{2-6}$-alkenylene group; and R$^{6a}$ and R$^{6b}$ can additionally together denote =O; or
R$^{4a}$ and R$^{4b}$, together with the carbon atom linking them, form a saturated ring which may be unsubstituted or substituted on at least one of its carbon ring members by at least one substituent independently selected from the group consisting of F, CF$_3$, C$_{1-6}$-alkyl, O—C$_{1-6}$-alkyl, OH, OCF$_3$, aryl and heteroaryl, wherein said ring is 3-, 4-, 5- or 6-membered and optionally may contain one or more oxygen atoms;
R$^7$ represents H, C$_{1-6}$-alkyl, —CN, —CF$_3$, OH, C$_{1-6}$-alkoxy, or —O—CF$_3$;
two of W$^1$, W$^2$ and W$^3$ represent N and the other represents CR$^{60}$;
wherein R$^{60}$ represents H, C$_{1-6}$-alkyl, halogen, —CN, CF$_3$, OH, C$_{1-6}$-alkoxy or —O—CF$_3$;
s is 0 or 1,
t is 0, 1, 2 or 3,
R$^8$ represents H; C$_{1-6}$-alkyl; C$_{3-8}$-cycloalkyl; aryl or heteroaryl; or C$_{3-8}$-cycloalkyl, aryl or heteroaryl bonded via a C$_{1-6}$-alkylene group;
R$^{9a}$ and R$^{9b}$ each independently represent H; F; Cl; OH; C$_{1-6}$-alkyl; O—C$_{1-6}$-alkyl; C$_{3-8}$-cycloalkyl; aryl or heteroaryl; C$_{3-8}$-cycloalkyl, aryl or heteroaryl bonded via a C$_{1-6}$-alkylene group;
A represents N or CH,
with the proviso that when s represents 1, and t represents 0, then A represents CH; and
with the proviso that when s and t each represent 0, then A represents N;
R$^{10}$, R$^{11}$ and A together represent a spirocyclic or cyclic group corresponding to formula II or formula III:

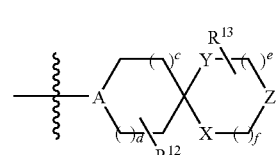

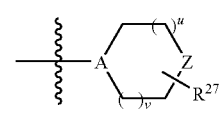

wherein
c, d, e, f, u and v each independently denote 0, 1 or 2;
R$^{12}$, R$^{13}$ and R$^{27}$ each independently represent from 0 to 4 substituents each independently selected from the group consisting of F; Cl; OH; =O; C$_{1-6}$-alkyl; O—C$_{1-6}$-alkyl; C$_{3-8}$-cycloalkyl; aryl, heteroaryl, and C$_{3-8}$-cycloalkyl, aryl or heteroaryl bonded via a C$_{1-6}$-alkylene group; or
two substituents R$^{27}$ optionally may together represent a C$_{1-3}$-alkylene bridge, so that the ring of formula III assumes a bicyclically bridged form; or
two adjacent substituents R$^{13}$ optionally may form a fused aryl or heteroaryl group; or
two adjacent substituents R$^{27}$ optionally may form a fused aryl or heteroaryl group;
X represents CR$^{14a}$R$^{14b}$, NR$^{15}$ or O;
Y represents CR$^{16a}$R$^{16b}$, NR$^{17}$ or O;
with the proviso that X is not NR$^{15}$ when Y is NR$^{17}$; and
with the proviso that X and Y do not simultaneously denote O;
wherein
R$^{14a}$, R$^{14b}$, R$^{16a}$ and R$^{16b}$ each independently denote H; F; Cl; OH; C$_{1-6}$-alkyl; O—C$_{1-6}$-alkyl; C$_{3-8}$-cycloalkyl; aryl, heteroaryl, or C$_{3-8}$-cycloalkyl, aryl or heteroaryl bonded via a C$_{1-6}$-alkylene group; or $R^{14a}$ and $R^{14b}$ optionally may together represent =O; or
$R^{16a}$ and $R^{16b}$ optionally may together represent =O;
$R^{15}$ and $R^{17}$ each independently represents H; $C_{1-6}$-alkyl; $C_{3-8}$-cycloalkyl, aryl, heteroaryl, or $C_{3-8}$-cycloalkyl, aryl or heteroaryl bonded via a $C_{1-6}$-alkylene group;

Z in formula II represents $CR^{18a}R^{18b}$, $NR^{19}$ or O; or

If in formula II, X represents O, and f is 0, then Z optionally may denote —$(C(R^{124})$—$C(R^{125}))$—, wherein
  $R^{124}$ and $R^{125}$, together with the carbon atoms linking them, form a fused aryl or heteroaryl group; or If in formula II, X represents O, and f is 0, then Z optionally may denote =(N—$(CR^{126})$)—, wherein the N atom is singly bonded to the O atom, and
  $R^{126}$ represents H; $C_{1-6}$-alkyl; $C_{3-8}$-cycloalkyl; aryl; heteroaryl; or $C_{3-8}$-cycloalkyl, aryl or heteroaryl bonded via a $C_{1-6}$-alkylene group; or Z in formula III represents $CR^{18a}R^{18b}$, $NR^{19}$, O, S, S(=O) or S(=O)$_2$; wherein
  $R^{18a}$ represents H; $C_{1-6}$-alkyl; $C_{3-8}$-cycloalkyl; aryl; heteroaryl; or $C_{3-8}$-cycloalkyl, aryl or heteroaryl bonded via a $C_{1-6}$-alkylene group; or
  $R^{18a}$ represents a group corresponding to formula IV:

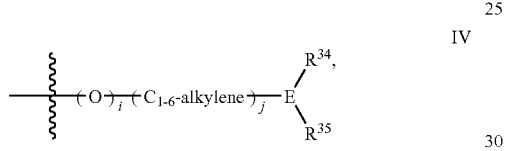

IV wherein
  i and j each independently represent 0 or 1;
  E represents N or CH,
    with the proviso that if i is 1, and j is 0, then E represents CH;
  $R^{34}$ and $R^{35}$ each independently represent H; $C_{1-6}$-alkyl; $C_{3-8}$-cycloalkyl; aryl; heteroaryl; or aryl, heteroaryl or $C_{3-8}$-cycloalkyl bonded via a $C_{1-3}$-alkylene group; or
  $R^{34}$, $R^{35}$ and E together form a 5- or 6-membered aryl or heteroaryl group; or
  $R^{34}$, $R^{35}$ and E together form a saturated heterocycle corresponding to formula V:

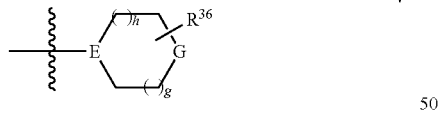

V wherein
  h and g each independently denote 0, 1 or 2;
  G represents $CR^{37a}R^{37b}$, $NR^{38}$, O, S, S=O or S(=O)$_2$, with the proviso that if E represents CH, then G does not denote $CR^{37a}R^{37b}$;
  $R^{36}$ represents from 0 to 4 substituents each independently selected from the group consisting of F; Cl; Br; I; OH; SH; =O; O—$C_{1-6}$-alkyl; $C_{1-6}$-alkyl; $C_{3-8}$-cycloalkyl; aryl; heteroaryl; or $C_{3-8}$-cycloalkyl, aryl or heteroaryl bonded via a $C_{1-6}$-alkylene group; or
  two adjacent substituents $R^{36}$ optionally may together represent a fused aryl or heteroaryl group;
  $R^{37a}$ and $R^{37b}$ each independently represent H; F; Cl; Br; I; OH; SH; =O; O—$C_{1-6}$-alkyl; $C_{1-6}$-alkyl; $C_{3-8}$-cycloalkyl; aryl; heteroaryl; or $C_{3-8}$-cycloalkyl, aryl or heteroaryl bonded via a $C_{1-6}$-alkylene group;

$R^{38}$ represents H; $C_{1-6}$-alkyl; $C_{3-8}$-cycloalkyl; aryl; heteroaryl; or aryl, heteroaryl or $C_{3-8}$-cycloalkyl bonded via a $C_{1-3}$-alkylene group;

$R^{18b}$ represents H; OH; $C_{1-6}$-alkyl; $C_{3-8}$-cycloalkyl; O—$C_{1-6}$-alkyl; O—($C_{3-8}$-cycloalkyl); ($C_{1-6}$-alkylene)-O—$C_{1-6}$-alkyl; ($C_{1-6}$-alkylene)-O—($C_{3-8}$-cycloalkyl); aryl or heteroaryl; O-aryl or O-heteroaryl; or aryl, O-aryl, heteroaryl or O-heteroaryl bonded via $C_{1-6}$-alkylene; or $R^{18b}$ represents a group corresponding to formula VI:

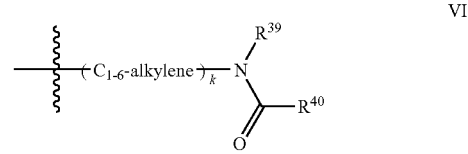

VI wherein
  k is 0 or 1;
  $R^{39}$ represents H; $C_{1-6}$-alkyl; $C_{3-8}$-cycloalkyl; aryl; heteroaryl; or $C_{3-8}$-cycloalkyl, aryl or heteroaryl bonded via a $C_{1-3}$-alkylene group;
  $R^{40}$ represents $C_{1-6}$-alkyl; $C_{3-8}$-cycloalkyl; aryl; heteroaryl; or $C_{3-8}$-cycloalkyl, aryl or heteroaryl bonded via a $C_{1-6}$-alkylene group; or
  $R^{39}$, $R^{40}$ and the N—C(=O) group linking them together form a ring corresponding to formula VII:

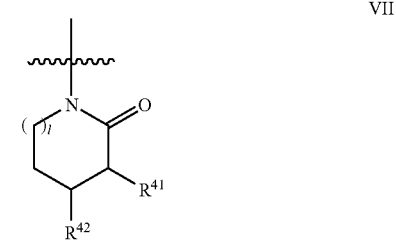

VII wherein
  l is 0, 1 or 2, and
  $R^{41}$, $R^{42}$ and the carbon atoms linking them together form a fused aryl or heteroaryl group;

$R^{19}$ represents H; or $(P)_z$—$R^{22}$, wherein
  z is 0 or 1;
  P represents (C=O), S(=O)$_2$ or C(=O)—N($R^{24}$); wherein
    the nitrogen atom in the C(=O)—N($R^{24}$) group is linked to $R^{22}$; and
  $R^{24}$ represents H; $C_{1-6}$-alkyl; $C_{3-8}$-cycloalkyl; aryl; heteroaryl; or $C_{3-8}$-cycloalkyl bonded via a $C_{1-3}$-alkylene group;
  $R^{22}$ represents $C_{1-6}$-alkyl; aryl; heteroaryl; or aryl or heteroaryl bonded via a $C_{1-6}$-alkylene group; or
  $R^{22}$ represents a group corresponding to formula VIII:

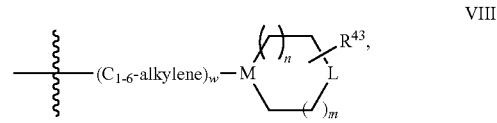

VIII wherein n is 0, 1 or 2;

m is 0, 1 or 2;

w is 0 or 1,

M represents CH or N;

with the proviso that if P represents $C(=O)-NR^{24}$, and w represents 0, then M represents CH; and with the proviso that if z and w both represent 0, then M represents CH;

L represents $CR^{44a}R^{44b}$, $NR^{45}$, O, S, $S=O$ or $S(=O)_2$; wherein $R^{44a}$ and $R^{44b}$ each independently represent H; F; Cl; Br; I; OH; $C_{1-6}$-alkyl; $O-C_{1-6}$-alkyl; $C_{3-8}$-cycloalkyl; aryl; heteroaryl; or $C_{3-8}$-cycloalkyl, aryl or heteroaryl bonded via a $C_{1-6}$-alkylene group; or $R^{44a}$ and $R^{44b}$ together optionally may represent $=O$;

$R^{45}$ represents H; $C_{1-6}$-alkyl; $C_{3-8}$-cycloalkyl; aryl; heteroaryl; or aryl, heteroaryl or $C_{3-8}$-cycloalkyl bonded via a $C_{1-3}$-alkylene group;

$R^{43}$ represents from 0 to 4 substituents each independently selected from the group consisting of F; Cl; OH; $=O$; $C_{1-6}$-alkyl; $O-C_{1-6}$-alkyl; $C_{3-8}$-cycloalkyl; aryl; heteroaryl; or $C_{3-8}$-cycloalkyl, aryl or heteroaryl bonded via a $C_{1-6}$-alkylene group; or two adjacent substituents $R^{43}$ optionally may together represent a fused aryl or heteroaryl group;

wherein the respective above-mentioned $C_{1-6}$-alkyl, $C_{1-3}$-alkylene, $C_{1-6}$-alkylene, $C_{2-6}$-alkenylene, $C_{2-6}$-alkynylene, $C_{3-6}$-cycloalkyl, $C_{3-8}$-cycloalkyl, aryl and heteroaryl groups each may each be unsubstituted or mono- or poly-substituted by identical or different substituents; and the respective above-mentioned $C_{1-6}$-alkyl, $C_{1-3}$-alkylene, $C_{1-6}$-alkylene, $C_{2-6}$-alkenylene and $C_{2-6}$-alkynylene groups may each be branched or unbranched;

or a pharmaceutically acceptable salt thereof.

2. A compound as claimed in claim 1, wherein said compound is in the form of an isolated stereoismer.

3. A compound as claimed in claim 1, wherein said compound is in the form of a mixture of stereoisomers in any mixing ratio.

4. A compound as claimed in claim 3, wherein said mixture is a racemic mixture.

5. A compound as claimed in claim 1, wherein $W^1$ and $W^3$ represent N and $W^2$ represents $CR^{60}$; or $W^1$ and $W^2$ represent N and $W^3$ represents $CR^{60}$.

6. A compound as claimed in claim 1, wherein V represents O.

7. A compound as claimed in claim 1, wherein $R^1$ represents a phenyl, naphthyl, indolyl, benzofuranyl, benzothiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl or $CH(phenyl)_2$ group, wherein said group may be unsubstituted or mono- or poly-substituted by identical or different substituents selected from the group consisting of $-O-C_{1-3}$-alkyl, $C_{1-6}$-alkyl, F, Cl, Br, I, $CF_3$, $OCF_3$, OH, SH, phenyl, naphthyl, furyl, thiazolyl, thienyl and pyridinyl.

8. A compound as claimed in claim 7, wherein $R^1$ represents a phenyl, naphthyl, benzothiophenyl, benzooxadiazolyl, thiophenyl, pyridinyl, imidazothiazolyl or dibenzofuranyl group.

9. A compound as claimed in claim 1, wherein in formula I, the partial structure (Ac I):

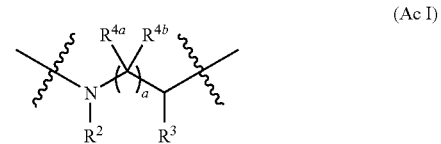

represents:

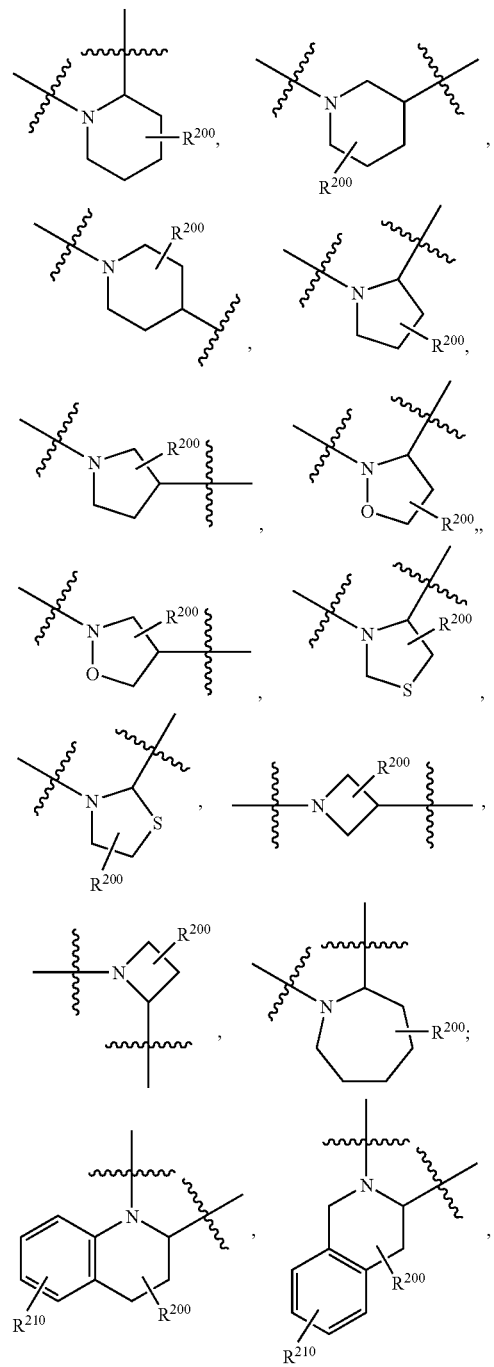

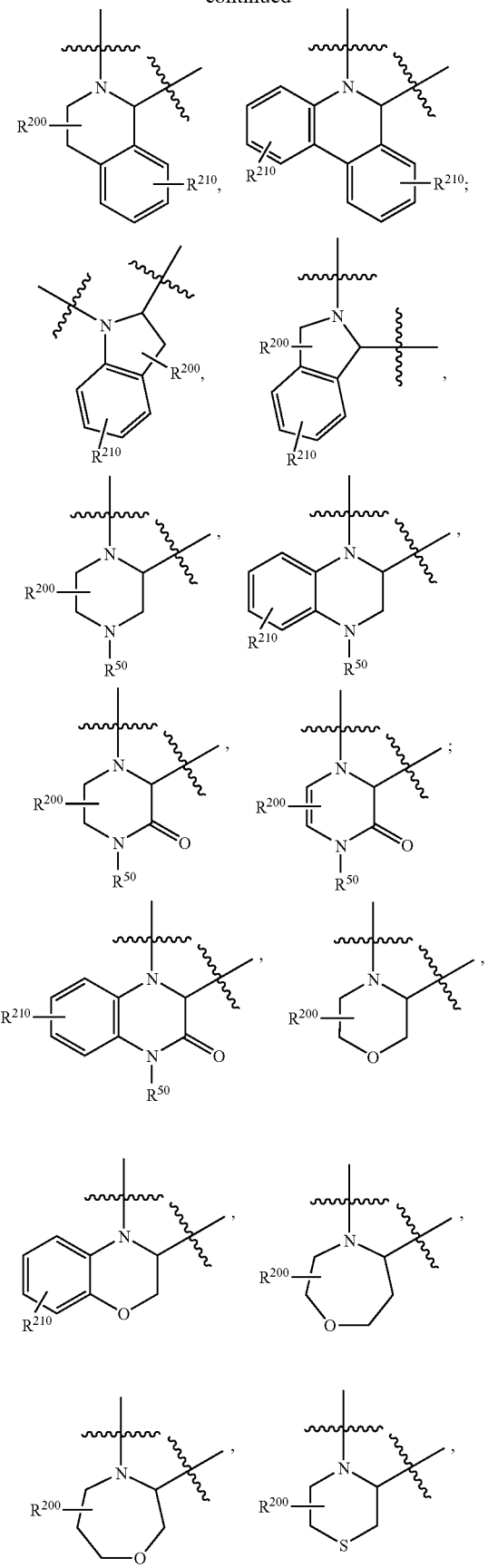

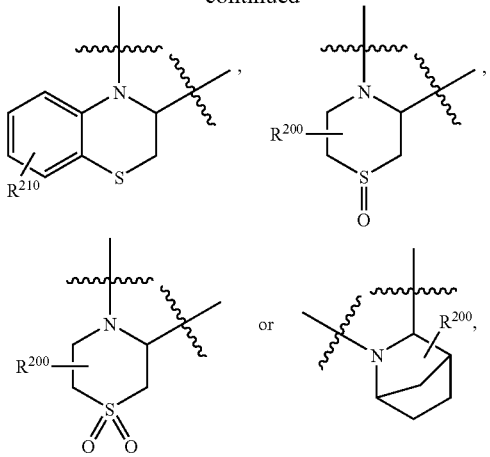

wherein
R²⁰⁰ represents from 0 to 4 substituents independently selected from the group consisting of F, Cl, —CF₃, =O, —O—CF₃, —OH, —O—C₁₋₆-alkyl and C₁₋₆-alkyl; or two substituents R²⁰⁰ optionally together represent a fused aryl group; and
R²¹⁰ represents from 0 to 4 substituents independently selected from the group consisting of —O—C₁₋₃-alkyl, C₁₋₆-alkyl, F, Cl, Br, I, CF₃, OCF₃, OH, SH, phenyl, naphthyl, furyl, thienyl and pyridinyl.

10. A compound as claimed in claim 1, wherein
R² represents H, C₁₋₆-alkyl, C₃₋₆-cycloalkyl, aryl, or a C₃₋₆-cycloalkyl or aryl bonded via a C₁₋₃-alkylene group, in each case unsubstituted or mono- or poly-substituted by identical or different substituents; and
R³ represents H, F, Cl, —CF₃, —OH, —O—C₁₋₆-alkyl, C₁₋₆-alkyl or aryl; or aryl bonded via a C₁₋₃-alkylene group, in each case unsubstituted or mono- or poly-substituted by identical or different substituents.

11. A compound as claimed in claim 10, wherein R² represents H, methyl, ethyl, n-propyl, isopropyl, n-butyl, isobutyl, tert-butyl, cyclopropyl, phenyl, pyridinyl, or phenyl or pyridinyl bonded via a C₁₋₃-alkylene group.

12. A compound as claimed in claim 1, wherein a+b=1.

13. A compound as claimed in claim 1, wherein
(a1) formula II has the structure of formula IIa:

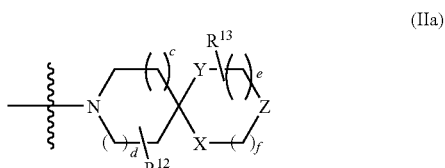

(IIa)

or
(a2) formula III has the structure of formula IIIa or IIIb:

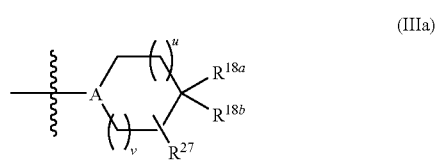

(IIIa)

14. A compound as claimed in claim 13, wherein
(a1) formula IIa has the structure of formula IIb:

(IIb)

or
(a2) formula IIIa or formula IIIb has the structure of formula IIIc, IIId or IIIe:

(IIIc)

(IIId)

(IIIe)

15. A compound as claimed in claim 8, wherein
(a1) formula IIa has the structure of formula IIb;
  $R^8$ represents H, $C_{1-6}$-alkyl, or $C_{2-6}$-cycloalkyl, in each case unsubstituted or mono- or poly-substituted by identical or different substituents, and
  $R^{9a}$ and $R^{9b}$ each represents H; or
(a2) formula IIIa or IIIb has the structure of formula IIIc or IIId, and s and t are each 0; or
(a3) formula IIIa or IIIb has the structure of formula IIIc or IIId, and two substituents $R^{27}$ together represent a $C_{1-3}$-alkylene bridge, so that the ring in formula IIIc or IIId has a bicyclically bridged form, and s and t are each 0; or
(a4) formula IIIa or IIIb has the structure of formula IIIc or IIIe;
  s is 1, and t is 1, 2 or 3; and
  $R^8$ represents H, $C_{1-6}$-alkyl or $C_{3-6}$-cycloalkyl, in each case unsubstituted or mono- or poly-substituted by identical or different substituents.

16. A compound as claimed in claim 15, wherein
(a1) formula IIb has the structure of formula IIc:

(IIc)

and s and t are each 0; or
(a2) formula IIIc or IIId has the structure of formula IIIf or IIIg:

(IIIf)

(IIIg)

wherein
  $R^{27}$ represents H or methyl or two adjacent substituents $R^{27}$ optionally form a fused aryl or heteroaryl group; or
(a3) formula IIIc or IIId has the structure of one of the following formulas A to H:

(A)

(B)

(C)

(D)

(E)

(F)

(G)

-continued

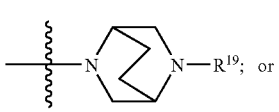
(H)

(a4) formula IIIc or IIIe has the structure of formulas IIIh or IIIi:

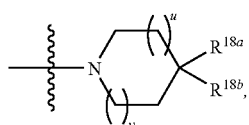
(IIIh)

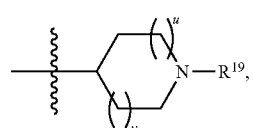
(IIIi)

and $R^{9a}$ and $R^{9b}$ each represent H.

17. A compound as claimed in claim 16, wherein
(a1) in formula IIc, $R^{16a}$ and $R^{16b}$ each represent H or together form =O; and
$R^{13}$ represents aryl or heteroaryl; or two substituents $R^{13}$ optionally together form =O; or
two adjacent substituents $R^{13}$ together form a fused aryl or heteroaryl group; or
(a2) in formula IIIf or IIIg,
$R^{18a}$ represents H; $C_{1-6}$-alkyl; $C_{3-8}$-cycloalkyl, —NH($C_{1-6}$-alkyl), —N($C_{1-6}$-alkyl)$_2$, phenyl, pyridyl, pyrimidinyl, thiazolyl, imidazolyl, triazolyl or thienyl, in each case unsubstituted or mono- or poly-substituted; or phenyl, pyridyl, pyrimidinyl, imidazolyl, triazolyl or thienyl bonded via a —(O)$_{0-1}$—$C_{1-6}$-alkylene group and in each case unsubstituted or mono- or poly-substituted; or
$R^{18a}$ represents a group corresponding to formula VIIa:

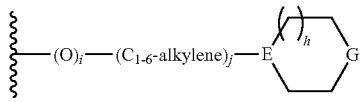
VIIa wherein
i is 0 or 1;
j is 0 or 1;
h is 0 or 1;
E represents N or CH;
with the proviso that if i is 1 and j is 0, then E represents CH;
G represents $CR^{37a}R^{37b}$ or $NR^{38}$; wherein
$R^{37a}$ and $R^{37b}$ each independently represent H; F or $C_{1-6}$-alkyl, in each case unsubstituted or mono- or poly-substituted by identical or different substituents;
$R^{38}$ represents H; $C_{3-6}$-cycloalkyl or pyridyl;
$R^{18b}$ represents H; OH; $C_{1-6}$-alkyl; phenyl, pyridyl, pyrimidinyl, imidazolyl, triazolyl, thienyl or thiazolyl; in each case unsubstituted or mono- or poly-substituted by identical or different substituents; phenyl, pyridyl, pyrimidinyl, O-phenyl, O-pyridyl, imidazolyl, triazolyl, thienyl or thiazolyl bonded via a $C_{1-6}$-alkylene group and in each case unsubstituted or mono- or substituted by identical or different substituents; or phenyl, pyridyl, pyrimidinyl, imidazolyl, triazolyl, thiazolyl or thienyl bridged via $C_{1-6}$-alkylene-NH(C=O) and in each case unsubstituted or substituted by identical or different substituents;
$R^{19}$ represents H; $C_{1-6}$-alkyl; $C_{3-8}$-cycloalkyl, or $C_{1-6}$-alkyl bonded via (C=O)$_{0-1}$; phenyl, pyridyl, thienyl, thiazolyl, triazolyl, pyrimidinyl or imidazolyl, in each case unsubstituted or mono- or poly-substituted by identical or different substituents; phenyl, pyridyl, thienyl, thiazolyl, pyrimidinyl, triazolyl or imidazolyl bonded via a $C_{1-6}$-alkylene group and in each case unsubstituted or mono- or poly-substituted by identical or different substituents; or
$R^{19}$ corresponds to formula VIIIa:

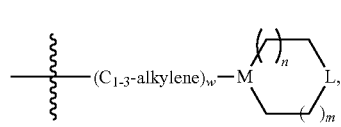
(VIIIa)

wherein
w is 0 or 1;
n is 0 or 1;
m is 0 or 1;
M represents CH or N, with the proviso that if w is 0, then M represents CH;
L represents $CR^{44a}R^{44b}$ or $NR^{45}$; wherein
$R^{44a}$ and $R^{44b}$ each independently represent H; F or $C_{1-6}$-alkyl, in each case unsubstituted or mono- or poly-substituted by identical or different substituents; and
$R^{45}$ represents H; $C_{1-6}$-alkyl, $C_{3-6}$-cycloalkyl or pyridyl; or
(a3) the formula IIIc or IIId has the structure of one of the following formulas A to H:

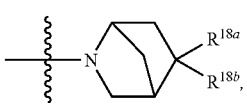
(A)

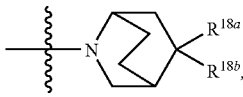
(B)

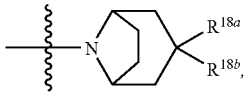
(C)

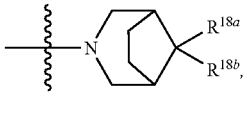
(D)

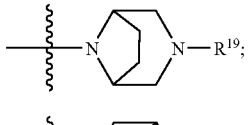
(E)

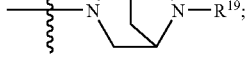
(F)

-continued

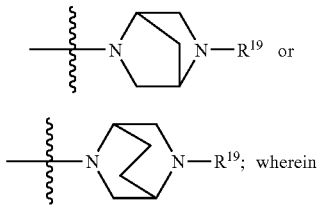
(G)

(H)

wherein

R$^{18a}$ represents H; C$_{1-6}$-alkyl; C$_{3-8}$-cycloalkyl, N(C$_{1-6}$-alkyl)$_2$; NH(C$_{1-6}$-alkyl); azetidinyl; pyrrolidinyl, piperidinyl, 4-(C$_{1-6}$-alkyl)-piperazinyl; phenyl, pyridyl, pyrimidinyl, imidazolyl, triazolyl, thiazolyl or thienyl, in each case unsubstituted or mono- or poly-substituted by identical or different substituents; or N(C$_{1-6}$-alkyl)$_2$; NH(C$_{1-6}$-alkyl); azetidinyl; pyrrolidinyl, piperidinyl, 4-(C$_{1-6}$-alkyl)-piperazinyl; phenyl, imidazolyl, triazolyl, thienyl, thiazolyl, pyrimidinyl or pyridyl bonded via a —(O)$_{0-1}$—C$_{1-6}$-alkylene group and in each case unsubstituted or mono- or poly-substituted by identical or different substituents;

R$^{18b}$ represents H; OH; C$_{1-6}$-alkyl; phenyl, pyridyl, pyrimidinyl, imidazolyl, triazolyl, thiazolyl or thienyl, in each case unsubstituted or mono- or poly-substituted by identical or different substituents; or phenyl, pyridyl, pyrimidinyl, imidazolyl, triazolyl, thiazolyl or thienyl bonded via a C$_{1-6}$-alkylene group and in each case unsubstituted or mono- or poly-substituted by identical or different substituents;

R$^{19}$ represents H; C$_{1-6}$-alkyl; C$_{3-8}$-cycloalkyl, phenyl, pyridyl, pyrimidinyl, thienyl, imidazolyl, thiazolyl or triazolyl, in each case unsubstituted or mono- or poly-substituted by identical or different substituents; or phenyl, pyridyl, pyrimidinyl, thienyl, imidazolyl, thiazolyl or triazolyl bonded via a C$_{1-6}$-alkylene group or a (C=O) group and in each case unsubstituted or mono- or poly-substituted by identical or different substituents; or (a4) in formula IIIh or IIIi R$^{18a}$ represents H; C$_{1-6}$-alkyl; C$_{3-8}$-cycloalkyl, N(C$_{1-6}$-alkyl)$_2$; NH(C$_{1-8}$-alkyl), azetidinyl; pyrrolidinyl, piperidinyl, 4-(C$_{1-6}$-alkyl)-piperazinyl; phenyl, pyridyl, pyrimidinyl, thienyl, imidazolyl, thiazolyl or triazolyl, in each case unsubstituted or mono- or poly-substituted by identical or different substituents; N(C$_{1-6}$-alkyl)$_2$; NH(C$_{1-6}$-alkyl), azetidinyl; pyrrolidinyl, piperidinyl, 4-(C$_{1-6}$-alkyl)-piperazinyl; phenyl, pyridyl, pyrimidinyl, thienyl, imidazolyl, thiazolyl or triazolyl bonded via a —(O)$_{0/1}$—C$_{1-6}$-alkylene group and in each case unsubstituted or mono- or poly-substituted by identical or different substituents;

R$^{18}$ represents H; OH; C$_{1-6}$-alkyl; phenyl, pyridyl, pyrimidinyl, thienyl, imidazolyl, thiazolyl or triazolyl, in each case unsubstituted or mono- or poly-substituted by identical or different substituents; or phenyl, pyridyl, pyrimidinyl, thienyl, imidazolyl, thiazolyl or triazolyl bonded via a C$_{1-6}$-alkylene group and in each case unsubstituted or mono- or poly-substituted by identical or different substituents;

R$^{19}$ represents H; C$_{1-6}$-alkyl; C$_{3-8}$-cycloalkyl, phenyl, pyridyl, pyrimidinyl, thienyl, imidazolyl, thiazolyl or triazolyl, in each case unsubstituted or mono- or poly-substituted by identical or different substituents; or phenyl, pyridyl, pyrimidinyl, thienyl, imidazolyl, thiazolyl or triazolyl bonded via a C$_{1-6}$-alkylene group or (C=O) group and in each case unsubstituted or mono- or poly-substituted by identical or different substituents.

18. A compound as claimed in claim 17, wherein (a1) formula IIc has the structure of one of the following formulas SP1 to SP34:

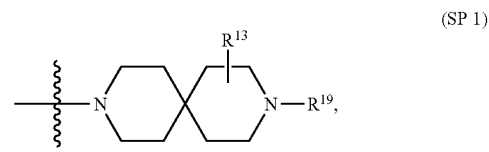
(SP 1)

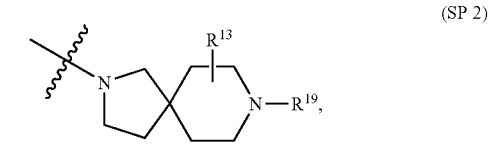
(SP 2)

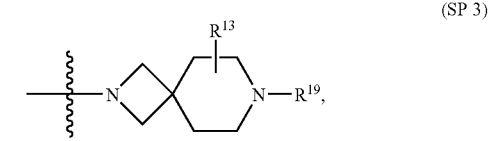
(SP 3)

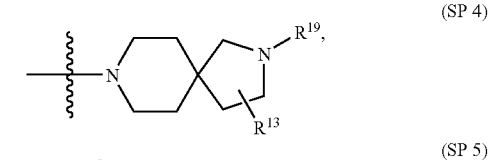
(SP 4)

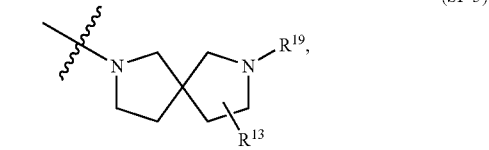
(SP 5)

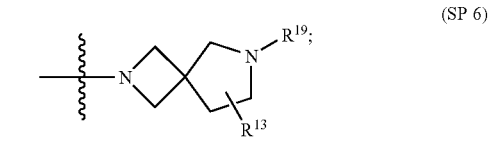
(SP 6)

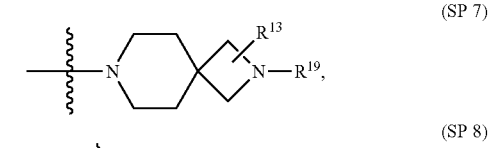
(SP 7)

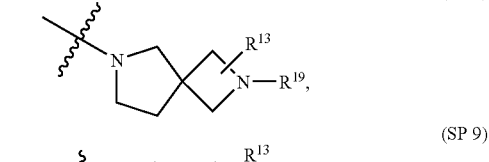
(SP 8)

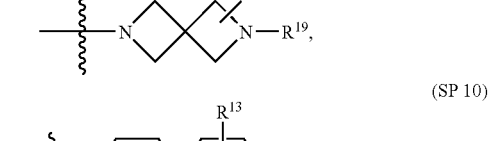
(SP 9)

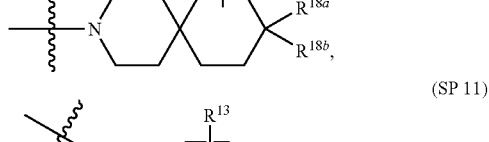
(SP 10)

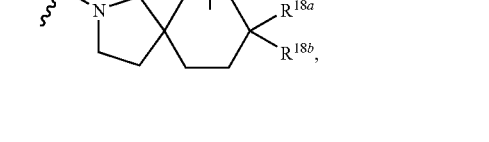
(SP 11)

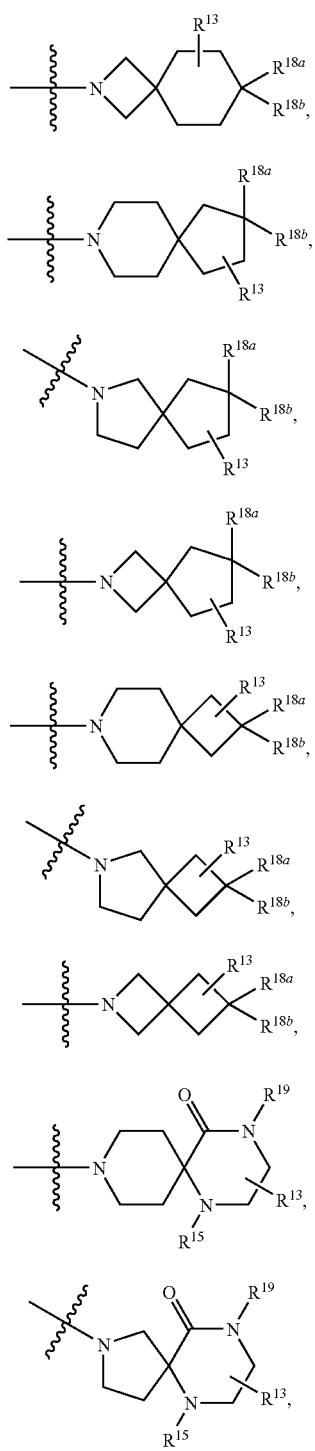
(SP 12)
(SP 13)
(SP 14)
(SP 16)
(SP 17)
(SP 18)
(SP 19)
(SP 20)
(SP 21)
(SP 22)
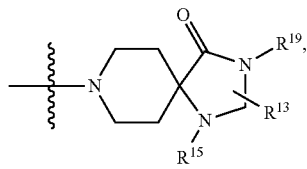 (SP 23)
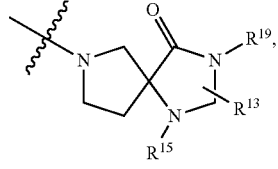 (SP 24)
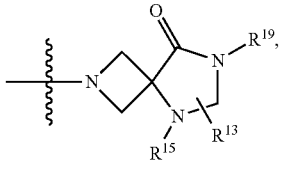 (SP 25)
 (SP 26)
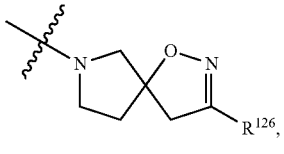 (SP 27)
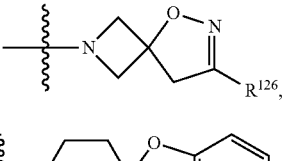 (SP 28)
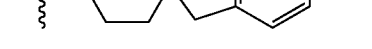 (SP 29)
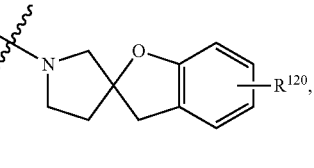 (SP 30)
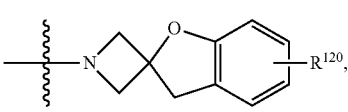 (SP 31)
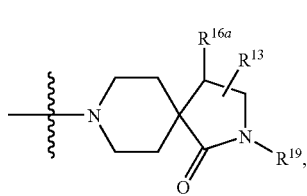 (SP 32)

-continued

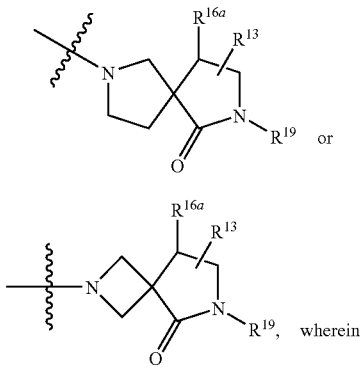
(SP 33)

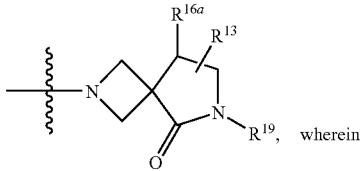
(SP 34), wherein $R^{13}$ represents H or phenyl, in each case unsubstituted or mono- or poly-substituted by identical or different substituents; or
two substituents $R^{13}$ optionally together form =O; or
two adjacent substituents $R^{13}$ together optionally form a fused aryl or heteroaryl;
$R^{15}$ represents H; $C_{1-6}$-alkyl; $C_{3-8}$-cycloalkyl, phenyl, pyridyl, pyrimidinyl, imidazolyl, triazolyl, thiazolyl or thienyl, in each case unsubstituted or mono- or poly-substituted by identical or different substituents; or phenyl, pyridyl, pyrimidinyl, imidazolyl, triazolyl, thiazolyl or thienyl bonded via a $C_{1-6}$-alkylene group and in each case unsubstituted or mono- or poly-substituted by identical or different substituents;
$R^{16a}$ represents H, $C_{1-6}$-alkyl, phenyl, pyridyl, pyrimidinyl, imidazolyl, triazolyl, thiazolyl or thienyl, in each case unsubstituted or mono- or poly-substituted by identical or different substituents;
$R^{18a}$ represents H; $C_{1-6}$-alkyl; $C_{3-8}$-cycloalkyl, $N(C_{1-6}$-alkyl$)_2$; NH($C_{1-6}$-alkyl), azetidinyl; pyrrolidinyl, piperidinyl, 4-($C_{1-6}$-alkyl)-piperazinyl; phenyl, pyridyl, pyrimidinyl, imidazolyl, triazolyl, thiazolyl or thienyl, in each case unsubstituted or mono- or poly-substituted by identical or different substituents; or N($C_{1-6}$-alkyl$)_2$; NH($C_{1-6}$-alkyl), azetidinyl; pyrrolidinyl, piperidinyl, 4-($C_{1-6}$-alkyl)-piperazinyl; phenyl, pyridyl, pyrimidinyl, imidazolyl, triazolyl, thiazolyl or thienyl bonded via a —(O)$_{0/1}$—$C_{1-6}$-alkylene group and in each case unsubstituted or mono- or poly-substituted by identical or different substituents;
$R^{18b}$ represents H; OH; $C_{1-6}$-alkyl; phenyl, pyridyl, pyrimidinyl, imidazolyl, triazolyl, thiazolyl or thienyl, in each case unsubstituted or mono- or poly-substituted by identical or different substituents; or phenyl, pyridyl, pyrimidinyl, imidazolyl, triazolyl, thiazolyl or thienyl bonded via a $C_{1-6}$-alkylene group and in each case unsubstituted or mono- or poly-substituted by identical or different substituents;
$R^{19}$ represents H; $C_{1-6}$-alkyl; $C_{3-8}$-cycloalkyl, phenyl, pyridyl, pyrimidinyl, imidazolyl, triazolyl, thiazolyl or thienyl, in each case unsubstituted or mono- or poly-substituted by identical or different substituents; or phenyl, pyridyl, pyrimidinyl, imidazolyl, triazolyl, thiazolyl or thienyl bonded via a $C_{1-6}$-alkylene group or (C=O) group and in each case unsubstituted or mono- or poly-substituted by identical or different substituents;
$R^{120}$ represents H; F; Cl; OH; OCH$_3$, $C_{1-6}$-alkyl; phenyl, in each case unsubstituted or mono- or poly-substituted by identical or different substituents; and $R^{126}$ represents H; $C_{1-6}$-alkyl; $C_{3-6}$-cycloalkyl; phenyl, pyridyl, pyrimidinyl, imidazolyl, triazolyl, thiazolyl or thienyl; or $C_{3-6}$-cycloalkyl, phenyl or pyridyl bonded via a $C_{1-3}$-alkylene group and in each case unsubstituted or mono- or poly-substituted by identical or different substituents.

19. A compound as claimed in claim 1, wherein in formula I, the partial structure (B):

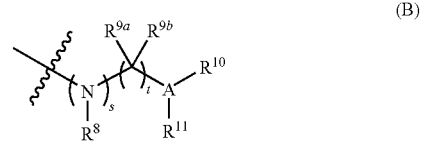
(B)

is selected from the group consisting of:

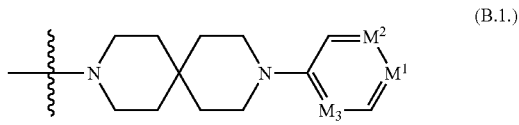
(B.1.)

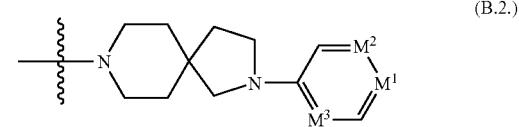
(B.2.)

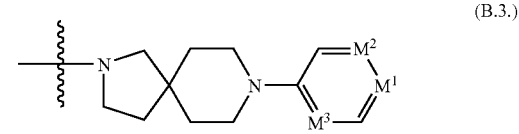
(B.3.)

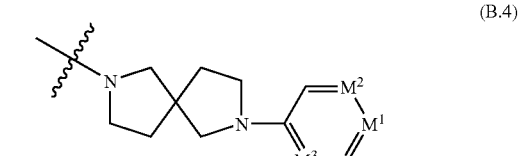
(B.4)

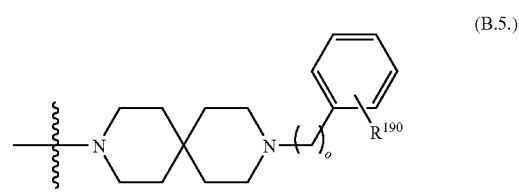
(B.5.)

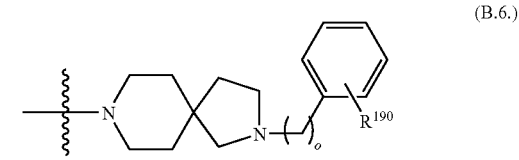
(B.6.)

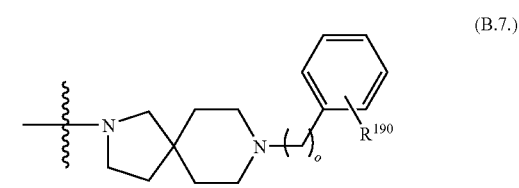
(B.7.)

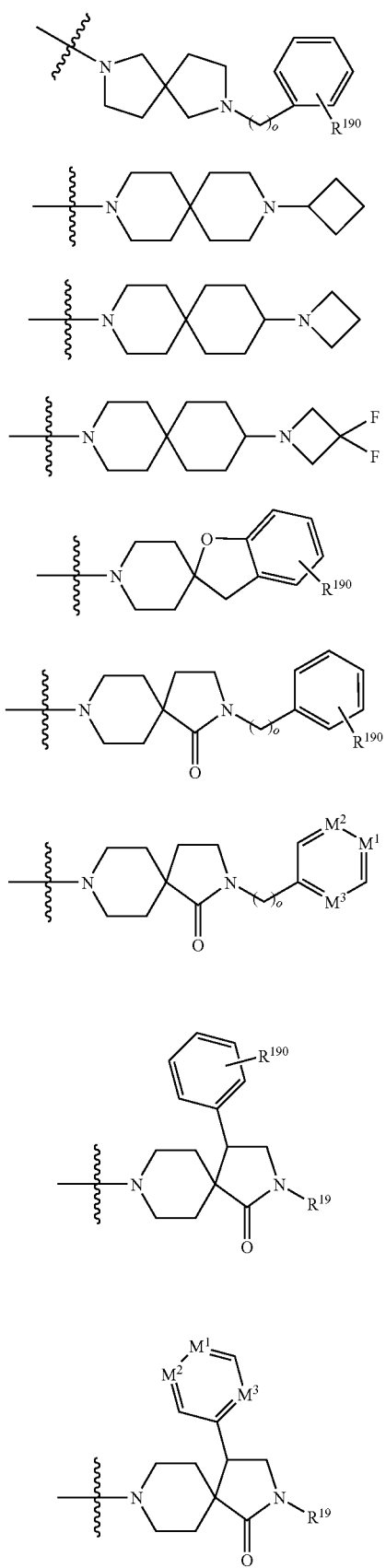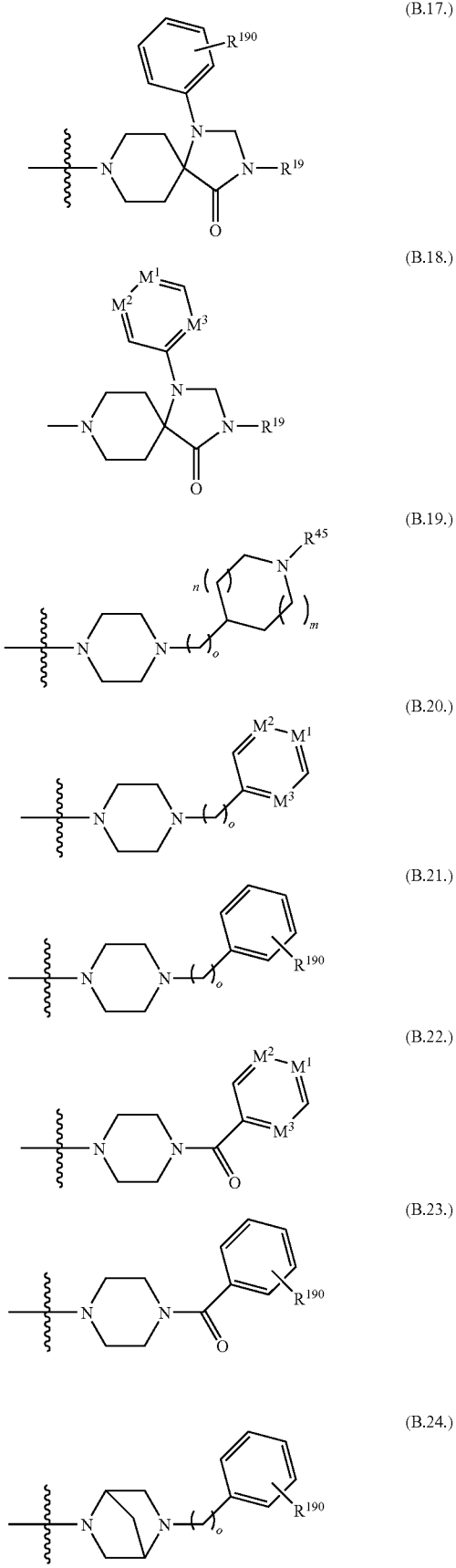

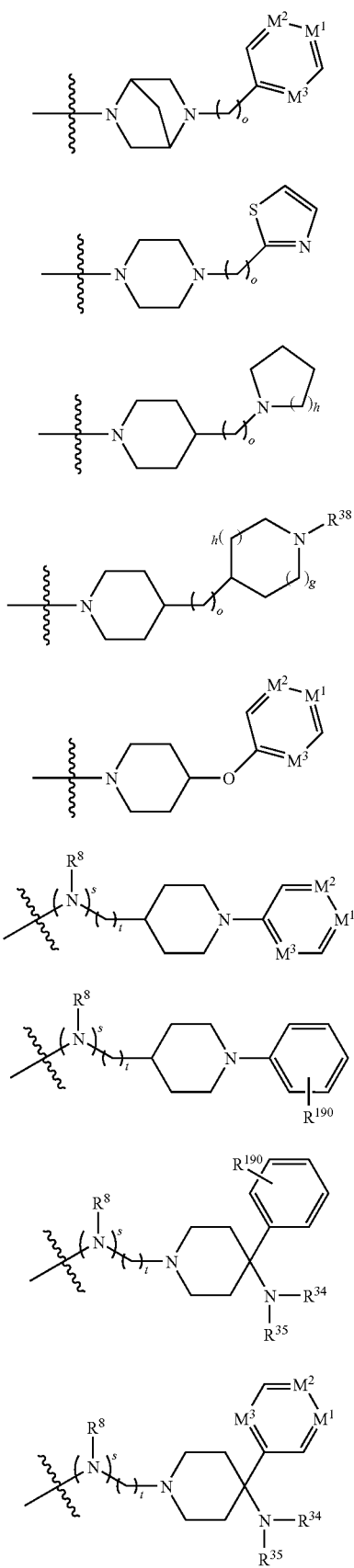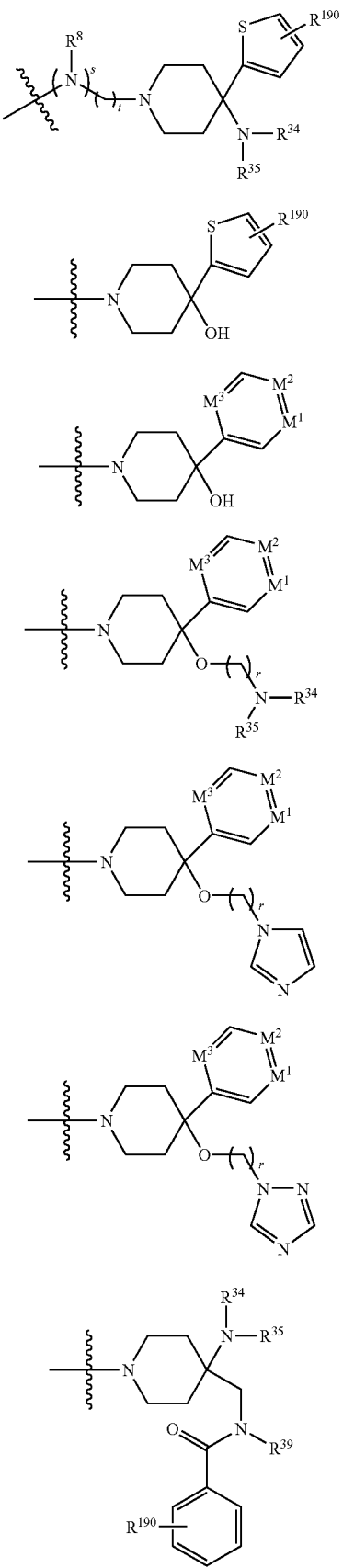

-continued

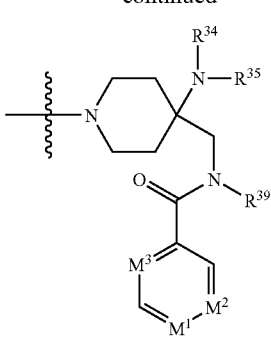
(B.40.)

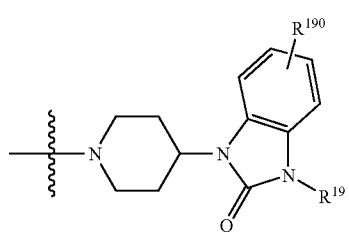
(B.41.)

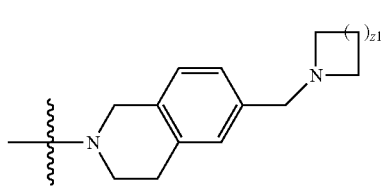
(B.42.)

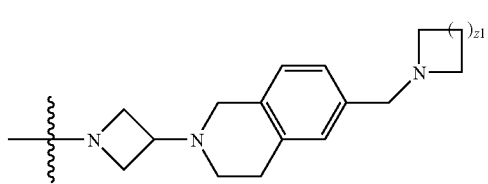
(B.43.)

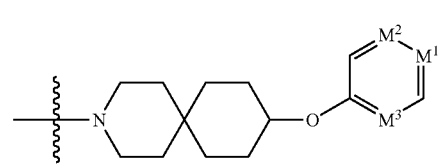
(B.44.)

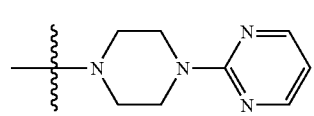
(B.45.)

wherein
h is 0 or 1;
g is 0 or 1;
m is 0 or 1;
n is 0 or 1;
o is 0, 1, 2 or 3;
r is 1, 2 or 3;
s is 0 or 1;
t is 0, 1, 2 or 3, with the proviso that if s is 0, then t is 0;
z1 is 0, 1, 2 or 3;
$M^1$, $M^2$ and $M^3$ each independently represent N or CH, with the proviso that one of $M^1$, $M^2$ and $M^3$ represents N, and the other two represent CH;
$R^8$ represents H; $C_{1-6}$-alkyl; or $C_{3-6}$-cycloalkyl; in each case unsubstituted or mono- or poly-substituted by identical or different substituents;
$R^{19}$ is selected from H; $C_{1-6}$-alkyl; or $C_{3-6}$-cycloalkyl; in each case unsubstituted or mono- or poly-substituted by identical or different substituents;

$R^{34}$ and $R^{35}$ are each independently methyl or ethyl, or together with the N atom linking them form an azetidinyl; pyrrolidinyl, or piperidinyl, 4-($C_{1-6}$-alkyl)-piperazinyl group; in each case unsubstituted or mono- or poly-substituted by identical or different substituents;

$R^{38}$ represents H, $C_{1-6}$-alkyl, $C_{3-6}$-cycloalkyl or pyridyl;

$R^{39}$ represents H; $C_{1-6}$-alkyl, or $C_{3-6}$-cycloalkyl; in each case unsubstituted or mono- or poly-substituted by identical or different substituents;

$R^{45}$ represents H, $C_{1-6}$-alkyl, $C_{3-6}$-cycloalkyl or pyridyl; and $R^{190}$ represents from 0 to 4 substituents independently selected from the group consisting of F, Cl, O—$CF_3$, $CF_3$ and CN.

20. A compound as claimed in claim 19, wherein r is 1 or 2;

t is 0, 1 or 2;

z1 is 1;

$R^8$ represents methyl, ethyl, n-propyl, isopropyl, n-butyl, sec-butyl, isobutyl, tert-butyl or cyclopropyl;

$R^{19}$ represents methyl, ethyl, n-propyl, isopropyl, n-butyl, sec-butyl, isobutyl, tert-butyl or cyclopropyl; and $R^{39}$ represents methyl, ethyl, n-propyl, isopropyl, n-butyl, sec-butyl, isobutyl, tert-butyl or cyclopropyl.

21. A compound as claimed in claim 1, corresponding to any one of the following formulas C1 to C21:

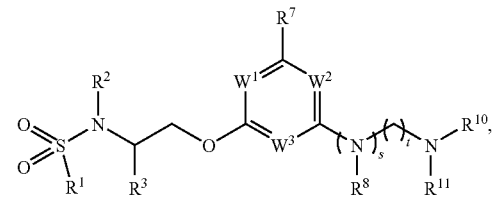
(C1)

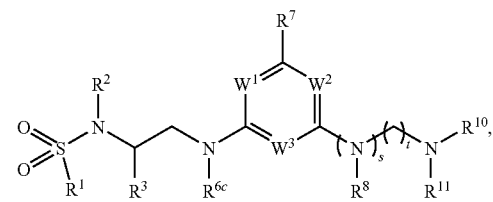
(C2)

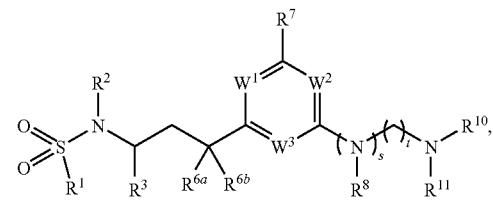
(C3)

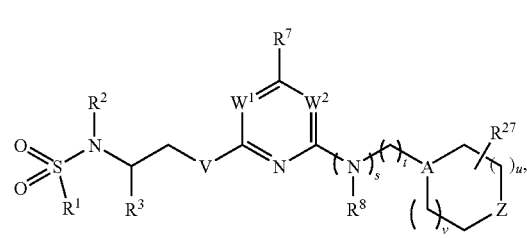
(C4)

(C5)
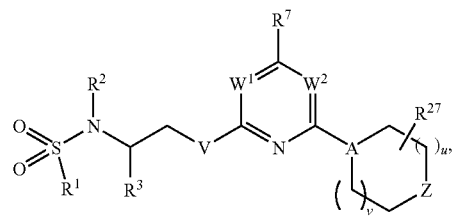
(C6)
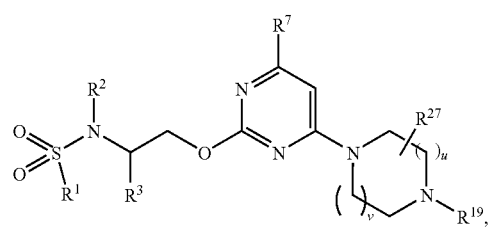
(C7)
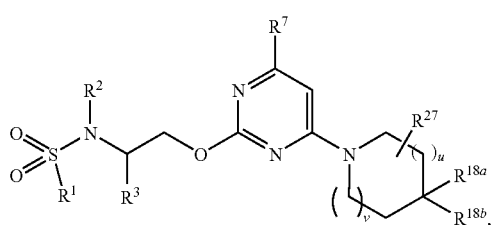
(C8)
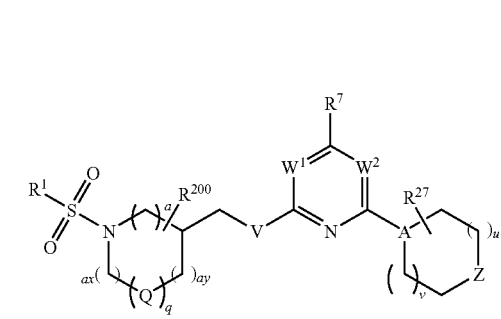
(C9)
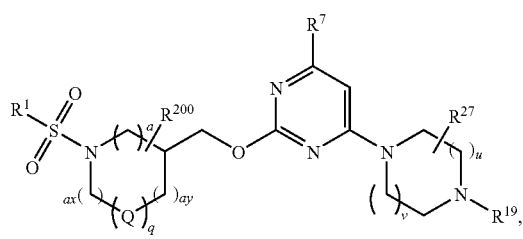
(C10)
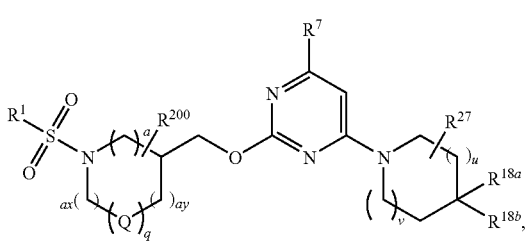
(C11)
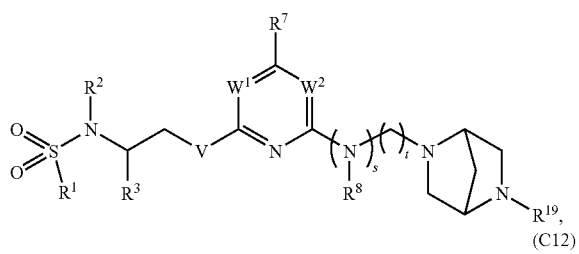
(C12)
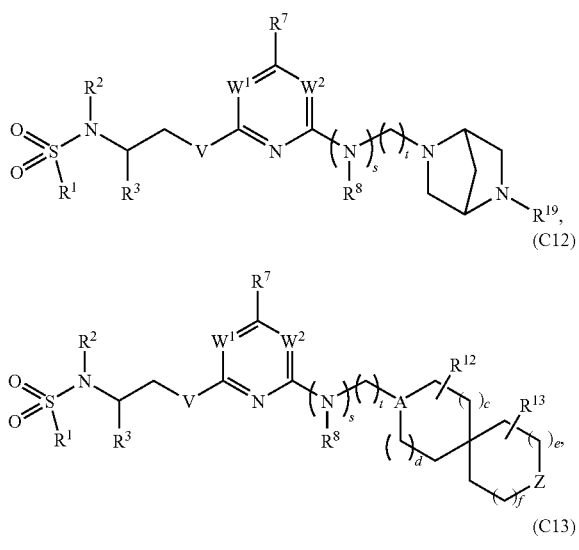
(C13)
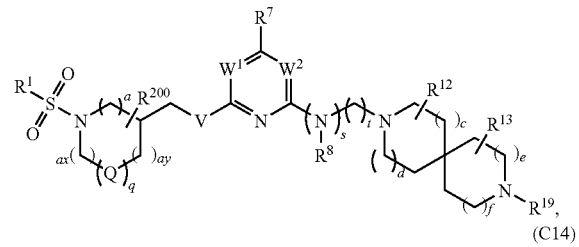
(C14)
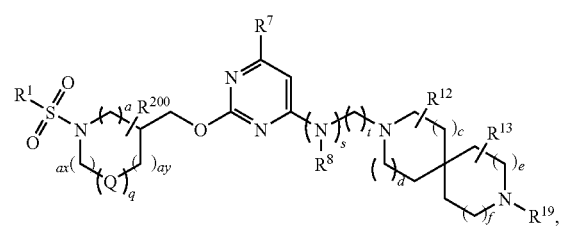
(C15)
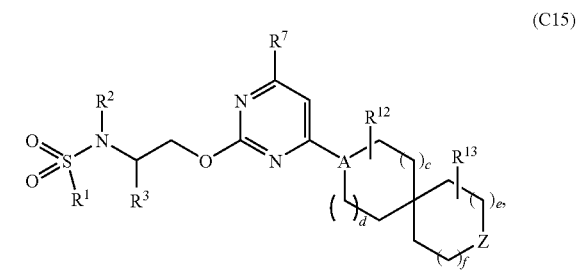
(C16)
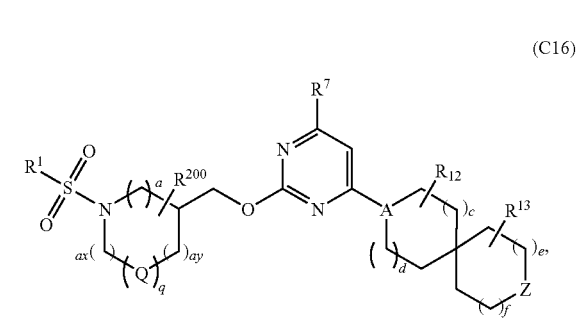

-continued

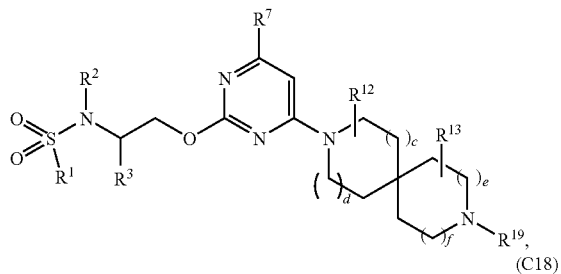
(C17)

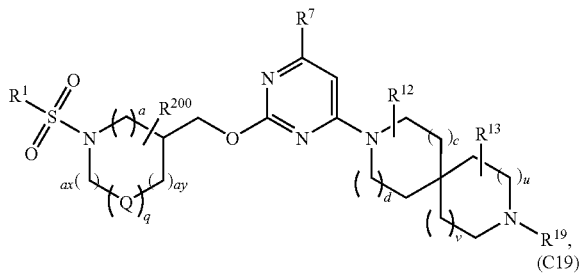
(C18)

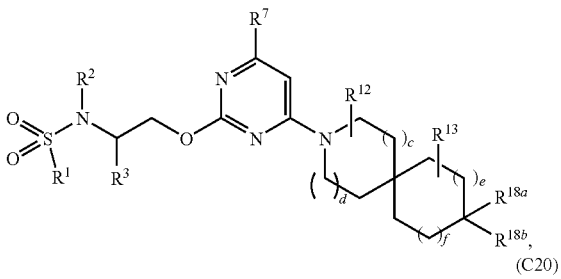
(C19)

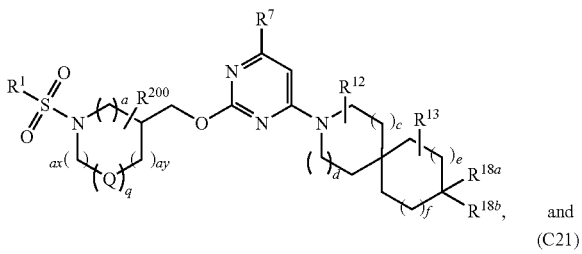
(C20)

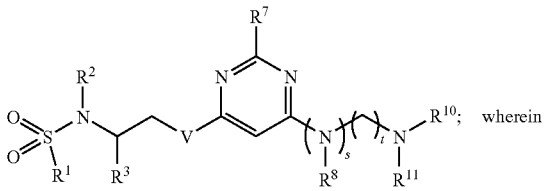
(C21)

q is 0 or 1,
a is 0, 1 or 2;
ax is 0, 1, 2 or 3;
ay is 0, 1 or 2;
q is 0 or 1;
with the proviso that a+ax+ay+q≧2;
Q represents $CH_2$, $NR^{50}$, O, S, S=O or $S(=O)_2$.

22. A compound as claimed in claim 1, wherein the compound is selected from the group consisting of:

4-methoxy-N,2,6-trimethyl-N-[2-[[4-[4-(2-1-pyrrolidinylethyl)-1-piperidinyl]-2-pyrimidinyl]oxy]ethyl]benzenesulfonamide, 4-methoxy-N,2,6-trimethyl-N-[2-[[4-[4-(4-pyridyl)-1-piperazinyl]-2-pyrimidinyl]oxy]ethyl]benzenesulfonamide, N-[2-[[4-[2-(4-dimethylamino-4-phenyl-1-piperidinyl)ethyl-methylamino]-2-pyrimidinyl]oxy]ethyl]-4-methoxy-N,2,6-trimethylbenzenesulfonamide, 2-[[1-(4-methoxy-2,6-dimethylphenyl)sulfonyl-2-piperidinyl]methoxy]-4-[4-(3-pyridyl)-4-(2-1-pyrrolidinylethoxy)-1-piperidinyl]pyrimidine, N-cyclopropyl-4-methoxy-2,6-dimethyl-N-[2-[[4-[9-(4-pyridyl)-3,9-diazaspiro[5.5]undecan-3-yl]-2-pyrimidinyl]oxy]ethyl]benzenesulfonamide hydrochloride, N-cyclopropyl-4-methoxy-2,6-dimethyl-N-[2-[[4-[2-[1-(4-pyridyl)-4-piperidinyl]ethylamino]-2-pyrimidinyl]oxy]ethyl]benzenesulfonamide, N-cyclopropyl-4-methoxy-2,6-dimethyl-N-[2-[[4-[4-(3-pyridyl)-4-(2-1-pyrrolidinylethoxy)-1-piperidinyl]-2-pyrimidinyl]oxy]ethyl]benzenesulfonamide, N-cyclopropyl-N-[2-[[4-[4-hydroxy-4-(3-pyridyl)-1-piperidinyl]-2-pyrimidinyl]oxy]ethyl]-4-methoxy-2,6-dimethylbenzenesulfonamide, 2-chloro-N-cyclopropyl-6-methyl-N-[2-[[4-[9-(4-pyridyl)-3,9-diazaspiro[5.5]undecan-3-yl]-2-pyrimidinyl]oxy]ethyl]benzenesulfonamide, N-cyclopropyl-N-[2-[[4-[9-(4-pyridyl)-3,9-diazaspiro[5.5]undecan-3-yl]-2-pyrimidinyl]oxy]ethyl]-2-(trifluoromethyl)benzenesulfonamide, 3-[2-[[(2S,4R)-4-fluoro-1-(4-methoxy-2,6-dimethylphenyl)sulfonyl-2-pyrrolidinyl]methoxy]-4-pyrimidinyl]-9-(4-pyridyl)-3,9-diazaspiro[5.5]undecane, N-cyclopropyl-4-methoxy-2,6-dimethyl-N-[2-[[4-[4-(4-pyridyloxy)-1-piperidinyl]-2-pyrimidinyl]oxy]ethyl]benzenesulfonamide, N-[2-[[4-[6-(1-azetidinylmethyl)-3,4-dihydro-1H-isoquinolin-2-yl]-2-pyrimidinyl]oxy]ethyl]-N-cyclopropyl-4-methoxy-2,6-dimethylbenzenesulfonamide, N-cyclopropyl-4-methoxy-2,6-dimethyl-N-[2-[[4-[8-(4-pyridyl)-3,8-diazaspiro[4.4]nonan-3-yl]-2-pyrimidinyl]oxy]ethyl]benzenesulfonamide, N-[2-[[4-[9-(1-azetidinyl)-3-azaspiro[5.5]undecan-3-yl]-2-pyrimidinyl]oxy]ethyl]-N-cyclopropyl-4-methoxy-2,6-dimethylbenzenesulfonamide hydrochloride, N-cyclopropyl-4-methoxy-2,6-dimethyl-N-[2-[[4-[9-(4-pyridyloxy)-3-azaspiro[5.5]undecan-3-yl]-2-pyrimidinyl]oxy]ethyl]benzenesulfonamide, N-cyclopropyl-N-[2-[[4-[9-(3,3-difluoro-1-azetidinyl)-3-azaspiro[5.5]undecan-3-yl]-2-pyrimidinyl]oxy]ethyl]-4-methoxy-2,6-dimethylbenzenesulfonamide, 3-[2-[[1-(4-methoxy-2,6-dimethylphenyl)sulfonyl-3-azetidinyl]oxy]-4-pyrimidinyl]-9-(4-pyridyl)-3,9-diazaspiro[5.5]undecane, N-cyclopropyl-4-methoxy-2,6-dimethyl-N-[2-[[4-[8-(4-pyridyl)-3,8-diazaspiro[4.5]decan-3-yl]-2-pyrimidinyl]oxy]ethyl]benzenesulfonamide, N-[2-[[4-[3-[6-(1-azetidinylmethyl)-3,4-dihydro-1H-isoquinolin-2-yl]-1-azetidinyl]-2-pyrimidinyl]oxy]ethyl]-N-cyclopropyl-4-methoxy-2,6-dimethylbenzenesulfonamide, 2,6-dichloro-N-cyclopropyl-3-methyl-N-[2-[4-(9-pyridin-4-yl-3,9-diazaspiro[5.5]undecan-3-yl)-pyrimidin-2-yl]oxy-ethyl]-benzenesulfonic acid amide, 4-methoxy-2,6-dimethyl-N-[1-[[4-(9-pyridin-4-yl-3,9-diazaspiro[5.5]undecan-3-yl)-pyrimidin-2-yl]oxy-methyl]-cyclobutyl]-benzenesulfonic acid amide, N-cyclopropyl-4-methoxy-2,6-dimethyl-N-[2-[4-[9-pyridin-3-yl-9-(2-pyrrolidin-1-yl-ethoxy)-3-azaspiro[5.5]undecan-3-yl]-pyrimidin-2-yl]oxy-ethyl]-benzenesulfonic acid amide, N-[1,1-dimethyl-2-[4-(9-pyridin-4-yl-3,9-diazaspiro[5.5]undecan-3-yl)-pyrimidin-2-yl]oxy-ethyl]-4-methoxy-2,6-dimethyl-benzenesulfonic acid amide, N-cyclopropyl-4-methoxy-2,6-dimethyl-N-[3-[4-(9-pyridin-4-yl-3,9-diazaspiro[5.5]undecan-3-yl)-pyrimidin-2-yl]oxy-propyl]-benzenesulfonic acid amide, 3-[2-[[(2S)-1-[(4-methoxy-2,6-dimethyl-phenyl)sulfonyl]-piperidin-2-yl]-methoxy]-pyrimidin-4-yl]-9-pyridin-4-yl-3,9-diazaspiro[5.5]undecane, 4-methoxy-N,2,6-trimethyl-N-[2-[[2-[4-(2-1-pyrrolidinylethyl)-1-piperidinyl]-4-pyrimidinyl]oxy]ethyl]benzenesulfonamide, 4-methoxy-N,2,6-trimethyl-N-[2-[[2-[4-(4-pyridyl)-1-piperazinyl]-4-pyrimidinyl]oxy]ethyl]benzenesulfonamide, N-[2-[[2-[2-(4-dimethylamino-4-phenyl-1-piperidinyl)ethyl-methylamino]-4-pyrimidinyl]oxy]ethyl]-4-methoxy-N,2,6-trimethylbenzenesulfonamide, N-[2-(4-dimethylamino-4-phenyl-1-piperidinyl)ethyl]-4-[[1-(4-methoxy-2,6-dimethylphenyl)sulfonyl-2-piperidinyl]methoxy]-N-methyl-2-pyrimidineamine, N-cyclopropyl-4-methoxy-2,6-dimethyl-N-[2-[[2-[4-(4-pyridyloxy)-1-piperidinyl]-4-pyrimidinyl]oxy]ethyl]benzenesulfonamide, 2-chloro-N-cyclopropyl-6-methyl-N-[2-[[2-[9-(4-pyridyl)-3,9-diazaspiro[5.5]undecan-3-yl]-4-pyrimidinyl]oxy]ethyl]benzenesulfonamide, 3-[4-[[1-(4-methoxy-2,6-dimethylphenyl)sulfonyl-3-azetidinyl]oxy]-2-pyrimidinyl]-9-(4-pyridyl)-3,9-diazaspiro[5.5]undecane, N-cyclopropyl-4-methoxy-2,6-dimethyl-N-[2-[[6-[9-(4-pyridyl)-3,9-diazaspiro[5.5]undecan-3-yl]-4-pyrimidinyl]oxy]ethyl]benzenesulfonamide, N-cyclopropyl-4-methoxy-2,6-dimethyl-N-[2-[methyl-[6-(9-pyridin-4-yl-3,9-diazaspiro[5.5]undecan-3-yl)-pyrazin-2-yl]-amino]-ethyl]-benzenesulfonic acid amide, N-cyclopropyl-4-methoxy-2,6-dimethyl-N-[2-[methyl-[6-(9-pyridin-4-yl-3,9-diazaspiro[5.5]undecan-3-yl)-pyrimidin-4-yl]-amino]-ethyl]-benzenesulfonic acid amide, N-cyclopropyl-4-methoxy-2,6-dimethyl-N-[2-[methyl-[2-(9-pyridin-4-yl-3,9-diazaspiro[5.5]undecan-3-yl)-pyrimidin-4-yl]-amino]-ethyl]-benzenesulfonic acid amide, N-cyclopropyl-4-methoxy-2,6-dimethyl-N-[2-[methyl-[4-(9-pyridin-4-yl-3,9-diazaspiro[5.5]undecan-3-yl)-pyrimidin-2-yl]-amino]-ethyl]-benzenesulfonic acid amide, N-cyclopropyl-4-methoxy-2,6-dimethyl-N-[3-[6-(9-pyridin-4-yl-3,9-diazaspiro[5.5]undecan-3-yl)-pyrazin-2-yl]-propyl]-benzenesulfonic acid amide, N-cyclopropyl-4-methoxy-2,6-dimethyl-N-[3-[2-(9-pyridin-4-yl-3,9-diazaspiro[5.5]undecan-3-yl)-pyrimidin-4-yl]-propyl]-benzenesulfonic acid amide, N-cyclopropyl-N-[3-[2-(9-pyridin-4-yl-3,9-diazaspiro[5.5]undecan-3-yl)-pyrimidin-4-yl]-propyl]-3-(trifluoromethyl)-benzenesulfonic acid amide, 4-methoxy-N,2,6-trimethyl-N-[2-[[4-[4-(1-methyl-4-piperidinyl)-1-piperazinyl]-2-pyrimidinyl]oxy]ethyl]benzenesulfonamide, 2-[[1-(4-methoxy-2,6-dimethylphenyl)sulfonyl-2-piperidinyl]methoxy]-4-[4-(1-methyl-4-piperidinyl)-1-piperazinyl]pyrimidine, 2-[[1-(4-methoxy-2,6-dimethylphenyl)sulfonyl-2-piperidinyl]methoxy]-4-[4-(2-1-pyrrolidinylethyl)-1-piperidinyl]pyrimidine, N-[2-(4-dimethylamino-4-phenyl-1-piperidinyl)ethyl]-2-[[1-(4-methoxy-2,6-dimethylphenyl)sulfonyl-2-piperidinyl]methoxy]-N-methyl-4-pyrimidineamine, N-[2-[[4-[4-(4-fluorophenyl)-1-piperazinyl]-2-pyrimidinyl]oxy]ethyl]-4-methoxy-N,2,6-trimethylbenzenesulfonamide, 4-methoxy-N,2,6-trimethyl-N-[2-[[4-[4-(4-methyl-1-piperazinyl)-1-piperidinyl]-2-pyrimidinyl]oxy]ethyl]benzenesulfonamide, 4-methoxy-N,2,6-trimethyl-N-[2-[[4-[4-[(1-methyl-4-piperidinyl)methyl]-1-piperazinyl]-2-pyrimidinyl]oxy]ethyl]benzenesulfonamide, N-[2-[[4-[4-hydroxy-4-(3-pyridyl)-1-piperidinyl]-2-pyrimidinyl]oxy]ethyl]-4-methoxy-N,2,6-trimethylbenzenesulfonamide, 2-[[1-(4-methoxy-2,6-dimethylphenyl)sulfonyl-2-piperidinyl]methoxy]-4-(4-methyl-1-piperazinyl)pyrimidine, 4-[4-(4-fluorophenyl)-1-piperazinyl]-2-[[1-(4-methoxy-2,6-dimethylphenyl)sulfonyl-2-piperidinyl]methoxy]pyrimidine, 2-[[1-(4-methoxy-2,6-dimethylphenyl)sulfonyl-2-piperidinyl]methoxy]-4-[4-(4-methyl-1-piperazinyl)-1-piperidinyl]pyrimidine, 2-[[1-(4-methoxy-2,6-dimethylphenyl)sulfonyl-2-piperidinyl]methoxy]-4-[4-(2-pyrimidinyl)-1-piperazinyl]pyrimidine, 2-[[1-(4-methoxy-2,6-dimethylphenyl)sulfonyl-2-piperidinyl]methoxy]-4-[4-(4-pyridyl)-1-piperazinyl]pyrimidine, 2-[[1-(4-methoxy-2,6-dimethylphenyl)sulfonyl-2-piperidinyl]methoxy]-4-[4-[(1-methyl-4-piperidinyl)methyl]-1-piperazinyl]pyrimidine, 2-[[(2S)-1-(4-methoxy-2,6-dimethylphenyl)sulfonyl-2-pyrrolidinyl]methoxy]-4-(4-methyl-1-piperazinyl)pyrimidine, 2-[[(2S)-1-(4-methoxy-2,6-dimethylphenyl)sulfonyl-2-pyrrolidinyl]methoxy]-4-[4-(2-1-pyrrolidinylethyl)-1-piperidinyl]pyrimidine, 2-[[(2S)-1-(4-methoxy-2,6-dimethylphenyl)sulfonyl-2-pyrrolidinyl]methoxy]-4-[4-(4-methyl-1-piperazinyl)-1-piperidinyl]pyrimidine, 2-[[(2S)-1-(4-methoxy-2,6-dimethylphenyl)sulfonyl-2-pyrrolidinyl]methoxy]-4-[4-(2-pyrimidinyl)-1-piperazinyl]pyrimidine, 2-[[(2S)-1-(4-methoxy-2,6-dimethylphenyl)sulfonyl-2-pyrrolidinyl]methoxy]-4-[4-(4-pyridyl)-1-piperazinyl]pyrimidine, 1-[2-[[(2S)-1-(4-methoxy-2,6-dimethylphenyl)sulfonyl-2-pyrrolidinyl]methoxy]-4-pyrimidinyl]-4-(3-pyridyl)-4-piperidinol, 1-[2-[[(2S)-1-(4-methoxy-2,6-dimethylphenyl)sulfonyl-2-pyrrolidinyl]methoxy]-4-pyrimidinyl]-4-(2-thienyl)-4-piperidinol, 3-benzyl-7-[2-[[1-(4-methoxy-2,6-dimethylphenyl)sulfonyl-2-piperidinyl]methoxy]-4-pyrimidinyl]-3,7-diazaspiro[4.4]nonane, 1'-[2-[[1-(4-methoxy-2,6-dimethylphenyl)sulfonyl-2-piperidinyl]methoxy]-4-pyrimidinyl]spiro[1H-isobenzofuran-3,4'-piperidine], 6-chloro-3-[1-[2-[[1-(4-methoxy-2,6-dimethylphenyl) sulfonyl-2-piperidinyl]methoxy]-4-pyrimidinyl]-4-piperidinyl]-1H-benzimidazol-2-one, 8-[2-[[1-(4-methoxy-2,6-dimethylphenyl)sulfonyl-2-piperidinyl]methoxy]-4-pyrimidinyl]-4-phenyl-2,4,8-triazaspiro[4.5]decan-1-one, 2-[[1-(4-methoxy-2,6-dimethylphenyl)sulfonyl-2-piperidinyl]methoxy]-4-[4-[2-(1-piperidyl)ethyl]-1-piperidinyl]pyrimidine, 2-[[1-(4-methoxy-2,6-dimethylphenyl)sulfonyl-3-piperidinyl]oxy]-4-[4-[2-(1-piperidyl)ethyl]-1-piperidinyl]pyrimidine, N-[2-[[4-(3-benzyl-3,7-diazaspiro[4.4]nonan-7-yl)-2-pyrimidinyl]oxy]ethyl]-4-methoxy-N,2,6-trimethylbenzenesulfonamide, 4-methoxy-N,2,6-trimethyl-N-[2-[[4-(1'-spiro[1H-isobenzofuran-3,4'-piperidin]yl)-2-pyrimidinyl]oxy] ethyl]benzenesulfonamide, 4-methoxy-N,2,6-trimethyl-N-[2-[[4-(1-oxo-4-phenyl-2, 4,8-triazaspiro[4.5]decan-8-yl)-2-pyrimidinyl]oxy] ethyl]benzenesulfonamide, 4-methoxy-N,2,6-trimethyl-N-[2-[[4-[4-[2-(1-piperidyl) ethyl]-1-piperidinyl]-2-pyrimidinyl]oxy]ethyl]benzenesulfonamide, 3-benzyl-7-[2-[[(2S)-1-(4-methoxy-2,6-dimethylphenyl) sulfonyl-2-pyrrolidinyl]methoxy]-4-pyrimidinyl]-3,7-diazaspiro[4.4]nonane, 1'-[2-[[(2S)-1-(4-methoxy-2,6-dimethylphenyl)sulfonyl-2-pyrrolidinyl]methoxy]-4-pyrimidinyl]spiro[1H-isobenzofuran-3,4'-piperidine], 6-chloro-3-[1-[2-[[(2S)-1-(4-methoxy-2,6-dimethylphenyl)sulfonyl-2-pyrrolidinyl]methoxy]-4-pyrimidinyl]-4-piperidinyl]-1H-benzimidazol-2-one, 8-[2-[[(2S)-1-(4-methoxy-2,6-dimethylphenyl)sulfonyl-2-pyrrolidinyl]methoxy]-4-pyrimidinyl]-4-phenyl-2,4, 8-triazaspiro[4.5]decan-1-one, 2-[[(2S)-1-(4-methoxy-2,6-dimethylphenyl)sulfonyl-2-pyrrolidinyl]methoxy]-4-[4-(1-methyl-4-piperidinyl)-1-piperazinyl]pyrimidine, 2-[[(2S)-1-(4-methoxy-2,6-dimethylphenyl)sulfonyl-2-pyrrolidinyl]methoxy]-4-[4-[2-(1-piperidyl)ethyl]-1-piperidinyl]pyrimidine, 3-(4-fluorophenyl)-8-[2-[[1-(4-methoxy-2,6-dimethylphenyl)sulfonyl-2-piperidinyl]methoxy]-4-pyrimidinyl]-3,8-diazaspiro[4.5]decan-4-one, 3-[(4-fluorophenyl)methyl]-8-[2-[[1-(4-methoxy-2,6-dimethylphenyl)sulfonyl-2-piperidinyl]methoxy]-4-pyrimidinyl]-3,8-diazaspiro[4.5]decan-4-one, 3-benzyl-8-[2-[[1-(4-methoxy-2,6-dimethylphenyl)sulfonyl-2-piperidinyl]methoxy]-4-pyrimidinyl]-3,8-diazaspiro[4.5]decan-4-one, 9-[2-[[1-(4-methoxy-2,6-dimethylphenyl)sulfonyl-3-piperidinyl]oxy]-4-pyrimidinyl]-3-(4-pyridyl)-3,9-diazaspiro[5.5]undecane, N-[2-[[4-[3-(4-fluorophenyl)-4-oxo-3,8-diazaspiro[4.5] decan-8-yl]-2-pyrimidinyl]oxy]ethyl]-4-methoxy-N,2, 6-trimethylbenzenesulfonamide, 4-methoxy-N,2,6-trimethyl-N-[2-[[4-[4-oxo-1-[3-(trifluoromethyl)phenyl]-3,8-diazaspiro[4.5]decan-8-yl]-2-pyrimidinyl]oxy]ethyl]benzenesulfonamide, N-[2-[[4-[1-(4-fluorophenyl)-3-methyl-4-oxo-3,8-diazaspiro[4.5]decan-8-yl]-2-pyrimidinyl]oxy]ethyl]-4-methoxy-N,2,6-trimethylbenzenesulfonamide, N-[2-[[4-[3-[(4-fluorophenyl)methyl]-4-oxo-3,8-diazaspiro[4.5]decan-8-yl]-2-pyrimidinyl]oxy]ethyl]-4-methoxy-N,2,6-trimethylbenzenesulfonamide, N-[2-[[4-(3-benzyl-4-oxo-3,8-diazaspiro[4.5]decan-8-yl)-2-pyrimidinyl]oxy]ethyl]-4-methoxy-N,2,6-trimethylbenzenesulfonamide, 4-methoxy-N,2,6-trimethyl-N-[2-[[4-[3-(4-pyridyl)-3,9-diazaspiro[5.5]undecan-9-yl]-2-pyrimidinyl]oxy]ethyl] benzenesulfonamide, 3-(4-fluorophenyl)-8-[2-[[(2S)-1-(4-methoxy-2,6-dimethylphenyl)sulfonyl-2-pyrrolidinyl]methoxy]-4-pyrimidinyl]-3,8-diazaspiro[4.5]decan-4-one, 8-[2-[[(2S)-1-(4-methoxy-2,6-dimethylphenyl)sulfonyl-2-pyrrolidinyl]methoxy]-4-pyrimidinyl]-1-[3-(trifluoromethyl)phenyl]-3,8-diazaspiro[4.5]decan-4-one, 1-(4-fluorophenyl)-842-[[(2S)-1-(4-methoxy-2,6-dimethylphenyl)sulfonyl-2-pyrrolidinyl]methoxy]-4-pyrimidinyl]-3-methyl-3,8-diazaspiro[4.5]decan-4-one, 3-[(4-fluorophenyl)methyl]-8-[2-[[(2S)-1-(4-methoxy-2, 6-dimethylphenyl)sulfonyl-2-pyrrolidinyl]methoxy]-4-pyrimidinyl]-3,8-diazaspiro[4.5]decan-4-one, 2-[[(2S)-1-(4-methoxy-2,6-dimethylphenyl)sulfonyl-2-pyrrolidinyl]methoxy]-4-[4-(4-pyridyloxy)-1-piperidinyl]pyrimidine, 3-benzyl-8-[2-[[(2S)-1-(4-methoxy-2,6-dimethylphenyl) sulfonyl-2-pyrrolidinyl]methoxy]-4-pyrimidinyl]-3,8-diazaspiro[4.5]decan-4-one, N-[[1-[2-[[(2R)-1-(4-methoxy-2,6-dimethylphenyl)sulfonyl-2-pyrrolidinyl]methoxy]-4-pyrimidinyl]-4-(4-methyl-1-piperazinyl)-4-piperidinyl]methyl]-4-pyridinecarboxamide, 9-[2-[[(2S)-1-(4-methoxy-2,6-dimethylphenyl)sulfonyl-2-pyrrolidinyl]methoxy]-4-pyrimidinyl]-3-(4-pyridyl)-3,9-diazaspiro[5.5]undecane, 5-[2-[[1-(4-methoxy-2,6-dimethylphenyl)sulfonyl-2-piperidinyl]methoxy]-4-pyrimidinyl]-2-(4-pyridylmethyl)-2,5-diazabicyclo[2.2.1]heptane, 5-[2-[[1-(4-methoxy-2,6-dimethylphenyl)sulfonyl-3-piperidinyl]oxy]-4-pyrimidinyl]-2-(4-pyridylmethyl)-2,5-diazabicyclo[2.2.1]heptane, 5-[2-[[(2S)-1-(4-methoxy-2,6-dimethylphenyl)sulfonyl-2-pyrrolidinyl]methoxy]-4-pyrimidinyl]-2-(4-pyridylmethyl)-2,5-diazabicyclo[2.2.1]heptane, 4-methoxy-N,2,6-trimethyl-N-[2-[[4-[4-(1-methyl-4-piperidinyl)-1-piperazinyl]-2-pyrimidinyl]oxy]-1-phenylethyl]benzenesulfonamide, N-[2-[[4-[3-[(4-fluorophenyl)methyl]-4-oxo-3,8-diazaspiro[4.5]decan-8-yl]-2-pyrimidinyl]oxy]-1-phenylethyl]-4-methoxy-N,2,6-trimethylbenzenesulfonamide, N-[2-[[4-(3-benzyl-4-oxo-3,8-diazaspiro[4.5]decan-8-yl)-2-pyrimidinyl]oxy]-1-phenylethyl]-4-methoxy-N, 2,6-trimethylbenzenesulfonamide, 4-methoxy-N,2,6-trimethyl-N-[1-phenyl-2-[[4-[4-(3-pyridyl)-4-(2-1-pyrrolidinylethoxy)-1-piperidinyl]-2-pyrimidinyl]oxy]ethyl]benzenesulfonamide, 4-methoxy-N,2,6-trimethyl-N-[1-phenyl-2-[[4-[4-(4-pyridyloxy)-1-piperidinyl]-2-pyrimidinyl]oxy]ethyl]benzenesulfonamide, 4-methoxy-N,2,6-trimethyl-N-[2-[[4-4-[oxo-(3-pyridyl) methyl]-1-piperazinyl]-2-pyrimidinyl]oxy]-1-phenylethyl]benzenesulfonamide, N-[2-[[4-2-[(4-fluorophenyl)methyl]-2,5-diazabicyclo [2.2.1]heptan-5-yl]-2-pyrimidinyl]oxy]-1-phenylethyl]-4-methoxy-N,2,6-trimethylbenzenesulfonamide, 2-[[1-(4-methoxy-2,6-dimethylphenyl)sulfonyl-2-piperidinyl]methoxy]-4-[4-(4-pyridyl)-1-piperazinyl]pyrimidine, 1-[2-[[1-(4-methoxy-2,6-dimethylphenyl)sulfonyl-2-piperidinyl]methoxy]-4-pyrimidinyl]-4-(3-pyridyl)-4-piperidinol,
N-[2-[[4-(3-benzyl-3,7-diazaspiro[4.4]nonan-7-yl)-2-pyrimidinyl]oxy]-1-phenylethyl]-4-methoxy-N,2,6-trimethylbenzenesulfonamide,
[4-butyl-1-[2-[[1-[(4-methoxy-2,6-dimethyl-phenyl)sulfonyl]-piperidin-2-yl]-methoxy]-pyrimidin-4-yl]-piperidin-4-yl]-dimethyl-amine,
[1-[2-[[1-[(4-methoxy-2,6-dimethyl-phenyl)sulfonyl]-piperidin-2-yl]-methoxy]-pyrimidin-4-yl]-4-thiophen-2-yl-piperidin-4-yl]-dimethyl-amine,
[2-[[1-[(4-methoxy-2,6-dimethyl-phenyl)sulfonyl]-piperidin-2-yl]-methoxy]-pyrimidin-4-yl]-methyl-[2-(4-phenyl-4-pyrrolidin-1-yl-piperidin-1-yl)-ethyl]-amine,
2-(4-butyl-4-dimethylamino-piperidin-1-yl)-ethyl-[2-[[1-[(4-methoxy-2,6-dimethyl-phenyl)sulfonyl]-piperidin-2-yl]-methoxy]-pyrimidin-4-yl]-methyl-amine,
3-(4-dimethylamino-4-phenyl-piperidin-1-yl)-propyl-[2-[[(2S)-1-[(4-methoxy-2,6-dimethyl-phenyl)sulfonyl]-pyrrolidin-2-yl]-methoxy]-pyrimidin-4-yl]-methyl-amine,
3-(4-dimethylamino-4-phenyl-piperidin-1-yl)-propyl-[2-[[(2S)-1-[(4-methoxy-2,6-dimethyl-phenyl)sulfonyl]-2,3-dihydro-1H-indol-2-yl]-methoxy]-pyrimidin-4-yl]-methyl-amine,
2-[1-[(4-methoxy-2,6-dimethyl-phenyl)sulfonyl]-azetidin-3-yl]oxy-4-[4-[(1-methyl-piperidin-4-yl)-methyl]-piperazin-1-yl]-pyrimidine,
2-[[1-[(4-methoxy-2,6-dimethyl-phenyl)sulfonyl]-piperidin-2-yl]-methoxy]-4-(4-pyridin-2-yloxy-piperidin-1-yl)-pyrimidine,
2-[[1-[(4-methoxy-2,6-dimethyl-phenyl)sulfonyl]-piperidin-2-yl]-methoxy]-4-(4-pyrazin-2-yloxy-piperidin-1-yl)-pyrimidine,
2-[[1-[(4-methoxy-2,6-dimethyl-phenyl)sulfonyl]-piperidin-2-yl]-methoxy]-4-[4-pyridin-3-yl-4-(3-pyrrolidin-1-yl-propyl)-piperidin-1-yl]-pyrimidine,
2-[[1-[(4-methoxy-2,6-dimethyl-phenyl)sulfonyl]-piperidin-2-yl]-methoxy]-4-[2-(pyridin-2-yl-methyl)-pyrrolidin-1-yl]-pyrimidine,
1-[2-[[1-[(4-methoxy-2,6-dimethyl-phenyl)sulfonyl]-piperidin-2-yl]-methoxy]-pyrimidin-4-yl]-4-pyridin-2-yl-piperidin-4-ol,
1-[2-[[(2S)-1-[(4-methoxy-2,6-dimethyl-phenyl)sulfonyl]-pyrrolidin-2-yl]-methoxy]pyrimidin-4-yl]-4-pyridin-2-yl-piperidin-4-ol,
2-[[(2R)-1-[(4-methoxy-2,6-dimethyl-phenyl)sulfonyl]-pyrrolidin-2-yl]-methoxy]-4-[2-(pyridin-2-yl-methyl)-pyrrolidin-1-yl]-pyrimidine,
5-[1-[2-[[(2S)-1-[(4-methoxy-2,6-dimethyl-phenyl)sulfonyl]-pyrrolidin-2-yl]-methoxy]-pyrimidin-4-yl]-piperidin-4-yl]-3-pyridin-4-yl-[1,2,4]oxadiazole,
4-[4-(3-fluorophenyl)-4-(2-pyrrolidin-1-yl-ethoxy)-piperidin-1-yl]-2-[[(2S)-1-[(4-methoxy-2,6-dimethyl-phenyl)sulfonyl]-pyrrolidin-2-yl]-methoxy]-pyrimidine,
[4-butyl-1-[2-[[(2S)-1-[(4-methoxy-2,6-dimethyl-phenyl)sulfonyl]-pyrrolidin-2-yl]-methoxy]-pyrimidin-4-yl]-piperidin-4-yl]-dimethyl-amine,
2-(4-dimethylamino-4-phenyl-piperidin-1-yl)-ethyl-[2-[[(2S)-1-[(4-methoxy-2,6-dimethyl-phenyl)sulfonyl]-pyrrolidin-2-yl]-methoxy]-pyrimidin-4-yl]-methyl-amine,
N-[2-[4-(4-butyl-4-dimethylamino-piperidin-1-yl)-pyrimidin-2-yl]oxy-ethyl]-4-methoxy-N,2,6-trimethyl-benzenesulfonic acid amide,
[2-[[(2S)-1-[(4-methoxy-2,6-dimethyl-phenyl)sulfonyl]-pyrrolidin-2-yl]-methoxy]-pyrimidin-4-yl]-methyl-[2-(4-phenyl-4-pyrrolidin-1-yl-piperidin-1-yl)-ethyl]-amine,
(2S)-1-[(4-methoxy-2,6-dimethyl-phenyl)sulfonyl]-2-[[4-(4-pyrazin-2-yloxy-piperidin-1-yl)-pyrimidin-2-yl]oxy-methyl]-2,3-dihydro-1H-indole,
[4-butyl-1-[2-[[(2S)-1-[(4-methoxy-2,6-dimethyl-phenyl)sulfonyl]-2,3-dihydro-1H-indol-2-yl]-methoxy]-pyrimidin-4-yl]-piperidin-4-yl]-dimethyl-amine,
2-(4-dimethylamino-4-phenyl-piperidin-1-yl)-ethyl-[2-[[(2S)-1-[(4-methoxy-2,6-dimethyl-phenyl)sulfonyl]-2,3-dihydro-1H-indol-2-yl]-methoxy]-pyrimidin-4-yl]-methyl-amine,
[2-[[(2S)-1-[(4-methoxy-2,6-dimethyl-phenyl)sulfonyl]-2,3-dihydro-1H-indol-2-yl]-methoxy]-pyrimidin-4-yl]-methyl-[2-(4-phenyl-4-pyrrolidin-1-yl-piperidin-1-yl)-ethyl]-amine,
2-(4-butyl-4-dimethylamino-piperidin-1-yl)-ethyl-[2-[[(2S)-1-[(4-methoxy-2,6-dimethyl-phenyl)sulfonyl]-2,3-dihydro-1H-indol-2-yl]-methoxy]-pyrimidin-4-yl]-methyl-amine,
N-[2-[4-[2-(4-dimethylamino-4-phenyl-piperidin-1-yl)-ethyl-methyl-amino]-pyrimidin-2-yl]oxy-ethyl]-4-methoxy-N,2,6-trimethyl-benzenesulfonic acid amide,
N-[2-[4-[3-(4-dimethylamino-4-phenyl-piperidin-1-yl)-propyl-methyl-amino]-pyrimidin-2-yl]oxy-ethyl]-4-methoxy-N,2,6-trimethyl-benzenesulfonic acid amide,
3-(4-dimethylamino-4-phenyl-piperidin-1-yl)-propyl-[2-[[1-[(4-methoxy-2,6-dimethyl-phenyl)sulfonyl]-piperidin-2-yl]-methoxy]-pyrimidin-4-yl]-methyl-amine,
5-[1-[2-[[1-[(4-methoxy-2,6-dimethyl-phenyl)sulfonyl]-piperidin-2-yl]-methoxy]-pyrimidin-4-yl]-piperidin-4-yl]-3-pyridin-4-yl-[1,2,4]oxadiazole,
4-[4-(3-fluorophenyl)-4-(4-methyl-piperazin-1-yl)-piperidin-1-yl]-2-[[1-[(4-methoxy-2,6-dimethyl-phenyl)sulfonyl]-piperidin-2-yl]-methoxy]-pyrimidine,
(1S,5R)-8-[2-[[1-[(4-methoxy-2,6-dimethyl-phenyl)sulfonyl]-piperidin-2-yl]-methoxy]-pyrimidin-4-yl]-3-pyridin-3-yloxy-8-azabicyclo[3.2.1]octane,
1-[2-[[2-[[1-[(4-methoxy-2,6-dimethyl-phenyl)sulfonyl]-piperidin-2-yl]-methoxy]-pyrimidin-4-yl]-methyl-amino]-ethyl]-4-pyridin-3-yl-piperidin-4-ol,
4-methoxy-N,2,6-trimethyl-N-[1-phenyl-2-[4-[(1S,5R)-3-pyridin-3-yloxy-8-azabicyclo[3.2.1]octan-8-yl]-pyrimidin-2-yl]oxy-ethyl]-benzenesulfonic acid amide,
4-methoxy-N,2,6-trimethyl-N-[1-phenyl-2-[4-[4-pyridin-3-yl-4-(3-pyrrolidin-1-yl-propyl)-piperidin-1-yl]-pyrimidin-2-yl]oxy-ethyl]-benzenesulfonic acid amide,
7-[2-[[(2S)-1-[(4-methoxy-2,6-dimethyl-phenyl)sulfonyl]-pyrrolidin-2-yl]-methoxy]-pyrimidin-4-yl]-2-(piperidin-1-yl-methyl)-5,6,7,8-tetrahydro-imidazo[1,2-a]pyrazine,
1-[2-[[1-[(4-methoxy-2,6-dimethyl-phenyl)sulfonyl]-piperidin-2-yl]-methoxy]-pyrimidin-4-yl]-4-pyridin-4-yl-piperidin-4-ol,
N-[2-[4-(4-hydroxy-4-pyridin-4-yl-piperidin-1-yl)-pyrimidin-2-yl]oxy-1-phenyl-ethyl]-4-methoxy-N,2,6-trimethyl-benzenesulfonic acid amide,
[1-[2-[[1-[(4-methoxy-2,6-dimethyl-phenyl)sulfonyl]-piperidin-2-yl]-methoxy]-pyrimidin-4-yl]-4-phenyl-piperidin-4-yl]-dimethyl-amine,
2-[1-[(4-methoxy-2,6-dimethyl-phenyl)sulfonyl]-piperidin-3-yl]oxy-4-(4-phenyl-4-pyrrolidin-1-yl-piperidin-1-yl)-pyrimidine, 2-[[(2S)-1-[(4-methoxy-2,6-dimethyl-phenyl)sulfonyl]-pyrrolidin-2-yl]-methoxy]-4-(4-phenyl-4-pyrrolidin-1-yl-piperidin-1-yl)-pyrimidine,
4-methoxy-N,2,6-trimethyl-N-[2-[4-(4-phenyl-4-pyrrolidin-1-yl-piperidin-1-yl)-pyrimidin-2-yl]oxy-ethyl]-benzenesulfonic acid amide,
N-[2-[4-(4-dimethylamino-4-phenyl-piperidin-1-yl)-pyrimidin-2-yl]oxy-ethyl]-4-methoxy-N,2,6-trimethyl-benzenesulfonic acid amide,
N-[2-[4-(4-dimethylamino-4-thiophen-2-yl-piperidin-1-yl)-pyrimidin-2-yl]oxy-ethyl]-4-methoxy-N,2,6-trimethyl-benzenesulfonic acid amide,
4-methoxy-N,2,6-trimethyl-N-[2-[4-[methyl-[2-(4-phenyl-4-pyrrolidin-1-yl-piperidin-1-yl)-ethyl]-amino]-pyrimidin-2-yl]oxy-ethyl]-benzenesulfonic acid amide,
N-[2-[4-[2-(4-butyl-4-dimethylamino-piperidin-1-yl)-ethyl-methyl-amino]-pyrimidin-2-yl]oxy-ethyl]-4-methoxy-N,2,6-trimethyl-benzenesulfonic acid amide,
2-[[1-[(4-methoxy-2,6-dimethyl-phenyl)sulfonyl]-piperidin-2-yl]-methoxy]-4-(4-phenyl-4-pyrrolidin-1-yl-piperidin-1-yl)-pyrimidine,
2-[1-[(4-methoxy-2,6-dimethyl-phenyl)sulfonyl]-azetidin-3-yl]oxy-4-(4-phenyl-4-pyrrolidin-1-yl-piperidin-1-yl)-pyrimidine,
2-(4-dimethylamino-4-phenyl-piperidin-1-yl)-ethyl-[2-[1-[(4-methoxy-2,6-dimethyl-phenyl)sulfonyl]-azetidin-3-yl]oxy-pyrimidin-4-yl]-methyl-amine,
[2-[1-[(4-methoxy-2,6-dimethyl-phenyl)sulfonyl]-azetidin-3-yl]oxy-pyrimidin-4-yl]-methyl-[2-(4-phenyl-4-pyrrolidin-1-yl-piperidin-1-yl)-ethyl]-amine,
[1-[2-[[(2S)-1-[(4-methoxy-2,6-dimethyl-phenyl)sulfonyl]-2,3-dihydro-1H-indol-2-yl]-methoxy]-pyrimidin-4-yl]-4-thiophen-2-yl-piperidin-4-yl]-dimethyl-amine,
3-(4-dimethylamino-4-phenyl-piperidin-1-yl)-propyl-[2-[1-[(4-methoxy-2,6-dimethyl-phenyl)sulfonyl]-azetidin-3-yl]oxy-pyrimidin-4-yl]-methyl-amine,
3-[4-[2-[1-[(4-methoxy-2,6-dimethyl-phenyl)sulfonyl]-azetidin-3-yl]oxy-pyrimidin-4-yl]-piperazin-1-yl]-propyl-dimethyl-amine,
1-[2-[1-[(4-methoxy-2,6-dimethyl-phenyl)sulfonyl]-azetidin-3-yl]oxy-pyrimidin-4-yl]-4-pyridin-3-yl-piperidin-4-ol,
2-[1-[(4-methoxy-2,6-dimethyl-phenyl)sulfonyl]-azetidin-3-yl]oxy-4-[4-(2-piperidin-1-yl-ethyl)-piperidin-1-yl]-pyrimidine,
(2S)-2-[[4-[2-[(4-fluorophenyl)-methyl]-2,5-diazabicyclo[2.2.1]heptan-5-yl]-pyrimidin-2-yl]oxy-methyl]-1-[(4-methoxy-2,6-dimethyl-phenyl)sulfonyl]-2,3-dihydro-1H-indole,
4-[1-[2-[[1-[(4-methoxy-2,6-dimethyl-phenyl)sulfonyl]-piperidin-2-yl]-methoxy]-pyrimidin-4-yl]-4-methyl-piperidin-4-yl]-morpholine,
4-methoxy-N,2,6-trimethyl-N-[1-phenyl-2-[4-[2-(pyridin-2-yl-methyl)-pyrrolidin-1-yl]-pyrimidin-2-yl]oxy-ethyl]-benzenesulfonic acid amide,
4-methoxy-N,2,6-trimethyl-N-[1-phenyl-2-[4-[4-(3-pyridin-4-yl-[1,2,4]oxadiazol-5-yl)-piperidin-1-yl]-pyrimidin-2-yl]oxy-ethyl]-benzenesulfonic acid amide,
N-[2-[4-[4-(3-fluorophenyl)-4-(4-methyl-piperazin-1-yl)-piperidin-1-yl]-pyrimidin-2-yl]oxy-1-phenyl-ethyl]-4-methoxy-N,2,6-trimethyl-benzenesulfonic acid amide,
4-methoxy-N,2,6-trimethyl-N-[1-phenyl-2-[4-(4-pyridin-2-yloxy-piperidin-1-yl)-pyrimidin-2-yl]oxy-ethyl]-benzenesulfonic acid amide,
4-methoxy-N,2,6-trimethyl-N-[2-[4-(4-methyl-4-morpholin-4-yl-piperidin-1-yl)-pyrimidin-2-yl]oxy-1-phenyl-ethyl]-benzenesulfonic acid amide,
N-[2-[4-[2-(4-hydroxy-4-pyridin-3-yl-piperidin-1-yl)-ethyl-methyl-amino]-pyrimidin-2-yl]oxy-1-phenyl-ethyl]-4-methoxy-N,2,6-trimethyl-benzenesulfonic acid amide,
4-[[1-(4-methoxy-2,6-dimethylphenyl)sulfonyl-2-piperidinyl]methoxy]-2-[4-(1-methyl-4-piperidinyl)-1-piperazinyl]pyrimidine,
4-[[1-(4-methoxy-2,6-dimethylphenyl)sulfonyl-2-piperidinyl]methoxy]-2-[4-(2-1-pyrrolidinylethyl)-1-piperidinyl]pyrimidine,
4-[[1-(4-methoxy-2,6-dimethylphenyl)sulfonyl-2-piperidinyl]methoxy]-2-(4-methyl-1-piperazinyl)pyrimidine,
4-[[1-(4-methoxy-2,6-dimethylphenyl)sulfonyl-2-piperidinyl]methoxy]-2-[4-(2-pyrimidinyl)-1-piperazinyl]pyrimidine,
4-[[1-(4-methoxy-2,6-dimethylphenyl)sulfonyl-2-piperidinyl]methoxy]-2-[4-(4-pyridyl)-1-piperazinyl]pyrimidine,
4-[[1-(4-methoxy-2,6-dimethylphenyl)sulfonyl-2-piperidinyl]methoxy]-2-[4-[(1-methyl-4-piperidinyl)methyl]-1-piperazinyl]pyrimidine,
1-[4-[[1-(4-methoxy-2,6-dimethylphenyl)sulfonyl-2-piperidinyl]methoxy]-2-pyrimidinyl]-4-(3-pyridyl)-4-piperidinol,
4-[[(2S)-1-(4-methoxy-2,6-dimethylphenyl)sulfonyl-2-pyrrolidinyl]methoxy]-2-(4-methyl-1-piperazinyl)pyrimidine,
4-[[(2S)-1-(4-methoxy-2,6-dimethylphenyl)sulfonyl-2-pyrrolidinyl]methoxy]-2-[4-(2-1-pyrrolidinylethyl)-1-piperidinyl]pyrimidine,
4-[[(2S)-1-(4-methoxy-2,6-dimethylphenyl)sulfonyl-2-pyrrolidinyl]methoxy]-2-[4-(4-methyl-1-piperazinyl)-1-piperidinyl]pyrimidine,
4-[[(2S)-1-(4-methoxy-2,6-dimethylphenyl)sulfonyl-2-pyrrolidinyl]methoxy]-2-[4-(2-pyrimidinyl)-1-piperazinyl]pyrimidine,
4-[[(2S)-1-(4-methoxy-2,6-dimethylphenyl)sulfonyl-2-pyrrolidinyl]methoxy]-2-[4-[(1-methyl-4-piperidinyl)methyl]-1-piperazinyl]pyrimidine,
1-[4-[[(2S)-1-(4-methoxy-2,6-dimethylphenyl)sulfonyl-2-pyrrolidinyl]methoxy]-2-pyrimidinyl]-4-(3-pyridyl)-4-piperidinol,
4-[[1-(4-methoxy-2,6-dimethylphenyl)sulfonyl-3-azetidinyl]oxy]-2-[4-(2-1-pyrrolidinylethyl)-1-piperidinyl]pyrimidine,
4-[[1-(4-methoxy-2,6-dimethylphenyl)sulfonyl-3-azetidinyl]oxy]-2-[4-(4-methyl-1-piperazinyl)-1-piperidinyl]pyrimidine,
(2S)-1-(4-methoxy-2,6-dimethylphenyl)sulfonyl-2-[[2-(4-methyl-1-piperazinyl)-4-pyrimidinyl]oxymethyl]indoline,
(2S)-1-(4-methoxy-2,6-dimethylphenyl)sulfonyl-2-[[2-[4-(2-1-pyrrolidinylethyl)-1-piperidinyl]-4-pyrimidinyl]oxymethyl]indoline,
(2S)-1-(4-methoxy-2,6-dimethylphenyl)sulfonyl-2-[[2-[4-(4-methyl-1-piperazinyl)-1-piperidinyl]-4-pyrimidinyl]oxymethyl]indoline,
(2S)-1-(4-methoxy-2,6-dimethylphenyl)sulfonyl-2-[[2-[4-(4-pyridyl)-1-piperazinyl]-4-pyrimidinyl]oxymethyl]indoline,
(2S)-1-(4-methoxy-2,6-dimethylphenyl)sulfonyl-2-[[2-[4-[(1-methyl-4-piperidinyl)methyl]-1-piperazinyl]-4-pyrimidinyl]oxymethyl]indoline,
3-benzyl-7-[4-[[1-(4-methoxy-2,6-dimethylphenyl)sulfonyl-2-piperidinyl]methoxy]-2-pyrimidinyl]-3,7-diazaspiro[4.4]nonane, 4-[[1-(4-methoxy-2,6-dimethylphenyl)sulfonyl-2-piperidinyl]methoxy]-2-[4-[2-(1-piperidyl)ethyl]-1-piperidinyl]pyrimidine,
3-benzyl-7-[4-[[(2S)-1-(4-methoxy-2,6-dimethylphenyl)sulfonyl-2-pyrrolidinyl]methoxy]-2-pyrimidinyl]-3,7-diazaspiro[4.4]nonane,
8-[4-[[(2S)-1-(4-methoxy-2,6-dimethylphenyl)sulfonyl-2-pyrrolidinyl]methoxy]-2-pyrimidinyl]-4-phenyl-2,4,8-triazaspiro[4.5]decan-1-one,
4-[[(2S)-1-(4-methoxy-2,6-dimethylphenyl)sulfonyl-2-pyrrolidinyl]methoxy]-2-[4-(1-methyl-4-piperidinyl)-1-piperazinyl]pyrimidine,
4-[[(2S)-1-(4-methoxy-2,6-dimethylphenyl)sulfonyl-2-pyrrolidinyl]methoxy]-2-[4-[2-(1-piperidyl)ethyl]-1-piperidinyl]pyrimidine,
(2S)-1-(4-methoxy-2,6-dimethylphenyl)sulfonyl-2-[[2-[4-(1-methyl-4-piperidinyl)-1-piperazinyl]-4-pyrimidinyl]oxymethyl]indoline,
(2S)-1-(4-methoxy-2,6-dimethylphenyl)sulfonyl-2-[[2-[4-[2-(1-piperidyl)ethyl]-1-piperidinyl]-4-pyrimidinyl]oxymethyl]indoline,
4-methoxy-N,2,6-trimethyl-N-[2-[[2-[3-(4-pyridyl)-3,9-diazaspiro[5.5]undecan-9-yl]-4-pyrimidinyl]oxy]ethyl]benzenesulfonamide,
3-[(4-fluorophenyl)methyl]-8-[4-[[1-(4-methoxy-2,6-dimethylphenyl)sulfonyl-2-piperidinyl]methoxy]-2-pyrimidinyl]-3,8-diazaspiro[4.5]decan-4-one,
N-[[1-[4-[[1-(4-methoxy-2,6-dimethylphenyl)sulfonyl-2-piperidinyl]methoxy]-2-pyrimidinyl]-4-(4-methyl-1-piperazinyl)-4-piperidinyl]methyl]-4-pyridinecarboxamide,
9-[4-[[1-(4-methoxy-2,6-dimethylphenyl)sulfonyl-2-piperidinyl]methoxy]-2-pyrimidinyl]-3-(4-pyridyl)-3,9-diazaspiro[5.5]undecane,
4-methoxy-N,2,6-trimethyl-N-[2-[[2-[4-(3-pyridyl)-4-(2-1-pyrrolidinylethoxy)-1-piperidinyl]-4-pyrimidinyl]oxy]ethyl]benzenesulfonamide,
4-methoxy-N,2,6-trimethyl-N-[2-[[2-[2-(4-pyridylmethyl)-2,5-diazabicyclo[2.2.1]heptan-5-yl]-4-pyrimidinyl]oxy]ethyl]benzenesulfonamide,
4-[[1-(4-methoxy-2,6-dimethylphenyl)sulfonyl-2-piperidinyl]methoxy]-2-[4-(3-pyridyl)-4-(2-1-pyrrolidinylethoxy)-1-piperidinyl]pyrimidine,
4-methoxy-N,2,6-trimethyl-N-[1-phenyl-2-[[2-[4-(4-pyridyl)-1-piperazinyl]-4-pyrimidinyl]oxy]ethyl]benzenesulfonamide,
4-methoxy-N,2,6-trimethyl-N-[1-phenyl-2-[[2-[3-(4-pyridyl)-3,9-diazaspiro[5.5]undecan-9-yl]-4-pyrimidinyl]oxy]ethyl]benzenesulfonamide,
N-methyl-N-[1-phenyl-2-[[2-[4-(3-pyridyl)-4-(2-1-pyrrolidinylethoxy)-1-piperidinyl]-4-pyrimidinyl]oxy]ethyl]-2-naphthalenesulfonamide,
N-[2-[[2-[3-[(4-fluorophenyl)methyl]-4-oxo-3,8-diazaspiro[4.5]decan-8-yl]-4-pyrimidinyl]oxy]ethyl]-4-methoxy-N,2,6-trimethylbenzenesulfonamide,
4-[[(2S)-1-(4-methoxy-2,6-dimethylphenyl)sulfonyl-2-pyrrolidinyl]methoxy]-2-[4-(3-pyridyl)-4-(2-1-pyrrolidinylethoxy)-1-piperidinyl]pyrimidine,
4-[[1-(4-methoxy-2,6-dimethylphenyl)sulfonyl-3-piperidinyl]oxy]-2-[4-[2-(1-piperidyl)ethyl]-1-piperidinyl]pyrimidine,
1-[4-[[1-[(4-methoxy-2,6-dimethyl-phenyl)sulfonyl]-piperidin-2-yl]-methoxy]-pyrimidin-2-yl]-4-(pyridin-2-yl-methyl)-[1,4]diazepan,
1-[4-[[(2R)-1-[(4-methoxy-2,6-dimethyl-phenyl)sulfonyl]-pyrrolidin-2-yl]-methoxy]-pyrimidin-2-yl]-4-(pyridin-2-yl-methyl)-[1,4]diazepan,
2-(4-dimethylamino-4-phenyl-piperidin-1-yl)-ethyl-[4-[[1-[(4-methoxy-2,6-dimethyl-phenyl)sulfonyl]-piperidin-2-yl]-methoxy]-pyrimidin-2-yl]-methyl-amine,
2-(4-butyl-4-dimethylamino-piperidin-1-yl)-ethyl-[4-[[1-[(4-methoxy-2,6-dimethyl-phenyl)sulfonyl]-piperidin-2-yl]-methoxy]-pyrimidin-2-yl]-methyl-amine,
3-(4-dimethylamino-4-phenyl-piperidin-1-yl)-propyl-[4-[[(2S)-1-[(4-methoxy-2,6-dimethyl-phenyl)sulfonyl]-pyrrolidin-2-yl]-methoxy]-pyrimidin-2-yl]-methyl-amine,
1-[4-[[(2S)-1-[(4-methoxy-2,6-dimethyl-phenyl)sulfonyl]-pyrrolidin-2-yl]-methoxy]-pyrimidin-2-yl]-4-pyridin-2-yl-piperidin-4-ol,
5-[1-[4-[[(2S)-1-[(4-methoxy-2,6-dimethyl-phenyl)sulfonyl]-pyrrolidin-2-yl]-methoxy]-pyrimidin-2-yl]-piperidin-4-yl]-3-pyridin-4-yl-[1,2,4]oxadiazole,
[4-[[1-[(4-methoxy-2,6-dimethyl-phenyl)sulfonyl]-piperidin-2-yl]-methoxy]-pyrimidin-2-yl]-methyl-[2-(4-pyridin-4-yloxy-piperidin-1-yl)-ethyl]-amine,
(1S,5R)-8-[4-[[1-[(4-methoxy-2,6-dimethyl-phenyl)sulfonyl]-piperidin-2-yl]-methoxy]-pyrimidin-2-yl]-3-pyridin-4-yloxy-8-azabicyclo[3.2.1]octane,
[4-[[(2S)-1-[(4-methoxy-2,6-dimethyl-phenyl)sulfonyl]-pyrrolidin-2-yl]-methoxy]-pyrimidin-2-yl]-methyl-[2-(4-pyridin-4-yloxy-piperidin-1-yl)-ethyl]-amine,
(1S,5R)-8-[4-[[(2S)-1-[(4-methoxy-2,6-dimethyl-phenyl)sulfonyl]-pyrrolidin-2-yl]-methoxy]-pyrimidin-2-yl]-3-pyridin-4-yloxy-8-azabicyclo[3.2.1]octane,
2-(4-butyl-4-dimethylamino-piperidin-1-yl)-ethyl-[4-[1-[(4-methoxy-2,6-dimethyl-phenyl)sulfonyl]-piperidin-3-yl]oxy-pyrimidin-2-yl]-methyl-amine,
2-(4-dimethylamino-4-phenyl-piperidin-1-yl)-ethyl-[4-[[(2S)-1-[(4-methoxy-2,6-dimethyl-phenyl)sulfonyl]-pyrrolidin-2-yl]-methoxy]-pyrimidin-2-yl]-methyl-amine,
[4-[[(2S)-1-[(4-methoxy-2,6-dimethyl-phenyl)sulfonyl]-pyrrolidin-2-yl]-methoxy]-pyrimidin-2-yl]methyl-[2-(4-phenyl-4-pyrrolidin-1-yl-piperidin-1-yl)-ethyl]-amine,
2-(4-butyl-4-dimethylamino-piperidin-1-yl)-ethyl-[4-[[(2S)-1-[(4-methoxy-2,6-dimethyl-phenyl)sulfonyl]-pyrrolidin-2-yl]-methoxy]-pyrimidin-2-yl]-methyl-amine,
2-(4-dimethylamino-4-phenyl-piperidin-1-yl)-ethyl-[4-[[(2S)-1-[(4-methoxy-2,6-dimethyl-phenyl)sulfonyl]-2,3-dihydro-1H-indol-2-yl]-methoxy]-pyrimidin-2-yl]-methyl-amine,
2-(4-butyl-4-dimethylamino-piperidin-1-yl)-ethyl-[4-[[(2S)-1-[(4-methoxy-2,6-dimethyl-phenyl)sulfonyl]-2,3-dihydro-1H-indol-2-yl]-methoxy]-pyrimidin-2-yl]-methyl-amine,
4-methoxy-N,2,6-trimethyl-N-[2-2-[methyl-[2-(4-phenyl-4-pyrrolidin-1-yl-piperidin-1-yl)-ethyl]-amino]-pyrimidin-4-yl]oxy-ethyl]-benzenesulfonic acid amide,
N-[2-[2-[2-(4-butyl-4-dimethylamino-piperidin-1-yl)-ethyl-methyl-amino]-pyrimidin-4-yl]oxy-ethyl]-4-methoxy-N,2,6-trimethyl-benzenesulfonic acid amide,
3-(4-dimethylamino-4-phenyl-piperidin-1-yl)-propyl-[4-[[1-[(4-methoxy-2,6-dimethyl-phenyl)sulfonyl]-piperidin-2-yl]-methoxy]-pyrimidin-2-yl]-methyl-amine,
[4-butyl-1-[4-[[1-[(4-methoxy-2,6-dimethyl-phenyl)sulfonyl]-piperidin-2-yl]-methoxy]-pyrimidin-2-yl]-piperidin-4-yl]-dimethyl-amine,
[4-[[1-[(4-methoxy-2,6-dimethyl-phenyl)sulfonyl]-piperidin-2-yl]-methoxy]-pyrimidin-2-yl]-methyl-[2-(4-phenyl-4-pyrrolidin-1-yl-piperidin-1-yl)-ethyl]-amine,

[1-[4-[1-[(4-methoxy-2,6-dimethyl-phenyl)sulfonyl]-piperidin-3-yl]oxy-pyrimidin-2-yl]-4-phenyl-piperidin-4-yl]-dimethyl-amine, 2-(4-dimethylamino-4-phenyl-piperidin-1-yl)-ethyl-[4-[1-[(4-methoxy-2,6-dimethyl-phenyl)sulfonyl]-piperidin-3-yl]oxy-pyrimidin-2-yl]-methyl-amine,

[4-[1-[(4-methoxy-2,6-dimethyl-phenyl)sulfonyl]-piperidin-3-yl]oxy-pyrimidin-2-yl]-methyl-[2-(4-phenyl-4-pyrrolidin-1-yl-piperidin-1-yl)-ethyl]-amine, N-[2-[2-[2-(4-dimethylamino-4-phenyl-piperidin-1-yl)-ethyl-methyl-amino]-pyrimidin-4-yl]oxy-ethyl]-4-methoxy-N,2,6-trimethyl-benzenesulfonic acid amide,

[4-butyl-1-[4-[[(2S)-1-[(4-methoxy-2,6-dimethyl-phenyl)sulfonyl]-pyrrolidin-2-yl]-methoxy]-pyrimidin-2-yl]-piperidin-4-yl]-dimethyl-amine, 2-(4-dimethylamino-4-phenyl-piperidin-1-yl)-ethyl-[4-[1-[(4-methoxy-2,6-dimethyl-phenyl)sulfonyl]-azetidin-3-yl]oxy-pyrimidin-2-yl]-methyl-amine,

[4-[1-[(4-methoxy-2,6-dimethyl-phenyl)sulfonyl]-azetidin-3-yl]oxy-pyrimidin-2-yl]-methyl-[2-(4-phenyl-4-pyrrolidin-1-yl-piperidin-1-yl)-ethyl]-amine, 2-(4-butyl-4-dimethylamino-piperidin-1-yl)-ethyl-[4-[1-[(4-methoxy-2,6-dimethyl-phenyl)sulfonyl]-azetidin-3-yl]oxy-pyrimidin-2-yl]-methyl-amine,

[4-[[(2S)-1-[(4-methoxy-2,6-dimethyl-phenyl)sulfonyl]-2,3-dihydro-1H-indol-2-yl]-methoxy]-pyrimidin-2-yl]-methyl-[2-(4-phenyl-4-pyrrolidin-1-yl-piperidin-1-yl)-ethyl]-amine, 3-(4-dimethylamino-4-phenyl-piperidin-1-yl)-propyl-[4-[1-[(4-methoxy-2,6-dimethyl-phenyl)sulfonyl]-piperidin-3-yl]oxy-pyrimidin-2-yl]-methyl-amine, 3-(4-dimethylamino-4-phenyl-piperidin-1-yl)-propyl-[4-[1-[(4-methoxy-2,6-dimethyl-phenyl)sulfonyl]-azetidin-3-yl]oxy-pyrimidin-2-yl]-methyl-amine, 3-(4-dimethylamino-4-phenyl-piperidin-1-yl)-propyl-[4-[[(2S)-1-[(4-methoxy-2,6-dimethyl-phenyl)sulfonyl]-2,3-dihydro-1H-indol-2-yl]-methoxy]-pyrimidin-2-yl]-methyl-amine, 1-[4-[1-[(4-methoxy-2,6-dimethyl-phenyl)sulfonyl]-azetidin-3-yl]oxy-pyrimidin-2-yl]-4-pyridin-3-yl-piperidin-4-ol, 1-[4-[1-[(4-methoxy-2,6-dimethyl-phenyl)sulfonyl]-azetidin-3-yl]oxy-pyrimidin-2-yl]-4-(pyridine-2-yl-methyl)-[1,4]diazepan, 4-[[1-[(4-methoxy-2,6-dimethyl-phenyl)sulfonyl]-piperidin-2-yl]-methoxy]-2-[2-(pyridin-2-yl-methyl)-pyrrolidin-1-yl]-pyrimidine, 4-[[1-[(4-methoxy-2,6-dimethyl-phenyl)sulfonyl]-piperidin-2-yl]-methoxy]-2-(4-pyridin-2-yloxy-piperidin-1-yl)-pyrimidine, 4-[[1-[(4-methoxy-2,6-dimethyl-phenyl)sulfonyl]-piperidin-2-yl]-methoxy]-2-(4-pyrazin-2-yloxy-piperidin-1-yl)-pyrimidine, 4-[1-[4-[[1-[(4-methoxy-2,6-dimethyl-phenyl)sulfonyl]-piperidin-2-yl]-methoxy]-pyrimidin-2-yl]-4-methyl-piperidin-4-yl]-morpholine, 4-[[1-[(4-methoxy-2,6-dimethyl-phenyl)sulfonyl]-piperidin-2-yl]-methoxy]-2-[4-pyridin-3-yl-4-(3-pyrrolidin-1-yl-propyl)-piperidin-1-yl]-pyrimidine, 1-[4-[[1-[(4-methoxy-2,6-dimethyl-phenyl)sulfonyl]-piperidin-2-yl]-methoxy]-pyrimidin-2-yl]-4-pyridin-2-yl-piperidin-4-ol, 4-[[(2R)-1-[(4-methoxy-2,6-dimethyl-phenyl)sulfonyl]-pyrrolidin-2-yl]-methoxy]-2-[2-(pyridin-2-yl-methyl)-pyrrolidin-1-yl]-pyrimidine,

[1-[4-[[(2S)-1-[(4-methoxy-2,6-dimethyl-phenyl)sulfonyl]-pyrrolidin-2-yl]-methoxy]-pyrimidin-2-yl]-4-phenyl-piperidin-4-yl]-dimethyl-amine,

[1-[4-[[(2S)-1-[(4-methoxy-2,6-dimethyl-phenyl)sulfonyl]-pyrrolidin-2-yl]-methoxy]-pyrimidin-2-yl]-4-thiophen-2-yl-piperidin-4-yl]-dimethyl-amine, 4-methoxy-N,2,6-trimethyl-N-[2-[2-[2-(pyridin-2-yl-methyl)-pyrrolidin-1-yl]-pyrimidin-4-yl]oxy-ethyl]-benzenesulfonic acid amide, 4-[[(2S)-1-[(4-methoxy-2,6-dimethyl-phenyl)sulfonyl]-pyrrolidin-2-yl]-methoxy]-2-[2-(pyridin-2-yl-methyl)-pyrrolidin-1-yl]-pyrimidine, 4-methoxy-N,2,6-trimethyl-N-[2-[2-[methyl-[2-(4-pyridin-4-yloxy-piperidin-1-yl)-ethyl]-amino]-pyrimidin-4-yl]oxy-ethyl]-benzenesulfonic acid amide, N-[2-[2-[4-(3-fluorophenyl)-4-(2-pyrrolidin-1-yl-ethoxy)-piperidin-1-yl]-pyrimidin-4-yl]oxy-ethyl]-4-methoxy-N,2,6-trimethyl-benzenesulfonic acid amide, 2-[4-(3-fluorophenyl)-4-(4-methyl-piperazin-1-yl)-piperidin-1-yl]-4-[[1-[(4-methoxy-2,6-dimethyl-phenyl)sulfonyl]-piperidin-2-yl]-methoxy]-pyrimidine, 2-[4-(3-fluorophenyl)-4-(2-pyrrolidin-1-yl-ethoxy)-piperidin-1-yl]-4-[[(2S)-1-[(4-methoxy-2,6-dimethyl-phenyl)sulfonyl]-pyrrolidin-2-yl]-methoxy]-pyrimidine, 4-methoxy-N,2,6-trimethyl-N-[1-phenyl-2-[2-[(1S,5R)-3-pyridin-4-yloxy-8-azabicyclo[3.2.1]octan-8-yl]-pyrimidin-4-yl]oxy-ethyl]-benzenesulfonic acid amide, and pharmaceutically acceptable salts of any of the foregoing compounds.

23. A pharmaceutical composition comprising a compound as claimed in claim 1, and at least one pharmaceutically acceptble carrier, additive or auxiliary substance.

24. A method of treating pain, in a subject in need thereof, said method comprising administering to said subject a pharmacologically effective amount of a compound as claimed in claim 1.

25. A method as claimed in claim 24, wherein said pain is selected from the group consisting of acute pain, visceral pain, neuropathic pain, chronic pain and inflammatory pain.

* * * * *